United States Patent
Berthelot et al.

(10) Patent No.: US 10,894,793 B2
(45) Date of Patent: Jan. 19, 2021

(54) BICYCLIC PYRIDINE, PYRAZINE, AND PYRIMIDINE DERIVATIVES AS PI3K BETA INHIBITORS

(71) Applicant: Janssen Pharmaceutica NV, Beerse (BE)

(72) Inventors: Didier Jean-Claude Berthelot, Issy-les-Moulineaux (FR); Laurence Anne Mevellec, Issy-les-Moulineaux (FR); Patrick Rene Angibaud, Issy-les-Moulineaux (FR); Sophie Coupa, Issy-les-Moulineaux (FR); Christophe Gabriel Marcel Demestre, Issy-les-Moulineaux (FR); Lieven Meerpoel, Beerse (BE); Guillaume Jean Maurice Mercey, Issy-les-Moulineaux (FR); Christophe Meyer, Issy-les-Moulineaux (FR); Elisabeth Therese Jeanne Pasquter, Issy-les-Moulineaux (FR); Isabelle Noelle Constance Pilatte, Issy-les-Moulineaux (FR); Virginie Sophie Poncelet, Issy-les-Moulineaux (FR); Olivier Alexis Georges Querolle, Issy-les-Moulineaux (FR)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/309,999

(22) PCT Filed: Jun. 15, 2017

(86) PCT No.: PCT/EP2017/064671
§ 371 (c)(1),
(2) Date: Dec. 14, 2018

(87) PCT Pub. No.: WO2017/216292
PCT Pub. Date: Dec. 21, 2017

(65) Prior Publication Data
US 2019/0169199 A1    Jun. 6, 2019

(30) Foreign Application Priority Data
Jun. 16, 2016   (EP) .................................. 16174715

(51) Int. Cl.
C07D 471/04    (2006.01)
C07D 487/04    (2006.01)
A61P 35/00     (2006.01)

(52) U.S. Cl.
CPC ............ C07D 487/04 (2013.01); A61P 35/00 (2018.01); C07D 471/04 (2013.01)

(58) Field of Classification Search
CPC ................... C07D 471/04; C07D 487/04
See application file for complete search history.

(56) References Cited

U.S. PATENT DOCUMENTS

| 2011/0110545 A1 | 5/2011 | Giese |
| 2013/0157977 A1 | 6/2013 | Rivero et al. |
| 2015/0191482 A1* | 7/2015 | Bentley ................ C07D 487/04 514/210.21 |

FOREIGN PATENT DOCUMENTS

| CN | 101663283 A | 4/2014 |
| WO | 2007/103756 | 9/2007 |
| WO | 2008/014219 | 1/2008 |
| WO | 2009/088990 | 7/2009 |
| WO | 2009/021083 A1 | 9/2009 |
| WO | 2011/022439 | 2/2011 |
| WO | 2011/041399 | 4/2011 |
| WO | 2011/110545 A1 | 9/2011 |
| WO | 2011/123751 | 10/2011 |
| WO | 2012/047538 | 4/2012 |
| WO | 2012/116237 | 8/2012 |
| WO | 2013/028263 | 2/2013 |
| WO | 2013/095761 A1 | 6/2013 |
| WO | 2014/009296 A1 | 1/2014 |
| WO | 2016/097347 | 6/2016 |
| WO | 2016/097359 | 6/2016 |
| WO | 2017/060406 A1 | 4/2017 |

OTHER PUBLICATIONS

B.Vanhasesbroeck et al, Signaling by distinct classes of phosphoinositide 3-kinases, Experimental Cell Research, 1999, pp. 239-254, 253.
David Stokoe et al, Dual role of phosphatidylinositol-3,4,5-trisphosphate in the activation of protein kinase B, Science, Jul. 25, 1997, pp. 567-570, 277.
Dr Calnan et al, The FoxO code, Oncogene, 2008, pp. 2276-2288, 27.
Kevin D. Courtney En Al, The PI3K pathways as drug target in human cancer, Journal of clinical oncology, Feb. 20, 2010, pp. 1075-1083, 28.
L Zhao et al, Class I PI3K in oncogenic cellular transformation, Oncogene, 2008, pp. 5486-5496, 27.

(Continued)

*Primary Examiner* — Bruck Kifle

(57) ABSTRACT

The present invention relates to bicyclic pyridine, pyrazine, and pyrimidine derivatives of Formula (I)

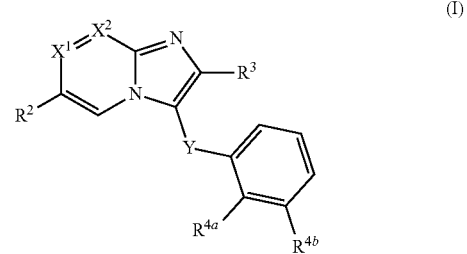

wherein the variables have the meaning defined in the claims. The compounds according to the present invention are useful as pI3Kβ inhibitors. The invention further relates to pharmaceutical compositions comprising said compounds as an active ingredient as well as the use of said compounds as a medicament.

5 Claims, No Drawings

(56) References Cited

OTHER PUBLICATIONS

Michael P. Myers, The lipid phosphatase activity of PTEN is crital for its tumor supressor function, Proc. Natl. Acad. Sci. USA, Nov. 1998, pp. 13513-13518, vol. 95.

Rute B. Marques et al, High Efficacy of Combination Therapy Using PI3K/AKT Inhibitors with Androgen Deprivation in Prostate Cancer Preclinical Models, European Urology, 2014, pp. 1177-1185, 67.

Shaun P Jackson, PI 3-kinase p 110b a new target for antithrombotic therapy, Nature medicine, May 2005, pp. 507-514, 11.

Shidong Jia et al, Essential roles of PI(3)K-p110B in cell growth, metabolism an tumorigenesis, Letters, Aug. 7, 2008, pp. 776-779, vol. 454.

Susan Wee et al, PTEN-deficient cancers depend on PIL3CB, PNAS, Sep. 2, 2008, pp. 13057-13062, 105.

W. Hickinbottom, corresponding part of the English edition Reactions of Organic Compounds, Chemical encyclopaedia, 1939, pp. 277-280, page number.

Wu Kui et al, Multisubstituted quinoxalines and pyrido[2,3-d]pyrimidines: Synthesis and SAR study as tyrosine kinase c-Met inhibitors, Bioorganic & Medicinal chemistry Letters, Aug. 27, 2012, pp. 6368-6372, vol. 22 No. 20.

* cited by examiner

BICYCLIC PYRIDINE, PYRAZINE, AND PYRIMIDINE DERIVATIVES AS PI3K BETA INHIBITORS

CROSS REFERENCE TO RELATED APPLICATIONS

This application is a national stage application of International Patent Application No. PCT/EP2017/064671, filed 15 Jun. 2017, which claims priority from EP Application 16174715.9 filed on 16 Jun. 2016. The complete disclosures of the aforementioned related patent applications are hereby incorporated herein by reference for all purposes.

FIELD OF THE INVENTION

The present invention relates to bicyclic pyridine, pyrazine, and pyrimidine derivatives useful as PI3Kβ inhibitors. The invention further relates to pharmaceutical compositions comprising said compounds as an active ingredient as well as the use of said compounds as a medicament.

BACKGROUND OF THE INVENTION

There are three classes of phosphoinositide-3-kinases (PI3Ks): class I, class II and class III. Class I PI3Ks are the most associated with human cancer [K. D Courtney, R. B. Corcoran and J. A. Engelman (2010), *Journal of Clinical Oncology.*, 28; 1075]. The class I phosphoinositide-3-kinases (PI3Ks) are divided into 2 subclasses: class IA, composed of a p110 catalytic subunit (p110a, p110b or p110d) and a p85 regulatory subunit (p85a, p55a and p50a, p85b or p55g) and class $1_B$ PI3K represented by the p110g catalytic subunit and the p101 and p84 regulatory subunits [B. Vanhaesebroeck and M. D. Waterfield (1999) *Experimental Cell Research.*, 253, 239-254]. The class IA PI3Ks are activated in a variety of solid and non-solid tumors via mutation or deletion of the tumor suppressor PTEN (phosphatase and tensin homolog) or in the case of p110a by activating mutations [K. D Courtney, R. B. Corcoran and J. A. Engelman (2010), *Journal of Clinical Oncology.*, 28; 1075]. PI3Ks can also be activated by receptor tyrosine kinases (RTKs); p110b can be activated by G-protein coupled receptors [K. D Courtney, R. B. Corcoran and J. A. Engelman (2010), *Journal of Clinical Oncology.*, 28; 1075]. Once activated the phosphoinositide-3-kinases catalyze the phosphorylation of phosphatidyl 4,5-diphosphate leading to the generation of phosphatidyl, 3, 4, 5-triphosphate (PIP3) [Zhao L., Vogt P. K. (2008) Oncogene 27, 5486-5496]. PTEN antagonizes the activity of the PI3Ks through the dephosphorylation of PIP3 [Myers M. P., Pass I., Batty I. H., Van der Kaay J., Stolarov J. P., Hemmings B. A., Wigler M. H., Downes C. P., Tonks N. K. (1998) *Proc. Natl. Acad. Sci. U.S.A.* 95, 13513-13518]. The PIP3 generated by activation of PI3K or sustained by the inactivation of PTEN binds to a subset of lipid-binding domains in downstream targets such as the pleckstrin homology domain of the oncogene Akt thereby recruiting it to the plasma membrane [Stokoe D., Stephens L. R., Copeland T., Gaffney P. R., Reese C. B., Painter G. F., Holmes A. B., McCormick F., Hawkins P. T. (1997) *Science* 277 567-570]. Once at the plasma membrane Akt phosphorylates several effector molecules that are involved in numerous biologically relevant processes such as metabolism, differentiation, proliferation, longevity and apoptosis [D. R. Calnan and A. Brunet (2008) *Oncogene* 27; 2276)].

Several studies suggest a key role for p1ll0b in PTEN-deficient tumors. For example the genetic knockout of p110b, but not p110a, is able to block tumor formation and Akt activation driven by Pten loss in the anterior prostate in a mouse model [Jia S, Liu Z, Zhang S, Liu P, Zhang L, Lee S H, Zhang J, Signoretti S, Loda M, Roberts T M, Zhao J J. *Nature* 2008; 454:776-9]. Furthermore other studies have shown that a subset of PTEN-deficient human tumor cell lines is sensitive to inactivation of p110b rather than p110a [Wee S, Wiederschain D, Maira S M, Loo A, Miller C, deBeaumont R, Stegmeier F, Yao Y M, Lengauer C (2008) *Proc. Natl. Acad Sci (USA)*; 105 13057]. PTEN deficiency either by genetic inactivation or reduced expression frequently occurs in human cancers such as GBM, endometrial, lung, breast cancers and prostate cancer among others [K. D Courtney, R. B. Corcoran and J. A. Engelman (2010), *Journal of Clinical Oncology.*, 28; 1075].

These studies suggest that treatment of PTEN-deficient cancer with agents that inhibit p110b may be therapeutically beneficial. In addition to its role in cancer, p110b may be a target for antithrombotic therapy. It has been reported in mouse models that PI3Kb inhibition can prevent stable integrin $a_{IIb}b_3$ adhesion contacts that eliminates occlusive thrombus formation without prolongation of bleed time [S. P. Jackson et al. (2005) *Nature Medicine.*, 11, 507-514].

Furthermore, the phosphatidylinositol-4,5-bisphosphate 3-kinase (PI3K)/AKT pathway is frequently activated during prostate cancer (PCa) progression through loss or mutation of the phosphatase and tensin homolog (PTEN) gene. Following the androgen receptor (AR) pathway, it is the second major driver of PCa growth. Combination with hormonal therapy improved efficacy of PI3K/AKT-targeted agents in PTEN-negative PCa models. Upregulation of AR-target genes upon PI3K/AKT inhibition suggests a compensatory crosstalk between the PI3K-AR pathways which, for optimal efficacy treatment, could require cotargeting of the AR axis [Marques R B, et al., High Efficacy of Combination Therapy Using PI3IK/AKT Inhibitors with Androgen Deprivation in Prostate Cancer Preclinical Models. *Eur Urol* (2014), http://dx.doi.org/10.1016/i.eururo.2014.08.053]. Therefore PI3Kβ inhibitors can be advantageously combined with anti-androgen therapies including androgen receptor antagonists and inhibitors of androgen biosynthesis in PTFN-negative prostate cancers.

WO 2012/116237 discloses heterocyclic entitites that modulate PI3 kinase activity.

WO 2011/123751 describes heterocyclic compounds as selective inhibitors of PI3K activity.

WO 2011/022439 discloses heterocyclic entities that modulate PI3 kinase activity.

WO 2008/014219 describes thiozolidinedione derivatives as PI3 kinase inhibitors.

WO 2013/028263 relates to pyrazolopyrimidine derivatives as PI3 kinase inhibitors.

WO 2012/047538 relates to benzimidazole derivatives as PI3 kinase inhibitors.

WO 2013/095761 relates to imidazopyridine derivatives as PI3 kinase inhibitors.

US 2013/0157977 relates to benzimidazole boronic acid derivatives as PI3 kinase inhibitors.

WO 2009/021083 describes quinoxaline derivatives as PI3 kinase inhibitors.

WO 2007/103756 describes the preparation of thiazolones for use as PI3 kinase inhibitors.

WO 2011/041399 describes benzimidazolyl (morpholinyl)purines and related compounds as PI3Kδ inhibitors and their preparation and use for the treatment of PI3K-mediated diseases.

WO 2009/088990 describes the preparation of pyrazolo pyrimidines and other heterocyclic compounds as therapeutic PI3 kinase modulators.

There is thus a strong need for novel PI3Kβ kinase inhibitors thereby opening new avenues for the treatment or prevention of cancer, in particular PTEN-deficient cancers, more in particular prostate cancer. It is accordingly an object of the present invention to provide such compounds.

SUMMARY OF THE INVENTION

It has been found that the compounds of the present invention are useful as PI3K3 inhibitors. The compounds according to the invention and compositions thereof, may be useful for the treatment or prevention, in particular for the treatment, of diseases such as cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, lung injuries and the like.

This invention concerns compounds of Formula (I)

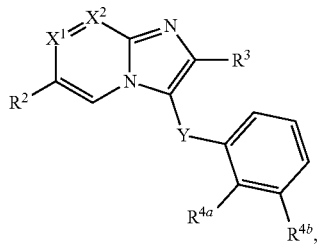

(I)

tautomers and stereoisomeric forms thereof, wherein
$X^1$ represents CH or N;
$X^2$ represents $CR^1$ or N;
provided that maximum one of $X^1$ and $X^2$ represents N;
$R^1$ represents hydrogen, —C(=O)OH, —C(=O)NH$_2$, —NH$_2$, —CH$_2$OH,

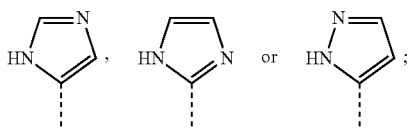

Y represents —CH$_2$— or —NH—;
$R^2$ represents

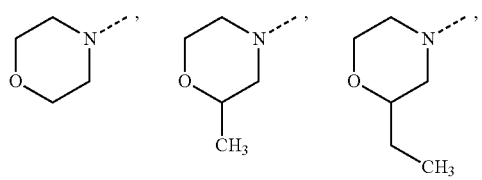

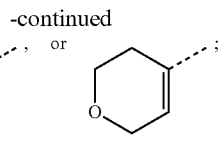

$R^3$ represents $C_{1-4}$alkyl; —C(=O)—O—$C_{1-4}$alkyl; —C(=O)—Het$^1$; —CH(OH)—CH$_2$—$R^q$; $C_{1-4}$alkyl substituted on the same carbon atom with one —OH and with one Het$^1$; or $C_{1-4}$alkyl substituted with one substituent selected from the group consisting of halo, —OH, —NH$_2$, —O—(C=O)—$C_{1-4}$alkyl, —(C=O)—O—$C_{1-4}$alkyl, —NH—(C=O)—$C_{1-4}$alkyl, —NH—(SO$_2$)—$C_{1-4}$alkyl, —N(CH$_3$)—$C_{1-4}$alkyl-SO$_2$—CH$_3$, —NH—$C_{1-4}$alkyl-SO$_2$—CH$_3$, —N(CH$_3$)—$C_{1-4}$alkyl-OH, —N(C=O—$C_{1-4}$alkyl)-$C_{1-4}$alkyl-OH, —(C=O)—NH—$C_{1-4}$alkyl-OH, —O—(C=O)—CH(NH$_2$)—$C_{1-4}$alkyl, —O—(C=O)—CH(NH$_2$)—$C_{1-4}$alkyl-Ar, —NH—$C_{1-4}$alkyl-OH, Het$^1$, —O—C(=O)—$C_{1-4}$alkyl-Het$^1$, —C(=O)—Het$^1$, and —NH—C(=O)—Het$^1$;
$R^q$ represents Het$^1$, halo, —OH, —NH$_2$, —O—(C=O)—$C_{1-4}$alkyl, —NH—(C=O)—$C_{1-4}$alkyl, —NH—(SO$_2$)—$C_{1-4}$alkyl, —N(CH$_3$)—$C_{1-4}$alkyl-SO$_2$—CH$_3$, —NH—$C_{1-4}$alkyl-SO$_2$—CH$_3$, —N(CH$_3$)—$C_{1-4}$alkyl-OH, —O—(C=O)—CH(NH$_2$)—$C_{1-4}$alkyl, —O—(C=O)—CH(NH$_2$)—$C_{1-4}$alkyl-Ar, or —NH—$C_{1-4}$alkyl-OH;
Ar represents phenyl optionally substituted with one hydroxy;
$R^{4a}$ represents hydrogen, $C_{1-4}$alkyl, Het$^a$, or $C_{1-4}$alkyl substituted with one or more substituents each independently selected from the group consisting of —OH, —NR$^5$R$^6$ and Het$^a$;
$R^{4b}$ represents hydrogen, halo, $C_{1-4}$alkyl, or $C_{1-4}$alkyl substituted with one or more halo substituents;
or $R^{4a}$ and $R^{4b}$ are taken together to form together with the phenyl ring to which they are attached a structure of Formula (a-1), (a-2), (a-3), (a-4) or (a-5):

(a-1)

-continued

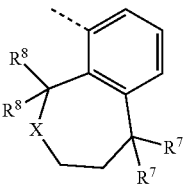
(a-2)

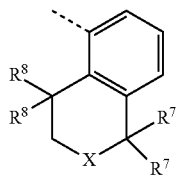
(a-3)

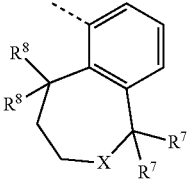
(a-4)

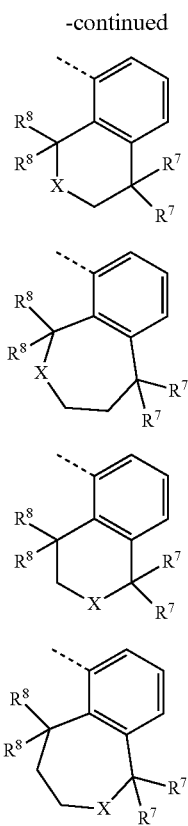
(a-5)

X represents —NH—, —O—, —N($C_{1-3}$alkyl)-, or —N(hydroxy$C_{1-3}$alkyl)-;

both $R^7$ substituents are the same and are selected from the group consisting of hydrogen, fluoro and methyl; or both $R^7$ substituents are taken together to form together with the common carbon atom to which they are attached a cyclopropyl, cyclobutyl or oxetanyl;

both $R^8$ substituents are the same and are selected from the group consisting of hydrogen and methyl; or both $R^8$ substituents are taken together to form together with the common carbon atom to which they are attached a cyclopropyl, cyclobutyl or oxetanyl;

$R^5$ represents hydrogen, $C_{1-6}$alkyl, or $C_{1-6}$alkyl substituted with one —OH;

$R^6$ represents hydrogen, $C_{1-6}$alkyl, or $C_{1-6}$alkyl substituted with one —OH;

$Het^1$ represents a 4-, 5- or 6-membered saturated heterocyclyl containing at least one heteroatom each independently selected from O, S, $S(=O)_p$ and N; said 4-, 5- or 6-membered saturated heterocyclyl is optionally substituted with one or two substituents each independently selected from the group consisting of halo, —NH$_2$, $C_{1-4}$alkyl, —S(=O)$_2$—$C_{1-6}$alkyl, —$C_{1-4}$alkyl-S(=O)$_2$—$C_{1-6}$alkyl, hydroxyl, $C_{1-4}$alkyloxy, fluoro, cyano and $C_{1-4}$alkyl substituted with one hydroxy; or two substituents on the same carbon atom of said 4-, 5- or 6-membered saturated heterocyclyl are taken together to form together with the common carbon atom to which they are attached Ring A;

Ring A represents cyclobutyl, cyclopentyl, cyclohexyl or a 4-, 5- or 6-membered saturated heterocyclyl containing at least one heteroatom each independently selected from O, S, $S(=O)_p$ and N; said cyclobutyl, cyclopentyl, cyclohexyl or 4-, 5- or 6-membered saturated heterocyclyl is optionally substituted with one or two $C_{1-4}$alkyl substituents, with one $C_{1-4}$alkyl and one hydroxy substituent, or with one hydroxy substituent;

each $Het^a$ independently represents a 4-, 5- or 6-membered saturated heterocyclyl containing at least one heteroatom each independently selected from O, S, $S(=O)_p$ and N; said 4-, 5- or 6-membered saturated heterocyclyl is optionally substituted with one or two substituents each independently selected from the group consisting of $C_{1-4}$alkyl, —S(=O)$_2$—$C_{1-6}$alkyl, hydroxy —$C_{1-4}$alkyl-S(=O)$_2$—$C_{1-6}$alkyl, and $C_{1-4}$alkyl substituted with one hydroxy; or two substituents on the same carbon atom of said 4-, 5- or 6-membered saturated heterocyclyl are taken together to form together with the common carbon atom to which they are attached Ring B;

Ring B represents cyclobutyl, cyclopentyl, cyclohexyl or a 4-, 5- or 6-membered saturated heterocyclyl containing at least one heteroatom each independently selected from O, S, $S(=O)_p$ and N; said cyclobutyl, cyclopentyl, cyclohexyl or 4-, 5- or 6-membered saturated heterocyclyl is optionally substituted with one or two $C_{1-4}$alkyl substituents, with one $C_{1-4}$alkyl and one hydroxy substituent, or with one hydroxy substituent;

p represents 1 or 2;

and the N-oxides, the pharmaceutically acceptable addition salts, and the solvates thereof.

The present invention also concerns methods for the preparation of compounds of the present invention and pharmaceutical compositions comprising them.

The compounds of the present invention were found to inhibit PI3Kβ per se or can undergo metabolism to a (more) active form in vivo (prodrugs), and therefore may be useful in the treatment or prevention, in particular in the treatment, of diseases such as cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, lung injuries and the like.

In view of the aforementioned pharmacology of the compounds of Formula (I) and N-oxides, pharmaceutically acceptable addition salts, and solvates thereof, it follows that they may be suitable for use as a medicament.

In particular the compounds of Formula (I) and N-oxides, pharmaceutically acceptable addition salts, and solvates thereof, may be suitable in the treatment or prevention, in particular in the treatment, of cancer.

The present invention also concerns the use of compounds of Formula (I) and N-oxides, pharmaceutically acceptable addition salts, and solvates thereof, for the manufacture of a medicament for the inhibition of PI3Kβ, for the treatment or prevention of cancer.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

When any variable occurs more than one time in any constituent or in any formula (e.g. Formula (I)), its definition in each occurrence is independent of its definition at every other occurrence.

Whenever the term "substituted" is used in the present invention, it is meant, unless otherwise is indicated or is clear from the context, to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

When two or more substituents are present on a moiety they may, unless otherwise is indicated or is clear from the context, replace hydrogens on the same atom or they may replace hydrogen atoms on different atoms in the moiety.

It will be clear for the skilled person that, unless otherwise is indicated or is clear from the context, a substituent on a heterocyclyl group may replace any hydrogen atom on a ring carbon atom or on a ring heteroatom.

The prefix "$C_{x-y}$" (where x and y are integers) as used herein refers to the number of carbon atoms in a given group. Thus, a $C_{1-6}$alkyl group contains from 1 to 6 carbon atoms, a $C_{1-4}$alkyl group contains from 1 to 4 carbon atoms, a $C_{1-3}$alkyl group contains from 1 to 3 carbon atoms, a $C_{3-6}$cycloalkyl group contains from 3 to 6 carbon atoms, and so on.

The term "halo" as a group or part of a group is generic for fluoro, chloro, bromo, iodo unless otherwise is indicated or is clear from the context.

The term "$C_{1-6}$alkyl" as a group or part of a group refers to a hydrocarbyl radical of Formula $C_nH_{2n+1}$ wherein n is a number ranging from 1 to 6. $C_{1-6}$alkyl groups comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes methyl, ethyl, n-propyl, i-propyl, 2-methyl-ethyl, butyl and its isomers (e.g. n-butyl, isobutyl and tert-butyl), and the like.

The term "$C_{1-3}$alkyl" as a group or part of a group refers to a hydrocarbyl radical of Formula $C_nH_{2n+1}$ wherein n is a number ranging from 1 to 3. $C_{1-3}$alkyl groups comprise from 1 to 3 carbon atoms, preferably 1 to 2 carbon atoms. $C_{1-3}$alkyl groups may be linear or branched and may be substituted as indicated herein. When a subscript is used herein following a carbon atom, the subscript refers to the number of carbon atoms that the named group may contain. $C_{1-3}$alkyl includes all linear, or branched alkyl groups with between 1 and 3 carbon atoms, and thus includes methyl, ethyl, n-propyl, i-propyl, 2-methyl-ethyl, and the like.

In an embodiment the expression 'at least one heteroatom' is restricted to '1, 2 or 3 heteroatoms', in a particular embodiment to '1 or 2 heteroatoms', in a more particular embodiment to '1 heteroatom'.

A 4-, 5- or 6-membered saturated heterocyclyl containing at least one heteroatom each independently selected from O, S, $S(=O)_p$ and N (as occurring for example in the definitions of $Het^1$, $Het^a$, Ring A and Ring B); in a particular embodiment is a 4-, 5- or 6-membered saturated heterocyclyl containing 1, 2 or 3 heteroatoms selected from O, S, $S(=O)_p$ and N; in a more particular embodiment a 4-, 5- or 6-membered saturated heterocyclyl containing 1 or 2 heteroatoms selected from O, S, $S(=O)_p$ and N.

Examples of a 4-, 5- or 6-membered saturated heterocyclyl containing at least one heteroatom each independently selected from O, S, $S(=O)_p$ and N, include, but are not limited to azetidinyl, morpholinyl, piperidinyl, pyrrolidinyl, 1,1-dioxido-thietanyl, 1,1-dioxido-thiomorpholinyl, piperazinyl, dioxolanyl, oxazolidinyl, oxetanyl, tetrahydrofuranyl, and the like.

$Het^1$ and $Het^a$ may be attached to the remainder of the molecule of Formula (I) through any available ring carbon atom or ring heteroatom as appropriate, if not otherwise specified.

It will be clear that when two substituents on the same carbon atom in the $Het^1$ or $Het^a$ definition are taken together to form together with the common carbon atom to which they are attached Ring A or Ring B respectively, a spiro moiety is formed.

For example, when $Het^1$ represents 1-piperidinyl wherein two substituents on the carbon atom in position β are taken together to form together with the common carbon atom to which they are attached ring A, the following spiro moiety is formed:

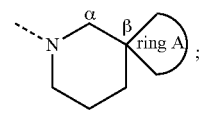

in particular if in the above example ring A represents 3-azetidinyl, the following spiro moiety is formed:

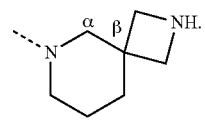

Examples of such spiro moieties, include, but are not limited to

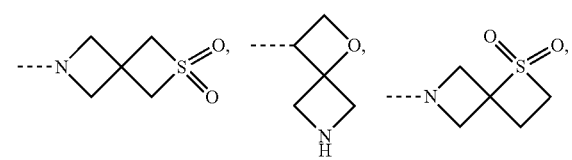

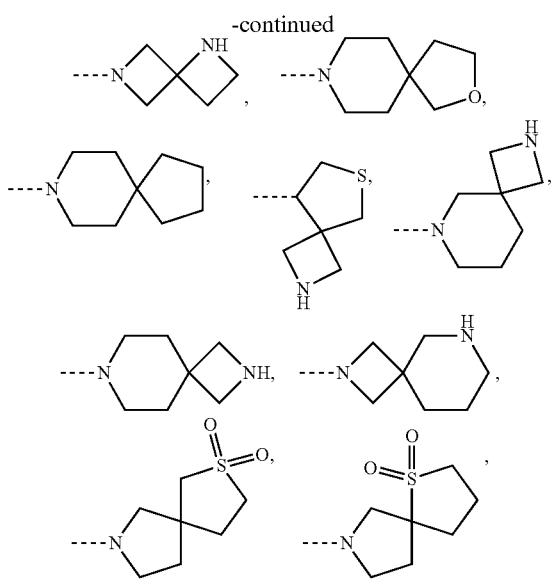

and the like.

Whenever substituents are represented by chemical structure, "---" represents the bond of attachment to the remainder of the molecule of Formula (I).

Whenever one of the ring systems, is substituted with one or more substituents, those substituents may replace, unless otherwise is indicated or is clear from the context, any hydrogen atom bound to a carbon or nitrogen atom of the ring system.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compounds of the invention" as used herein, is meant to include the compounds of Formula (I) and N-oxides, pharmaceutically acceptable addition salts, and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds of Formula (I) may also exist in their tautomeric form. Such forms in so far as they may exist, are intended to be included within the scope of the present invention. It follows that a single compound may exist in both stereoisomeric and tautomeric form.

For example, it will be clear for the skilled person that when $R^1$ represents

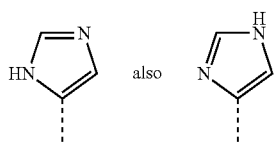

is included in the scope of the invention.

For therapeutic use, salts of the compounds of Formula (I), N-oxides and solvates thereof, are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove or hereinafter are meant to comprise the therapeutically active non-toxic acid and base addition salt forms which the compounds of Formula (I), N-oxides and solvates thereof, are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I), N-oxides and solvates thereof containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as N-oxides and pharmaceutically acceptable addition salts thereof. Examples of such forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and N-oxides, pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, an element, in particular when mentioned in relation to a compound of Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^2$H, $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^2$H, $^3$H, $^{11}$C and $^{18}$F. More preferably, the radioactive isotope is $^2$H. In particular, deuterated compounds are intended to be included within the scope of the present invention.

In an embodiment, the present invention concerns novel compounds of Formula (I), tautomers and stereoisomeric forms thereof, wherein
$X^1$ represents CH or N;
$X^2$ represents $CR^1$ or N;
provided that maximum one of $X^1$ and $X^2$ represents N;
$R^1$ represents hydrogen, —C(=O)OH, —C(=O)NH$_2$, —NH$_2$, —CH$_2$OH,

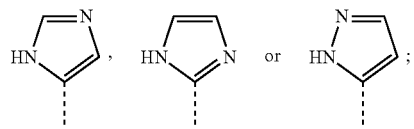

Y represents —CH$_2$— or —NH—;
$R^2$ represents

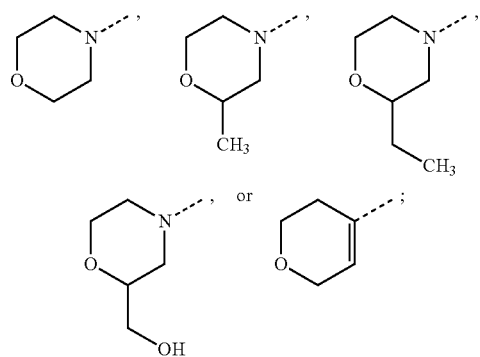

$R^3$ represents $C_{1-4}$alkyl; —C(=O)—Het$^1$; $C_{1-4}$alkyl substituted on the same carbon atom with one —OH and with one Het$^1$; or $C_{1-4}$alkyl substituted with one substituent selected from the group consisting of halo, —OH, —NH$_2$, —O—(C=O)—$C_{1-4}$alkyl, —(C=O)—O—$C_{1-4}$alkyl, —NH—(C=O)—$C_{1-4}$alkyl, —NH—(SO$_2$)—$C_{1-4}$alkyl, —N(CH$_3$)—$C_{1-4}$alkyl-SO$_2$—CH$_3$, —NH—$C_{1-4}$alkyl-SO$_2$—CH$_3$, —N(CH$_3$)—$C_{1-4}$alkyl-OH, —N(C=O—$C_{1-4}$alkyl)-$C_{1-4}$alkyl-OH, —(C=O)—NH—$C_{1-4}$alkyl-OH, —O—(C=O)—CH(NH$_2$)—$C_{1-4}$alkyl,

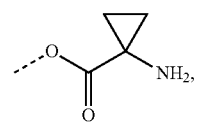

—NH—$C_{1-4}$alkyl-OH, Het$^1$, —O—C(=O)—$C_{1-4}$alkyl-Het$^1$, —C(=O)—Het$^1$, and —NH—C(=O)—Het$^1$;

$R^{4a}$ represents hydrogen, $C_{1-4}$alkyl, $Het^a$, or $C_{1-4}$alkyl substituted with one or more substituents each independently selected from the group consisting of —OH, —$NR^5R^6$ and $Het^a$;

$R^{4b}$ represents hydrogen, halo, $C_{1-4}$alkyl, or $C_{1-4}$alkyl substituted with one or more halo substituents;

$R^5$ represents hydrogen, $C_{1-6}$alkyl, or $C_{1-6}$alkyl substituted with one —OH;

$R^6$ represents hydrogen, $C_{1-6}$alkyl, or $C_{1-6}$alkyl substituted with one —OH;

$Het^1$ represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of halo, —$NH_2$, $C_{1-4}$alkyl, —S(=O)$_2$—$C_{1-6}$alkyl, —$C_{1-4}$alkyl-S(=O)$_2$—$C_{1-6}$alkyl, hydroxyl, $C_{1-4}$alkyloxy, fluoro, cyano and $C_{1-4}$alkyl substituted with one hydroxy; or two substituents on the same carbon atom of said 4-, 5- or 6-membered saturated heterocyclyl are taken together to form together with the common carbon atom to which they are attached Ring A;

Ring A represents cyclobutyl, cyclopentyl, cyclohexyl or a 4-, 5- or 6-membered saturated heterocyclyl containing at least one heteroatom each independently selected from O, S, S(=O)$_p$ and N; said cyclobutyl, cyclopentyl, cyclohexyl or 4-, 5- or 6-membered saturated heterocyclyl is optionally substituted with one or two $C_{1-4}$alkyl substituents, with one $C_{1-4}$alkyl and one hydroxy substituent, or with one hydroxy substituent;

each $Het^a$ independently represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of $C_{1-4}$alkyl, —S(=O)$_2$—$C_{1-6}$alkyl, hydroxy, —$C_{1-4}$alkyl-S(=O)$_2$—$C_{1-6}$alkyl, and $C_{1-4}$alkyl substituted with one hydroxy;

p represents 1 or 2;

and the N-oxides, the pharmaceutically acceptable addition salts, and the solvates thereof.

In an embodiment, the present invention concerns novel compounds of Formula (I), tautomers and stereoisomeric forms thereof, wherein $X^1$ represents CH or N;

$X^2$ represents $CR^1$ or N;

provided that maximum one of $X^1$ and $X^2$ represents N;

$R^1$ represents hydrogen, —C(=O)OH, —C(=O)$NH_2$, —$NH_2$, —$CH_2OH$,

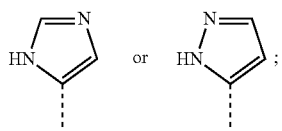

or

Y represents —$CH_2$— or —NH—;

$R^2$ represents

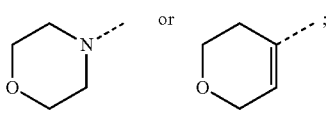

$R^3$ represents $C_{1-4}$alkyl; or $C_{1-4}$alkyl substituted with one substituent selected from the group consisting of halo, —OH, —O—(C=O)—$C_{1-4}$alkyl, —(C=O)—O—$C_{1-4}$alkyl, —N(CH$_3$)—$C_{1-4}$alkyl-OH, —N(C=O—$C_{1-4}$alkyl)-$C_{1-4}$alkyl-OH, —NH—$C_{1-4}$alkyl-OH, $Het^1$, and —C(=O)—$Het^1$;

$R^{4a}$ represents $C_{1-4}$alkyl, or $Het^a$;

$R^{4b}$ represents halo, or $C_{1-4}$alkyl substituted with one or more halo substituents;

$Het^1$ represents a 4-, 5- or 6-membered saturated heterocyclyl containing at least one heteroatom each independently selected from S(=O)$_p$ and N; said 4-, 5- or 6-membered saturated heterocyclyl is optionally substituted with one or two substituents each independently selected from the group consisting of $C_{1-4}$alkyl, and $C_{1-4}$alkyl substituted with one hydroxy; or two substituents on the same carbon atom of said 4-, 5- or 6-membered saturated heterocyclyl are taken together to form together with the common carbon atom to which they are attached Ring A;

Ring A represents cyclobutyl, cyclopentyl, cyclohexyl or a 4-, 5- or 6-membered saturated heterocyclyl containing at least one heteroatom each independently selected from S(=O)$_p$ and N;

each $Het^a$ independently represents a 4-, 5- or 6-membered saturated heterocyclyl containing at least one N-atom; said 4-, 5- or 6-membered saturated heterocyclyl is optionally substituted with one or two $C_{1-4}$alkyl substituents p represents 2;

and the N-oxides, the pharmaceutically acceptable addition salts, and the solvates thereof.

In an embodiment, the present invention concerns novel compounds of Formula (I), tautomers and stereoisomeric forms thereof, wherein $X^1$ represents CH or N;

$X^2$ represents $CR^1$ or N;

provided that maximum one of $X^1$ and $X^2$ represents N;

$R^1$ represents hydrogen, —$NH_2$, —$CH_2OH$, or

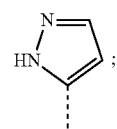

Y represents —$CH_2$— or —NH—;

$R^2$ represents

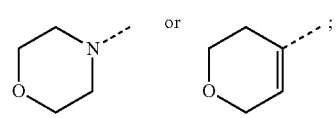

$R^3$ represents $C_{1-4}$alkyl; or $C_{1-4}$alkyl substituted with one substituent selected from the group consisting of —OH and $Het^1$;

$R^{4a}$ represents $C_{1-4}$alkyl;

$R^{4b}$ represents halo, or $C_{1-4}$alkyl substituted with one or more halo substituents;

Het¹ represents

and the N-oxides, the pharmaceutically acceptable addition salts, and the solvates thereof.

Another embodiment of the present invention relates to those compounds of Formula (I) and the N-oxides, the pharmaceutically acceptable addition salts, and the solvates thereof, or any subgroup thereof as mentioned in any of the other embodiments wherein one or more of the following restrictions apply:

(i) R¹ represents hydrogen, —C(=O)OH, —C(=O)NH₂, —NH₂, —CH₂OH,

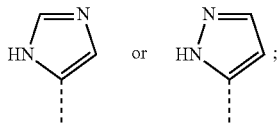

(ii) R² represents

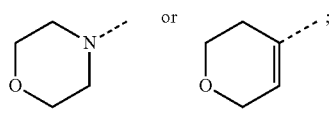

(iii) R³ represents $C_{1-4}$alkyl; or $C_{1-4}$alkyl substituted with one substituent selected from the group consisting of halo, —OH, —O—(C=O)—$C_{1-4}$alkyl, —(C=O)—O—$C_{1-4}$alkyl, —N(CH₃)—$C_{1-4}$alkyl-OH, —N(C=O—$C_{1-4}$alkyl)-$C_{1-4}$alkyl-OH, —NH—$C_{1-4}$alkyl-OH, Het¹, and —C(=O)—Het¹;

(iv) $R^{4a}$ represents $C_{1-4}$alkyl or Het$^a$;

(v) $R^{4b}$ represents halo, or $C_{1-4}$alkyl substituted with one or more halo substituents;

(vi) Het¹ represents a 4-, 5- or 6-membered saturated heterocyclyl containing at least one heteroatom each independently selected from $S(=O)_p$ and N; said 4-, 5- or 6-membered saturated heterocyclyl is optionally substituted with one or two substituents each independently selected from the group consisting of $C_{1-4}$alkyl, and $C_{1-4}$alkyl substituted with one hydroxy; or two substituents on the same carbon atom of said 4-, 5- or 6-membered saturated heterocyclyl are taken together to form together with the common carbon atom to which they are attached Ring A;

(vii) Ring A represents cyclobutyl, cyclopentyl, cyclohexyl or a 4-, 5- or 6-membered saturated heterocyclyl containing at least one heteroatom each independently selected from $S(=O)_p$ and N;

(viii) each Het$^a$ independently represents a 4-, 5- or 6-membered saturated heterocyclyl containing at least one N-atom; said 4-, 5- or 6-membered saturated heterocyclyl is optionally substituted with one or two $C_{1-4}$alkyl substituents (ix) p represents 2.

In an embodiment, the present invention relates to those compounds of Formula (I) and the N-oxides, the pharmaceutically acceptable addition salts, and the solvates thereof, or any subgroup thereof as mentioned in any of the other embodiments, wherein
R¹ represents —NH₂;
R² represents

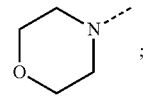

Y represents —CH₂—.

In an embodiment, the present invention relates to those compounds of Formula (I) and the N-oxides, the pharmaceutically acceptable addition salts, and the solvates thereof, or any subgroup thereof as mentioned in any of the other embodiments, wherein X¹ represents CH, and X² represents CR.

In an embodiment, the present invention relates to those compounds of Formula (I) and the N-oxides, the pharmaceutically acceptable addition salts, and the solvates thereof, or any subgroup thereof as mentioned in any of the other embodiments, wherein X¹ represents CH, and X² represents N.

In an embodiment, the present invention relates to those compounds of Formula (I) and the N-oxides, the pharmaceutically acceptable addition salts, and the solvates thereof, or any subgroup thereof as mentioned in any of the other embodiments, wherein X¹ represents N, and X² represents CR¹.

In an embodiment, the present invention relates to those compounds of Formula (I) and the N-oxides, the pharmaceutically acceptable addition salts, and the solvates thereof or any subgroup thereof as mentioned in any of the other embodiments, wherein X² represents CR¹; in particular wherein X² represents CH.

In an embodiment, the present invention relates to those compounds of Formula (I) and the N-oxides, the pharmaceutically acceptable addition salts, and the solvates thereof, or any subgroup thereof as mentioned in any of the other embodiments, wherein Y represents —CH₂—.

In an embodiment, the present invention relates to those compounds of Formula (I) and the N-oxides, the pharmaceutically acceptable addition salts, and the solvates thereof, or any subgroup thereof as mentioned in any of the other embodiments, wherein Y represents —NH—.

In an embodiment, the present invention relates to those compounds of Formula (I) and the N-oxides, the pharmaceutically acceptable addition salts, and the solvates thereof, or any subgroup thereof as mentioned in any of the other embodiments, wherein
Y represents —NH—; and
R³ represents $C_{1-4}$alkyl; or $C_{1-4}$alkyl substituted with one —OH substituent.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^{4a}$ represents hydrogen, $C_{1-4}$alkyl, or $C_{1-4}$alkyl substituted with one or more substituents each independently selected from the group consisting of —NR⁵R⁶ and Het$^a$;
$R^{4b}$ represents hydrogen, halo, $C_{1-4}$alkyl, or $C_{1-4}$alkyl substituted with one or more halo substituents.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^{4a}$ represents $C_{1-4}$alkyl; in particular $R^{4a}$ represents methyl;
$R^{4b}$ represents $C_{1-4}$alkyl substituted with one or more halo substituents; in particular $R^{4b}$ represents $CF_3$.

In an embodiment, the present invention relates to those compounds of Formula (I) and the N-oxides, the pharmaceutically acceptable addition salts, and the solvates thereof or any subgroup thereof as mentioned in any of the other embodiments, wherein $R^{4a}$ represents $C_{1-4}$alkyl; in particular $R^{4a}$ represents methyl.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^{4a}$ represents hydrogen, $C_{1-4}$alkyl, Het$^a$, or $C_{1-4}$alkyl substituted with one substituent selected from the group consisting of —OH, —NR$^5$R$^6$ and Het$^a$.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^{4b}$ represents $C_{1-4}$alkyl substituted with one or more halo substituents;
in particular $R^{4b}$ represents $CF_3$.

In an embodiment, the present invention relates to those compounds of Formula (I) and the N-oxides, the pharmaceutically acceptable addition salts, and the solvates thereof or any subgroup thereof as mentioned in any of the other embodiments, wherein $R^{4a}$ and $R^{4b}$ are other than hydrogen.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^{4a}$ and $R^{4b}$ are taken together to form together with the phenyl ring to which they are attached a structure of Formula (a-1), (a-2), (a-3), (a-4) or (a-5); in particular a structure of Formula (a-2) or (a-4); more in particular a structure of Formula (a-2).

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^{4a}$ represents $C_{1-4}$alkyl, Het$^a$, or $C_{1-4}$alkyl substituted with one or more substituents each independently selected from the group consisting of —OH, —NR$^5$R$^6$ and Het$^a$;
$R^{4b}$ represents hydrogen, halo, $C_{1-4}$alkyl, or $C_{1-4}$alkyl substituted with one or more halo substituents;
or $R^{4a}$ and $R^{4b}$ are taken together to form together with the phenyl ring to which they are attached a structure of Formula (a-2) or (a-4).

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^{4a}$ represents $C_{1-4}$alkyl, Het$^a$, or $C_{1-4}$alkyl substituted with one or more substituents each independently selected from the group consisting of —OH, —NR$^5$R$^6$ and Het$^a$;
$R^{4b}$ represents $C_{1-4}$alkyl, or $C_{1-4}$alkyl substituted with one or more halo substituents.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^{4a}$ represents $C_{1-4}$alkyl, Het$^a$, or $C_{1-4}$alkyl substituted with one or more substituents each independently selected from the group consisting of —OH, —NR$^5$R$^6$ and Het$^a$;
$R^{4b}$ represents $C_{1-4}$alkyl.

In an embodiment, the present invention relates to those compounds of Formula (I) and the N-oxides, the pharmaceutically acceptable addition salts, and the solvates thereof or any subgroup thereof as mentioned in any of the other embodiments, wherein
$R^{4a}$ represents $C_{1-4}$alkyl, Het$^a$, or $C_{1-4}$alkyl substituted with one or more substituents each independently selected from the group consisting of —OH, —NR$^5$R$^6$ and Het$^a$;
$R^{4b}$ represents $C_{1-4}$alkyl, or $C_{1-4}$alkyl substituted with one or more halo substituents;
or $R^{4a}$ and $R^{4b}$ are taken together to form together with the phenyl ring to which they are attached a structure of Formula (a-2) or (a-4).

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl; —C(=O)—Het$^1$; —CH(OH)—CH$_2$—R$^q$; $C_{1-4}$alkyl substituted on the same carbon atom with one —OH and with one Het$^1$; or $C_{1-4}$alkyl substituted with one substituent selected from the group consisting of halo, —OH, —NH$_2$, —O—(C=O)—$C_{1-4}$alkyl, —(C=O)—O—$C_{1-4}$alkyl, —NH—(C=O)—$C_{1-4}$alkyl, —NH—(SO$_2$)—$C_{1-4}$alkyl, —N(CH$_3$)—$C_{1-4}$alkyl-SO$_2$—CH$_3$, —NH—$C_{1-4}$alkyl-SO$_2$—CH$_3$, —N(CH$_3$)—$C_{1-4}$alkyl-OH, —N(C=O—$C_{1-4}$alkyl)-$C_{1-4}$alkyl-OH, —(C=O)—NH—$C_{1-4}$alkyl-OH, —O—(C=O)—CH(NH$_2$)—$C_{1-4}$alkyl, —O—(C=O)—CH(NH$_2$)—$C_{1-4}$alkyl-Ar,

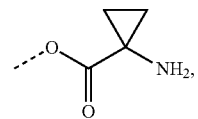

—NH—$C_{1-4}$alkyl-OH, Het$^1$, —O—C(=O)—$C_{1-4}$alkyl-Het$^1$, —C(=O)—Het$^1$, and —NH—C(=O)—Het$^1$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl; or $C_{1-4}$alkyl substituted with one substituent selected from the group consisting of halo, —OH, —NH$_2$, —O—(C=O)—$C_{1-4}$alkyl, —NH—(C=O)—$C_{1-4}$alkyl, —NH—(SO$_2$)—$C_{1-4}$alkyl, —N(CH$_3$)—$C_{1-4}$alkyl-SO$_2$—CH$_3$, —NH—$C_{1-4}$alkyl-SO$_2$—CH$_3$, —N(CH$_3$)—$C_{1-4}$alkyl-OH, —(C=O)—NH—$C_{1-4}$alkyl-OH, —O—(C=O)—CH(NH$_2$)—$C_{1-4}$alkyl, —O—(C=O)—CH(NH$_2$)—$C_{1-4}$alkyl-Ar,

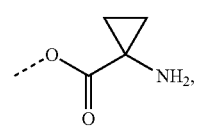

and —NH—$C_{1-4}$alkyl-OH.

In an embodiment, the present invention relates to those compounds of Formula (I) and the N-oxides, the pharmaceutically acceptable addition salts, and the solvates thereof, or any subgroup thereof as mentioned in any of the other embodiments, wherein R³ represents $C_{1-4}$alkyl; —CH(OH)—CH₂—R$^q$; or $C_{1-4}$alkyl substituted with one substituent selected from the group consisting of halo, —OH, —NH₂, —NH—(C=O)—$C_{1-4}$alkyl, —NH—(SO₂)—$C_{1-4}$alkyl, —N(CH₃)—$C_{1-4}$alkyl-SO₂—CH₃, —NH—$C_{1-4}$alkyl-SO₂—CH₃, —N(CH₃)—$C_{1-4}$alkyl-OH, —(C=O)—NH—$C_{1-4}$alkyl-OH, and —NH—$C_{1-4}$alkyl-OH; R$^q$ represents —OH, or —NH₂.

In an embodiment, the present invention relates to those compounds of Formula (I) and the N-oxides, the pharmaceutically acceptable addition salts, and the solvates thereof, or any subgroup thereof as mentioned in any of the other embodiments, wherein R³ represents $C_{1-4}$alkyl substituted with one substituent selected from the group consisting of halo, —OH, —NH₂, —O—(C=O)—$C_{1-4}$alkyl, —NH—(C=O)—$C_{1-4}$alkyl, —NH—(SO₂)—$C_{1-4}$alkyl, —N(CH₃)—$C_{1-4}$alkyl-SO₂—CH₃, —NH—$C_{1-4}$alkyl-SO₂—CH₃, —N(CH₃)—$C_{1-4}$alkyl-OH, —(C=O)—NH—$C_{1-4}$alkyl-OH, —(C=O)—CH(NH₂)—$C_{1-4}$alkyl, —O—(C=O)—CH(NH₂)—$C_{1-4}$alkyl-Ar,

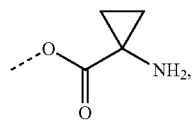

and —NH—$C_{1-4}$alkyl-OH.

In an embodiment, the present invention relates to those compounds of Formula (I) and the N-oxides, the pharmaceutically acceptable addition salts, and the solvates thereof, or any subgroup thereof as mentioned in any of the other embodiments, wherein R³ represents $C_{1-4}$alkyl; or $C_{1-4}$alkyl substituted with one substituent selected from the group consisting of halo, —OH, —NH₂, —O—(C=O)—$C_{1-4}$alkyl, —NH—(C=O)—$C_{1-4}$alkyl, —N(CH₃)—$C_{1-4}$alkyl-SO₂—CH₃, —NH—$C_{1-4}$alkyl-SO₂—CH₃, —O—(C=O)—CH(NH₂)—$C_{1-4}$alkyl, —O—(C=O)—CH(NH₂)—$C_{1-4}$alkyl-Ar,

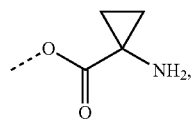

and —NH—$C_{1-4}$alkyl-OH.

In an embodiment, the present invention relates to those compounds of Formula (I) and the N-oxides, the pharmaceutically acceptable addition salts, and the solvates thereof or any subgroup thereof as mentioned in any of the other embodiments, wherein R³ represents —CH(OH)—CH₂—R$^q$; or $C_{1-4}$alkyl substituted with one substituent selected from the group consisting of halo, —OH, —NH₂, —O—(C=O)—$C_{1-4}$alkyl, —NH—(C=O)—$C_{1-4}$alkyl, —NH—(SO₂)—$C_{1-4}$alkyl, —N(CH₃)—$C_{1-4}$alkyl-SO₂—CH₃, —NH—$C_{1-4}$alkyl-SO₂—CH₃, —N(CH₃)—$C_{1-4}$alkyl-OH, —(C=O)—NH—$C_{1-4}$alkyl-OH, —O—(C=O)—CH(NH₂)—$C_{1-4}$alkyl, —O—(C=O)—CH(NH₂)—$C_{1-4}$alkyl-Ar,

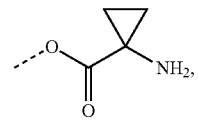

and —NH—$C_{1-4}$alkyl-OH.

In an embodiment, the present invention relates to those compounds of Formula (I) and the N-oxides, the pharmaceutically acceptable addition salts, and the solvates thereof, or any subgroup thereof as mentioned in any of the other embodiments, wherein R³ represents $C_{1-4}$alkyl substituted with one substituent as defined in any of the other embodiments.

In an embodiment, the present invention relates to those compounds of Formula (I) and the N-oxides, the pharmaceutically acceptable addition salts, and the solvates thereof, or any subgroup thereof as mentioned in any of the other embodiments, wherein R² represents

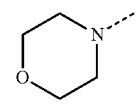

In an embodiment, the present invention relates to those compounds of Formula (I) and the N-oxides, the pharmaceutically acceptable addition salts, and the solvates thereof, or any subgroup thereof as mentioned in any of the other embodiments, wherein R² represents

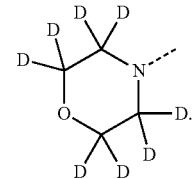

In an embodiment, the present invention relates to those compounds of Formula (I) and the N-oxides, the pharmaceutically acceptable addition salts, and the solvates thereof, or any subgroup thereof as mentioned in any of the other embodiments, wherein R³ represents $C_{1-4}$alkyl substituted with one —OH substituent; in particular R³ represents —CH₂—OH.

In an embodiment, the present invention relates to those compounds of Formula (I) and the N-oxides, the pharmaceutically acceptable addition salts, and the solvates thereof, or any subgroup thereof as mentioned in any of the other embodiments, wherein R¹ represents —C(=O)NH₂, —NH₂,

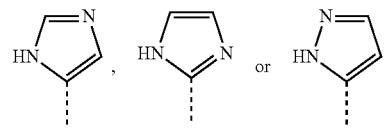

In an embodiment, the present invention relates to those compounds of Formula (I) and the N-oxides, the pharmaceutically acceptable addition salts, and the solvates thereof, or any subgroup thereof as mentioned in any of the other embodiments, wherein R¹ represents —C(=O)NH₂, —NH₂,

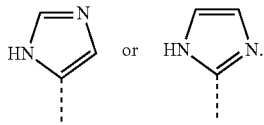

In an embodiment, the present invention relates to those compounds of Formula (I) and the N-oxides, the pharmaceutically acceptable addition salts, and the solvates thereof, or any subgroup thereof as mentioned in any of the other embodiments, wherein R¹ represents

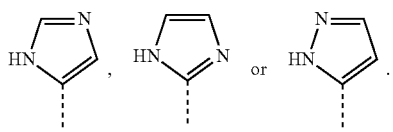

In an embodiment, the present invention relates to those compounds of Formula (I) and the N-oxides, the pharmaceutically acceptable addition salts, and the solvates thereof, or any subgroup thereof as mentioned in any of the other embodiments, wherein R¹ represents —C(=O)OH, —C(=O)NH₂, or —NH₂.

In an embodiment, the present invention relates to those compounds of Formula (I) and the N-oxides, the pharmaceutically acceptable addition salts, and the solvates thereof, or any subgroup thereof as mentioned in any of the other embodiments, wherein R¹ represents —C(=O)NH₂ or —NH₂.

In an embodiment, the present invention relates to those compounds of Formula (I) and the N-oxides, the pharmaceutically acceptable addition salts, and the solvates thereof, or any subgroup thereof as mentioned in any of the other embodiments, wherein R¹ represents —NH₂.

In an embodiment, the present invention relates to those compounds of Formula (I) and the N-oxides, the pharmaceutically acceptable addition salts, and the solvates thereof, or any subgroup thereof as mentioned in any of the other embodiments, wherein R¹ represents hydrogen.

In an embodiment, the present invention relates to those compounds of Formula (I) and the N-oxides, the pharmaceutically acceptable addition salts, and the solvates thereof, or any subgroup thereof as mentioned in any of the other embodiments, wherein R¹ represents other than hydrogen.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^q$ represents halo, —OH, —NH₂, —O—(C=O)—C₁₋₄alkyl, —NH—(C=O)—C₁₋₄alkyl, —NH—(SO₂)—C₁₋₄alkyl, —N(CH₃)—C₁₋₄alkyl-SO₂—CH₃, —NH—C₁₋₄alkyl-SO₂—CH₃, —N(CH₃)—C₁₋₄alkyl-OH, —O—(C=O)—CH(NH₂)—C₁₋₄alkyl, or —NH—C₁₋₄alkyl-OH.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^q$ represents —OH or —NH₂; in particular wherein $R^q$ represents —NH₂.

In an embodiment, the present invention relates to those compounds of Formula (I) and the N-oxides, the pharmaceutically acceptable addition salts, and the solvates thereof, or any subgroup thereof as mentioned in any of the other embodiments, wherein
R³ represents C₁₋₄alkyl; or C₁₋₄alkyl substituted with one substituent selected from the group consisting of halo, —OH, —O—(C=O)—C₁₋₄alkyl, —NH—(SO₂)—C₁₋₄alkyl, —N(CH₃)—C₁₋₄alkyl-SO₂—CH₃, —NH—C₁₋₄alkyl-SO₂—CH₃, —N(CH₃)—C₁₋₄alkyl-OH, —(C=O)—NH—C₁₋₄alkyl-OH and —NH—C₁₋₄alkyl-OH;
in particular wherein R³ represents C₁₋₄alkyl; or C₁₋₄alkyl substituted with one substituent selected from the group consisting of halo, —OH, —N(CH₃)—C₁₋₄alkyl-SO₂—CH₃, —NH—C₁₋₄alkyl-SO₂—CH₃, —N(CH₃)—C₁₋₄alkyl-OH, and —NH—C₁₋₄alkyl-OH; more in particular wherein R³ represents C₁₋₄alkyl; or C₁₋₄alkyl substituted with one substituent selected from the group consisting of halo and —OH; even more in particular wherein R³ represents C₁₋₄alkyl; or C₁₋₄alkyl substituted with one —OH substituent;
still more in particular wherein R³ represents C₁₋₄alkyl.

In an embodiment, the present invention relates to those compounds of Formula (I) and the N-oxides, the pharmaceutically acceptable addition salts, and the solvates thereof, or any subgroup thereof as mentioned in any of the other embodiments, wherein each $Het^a$ independently represents

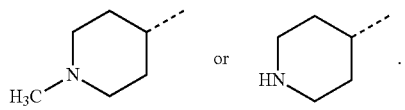

In an embodiment, the present invention relates to those compounds of Formula (I) and the N-oxides, the pharmaceutically acceptable addition salts, and the solvates thereof, or any subgroup thereof as mentioned in any of the other embodiments, wherein both R⁷ substituents are hydrogen; and wherein both R⁸ substituents are hydrogen.

In an embodiment, the present invention relates to those compounds of Formula (I) and the N-oxides, the pharmaceutically acceptable addition salts, and the solvates thereof, or any subgroup thereof as mentioned in any of the other embodiments, wherein
both R⁷ substituents are the same and are selected from the group consisting of hydrogen, fluoro and methyl; and wherein
both R⁸ substituents are the same and are selected from the group consisting of hydrogen and methyl.

In an embodiment, the present invention relates to those compounds of Formula (I) and the N-oxides, the pharmaceutically acceptable addition salts, and the solvates thereof, or any subgroup thereof as mentioned in any of the other embodiments, wherein R² represents

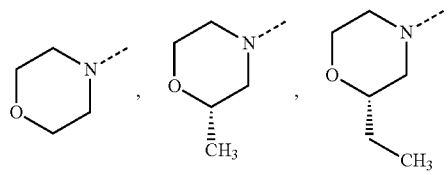

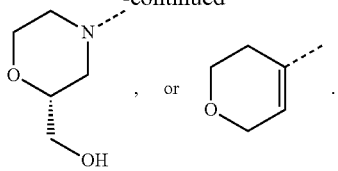

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^2$ represents

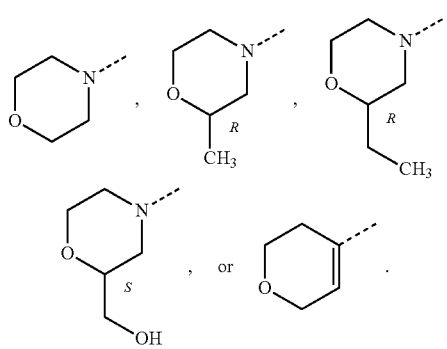

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^2$ representing

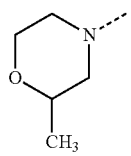

is limited to

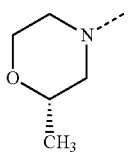

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^2$ representing

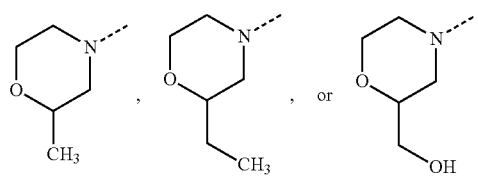

are limited respectively to

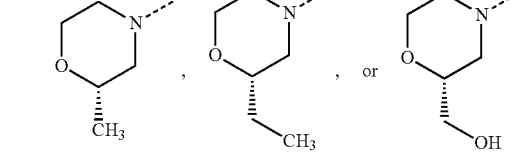

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl substituted with one substituent selected from the group consisting of $Het^{1a}$, —C(=O)—$Het^1$, and —NH—C(=O)—$Het^{1b}$; or $C_{1-4}$alkyl substituted on the same carbon atom with one —OH and with one $Het^{1b}$;

$Het^1$ represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of halo, —$NH_2$, $C_{1-4}$alkyl, —S(=O)$_2$—$C_{1-6}$alkyl, —$C_{1-4}$alkyl-S(=O)$_2$—$C_{1-6}$alkyl, hydroxy and $C_{1-4}$alkyl substituted with one hydroxy; or two substituents on the same carbon atom of said 4-, 5- or 6-membered saturated heterocyclyl are taken together to form together with the common carbon atom to which they are attached Ring A;

$Het^{1a}$ is defined as $Het^1$ provided however that $Het^{1a}$ is always attached to the remainder of $R^3$ through a ring nitrogen atom;

$Het^{1b}$ is defined as $Het^1$ provided however that $Het^{1b}$ is always attached to the remainder of $R^3$ through a ring carbon atom.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl substituted with one substituent selected from the group consisting of $Het^{1a}$, —O—C(=O)—$C_{1-4}$alkyl-$Het^{1a}$, —C(=O)-$Het^1$, and —NH—C(=O)-$Het^{1b}$; —CH(OH)—$CH_2$-$Het^{1a}$; or $C_{1-4}$alkyl substituted on the same carbon atom with one —OH and with one $Het^{1b}$;

$Het^1$ represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of halo, —$NH_2$, $C_{1-4}$alkyl, —S(=O)$_2$—$C_{1-6}$alkyl, —$C_{1-4}$alkyl-S(=O)$_2$—$C_{1-6}$alkyl, hydroxy and $C_{1-4}$alkyl substituted with one hydroxy; or two substituents on the same carbon atom of said 4-, 5- or 6-membered saturated heterocyclyl are taken together to form together with the common carbon atom to which they are attached Ring A;

$Het^{1a}$ is defined as $Het^1$ provided however that $Het^{1a}$ is always attached to the remainder of $R^3$ through a ring nitrogen atom;

$Het^{1b}$ is defined as $Het^1$ provided however that $Het^{1b}$ is always attached to the remainder of $R^3$ through a ring carbon atom.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^1$ represents other than —C(=O)OH.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^3$ represents $C_{1-4}$alkyl substituted with one substituent selected from the group consisting of $Het^1$, —C(=O)—$Het^1$, and —NH—C(=O)—$Het^1$; or
$C_{1-4}$alkyl substituted on the same carbon atom with one —OH and with one $Het^1$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl substituted with one substituent selected from the group consisting of $Het^1$, —C(=O)-$Het^1$, and —NH—C(=O)—$Het^1$; —CH(OH)—$CH_2$-$Het^1$; or $C_{1-4}$alkyl substituted on the same carbon atom with one —OH and with one $Het^1$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl substituted with one substituent selected from the group consisting of $Het^1$, —O—C(=O)—$C_{1-4}$alkyl-$Het^1$, —C(=O)—$Het^1$, and —NH—C(=O)—$Het^1$; or —CH(OH)—$CH_2$-$Het^1$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl substituted with one substituent selected from the group consisting of $Het^1$, —C(=O)—$Het^1$, and —NH—C(=O)—$Het^1$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl substituted with one substituent selected from the group consisting of $Het^1$ and —C(=O)—$Het^1$;
in particular $R^3$ represents $C_{1-4}$alkyl substituted with one $Het^1$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl substituted with one substituent selected from the group consisting of $Het^1$, —C(=O)—$Het^1$, and —NH—C(=O)—$Het^1$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl substituted with one $Het^1$ substituent; in particular $R^3$ represents $C_{1-4}$alkyl substituted with one $Het^{1a}$ substituent wherein $Het^{1a}$ is defined as $Het^1$ provided however that $Het^{1a}$ is always attached to $C_{1-4}$alkyl through a ring nitrogen atom.

In an embodiment, the present invention relates to those compounds of Formula (I) and the N-oxides, the pharmaceutically acceptable addition salts, and the solvates thereof, or any subgroup thereof as mentioned in any of the other embodiments, wherein the following proviso is applicable: when Y represents —NH—; then $R^3$ represents $C_{1-4}$alkyl substituted with one $Het^1$ substituent; in particular when Y represents —NH—, then $R^3$ represents $C_{1-4}$alkyl substituted with one $Het^{1a}$ substituent wherein $Het^{1a}$ is defined as $Het^1$ provided however that $Het^{1a}$ is always attached to $C_{1-4}$alkyl through a ring nitrogen atom.

In an embodiment, the present invention relates to those compounds of Formula (I) and the N-oxides, the pharmaceutically acceptable addition salts, and the solvates thereof, or any subgroup thereof as mentioned in any of the other embodiments, wherein the following proviso is applicable: when Y represents —NH—;
then $R^3$ represents $C_{1-4}$alkyl; or $C_{1-4}$alkyl substituted with one —OH substituent.

In an embodiment, the present invention relates to those compounds of Formula (I) and the N-oxides, the pharmaceutically acceptable addition salts, and the solvates thereof, or any subgroup thereof as mentioned in any of the other embodiments, wherein $Het^1$ represents a 4-, 5- or 6-membered saturated heterocyclyl containing at least one heteroatom each independently selected from $S(=O)_p$ and N; said 4-, 5- or 6-membered saturated heterocyclyl is optionally substituted with one or two substituents each independently selected from the group consisting of —$NH_2$, $C_{1-4}$alkyl, —$S(=O)_2$—$C_{1-6}$alkyl, hydroxy and $C_{1-4}$alkyl substituted with one hydroxy; or two substituents on the same carbon atom of said 4-, 5- or 6-membered saturated heterocyclyl are taken together to form together with the common carbon atom to which they are attached Ring A.

In an embodiment, the present invention relates to those compounds of Formula (I) and the N-oxides, the pharmaceutically acceptable addition salts, and the solvates thereof, or any subgroup thereof as mentioned in any of the other embodiments, wherein $Het^1$ represents a 4-, 5- or 6-membered saturated heterocyclyl containing at least one heteroatom each independently selected from $S(=O)_p$ and N; said 4-, 5- or 6-membered saturated heterocyclyl is optionally substituted with one or two substituents each independently selected from the group consisting of —$NH_2$, $C_{1-4}$alkyl, —$S(=O)_2$—$C_{1-6}$alkyl, hydroxy and $C_{1-4}$alkyl substituted with one hydroxy.

In an embodiment, the present invention relates to those compounds of Formula (I) and the N-oxides, the pharmaceutically acceptable addition salts, and the solvates thereof, or any subgroup thereof as mentioned in any of the other embodiments, wherein Ring A represents a 4-, 5- or 6-membered saturated heterocyclyl containing at least one heteroatom each independently selected from $S(=O)_p$ and N.

In an embodiment, the present invention relates to those compounds of Formula (I) and the N-oxides, the pharmaceutically acceptable addition salts, and the solvates thereof, or any subgroup thereof as mentioned in any of the other embodiments, wherein Ring A represents cyclobutyl, cyclopentyl, cyclohexyl or a 4-, 5- or 6-membered saturated heterocyclyl containing at least one heteroatom each independently selected from $S(=O)_p$ and N; said cyclobutyl, cyclopentyl, cyclohexyl or 4-, 5- or 6-membered saturated heterocyclyl is optionally substituted with one hydroxy substituent.

In an embodiment, the present invention relates to those compounds of Formula (I) and the N-oxides, the pharmaceutically acceptable addition salts, and the solvates thereof, or any subgroup thereof as mentioned in any of the other embodiments, wherein $Het^1$ represents a 4-, 5- or 6-membered saturated heterocyclyl containing at least one heteroatom each independently selected from O, S, S(=O)$_p$ and N; and 2 substituents on the same carbon atom of said 4-, 5- or 6-membered saturated heterocyclyl are taken together to form together with the common carbon atom to which they are attached Ring A.

In an embodiment, the present invention relates to those compounds of Formula (I) and the N-oxides, the pharmaceutically acceptable addition salts, and the solvates thereof, or any subgroup thereof as mentioned in any of the other embodiments, wherein Het$^1$ represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of —NH$_2$, C$_{1-4}$alkyl, —S(=O)$_2$—C$_{1-6}$alkyl, —C$_{1-4}$alkyl-S(=O)$_2$—C$_{1-6}$alkyl, hydroxy and C$_{1-4}$alkyl substituted with one hydroxy.

In an embodiment, the present invention relates to those compounds of Formula (I) and the N-oxides, the pharmaceutically acceptable addition salts, and the solvates thereof, or any subgroup thereof as mentioned in any of the other embodiments, wherein Het$^1$ represents a 4-, 5- or 6-membered saturated heterocyclyl containing at least one heteroatom each independently selected from O, S, S(=O)$_p$ and N; p represents 2.

In an embodiment, the present invention relates to those compounds of Formula (I) and the N-oxides, the pharmaceutically acceptable addition salts, and the solvates thereof or any subgroup thereof as mentioned in any of the other embodiments, wherein Het$^1$ represents a 4-, 5- or 6-membered saturated heterocyclyl containing one S(=O)$_p$ and also containing one N; p represents 2.

In an embodiment, the present invention relates to those compounds of Formula (I) and the N-oxides, the pharmaceutically acceptable addition salts, and the solvates thereof or any subgroup thereof as mentioned in any of the other embodiments, wherein Het$^1$ represents a 4-, 5- or 6-membered saturated heterocyclyl containing one S(=O)$_p$ and also containing one N; said 4-, 5- or 6-membered saturated heterocyclyl is optionally substituted with one or two substituents each independently selected from the group consisting of —NH$_2$, C$_{1-4}$alkyl, —S(=O)$_2$—C$_{1-6}$alkyl, —C$_{1-4}$alkyl-S(=O)$_2$—C$_{1-6}$alkyl, hydroxy and C$_{1-4}$alkyl substituted with one hydroxy; p represents 2.

In an embodiment, the present invention relates to those compounds of Formula (I) and the N-oxides, the pharmaceutically acceptable addition salts, and the solvates thereof, or any subgroup thereof as mentioned in any of the other embodiments, wherein
Het$^1$ represents

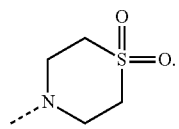

In an embodiment, the present invention relates to those compounds of Formula (I) and the N-oxides, the pharmaceutically acceptable addition salts, and the solvates thereof, or any subgroup thereof as mentioned in any of the other embodiments, wherein Het$^1$ represents

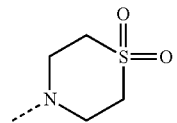

optionally substituted with one or two substituents each independently selected from the group consisting of —NH$_2$, C$_{1-4}$alkyl, —S(=O)$_2$—C$_{1-6}$alkyl, —C$_{1-4}$alkyl-S(=O)$_2$—C$_{1-6}$alkyl, hydroxy and C$_{1-4}$alkyl substituted with one hydroxy.

In an embodiment, the present invention relates to those compounds of Formula (I) and the N-oxides, the pharmaceutically acceptable addition salts, and the solvates thereof, or any subgroup thereof as mentioned in any of the other embodiments, wherein Het$^1$ represents

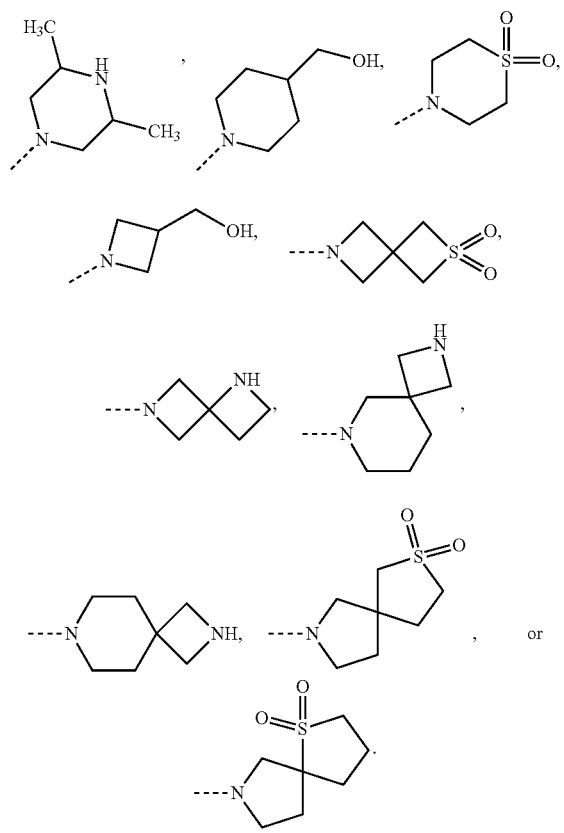

In an embodiment, the present invention relates to those compounds of Formula (I) and the N-oxides, the pharmaceutically acceptable addition salts, and the solvates thereof or any subgroup thereof as mentioned in any of the other embodiments, wherein R$^3$ represents C$_{1-4}$alkyl; —CH(OH)—CH$_2$—R$^q$; or C$_{1-4}$alkyl substituted with one substituent selected from the group consisting of halo, —OH, —NH$_2$, —O—(C=O)—C$_{1-4}$alkyl, —(C=O)—O—C$_{1-4}$alkyl, —NH—(C=O)—C$_{1-4}$alkyl, —NH—(SO$_2$)—C$_{1-4}$alkyl, —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, —N(C=O—C$_{1-4}$alkyl)-C$_{1-4}$alkyl-OH, —(C=O)—NH—C$_{1-4}$alkyl-OH, —O—(C=O)—CH(NH$_2$)—C$_{1-4}$alkyl, —O—(C=O)—CH(NH$_2$)—C$_{1-4}$alkyl-Ar,

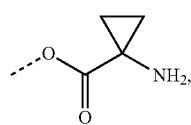

—NH—C$_{1-4}$alkyl-OH, Het$^1$, and —C(=O)—Het$^1$;
and wherein Het$^1$ represents

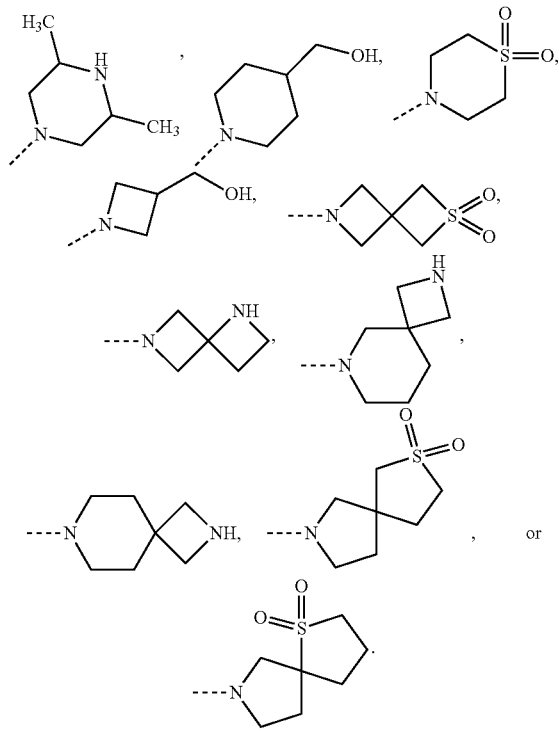

In an embodiment, the present invention relates to those compounds of Formula (I) and the N-oxides, the pharmaceutically acceptable addition salts, and the solvates thereof, or any subgroup thereof as mentioned in any of the other embodiments, wherein Het$^1$ represents

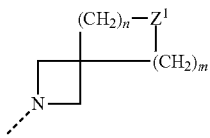

Z$^1$ represents —NH—, —S—, —O— or —S(O)$_2$—; in particular Z$^1$ represents —S(O)$_2$—;
n represents 0, 1 or 2;
m represents 1, 2 or 3; provided however that m does not have value 1 when n is 0.

In a particular embodiment, the present invention relates to those compounds of Formula (I) and the N-oxides, the pharmaceutically acceptable addition salts, and the solvates thereof, or any subgroup thereof as mentioned in any of the other embodiments, wherein Het$^1$ is attached to the remainder of the molecule of Formula (I) through a nitrogen atom.

In a particular embodiment, the present invention relates to those compounds of Formula (I) and the N-oxides, the pharmaceutically acceptable addition salts, and the solvates thereof, or any subgroup thereof as mentioned in any of the other embodiments, wherein Het$^1$ is attached to the remainder of the molecule of Formula (I) through a carbon atom.

In a particular embodiment, the present invention relates to those compounds of Formula (I) and the N-oxides, the pharmaceutically acceptable addition salts, and the solvates thereof, or any subgroup thereof as mentioned in any of the other embodiments, wherein
R$^3$ represents C$_{1-4}$alkyl; —C(=O)-Het$^1$; C$_{1-4}$alkyl substituted on the same carbon atom with one —OH and with one Het$^1$; or C$_{1-4}$alkyl substituted with one substituent selected from the group consisting of halo, —OH, —NH$_2$, —O—(C=O)—C$_{1-4}$alkyl, —(C=O)—O—C$_{1-4}$alkyl, —NH—(C=O)—C$_{1-4}$alkyl, —NH—(SO$_2$)—C$_{1-4}$alkyl, —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, —N(C=O—C$_{1-4}$alkyl)-C$_{1-4}$alkyl-OH, —(C=O)—NH—C$_{1-4}$alkyl-OH, —O—(C=O)—CH(NH$_2$)—C$_{1-4}$alkyl, —O—(C=O)—CH(NH$_2$)—C$_{1-4}$alkyl-Ar,

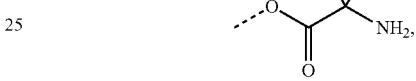

—NH—C$_{1-4}$alkyl-OH, Het$^1$, and —C(=O)—Het$^1$;
wherein Het$^1$ is attached to the remainder of the molecule of Formula (I) through a nitrogen atom.

In an embodiment, the present invention relates to those compounds of Formula (I) and the N-oxides, the pharmaceutically acceptable addition salts, and the solvates thereof or any subgroup thereof as mentioned in any of the other embodiments, wherein R$^3$ represents C$_{1-4}$alkyl; —CH(OH)—CH$_2$—R$^q$; or C$_{1-4}$alkyl substituted with one substituent selected from the group consisting of halo, —OH, —NH$_2$, —O—(C=O)—C$_{1-4}$alkyl, —(C=O)—O—C$_{1-4}$alkyl, —NH—(C=O)—C$_{1-4}$alkyl, —NH—(SO$_2$)—C$_{1-4}$alkyl, —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, —N(C=O—C$_{1-4}$alkyl)-C$_{1-4}$alkyl-OH, —(C=O)—NH—C$_{1-4}$alkyl-OH, —O—(C=O)—CH(NH$_2$)—C$_{1-4}$alkyl, —O—(C=O)—CH(NH$_2$)—C$_{1-4}$alkyl-Ar,

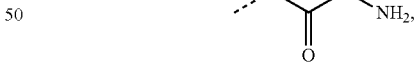

—NH—C$_{1-4}$alkyl-OH, Het$^1$, and —C(=O)—Het$^1$;
wherein Het$^1$ is attached to the remainder of the molecule of Formula (I) through a nitrogen atom.

In a particular embodiment, the present invention relates to those compounds of Formula (I) and the N-oxides, the pharmaceutically acceptable addition salts, and the solvates thereof, or any subgroup thereof as mentioned in any of the other embodiments, wherein
R$^3$ represents C$_{1-4}$alkyl; —C(=O)—Het$^1$; —CH(OH)—CH$_2$—R$^q$; C$_{1-4}$alkyl substituted on the same carbon atom with one —OH and with one Het$^{1b}$; or C$_{1-4}$alkyl substituted with one substituent selected from the group consisting of halo, —OH, —NH$_2$, —O—(C=O)—C$_{1-4}$alkyl, —(C=O)—O—C$_{1-4}$alkyl, —NH—(C=O)—C$_{1-4}$alkyl, —NH—(SO$_2$)—C$_{1-4}$alkyl, —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, —N(C=O—C$_{1-4}$alkyl)-C$_{1-4}$alkyl-OH, —(C=O)—NH—C$_{1-4}$alkyl-OH, —O—(C=O)—CH(NH$_2$)—C$_{1-4}$alkyl, —O—(C=O)—CH(NH$_2$)—C$_{1-4}$alkyl-Ar,

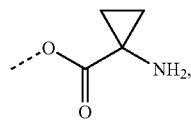

—NH—C$_{1-4}$alkyl-OH, Het$^{1a}$, —O—C(=O)—C$_{1-4}$alkyl-Het$^{1a}$, —C(=O)—Het$^1$, and —NH—C(=O)—Het$^{1b}$;

R$^q$ represents Het$^{1a}$, halo, —OH, —NH$_2$, —O—(C=O)—C$_{1-4}$alkyl, —NH—(C=O)—C$_{1-4}$alkyl, —NH—(SO$_2$)—C$_{1-4}$alkyl, —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, —O—(C=O)—CH(NH$_2$)—C$_{1-4}$alkyl, —O—(C=O)—CH(NH$_2$)—C$_{1-4}$alkyl-Ar,

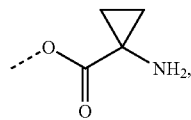

or —NH—C$_{1-4}$alkyl-OH;

Het$^1$ represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of halo, —NH$_2$, C$_{1-4}$alkyl, —S(=O)$_2$—C$_{1-6}$alkyl, —C$_{1-4}$alkyl-S(=O)$_2$—C$_{1-6}$alkyl, hydroxy and C$_{1-4}$alkyl substituted with one hydroxy; or two substituents on the same carbon atom of said 4-, 5- or 6-membered saturated heterocyclyl are taken together to form together with the common carbon atom to which they are attached Ring A;

Het$^{1a}$ is defined as Het$^1$ provided however that Het$^{1a}$ is always attached to the remainder of R$^3$ through a ring nitrogen atom;

Het$^{1b}$ is defined as Het$^1$ provided however that Het$^{1b}$ is always attached to the remainder of R$^3$ through a ring carbon atom.

In an embodiment the compound of Formula (I) is selected from the group consisting of compounds 1, 21, 39 and 46, tautomers and stereoisomeric forms thereof, and the N-oxides, the pharmaceutically acceptable addition salts, and the solvates thereof.

In an embodiment the compound of Formula (I) is selected from the group consisting of compounds 1, 21, 39 and 46.

All possible combinations of the above-indicated embodiments are considered to be embraced within the scope of this invention.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry. For example, the skilled person will realize that for some general schemes, analogous chemistry as reported for X$^2$ being limited to N or CH, can also be adapted for X$^2$ being CR$^1$ in general. It should be understood that suitable protecting groups might have to be applied. Although the schemes below are focussed on compounds of Formula (I) wherein Y represents —CH$_2$—, the skilled person will realize that analogous chemistry can be applied in combination with standard synthetic processes to synthesize compound of Formula (I) wherein Y represents —NH— (see also Scheme 19).

The skilled person will realize that in the reactions described in the Schemes, it may be necessary to protect reactive functional groups, for example hydroxy, amino, or carboxy groups, where these are desired in the final product, to avoid their unwanted participation in the reactions. Conventional protecting groups can be used in accordance with standard practice. This is illustrated in the specific examples. The protecting groups may be removed at a convenient subsequent stage using methods known from the art.

The skilled person will realize that in the reactions described in the Schemes, it may be advisable or necessary to perform the reaction under an inert atmosphere, such as for example under N$_2$-gas atmosphere.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

Reaction conditions in the general schemes that refer to 'sealed conditions', refer to a sealed reaction vessel wherein the pressure increases as the solvent becomes more volatile. Although typically this is not an absolute requirement to succeed the reactions in the schemes below, this will typically lead to reduced reaction times.

The skilled person will realize that another sequence of the chemical reactions shown in the Schemes below, may also result in the desired compound of Formula (I).

The skilled person will realize that intermediates and final compounds shown in the schemes below may be further functionalized according to methods well-known by the person skilled in the art.

As mentioned before, the prefix "C$_{x-y}$" (where x and y are integers) as used herein refers to the number of carbon atoms in a given group. The skilled person will realize that C$_0$ corresponds to a covalent bond. Thus the term "C$_{0-3}$alkyl" as a group or part of a group refers to a covalent bond (C$_0$) and a hydrocarbyl radical of Formula C$_n$H$_{2n+1}$ wherein n is a number ranging from 1 to 3.

Some compounds in the general schemes might be illustrative examples.

In general, compounds of Formula (I) wherein R$^1$ is restricted to hydrogen, and wherein the other variables are as shown in Formula (Ia), can be prepared according to the following reaction Scheme 1, wherein $W^1$ and $W^2$ represent a leaving group such as Cl, Br or I. All other variables in Scheme 1 are defined according to the scope of the present invention.

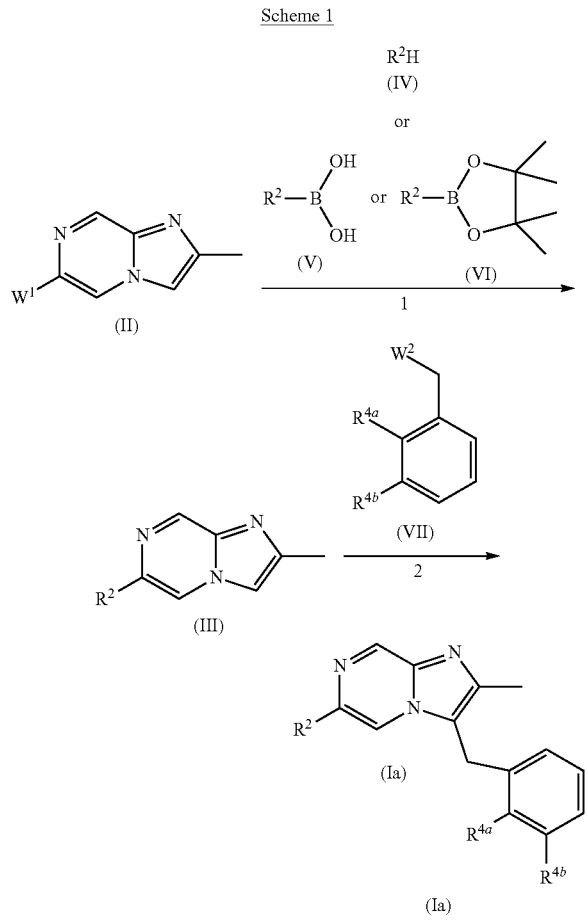

In Scheme 1, the following reaction conditions apply:

1: in case of $R_2H$:

Without solvent at a suitable temperature such as 100° C.

Alternatively in the presence of a suitable ligand such as 2-dicyclohexylphosphino-2',6'-diisopropoxybiphenyl (Ruphos) or 2-Dicyclohexylphosphino-2'-(N,N-dimethylamino)biphenyl (Davephos), a suitable catalyst such as for example tris(dibenzylideneacetone)dipalladium ($Pd_2dba_3$) or palladium acetate, a suitable base such as for example $Cs_2CO_3$, and a suitable solvent such as for example 2-methyl-2-butanol or dioxane, at a suitable temperature such as for example between 100 and 120° C.;

in case of $R_2B(OH)_2$ or $R_2$(4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium phosphate, and a suitable solvent such as for example a mixture dioxane and water, at a suitable temperature ranged between 80° C. and 105° C.;

2: in the presence of a suitable catalyst such as for example palladium acetate ($Pd(OAc)_2$), a suitable ligand such as for example tetrakistriphenyl phosphine ($P(Ph)_3$), a suitable base such as for example potassium carbonate ($K_2CO_3$), in a suitable solvent such as for example 1,4-dioxane at a suitable temperature such as for example 100° C., in sealed conditions.

In general, compounds of Formula (I) wherein $R^1$ is restricted to an hydrogen, and wherein the other variables are as shown in Formula (Ib), (Ica), (Icb) and (Id) can be prepared according to the following reaction Scheme 2, wherein $W^3$ represent a leaving group such as Cl, Br or I. All other variables in Scheme 2 are defined according to the scope of the present invention or as defined hereinbefore.

Scheme 2
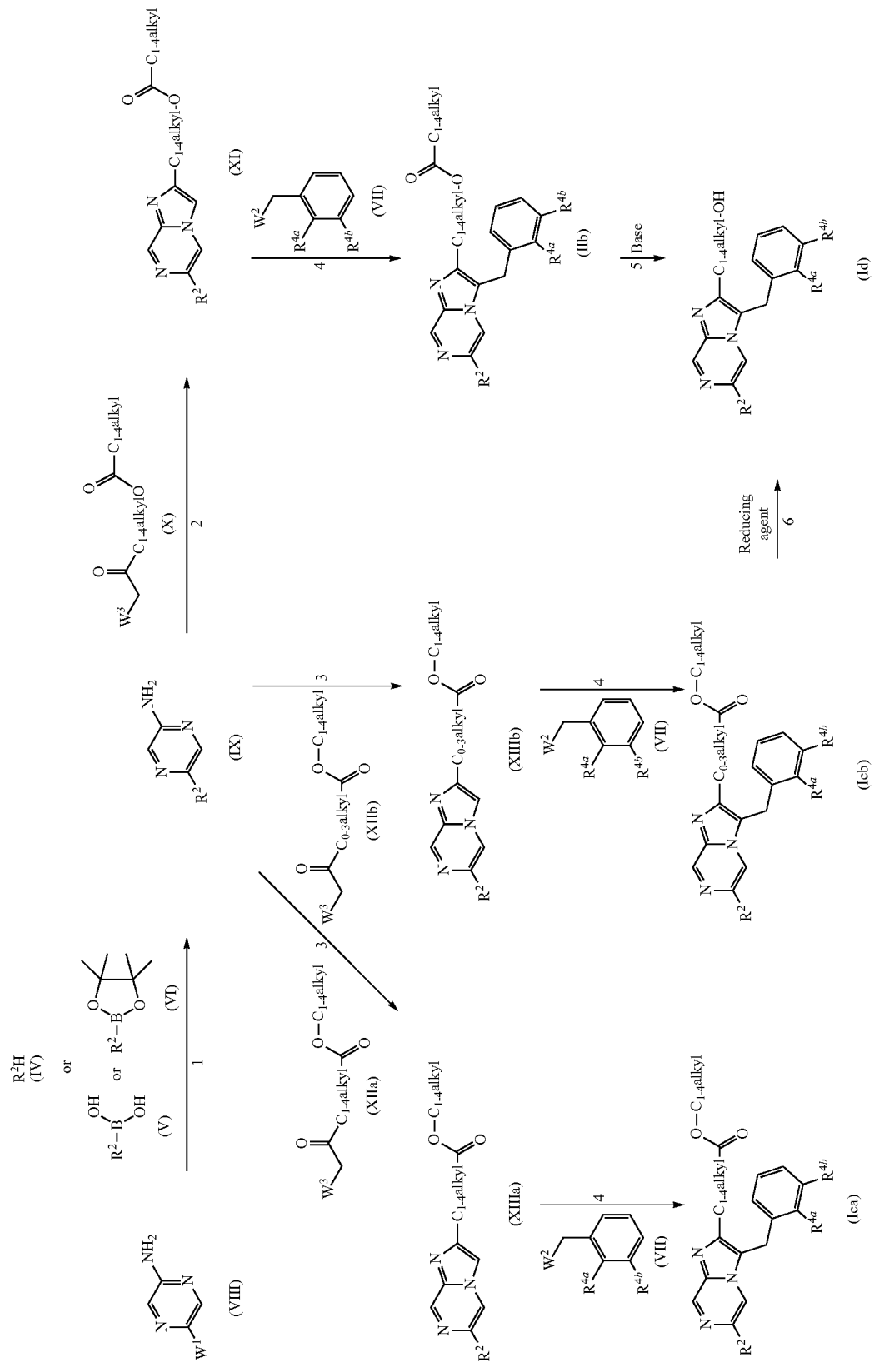

In Scheme 2, the following reaction conditions apply:
1: in case of $R_2H$:
Without solvent at a suitable temperature such as 100° C. Alternatively in the presence of a suitable ligand such as 2-dicyclohexylphosphino-2',6'-diisopropoxybiphenyl (Ruphos) or 2-Dicyclohexylphosphino-2'-(N,N-dimethylamino)biphenyl (Davephos), a suitable catalyst such as for example tris(dibenzylideneacetone)dipalladium ($Pd_2dba_3$) or palladium acetate, a suitable base such as for example $Cs_2CO_3$, and a suitable solvent such as for example 2-methyl-2-butanol or dioxane, at a suitable temperature such as for example between 100 and 120° C.;

in case of $R_2B(OH)_2$ or $R_2$(4,4,5,5-tetramethyl-1,3,2-dioxaborolane), in the presence of a suitable catalyst such as for example 1,1'-bis(diphenylphosphino)ferrocene palladium(II)dichloride dichloromethane adduct or RuPhos palladacycle, a suitable base such as for example potassium phosphate, and a suitable solvent such as for example a mixture dioxane and water, at a suitable temperature ranged between 80° C. and 105° C.;

2: in sealed conditions, in the presence of molecular sieve (4 Å), in a suitable solvent such as for example ethylene glycol dimethyl ether (DME), at suitable temperature such as for example 80° C.;

3: in sealed conditions, optionally in the presence of a suitable base such as for example sodium hydrogenocarbonate ($NaHCO_3$), in a suitable solvent such as for example ethylene glycol dimethyl ether (DME) or acetonitrile (ACN), at suitable temperature such ranged between 60 to 80° C., optionally in the presence of molecular sieve (4 Å);

4: in sealed conditions, in the presence of a suitable catalyst such as for example palladium acetate ($Pd(OAc)_2$, a suitable ligand such as for example tetrakistriphenyl phosphine ($P(Ph)_3$), a suitable base such as for example potassium carbonate ($K_2CO_3$), in a suitable solvent such as for example 1,4-dioxane at a suitable temperature such as for example 100° C.;

5: in the presence of a suitable base such as for example lithium hydroxide, in a suitable solvent such as for example a mixture of methanol and water, at a suitable temperature such as for example room temperature;

6: In the presence of a suitable reducing agent such as for example lithium aluminium hydride or lithium borohydride, in a suitable solvent such as for example tetrahydrofuran, at a suitable temperature ranged between 0 to room temperature.

In general, compounds of Formula (I) wherein $R^1$ is restricted to COOH, $CONH_2$ and $CH_2OH$, and wherein the other variables are as shown in Formula (Ie), (If) and (Ig) can be prepared according to the following reaction Scheme 3, wherein $W^4$ represent a leaving group such as Cl or Br. All other variables in Scheme 3 are defined according to the scope of the present invention or as defined hereinbefore.

Scheme 3

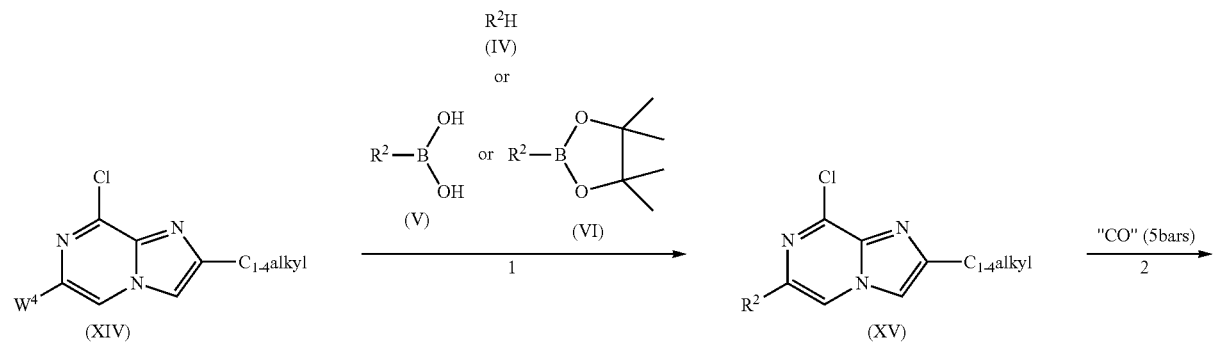

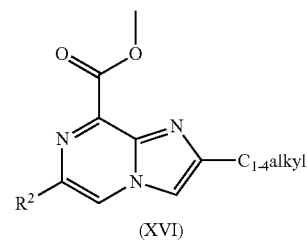

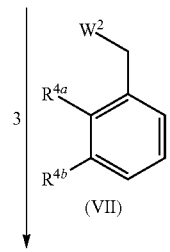

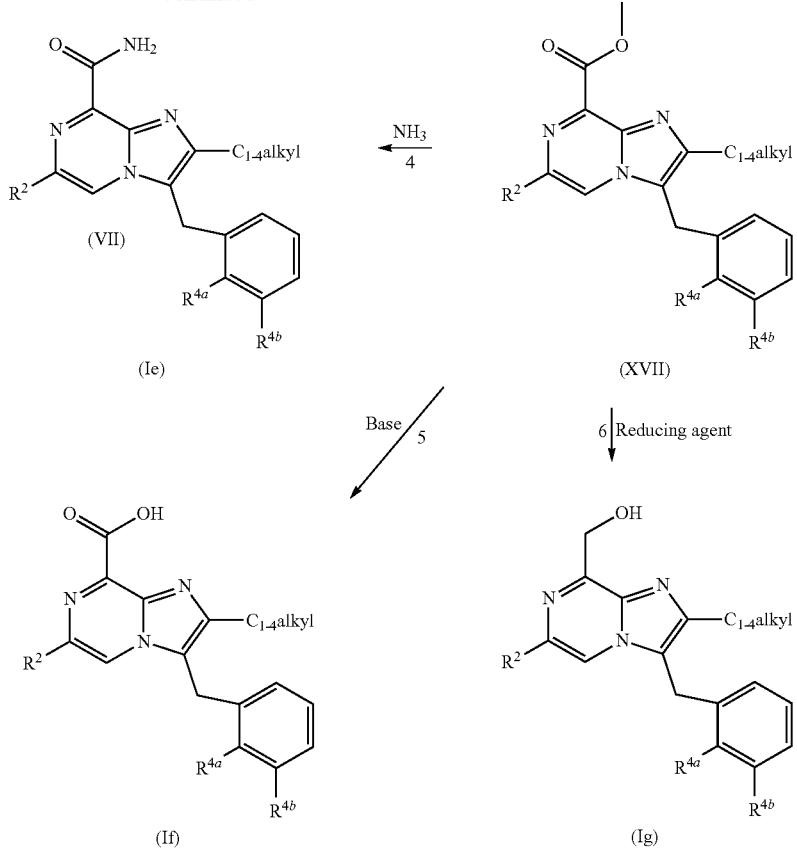

In Scheme 3, the following reaction conditions apply:
1: in case of $R_2H$:
Without solvent at a suitable temperature such as 100° C.
Alternatively in the presence of a suitable ligand such as 2-dicyclohexylphosphino-2',6'-diisopropoxybiphenyl (Ruphos) or 2-Dicyclohexylphosphino-2'-(N,N-dimethylamino)biphenyl (Davephos), a suitable catalyst such as for example tris(dibenzylideneacetone)dipalladium ($Pd_2dba_3$) or palladium acetate, a suitable base such as for example $Cs_2CO_3$, and a suitable solvent such as for example 2-methyl-2-butanol or dioxane, at a suitable temperature such as for example between 100 and 120° C.;
in case of $R_2B(OH)_2$ or $R_2$(4,4,5,5-tetramethyl-1,3,2-dioxaborolane), in the presence of a suitable catalyst such as for example 1,1'-bis(diphenylphosphino)ferrocene palladium(II)dichloride dichloromethane adduct or RuPhos palladacycle, a suitable base such as for example potassium phosphate, and a suitable solvent such as for example a mixture dioxane and water, at a suitable temperature ranged between 80° C. and 105° C.;
2: in an autoclave, in the presence of a suitable catalyst such as for example palladium acetate, a suitable ligand such as for example 1,3-bis(diphenylphosphino)propane, in the presence of a suitable base such as for example potassium acetate in a suitable solvent such as for example methanol, at a suitable temperature such as for example room temperature;
3: in sealed conditions, in the presence of a suitable catalyst such as for example palladium acetate ($Pd(OAc)_2$, a suitable ligand such as for example tetrakistriphenyl phosphine ($P(Ph)_3$), a suitable base such as for example potassium carbonate ($K_2CO_3$), in a suitable solvent such as for example 1,4-dioxane at a suitable temperature such as for example 100° C.;
4: in sealed conditions, in a suitable solvent such as for example methanol, at a suitable temperature such as for example 90° C.;
5: in the presence of a suitable base such as for example lithium hydroxide, in a suitable solvent such as for example a mixture of tetrahydrofuran and water, at a suitable temperature such as for example room temperature;
6: in the presence of a suitable reducing agent such as for example lithium aluminium hydride, in a suitable solvent such as for example tetrahydrofuran, at a suitable temperature such as for example room temperature.

In general, compounds of Formula (I) wherein $R^1$ is restricted to $NH_2$ and $R^{1a}$ being

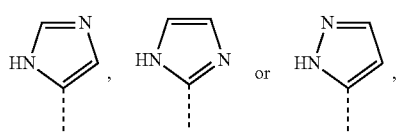

and wherein the other variables are as shown in Formula (Ih) and (Ii) can be prepared according to the following reaction Scheme 4. PG is defined as a protective group such as for example a N,N-dimethylsulfonamidyl or 2-tetrahydropyranyl moiety. All other variables in Scheme 4 are defined according to the scope of the present invention or as defined hereinbefore.

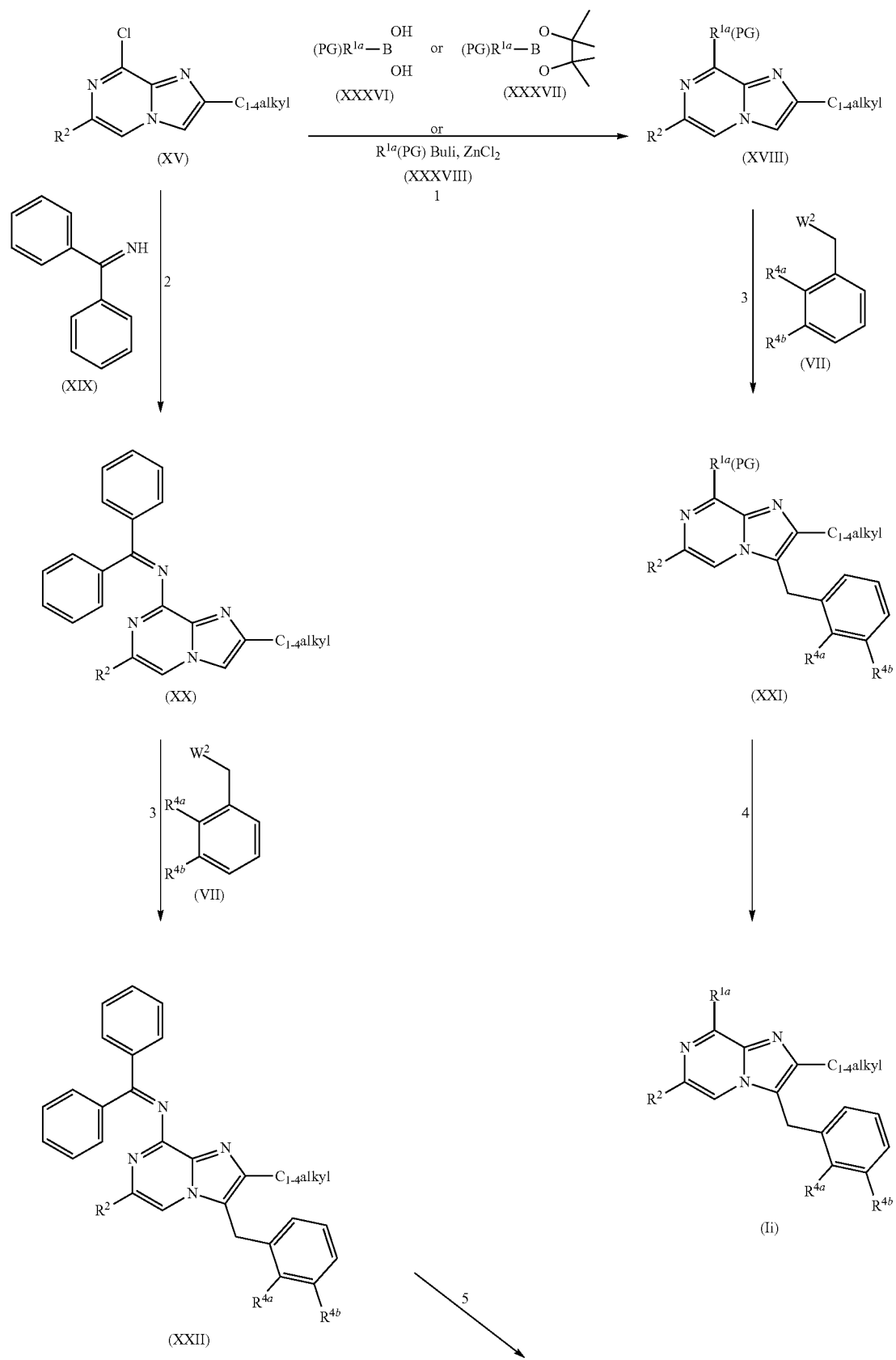

-continued

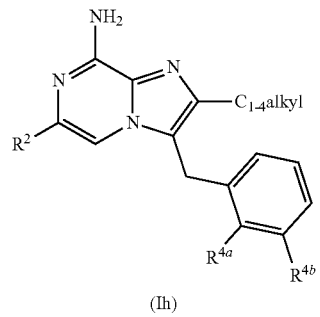

(Ih)

In Scheme 4, the following reaction conditions apply:

1: in case of (PG)R$^{1a}$B(OH)$_2$ or (PG)R$^{1a}$(4,4,5,5-tetramethyl-1,3,2-dioxaborolane), in the presence of a suitable catalyst such as for example 1,1'-bis(diphenylphosphino)-ferrocene palladium(II)dichloride dichloromethane adduct, a suitable base such as for example potassium phosphate, and a suitable solvent such as for example a mixture of dioxane and water, at a suitable temperature ranging from 80 to 100° C.;

In case of R$^{1a}$(PG), first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (L), optionally in solution in THF, and a suitable catalyst such as for example Pd(PPh$_3$)$_4$, heating at a suitable temperature ranging from 60 to 100° C.;

2: in the presence of a suitable catalyst such as for example palladium acetate, in the presence of a suitable ligand such as for example 2,2'-bis(diphenylphosphino)-1,1'-binaphtyle (BINAP), a suitable base such as for example cesium carbonate, at a suitable temperature such as for example 100° C., in sealed conditions;

3: in sealed conditions, in the presence of a suitable catalyst such as for example palladium acetate (Pd(OAc)$_2$, a suitable ligand such as for example tetrakistriphenyl phosphine (P(Ph)$_3$), a suitable base such as for example potassium carbonate (K$_2$CO$_3$), in a suitable solvent such as for example 1,4-dioxane at a suitable temperature such as for example 100° C.;

4: in the presence of a suitable acid such as for example hydrochloric acid, in a suitable solvent such as for example tetrahydrofuran, at a suitable temperature such as for example 60° C.;

5: in the presence of a suitable acid such as for example hydrochloric acid, in a suitable solvent such as for example tetrahydrofuran, at a suitable temperature ranging from room temperature to 60° C.

In general, compounds of Formula (I) wherein the other variables are as shown in Formula (Ii), can be prepared according to the following reaction Scheme 5, wherein W$^5$ represent a leaving group such as Br or I. All other variables in Scheme 5 are defined as above or according to the scope of the present invention.

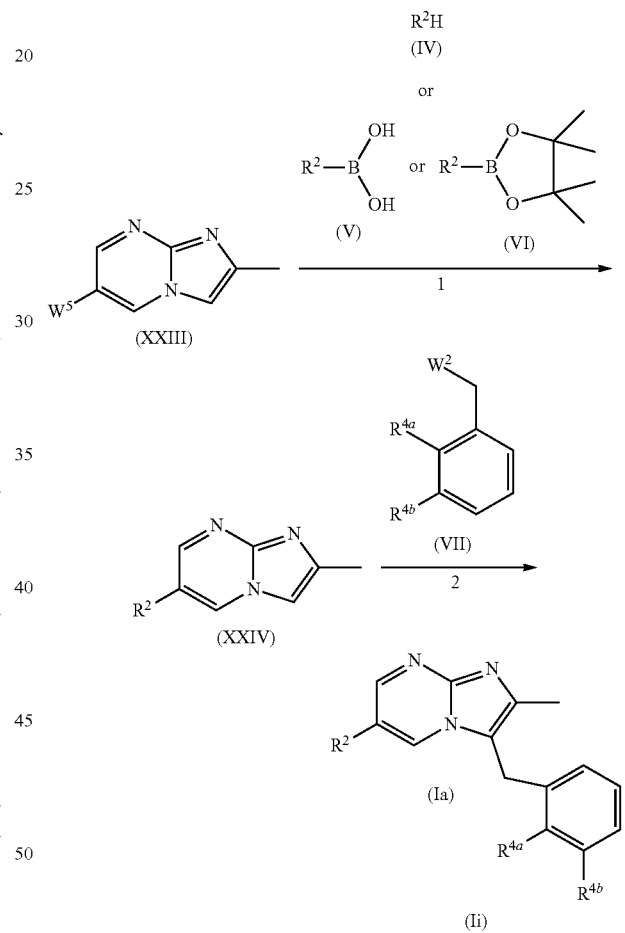

In Scheme 5, the following reaction conditions apply:

1: in case of R$_2$H:

Without solvent at a suitable temperature such as ranged between 100° C. and 175° C. in sealed conditions or under microwave irradiation;

Alternatively in the presence of a suitable ligand such as 2-dicyclohexylphosphino-2',6'-diisopropoxybiphenyl (Ruphos), a suitable catalyst such as for example chloro [2-(dicyclohexylphosphino)-3,6-dimethoxy-2',4',6'-tri-i-propyl-1,1'-biphenyl][2-(2-aminoethyl)phenyl]palladium(II) (Brettphos precatalyst first gen), a suitable base such as for example potassium tertButylate, and a suitable solvent such as for example dioxane, at a suitable temperature such as for example between 120° C., in sealed conditions;

in case of R$_2$B(OH)$_2$ or R$_2$(4,4,5,5-tetramethyl-1,3,2-dioxaborolane), in the presence of a suitable catalyst such as for example 1,1'-bis(diphenylphosphino)ferrocene palladium(II)dichloride dichloromethane adduct or RuPhos palladacycle, a suitable base such as for example potassium phosphate, and a suitable solvent such as for example a mixture dioxane and water, at a suitable temperature ranged between 80° C. and 105° C.;

2: in the presence of a suitable catalyst such as for example palladium acetate (Pd(OAc)$_2$, a suitable ligand such as for example tetrakistriphenyl phosphine (P(Ph)$_3$), a suitable base such as for example potassium carbonate (K$_2$CO$_3$), in a suitable solvent such as for example 1,4-dioxane at a suitable temperature such as for example ranged between 100 to 140° C., eventually under microwave conditions.

In general, compounds of Formula (I) wherein the other variables are as shown in Formula (Ija), (Ijb) and (Ik) can be prepared according to the following reaction Scheme 6. All other variables in Scheme 6 are defined according as above or to the scope of the present invention.

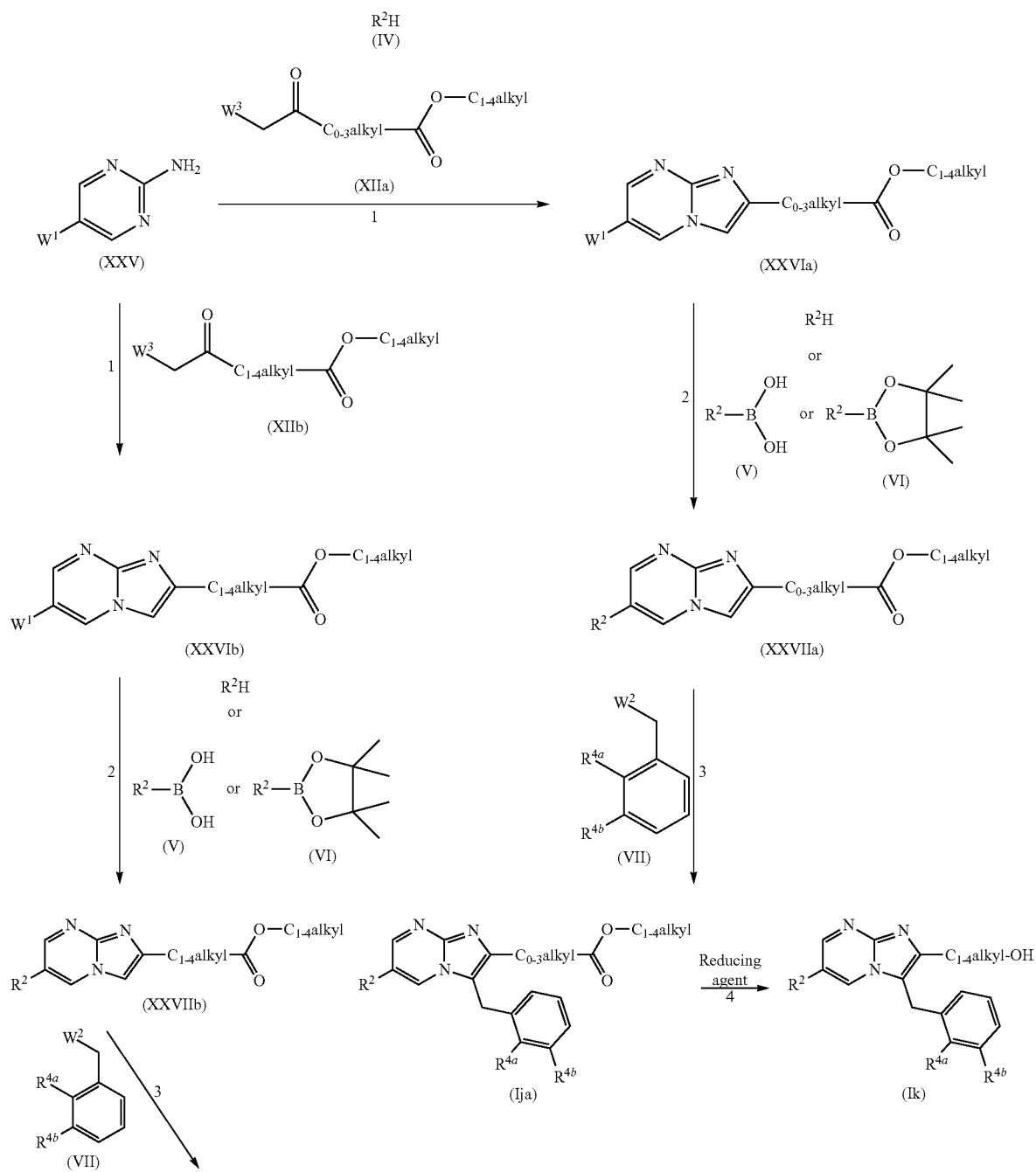

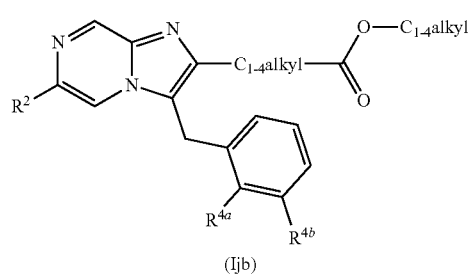

(Ijb)

In Scheme 6, the following reaction conditions apply:

1: in a suitable solvent such as for example dimethylformide, at a suitable temperature such as for example room temperature 2: in case of $R_2H$:

In the presence of a suitable base, without solvent at a suitable temperature such as room temperature Alternatively in the presence of a suitable ligand such as 2-dicyclohexylphosphino-2',6'-diisopropoxybiphenyl (Ruphos) or 2-Dicyclohexylphosphino-2'-(N,N-dimethylamino)biphenyl (Davephos), a suitable catalyst such as for example tris(dibenzylideneacetone)dipalladium ($Pd_2dba_3$) or palladium acetate or chloro[2-(dicyclohexylphosphino)-3,6-dimethoxy-2',4',6'-tri-i-propyl-1,1'-biphenyl][2-(2-aminoethyl)phenyl]-palladium (II) (Brettphos precatalyst first gen), a suitable base such as for example $Cs_2CO_3$ or potassium tertbutoxide, and a suitable solvent such as for example 2-methyl-2-butanol or dioxane, at a suitable temperature such as for example between 100 and 120° C., optionally in sealed conditions;

in case of $R_2B(OH)_2$ or $R_2$(4,4,5,5-tetramethyl-1,3,2-dioxaborolane), in the presence of a suitable catalyst such as for example 1,1'-bis(diphenylphosphino)ferrocene palladium(II)dichloride dichloromethane adduct or RuPhos palladacycle, a suitable base such as for example potassium phosphate, and a suitable solvent such as for example a mixture dioxane and water, at a suitable temperature ranged between 80° C. and 105° C.;

3: in sealed conditions, in the presence of a suitable catalyst such as for example palladium acetate ($Pd(OAc)_2$, a suitable ligand such as for example tetrakistriphenyl phosphine ($P(Ph)_3$), a suitable base such as for example potassium carbonate ($K_2CO_3$), in a suitable solvent such as for example 1,4-dioxane at a suitable temperature such as for example 100° C.;

4: In the presence of a suitable reducing agent such as for example diisobutylaluminium hydride, in a suitable solvent such as for example tetrahydrofuran, at a suitable temperature as for example between 0° C. and room temperature.

In general, compounds of Formula (I) wherein $R^1$ is restricted to an hydrogen, and wherein the other variables are as shown in Formula (II), can be prepared according to the following reaction Scheme 7. All other variables in Scheme 7 are defined as above or according to the scope of the present invention.

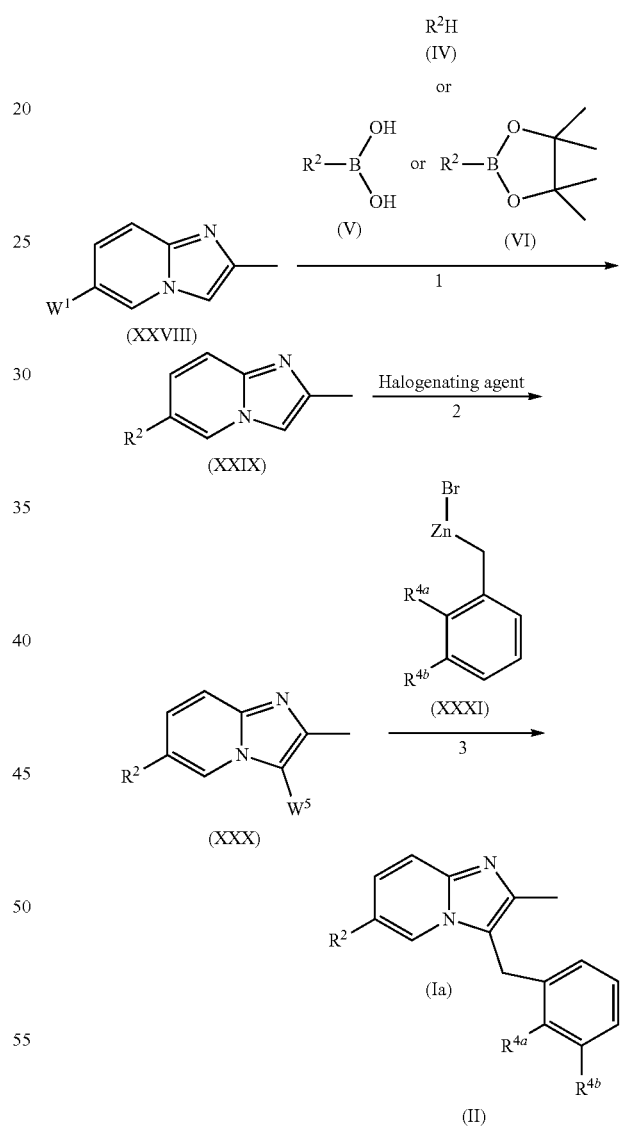

In Scheme 7, the following reaction conditions apply:

1: in case of $R_2H$:

Alternatively in the presence of a suitable ligand such as 2-dicyclohexylphosphino-2',6'-diisopropoxybiphenyl (Ruphos), a suitable catalyst such as for example chloro[2-(dicyclohexylphosphino)-3,6-dimethoxy-2',4',6'-tri-i-propyl-1,1'-biphenyl][2-(2-aminoethyl)phenyl]palladium(II) (Brettphos precatalyst first gen), a suitable base such as for example cesium carbonate, and a suitable solvent such as for example 2-methyl-2butanol at a suitable temperature such as for example between 100° C., in a schlenk reactor;

in case of $R_2B(OH)_2$ or $R_2(4,4,5,5$-tetramethyl-1,3,2-dioxaborolane), in the presence of a suitable catalyst such as for example 1,1'-bis(diphenylphosphino)ferrocene palladium(II)dichloride dichloromethane adduct or RuPhos palladacycle, a suitable base such as for example potassium phosphate, and a suitable solvent such as for example a mixture dioxane and water, at a suitable temperature ranged between 80° C. and 105° C.;

2: in the presence of an halogenating agent such as for example N-bromosuccinimide or N-iodosuccinimide, in a suitable solvent such as for example acetonitrile at a suitable temperature such as for example 0° C.;

3: in the presence of a suitable catalyst such as for example bis(tri-tert-butylphosphine palladium (0), in a suitable solvent such as for example tetrahydrofuran at a suitable temperature such as for example 60° C., in a schlenk reactor.

In general, compounds of Formula (I) wherein $R^1$ is restricted to hydrogen, and wherein the other variables are as shown in Formula (Im) and (In), can be prepared according to the following reaction Scheme 8. In scheme 8, $R^x$ and $R^y$ represent $C_{1-4}$alkyl, and $R^z$ represents $C_{1-4}$alkyl or phenyl, for instance $R^x$ and $R^y$ represent $CH_3$ and $R^z$ represents $C(CH_3)_3$ or phenyl. All other variables in Scheme 8 are defined as above or according to the scope of the present invention.

Scheme 8

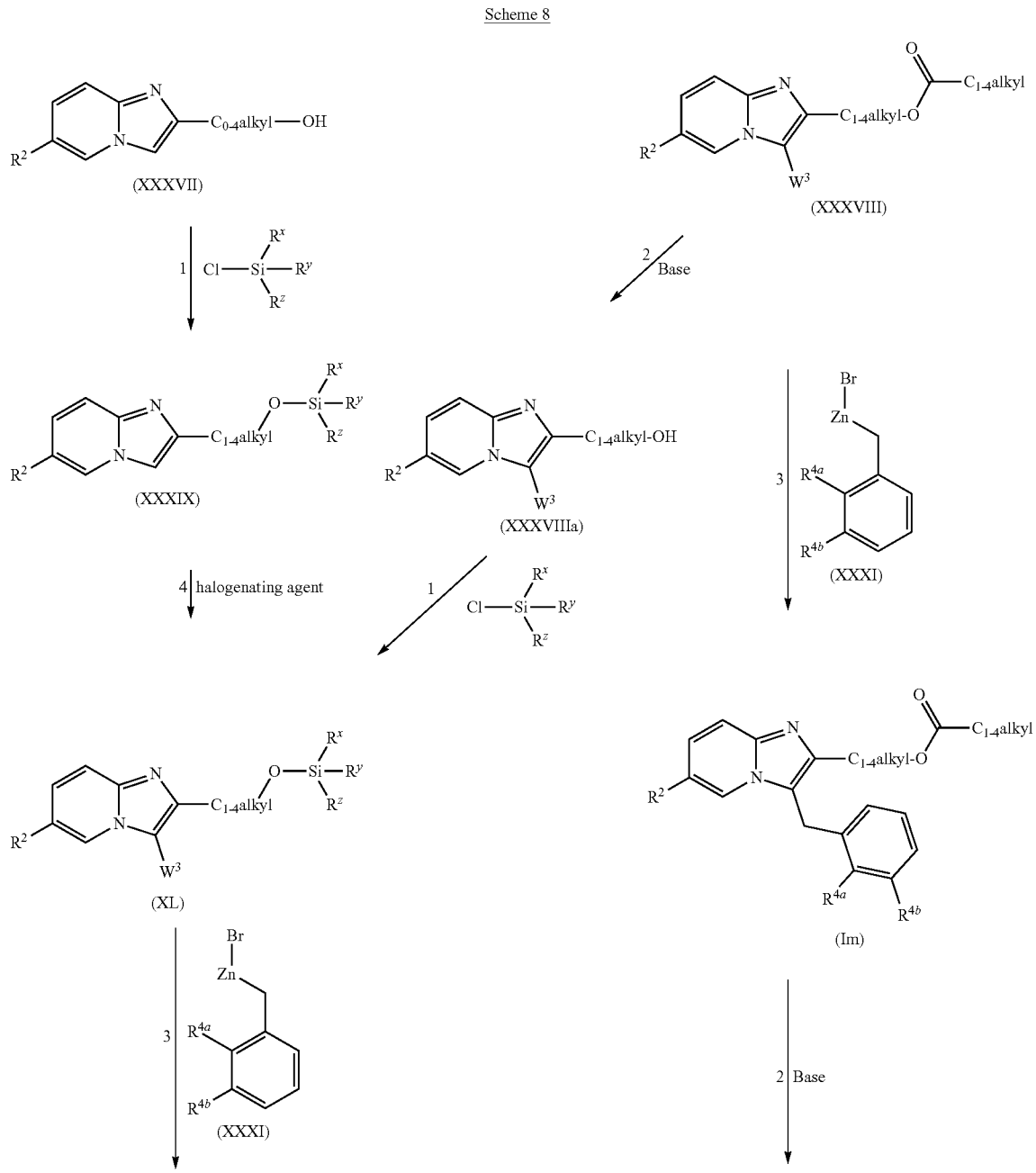

51

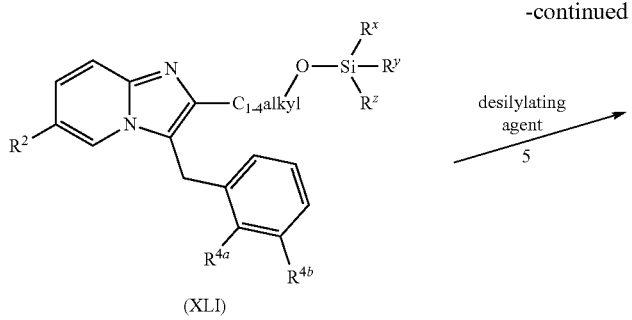
(XLI)

desilylating agent
5

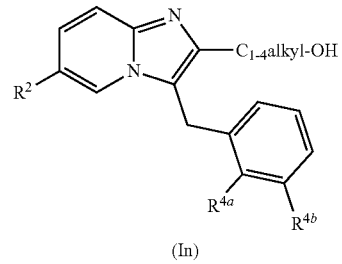
(In)

52

-continued

In Scheme 8, the following reaction conditions apply:

1: in the presence of a suitable reagent such as for example imidazole, in a suitable solvent such as for example dimethylformamide, at a suitable temperature such as for example room temperature;

2: in the presence of a base such as for example aqueous sodium hydroxide, in a suitable solvent such as for example tetrahydrofuran or a mixture of tetrahydrofuran and ethanol, at a suitable temperature such as for example room temperature;

3: in the presence of a suitable catalyst such as for example bis(tri-tert-butylphosphine-àpalladium (0), in a suitable solvent such as for example tetrahydrofuran at a suitable temperature such as for example 60° C., in a schlenk reactor;

4: in the presence of a halogenating agent such as for example N-bromosuccinimide or N-iodosuccinimide, in a suitable solvent such as for example acetonitrile at a suitable temperature such as for example 0° C.;

5: in the presence of a suitable desilylating reagent such as for example tetrabutylammonium fluoride, in a suitable solvent such as for example tetrahydrofuran, at a suitable temperature such as for example room temperature.

In general, intermediates of Formula (XXXVII) and (XXXVIII) wherein $R^1$ is restricted to an hydrogen, can be prepared according to the following reaction Scheme 9. All other variables in Scheme 9 are defined according to the scope of the present invention.

Scheme 9

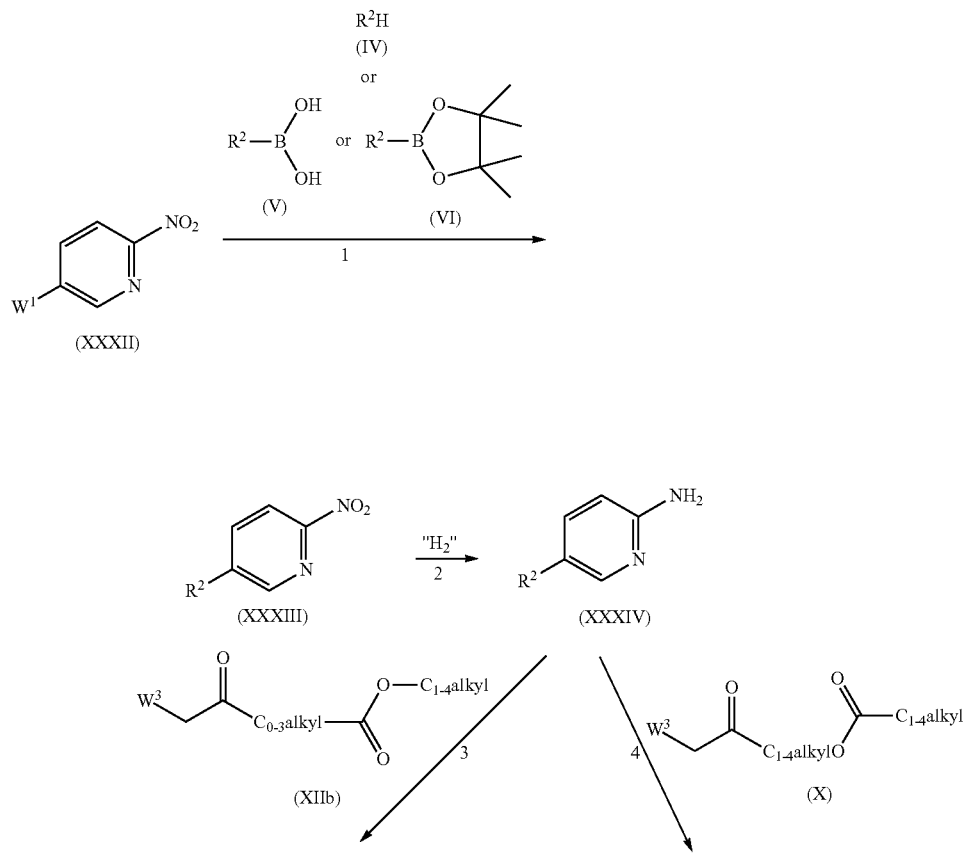

-continued

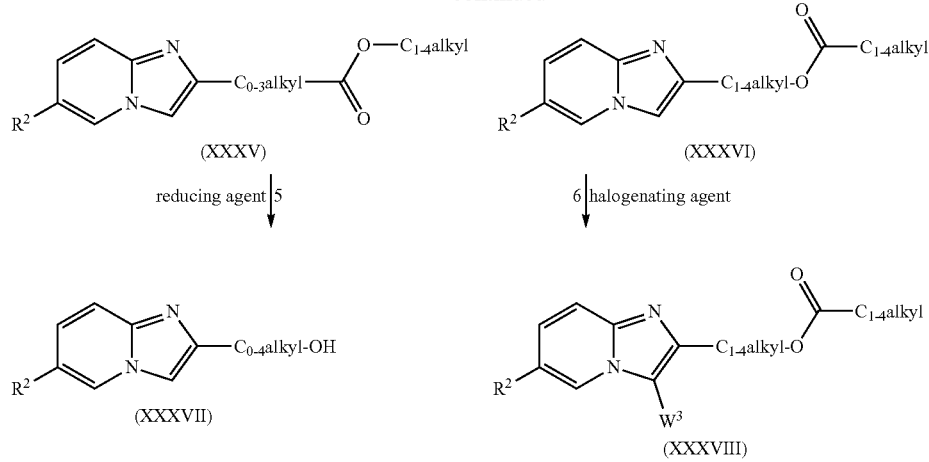

In Scheme 9, the following reaction conditions apply:
1: in case of $R_2H$:
Without solvent, at a suitable temperature such as 110° C.;
Alternatively, in the presence of a suitable base such as for example trimethylamine or diisopropylethylamine, in a suitable solvent such as for example dimethylsulfoxide or acetonitrile, at a suitable temperature ranged between 80 and 120° C.;
Alternatively in the presence of a suitable ligand such as 2-dicyclohexylphosphino-2',6'-diisopropoxybiphenyl (Ruphos) or 2-Dicyclohexylphosphino-2'-(N,N-dimethylamino)biphenyl (Davephos), a suitable catalyst such as for example tris(dibenzylideneacetone)dipalladium ($Pd_2dba_3$) or palladium acetate, a suitable base such as for example $Cs_2CO_3$, and a suitable solvent such as for example 2-methyl-2-butanol or dioxane, at a suitable temperature such as for example between 100 and 120° C.;
in case of $R_2B(OH)_2$ or $R_2$(4,4,5,5-tetramethyl-1,3,2-dioxaborolane), in the presence of a suitable catalyst such as for example Bis(triphenylphosphine)-palladium(II)-chloride or 1,1'-bis(diphenylphosphino)ferrocene palladium(II)dichloride dichloromethane adduct, a suitable base such as for example potassium sodium carbonate or potassium phosphate, and a suitable solvent such as for example a mixture dioxane and water, at a suitable temperature such as for example 80° C.;
2: in the presence of a suitable catalyst such as for example palladium on charcoal, in a suitable solvent such as for example tetrahydrofuran or ethanol, under 1 to 3 bars of hydrogen, Alternatively, in the presence of a suitable metal such as for example zinc, a suitable salt such as for example ammonium chloride, in a suitable solvent such as for example methanol, at a suitable temperature such as ranged between 0 to 5° C.;

3: optionally in the presence of a suitable base such as for example sodium hydrogenocarbonate ($NaHCO_3$), in a suitable solvent such as for example ethylene glycol dimethyl ether (DME) or acetonitrile (ACN) or ethanol, at suitable temperature such ranged between 60 to 120° C., optionally in the presence of molecular sieve (4 Å), in sealed conditions or under microwave irradiation;

4: in a schlenck reactor, in a suitable solvent such as for dimethylformamide, at suitable temperature such as for example 120° C.;

5: in the presence of a suitable reducing reagent such as for example lithium borohydride, in a suitable solvent such as for example tetrahydrofuran, at a suitable temperature such as for example 50° C.; optionally in sealed conditions;

6: in the presence of an halogenating agent such as for example N-bromosuccinimide or N-iodosuccinimide, in a suitable solvent such as for example acetonitrile at a suitable temperature such as for example 0° C.

Alternatively, intermediates of Formula (XXXIX) wherein $R^1$ is restricted to a hydrogen, can be prepared according to the following reaction Scheme 10. All other variables in Scheme 10 are defined according to the scope of the present invention or as defined hereinbefore.

Scheme 10

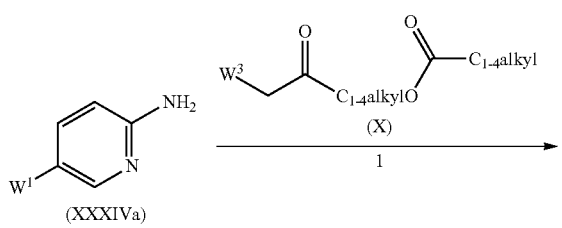

-continued

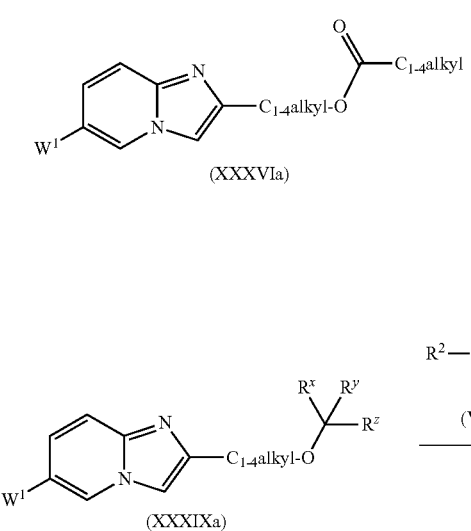
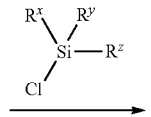

In Scheme 10, the following reaction conditions apply:

1: in a schlenck reactor, in or without a suitable solvent such as for dimethylformamide, at suitable temperature such as for example 120° C.;

2: in the presence of a base such as for example aqueous sodium hydroxide, in a suitable solvent such as for example tetrahydrofuran, ethanol or a mixture of tetrahydrofuran and ethanol, at a suitable temperature such as for example room temperature;

3: in the presence of a suitable reagent such as for example imidazole, in a suitable solvent such as for example dimethylformamide or dichloromethane, at a suitable temperature such as for example room temperature;

4: in case of R$_2$H:
  Without solvent, at a suitable temperature such as 110° C.;
  Alternatively, in the presence of a suitable base such as for example trimethylamine or diisopropylethylamine, in a suitable solvent such as for example dimethylsulfoxide or acetonitrile, at a suitable temperature ranged between 80 and 120° C.;
  Alternatively in the presence of a suitable ligand such as 2-dicyclohexylphosphino-2',6'-diisopropoxybiphenyl (Ruphos) or 2-Dicyclohexylphosphino-2'-(N,N-dimethylamino)biphenyl (Davephos), a suitable catalyst such as for example tris(dibenzylideneacetone)dipalladium (Pd$_2$dba$_3$) or palladium acetate, a suitable base such as for example Cs$_2$CO$_3$, and a suitable solvent such as for example 2-methyl-2-butanol or dioxane, at a suitable temperature such as for example between 100 and 120° C.;

in case of R$_2$B(OH)$_2$ or R$_2$(4,4,5,5-tetramethyl-1,3,2-dioxaborolane), in the presence of a suitable catalyst such as for example Bis(triphenylphosphine)-palladium(II)-chloride or 1,1'-bis(diphenylphosphino)ferrocene palladium(II)dichloride dichloromethane adduct, a suitable base such as for example potassium sodium carbonate or potassium phosphate, and a suitable solvent such as for example a mixture dioxane and water, at a suitable temperature such as for example 80° C.

In general, compounds of Formula (I) wherein R$^1$ is restricted to an hydrogen, and wherein the other variables are as shown in Formula (Io), can be prepared according to the following reaction Scheme 11. All other variables in Scheme 11 are defined as above or according to the scope of the present invention or as defined hereinbefore.

Scheme 11

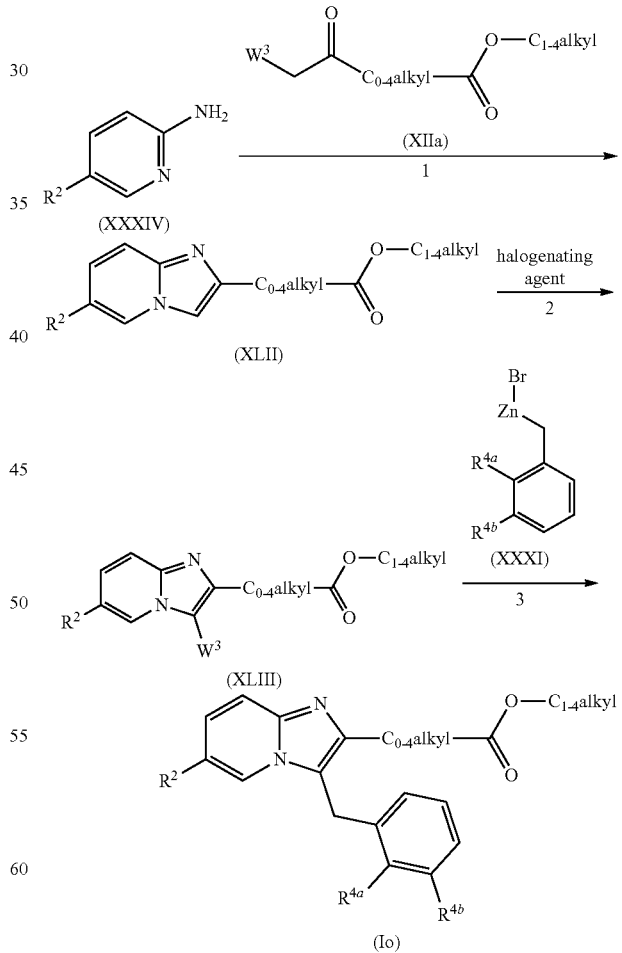

In Scheme 11, the following reaction conditions apply:

1: optionally in the presence of a suitable base such as for example sodium hydrogenocarbonate (NaHCO$_3$), in a suitable solvent such as for example ethylene glycol dimethyl ether (DME) or acetonitrile (ACN) or ethanol, at suitable temperature such ranged between 60 to 120° C., optionally in the presence of molecular sieve (4 Å), in sealed conditions or under microwave irradiation;

2: in the presence of an halogenating agent such as for example N-bromosuccinimide or N-iodosuccinimide, in a suitable solvent such as for example acetonitrile at a suitable temperature such as for example 0° C.;

3: in the presence of a suitable catalyst such as for example bis(tri-tert-butylphosphine-palladium (0), in a suitable solvent such as for example tetrahydrofuran at a suitable temperature such as for example 60° C., in a schlenk reactor.

In general, compounds of Formula (I) wherein $R^1$ is restricted to $R^{1a}$ being

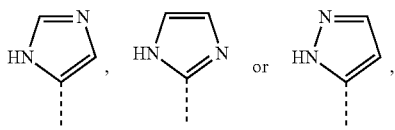

and wherein the other variables are as shown in Formula (Ip), can be prepared according to the following reaction Scheme 12. All other variables in Scheme 12 are defined as above or according to the scope of the present invention.

Scheme 12

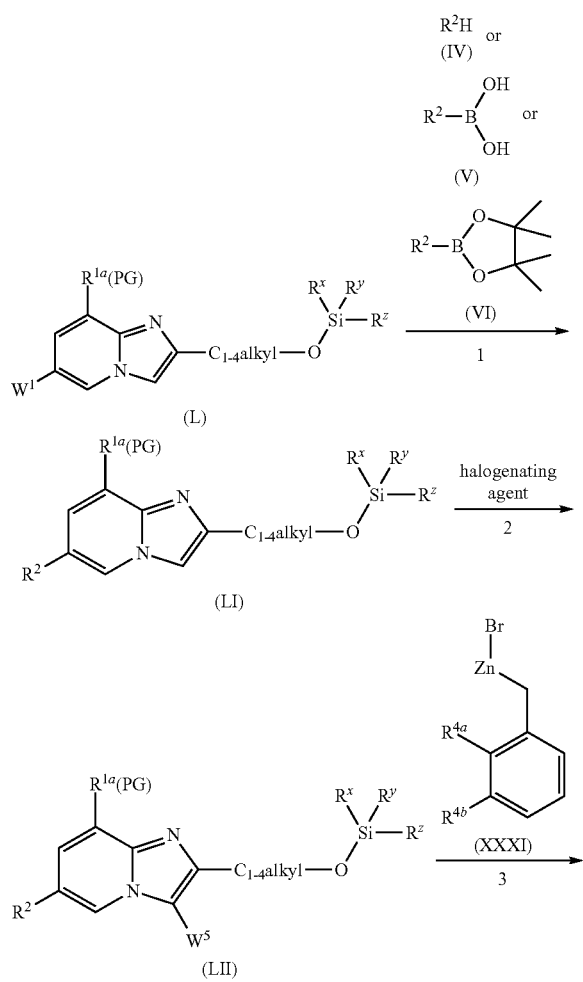

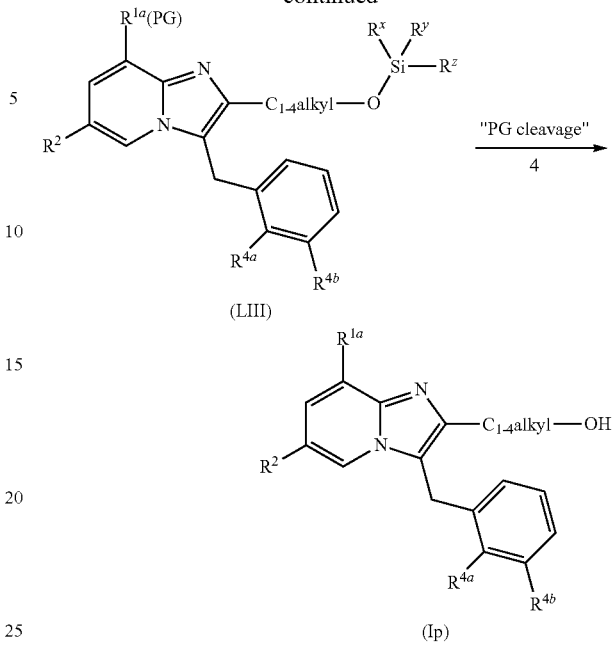

In Scheme 12, the following reaction conditions apply:

1: in case of $R_2H$:
Without solvent, at a suitable temperature such as 110° C.;
Alternatively, in the presence of a suitable base such as for example trimethylamine or diisopropylethylamine, in a suitable solvent such as for example dimethylsulfoxide or acetonitrile, at a suitable temperature ranged between 80 and 120° C.;
Alternatively in the presence of a suitable ligand such as 2-dicyclohexylphosphino-2',6'-diisopropoxybiphenyl (Ruphos) or 2-Dicyclohexylphosphino-2'-(N,N-dimethylamino)biphenyl (Davephos), a suitable catalyst such as for example chloro[2-(dicyclohexylphosphino)-3,6-dimethoxy-2',4',6'-tri-i-propyl-1,1'-biphenyl][2-(2-aminoethyl)phenyl]-palladium(II) (Brettphos precatalyst first gen), a suitable base such as for example $Cs_2CO_3$, and a suitable solvent such as for example 2-methyl-2-butanol, at a suitable temperature such as for example between 100 and 120° C., in sealed conditions;
in case of $R_2B(OH)_2$ or $R_2(4,4,5,5$-tetramethyl-1,3,2-dioxaborolane), in the presence of a suitable catalyst such as for example Bis(triphenylphosphine)-palladium(II)-chloride, a suitable base such as for example potassium sodium carbonate, and a suitable solvent such as for example a mixture dioxane and water, at a suitable temperature such as for example 80° C.;

2: in the presence of an halogenating agent such as for example N-bromosuccinimide or N-iodosuccinimide, in a suitable solvent such as for example dichloromethane at a suitable temperature such as for example room temperature;

3: in the presence of a suitable catalyst such as for example bis(tri-tert-butylphosphine)-palladium (0), in a suitable solvent such as for example tetrahydrofuran at a suitable temperature such as for example 60° C., in a schlenk reactor;

4: in the presence of a suitable acid such as for example hydrochloric acid, in a suitable solvent such as for example tetrahydrofuran, at a suitable temperature such as for example 60° C.

In general, intermediates of Formula (L) wherein $R^1$ is restricted to is restricted to $R^{1a}$ being

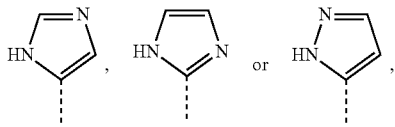

can be prepared according to the following reaction Scheme 13. All other variables in Scheme 13 are defined according to the scope of the present invention or as defined hereinbefore.

In Scheme 13, the following reaction conditions apply:
1: at a temperature ranging from 60 to 80° C., in sealed conditions;
2: in case of $(PG)R^{1a}B(OH)_2$ or $(PG)R^{1a}(4,4,5,5$-tetramethyl-1,3,2-dioxaborolane), in the presence of a suitable catalyst such as for example 1,1'-bis(diphenylphosphino)-ferrocene palladium(II)dichloride dichloromethane adduct, a suitable base such as for example potassium phosphate, and a suitable solvent such as for example a mixture of dioxane and water, at a suitable temperature ranging from 80 to 100° C.;
In case of $R^{1a}(PG)$, first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (L), optionally in solution in THF, and a suitable catalyst such as for example $Pd(PPh_3)_4$, heating at a suitable temperature ranging from 60 to 100° C.;

Scheme 13

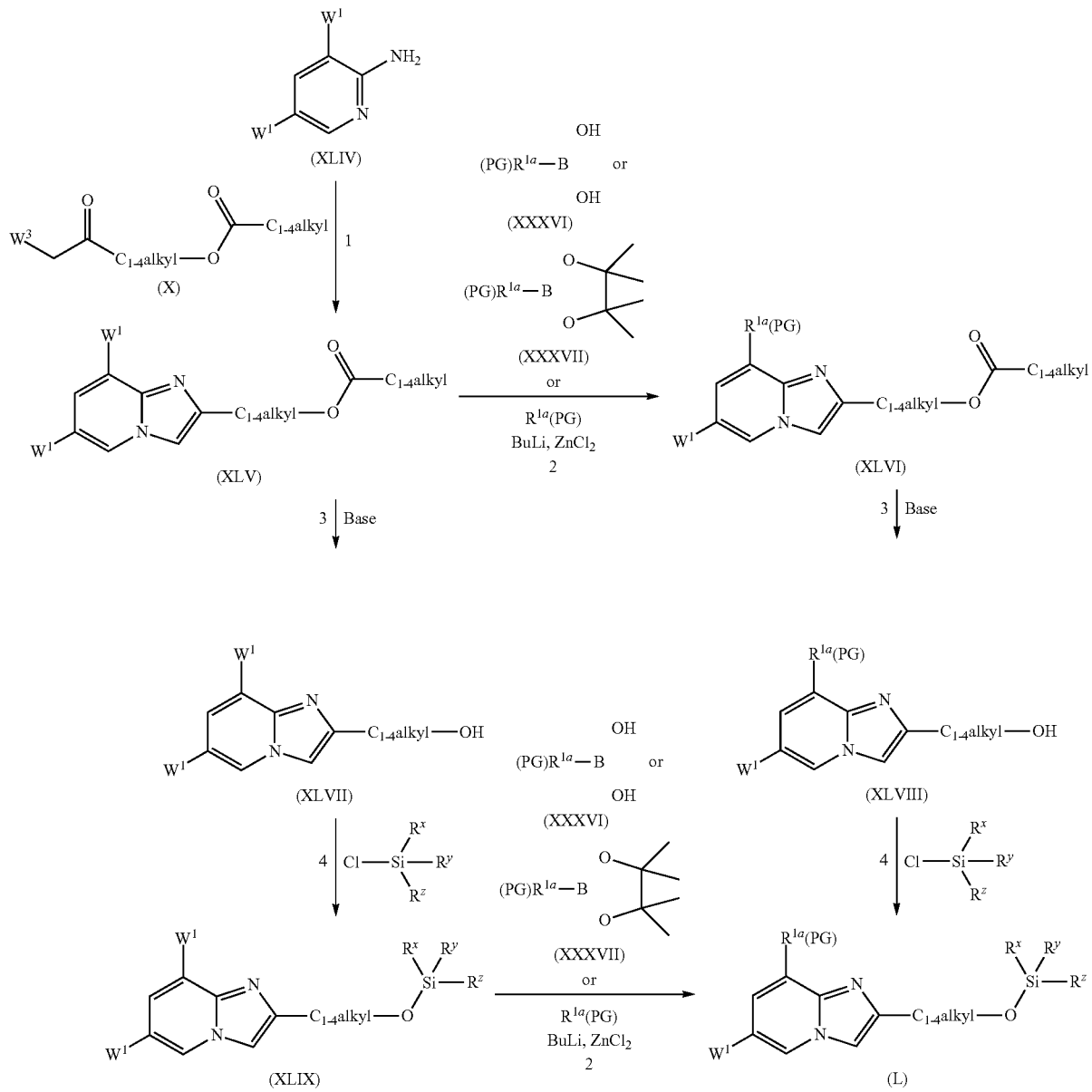

3: in the presence of a base such as for example aqueous sodium hydroxide, in a suitable solvent such as for example tetrahydrofuran, ethanol or a mixture of tetrahydrofuran and ethanol, at a suitable temperature such as for example room temperature;

4: in the presence of a suitable reagent such as for example imidazole, in a suitable solvent such as for example dimethylformamide or dichloromethane, at a suitable temperature such as for example room temperature.

In general, compounds of Formula (I) wherein $R^1$ is restricted to $R^{1a}$ being

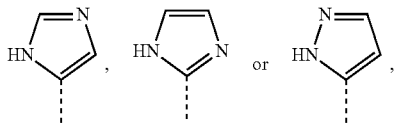

and wherein the other variables are as shown in Formula (Iq), can be prepared according to the following reaction Scheme 14. All other variables in Scheme 14 are defined as above or according to the scope of the present invention.

Scheme 14

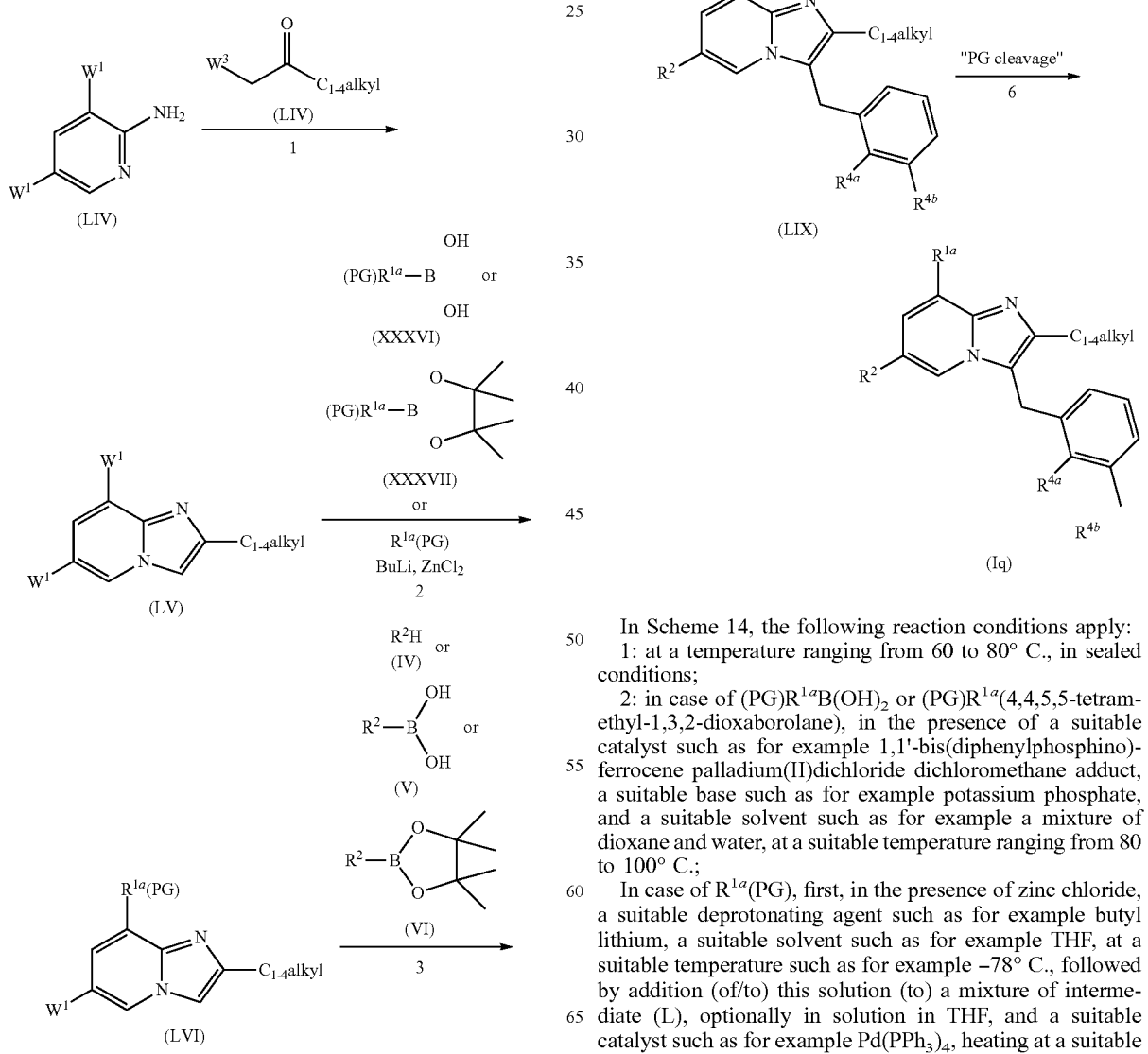

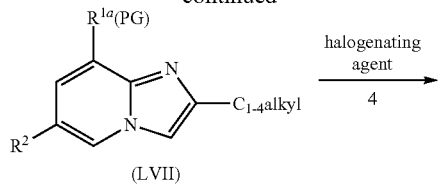

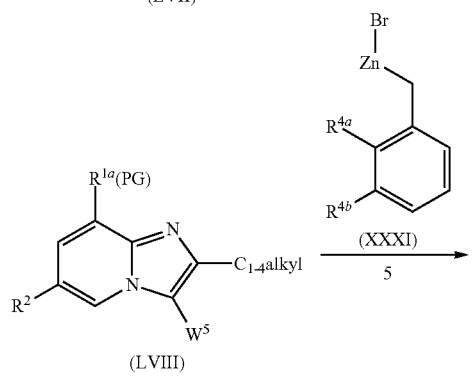

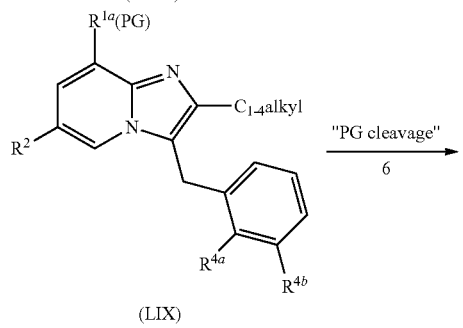

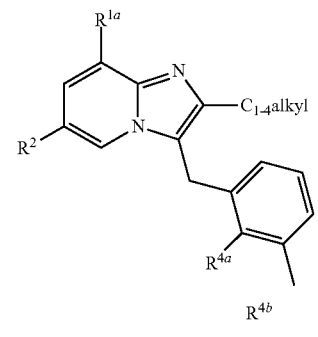

In Scheme 14, the following reaction conditions apply:

1: at a temperature ranging from 60 to 80° C., in sealed conditions;

2: in case of $(PG)R^{1a}B(OH)_2$ or $(PG)R^{1a}$(4,4,5,5-tetramethyl-1,3,2-dioxaborolane), in the presence of a suitable catalyst such as for example 1,1'-bis(diphenylphosphino)-ferrocene palladium(II)dichloride dichloromethane adduct, a suitable base such as for example potassium phosphate, and a suitable solvent such as for example a mixture of dioxane and water, at a suitable temperature ranging from 80 to 100° C.;

In case of $R^{1a}$(PG), first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (L), optionally in solution in THF, and a suitable catalyst such as for example Pd(PPh₃)₄, heating at a suitable temperature ranging from 60 to 100° C.;

4: in the presence of an halogenating agent such as for example N-bromosuccinimide or N-iodosuccinimide, in a suitable solvent such as for example dichloromethane at a suitable temperature such as for example room temperature;

5: in the presence of a suitable catalyst such as for example bis(tri-tert-butylphosphine-palladium (0), in a suitable solvent such as for example tetrahydrofuran at a suitable temperature such as for example 60° C., in a schlenk reactor;

6: in the presence of a suitable acid such as for example hydrochloric acid, in a suitable solvent such as for example tetrahydrofuran, at a suitable temperature such as for example 60° C.

In general, compounds of Formula (I) wherein $R^1$ is restricted to $CH_2$—OH and wherein the other variables are as shown in Formula (Ir), can be prepared according to the following reaction Scheme 15, wherein $PG^2$ is a tetrahydropyranyl or —$SiR^xR^yR^z$. In All other variables in Scheme 15 are defined as above or according to the scope of the present invention.

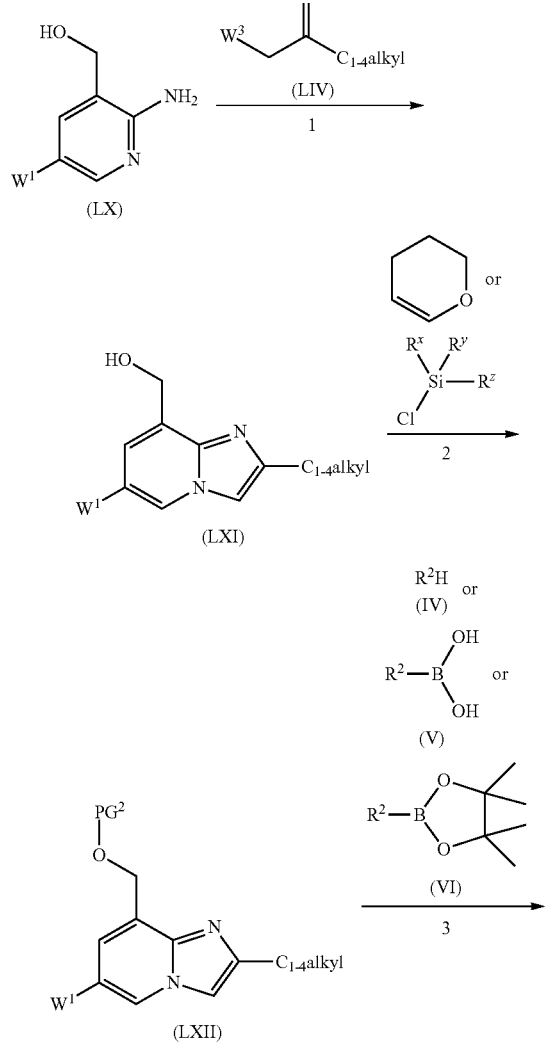

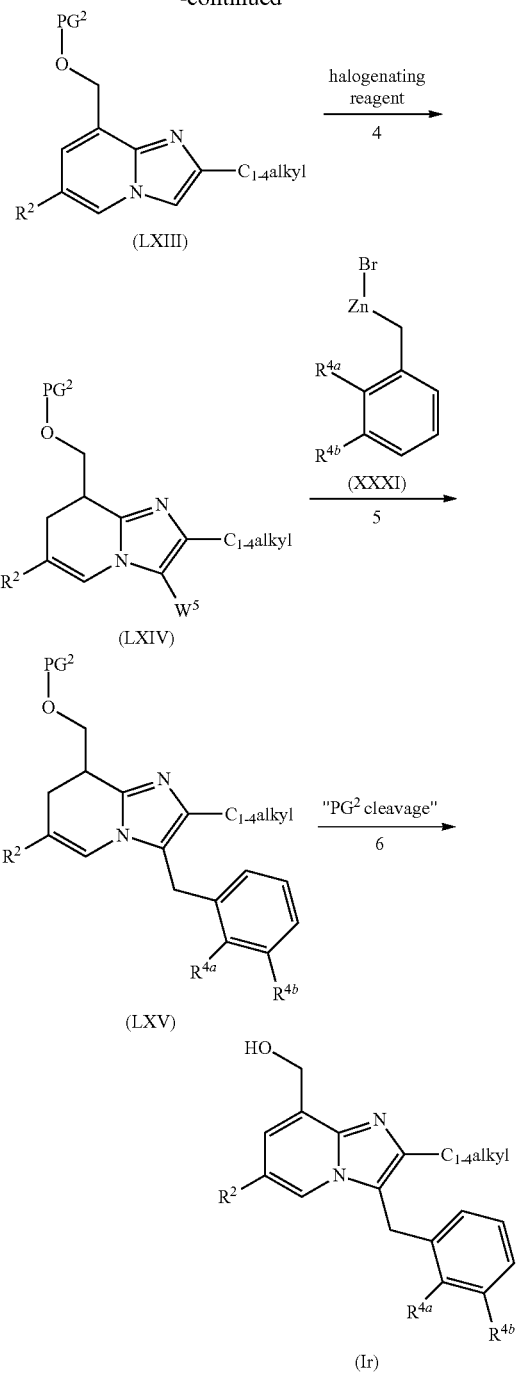

In Scheme 15, the following reaction conditions apply:

1: in the presence of a suitable base such as for example diisopropylethylamine, in a suitable solvent such as for example dimethylformamide, at a temperature ranging from 100 to 130° C., in sealed conditions;

2: in the presence of a suitable acid such as for example pyridiniump-toluene sulfonate, in a suitable solvent such as for example dichloromethane, at a suitable temperature such as 50° C. or in the presence of a suitable reagent such as for example imidazole, in a suitable solvent such as for example dimethylformamide or dichloromethane, at a suitable temperature such as for example room temperature;

3: in case of R₂H:

Without solvent, at a suitable temperature such as 110° C.;

Alternatively, in the presence of a suitable base such as for example trimethylamine or diisopropylethylamine, in a suitable solvent such as for example dimethylsulfoxide or acetonitrile, at a suitable temperature ranged between 80 and 120° C.;

Alternatively in the presence of a suitable ligand such as 2-dicyclohexylphosphino-2',6'-diisopropoxybiphenyl (Ruphos) or 2-Dicyclohexylphosphino-2'-(N,N-dimethylamino)biphenyl (Davephos), a suitable catalyst such as for example chloro[2-(dicyclohexylphosphino)-3,6-dimethoxy-2',4',6'-tri-i-propyl-1,1'-biphenyl][2-(2-aminoethyl)phenyl]palladium(II) (Brettphos precatalyst first gen), a suitable base such as for example Cs₂CO₃, and a suitable solvent such as for example 2-methyl-2-butanol, at a suitable temperature such as for example between 100 and 120° C., in sealed conditions;

in case of R₂B(OH)₂ or R₂(4,4,5,5-tetramethyl-1,3,2-dioxaborolane), in the presence of a suitable catalyst such as for example Bis(triphenylphosphine)-palladium(II-chloride, a suitable base such as for example potassium sodium carbonate, and a suitable solvent such as for example a mixture dioxane and water, at a suitable temperature such as for example 80° C.;

4: in the presence of an halogenating agent such as for example N-bromosuccinimide or N-iodosuccinimide, in a suitable solvent such as for example acetonitrile at a suitable temperature such as for example 0° C.;

5: in the presence of a suitable catalyst such as for example bis(tri-tert-butylphosphine-palladium (0), in a suitable solvent such as for example tetrahydrofuran at a suitable temperature such as for example 60° C., in a schlenk reactor;

6: in the presence of a suitable acid such as for example hydrochloric acid, in a suitable solvent such as for example tetrahydrofuran, at a suitable temperature ranging from room temperature to 60° C.

In general, compounds of Formula (I) wherein R¹ is restricted to CH₂—OH and wherein the other variables are as shown in Formula (Is), can be prepared according to the following reaction Scheme 16. All other variables in Scheme 16 are defined as above or according to the scope of the present invention.

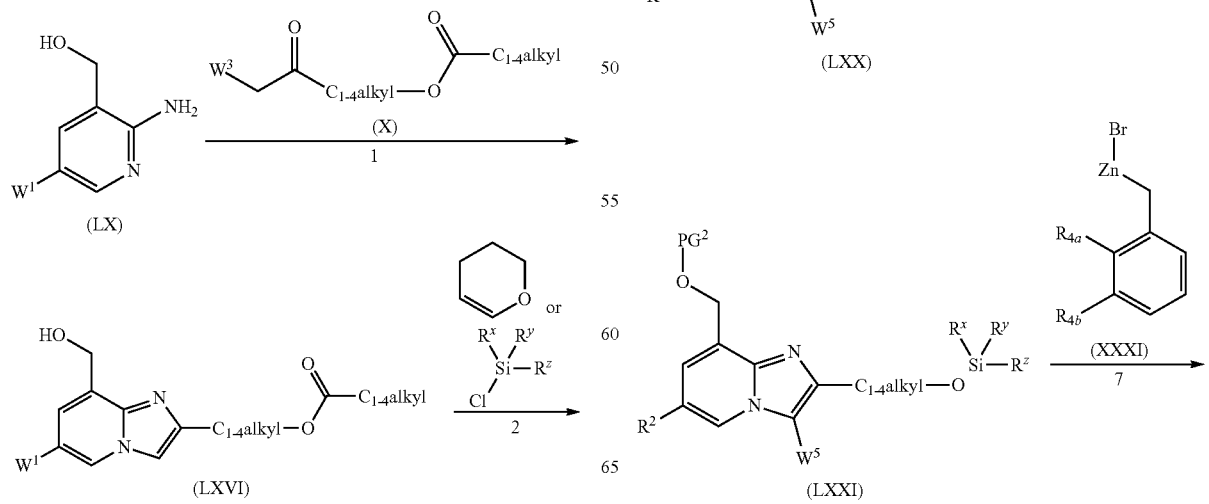

-continued

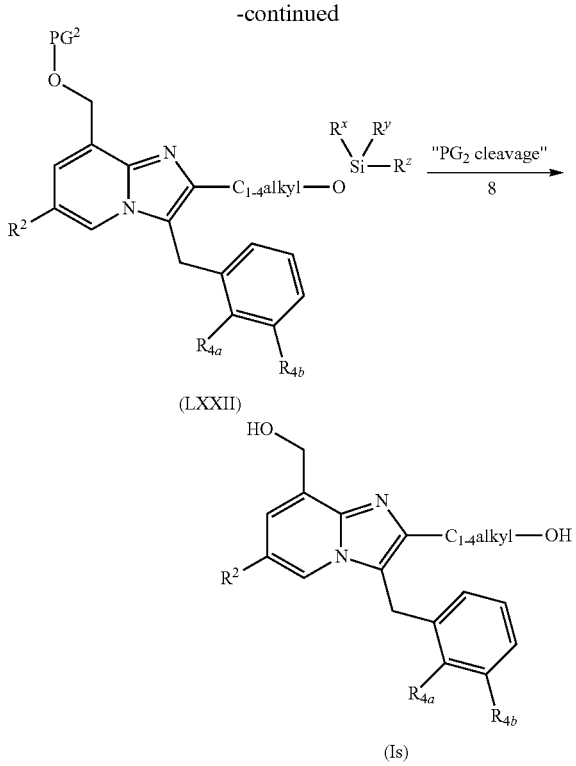

In Scheme 16, the following reaction conditions apply:
1: in the presence of a suitable base such as for example diisopropylethylamine, in a suitable solvent such as for example dimethylformamide, at a temperature ranging from 100 to 130 C, in sealed conditions;
2: in the presence of a suitable acid such as for example pyridinium p-toluene sulfonate, in a suitable solvent such as for example dichloromethane, at a suitable temperature such as 50° C. or in the presence of a suitable reagent such as for example imidazole, in a suitable solvent such as for example dimethylformamide or dichloromethane, at a suitable temperature such as for example room temperature;
3: in case of R₂H:
  Without solvent, at a suitable temperature such as 110° C.;
  Alternatively, in the presence of a suitable base such as for example trimethylamine or diisopropylethylamine, in a suitable solvent such as for example dimethylsulfoxide or acetonitrile, at a suitable temperature ranged between 80 and 120° C.;
  Alternatively in the presence of a suitable ligand such as 2-dicyclohexylphosphino-2',6'-diisopropoxybiphenyl (Ruphos) or 2-Dicyclohexylphosphino-2'-(N,N-dimethylamino)biphenyl (Davephos), a suitable catalyst such as for example chloro[2-(dicyclohexylphosphino)-3,6-dimethoxy-2',4',6'-tri-i-propyl-1,1'-biphenyl][2-(2-aminoethyl)phenyl]palladium(II) (Brettphos precatalyst first gen), a suitable base such as for example Cs₂CO₃, and a suitable solvent such as for example 2-methyl-2-butanol, at a suitable temperature such as for example between 100 and 120° C., in sealed conditions;
in case of R₂B(OH)₂ or R₂(4,4,5,5-tetramethyl-1,3,2-dioxaborolane), in the presence of a suitable catalyst such as for example Bis(triphenylphosphine)-palladium(II)-chloride, a suitable base such as for example potassium sodium carbonate, and a suitable solvent such as for example a mixture dioxane and water, at a suitable temperature such as for example 80° C.;
4: in the presence of an halogenating agent such as for example N-bromosuccinimide or N-iodosuccinimide, in a suitable solvent such as for example acetonitrile at a suitable temperature such as for example 0° C.;
5: in the presence of a base such as for example aqueous sodium hydroxide, in a suitable solvent such as for example tetrahydrofuran, ethanol or a mixture of tetrahydrofuran and ethanol, at a suitable temperature such as for example room temperature;
6: in the presence of a suitable catalyst such as for example bis(tri-tert-butylphosphine-palladium (0), in a suitable solvent such as for example tetrahydrofuran at a suitable temperature such as for example 60° C., in a schlenk reactor;
7: in the presence of a suitable acid such as for example hydrochloric acid, in a suitable solvent such as for example tetrahydrofuran, at a suitable temperature ranging from room temperature to 60° C.

In general, compounds of Formula (I) wherein $R^1$ is restricted to $NH_2$ and wherein the other variables are as shown in Formula (It), can be prepared according to the following reaction Scheme 17. All other variables in Scheme 17 are defined as above or according to the scope of the present invention.

Scheme 17

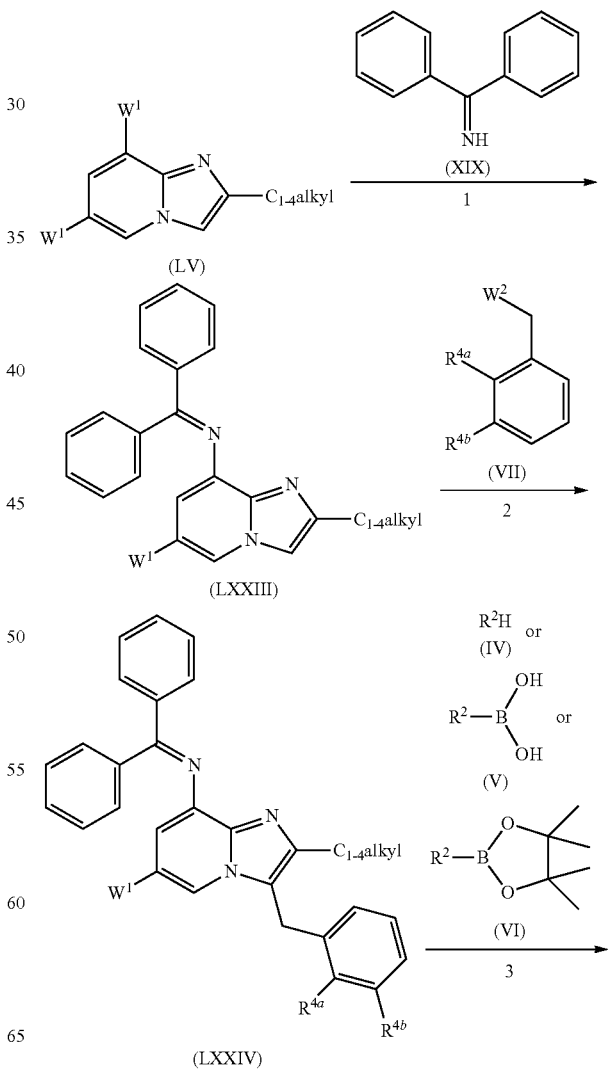

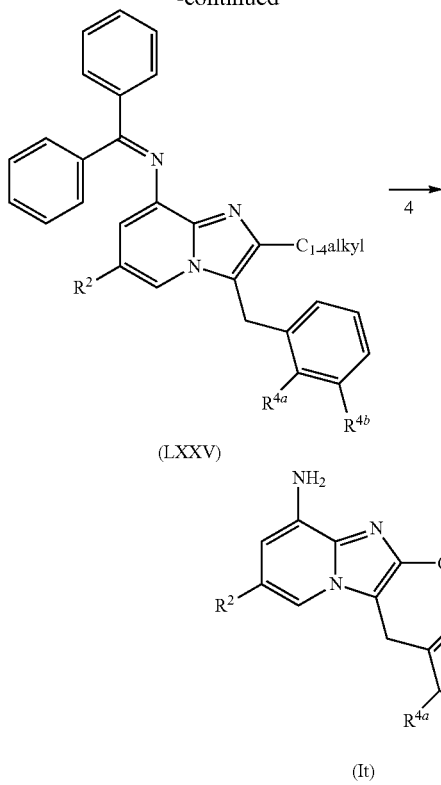

(LXXV)

(It)

In Scheme 17, the following reaction conditions apply:

1: in the presence of a suitable catalyst such as for example palladium acetate, in the presence of a suitable ligand such as for example 2,2'-bis(diphenylphosphino)-1,1'-binaphtyle (BINAP), a suitable base such as for example cesium carbonate, at a suitable temperature such as for example 100° C., in sealed conditions;

2: in sealed conditions, in the presence of a suitable catalyst such as for example palladium acetate (Pd(OAc)$_2$, a suitable ligand such as for example tetrakistriphenyl phosphine (P(Ph)$_3$), a suitable base such as for example potassium carbonate (K$_2$CO$_3$), in a suitable solvent such as for example 1,4-dioxane at a suitable temperature such as for example 100° C.;

3: in case of R$_2$H:

Without solvent, at a suitable temperature such as 110° C.;

Alternatively, in the presence of a suitable base such as for example trimethylamine or diisopropylethylamine, in a suitable solvent such as for example dimethylsulfoxide or acetonitrile, at a suitable temperature ranged between 80 and 120° C.;

Alternatively in the presence of a suitable ligand such as 2-dicyclohexylphosphino-2',6'-diisopropoxybiphenyl (Ruphos) or 2-Dicyclohexylphosphino-2'-(N,N-dimethylamino)biphenyl (Davephos), a suitable catalyst such as for example chloro[2-(dicyclohexylphosphino)-3,6-dimethoxy-2',4',6'-tri-i-propyl-1,1'-biphenyl][2-(2-aminoethyl)phenyl]palladium(II) (Brettphos palladacycle), a suitable base such as for example Cs$_2$CO$_3$, and a suitable solvent such as for example 2-methyl-2-butanol, at a suitable temperature such as for example between 100 and 120° C., in sealed conditions;

in case of R$_2$B(OH)$_2$ or R$_2$(4,4,5,5-tetramethyl-1,3,2-dioxaborolane), in the presence of a suitable catalyst such as for example Bis(triphenylphosphine)-palladium(II)-chloride, a suitable base such as for example potassium sodium carbonate, and a suitable solvent such as for example a mixture dioxane and water, at a suitable temperature such as for example 80° C.;

4: in the presence of a suitable acid such as for example hydrochloric acid, in a suitable solvent such as for example tetrahydrofuran, at a suitable temperature ranging from room temperature to 60° C.

In general, compounds of Formula (I) wherein R$^1$ is restricted to NH$_2$ and wherein the other variables are as shown in Formula (Iu), can be prepared according to the following reaction Scheme 18. All other variables in Scheme 18 are defined as above or according to the scope of the present invention.

Scheme 18

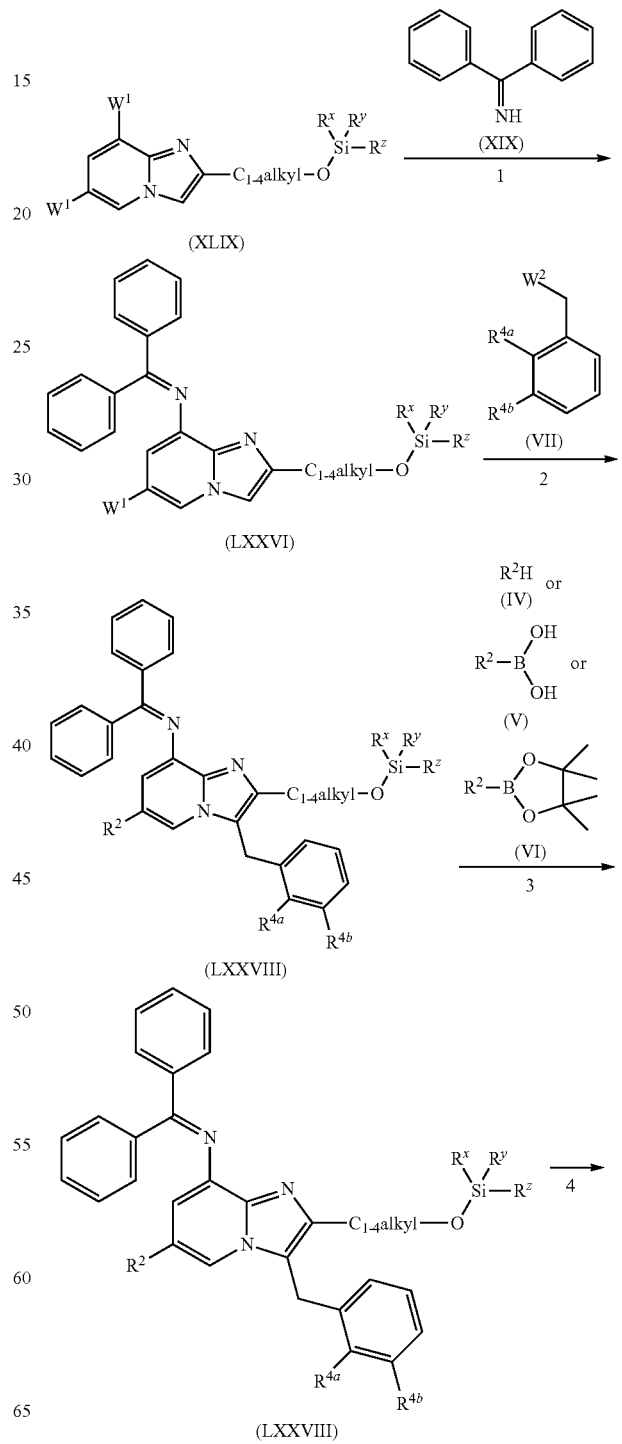

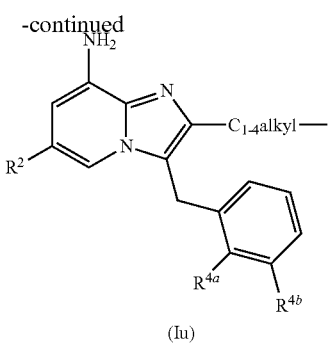

(Iu)

In Scheme 18, the following reaction conditions apply:

1: in the presence of a suitable catalyst such as for example palladium acetate, in the presence of a suitable ligand such as for example 2,2'-bis(diphenylphosphino)-1,1'-binaphtyle (BINAP), a suitable base such as for example cesium carbonate, at a suitable temperature such as for example 100° C., in sealed conditions;

2: in sealed conditions, in the presence of a suitable catalyst such as for example palladium acetate (Pd(OAc)$_2$, a suitable ligand such as for example tetrakistriphenyl phosphine (P(Ph)$_3$), a suitable base such as for example potassium carbonate (K$_2$CO$_3$), in a suitable solvent such as for example 1,4-dioxane at a suitable temperature such as for example 100*C;

3: in case of R$_2$H:

Without solvent, at a suitable temperature such as 110° C.;

Alternatively, in the presence of a suitable base such as for example trimethylamine or diisopropylethylamine, in a suitable solvent such as for example dimethylsulfoxide or acetonitrile, at a suitable temperature ranged between 80 and 120° C.;

Alternatively in the presence of a suitable ligand such as 2-dicyclohexylphosphino-2',6'-diisopropoxybiphenyl (Ruphos) or 2-Dicyclohexylphosphino-2'-(N,N-dimethylamino)biphenyl (Davephos), a suitable catalyst such as for example chloro[2-(dicyclohexylphosphino)-3,6-dimethoxy-2',4',6'-tri-i-propyl-1,1'-biphenyl][2-(2-aminoethyl)phenyl]palladium(II) (Brettphos precatalyst first gen), a suitable base such as for example Cs$_2$CO$_3$, and a suitable solvent such as for example 2-methyl-2-butanol, at a suitable temperature such as for example between 100 and 120° C., in sealed conditions;

in case of R$_2$B(OH)$_2$ or R$_2$(4,4,5,5-tetramethyl-1,3,2-dioxaborolane), in the presence of a suitable catalyst such as for example Bis(triphenylphosphine)-palladium(II)-chloride, a suitable base such as for example potassium sodium carbonate, and a suitable solvent such as for example a mixture dioxane and water, at a suitable temperature such as for example 80° C.;

4: in the presence of a suitable acid such as for example hydrochloric acid, in a suitable solvent such as for example tetrahydrofuran, at a suitable temperature ranging from room temperature to 60° C.

In general, compounds of Formula (I) wherein R$^1$ is restricted to an hydrogen and wherein the other variables are as shown in Formula (Iv), can be prepared according to the following reaction Scheme 19. All other variables in Scheme 19 are defined as above or according to the scope of the present invention.

Scheme 19

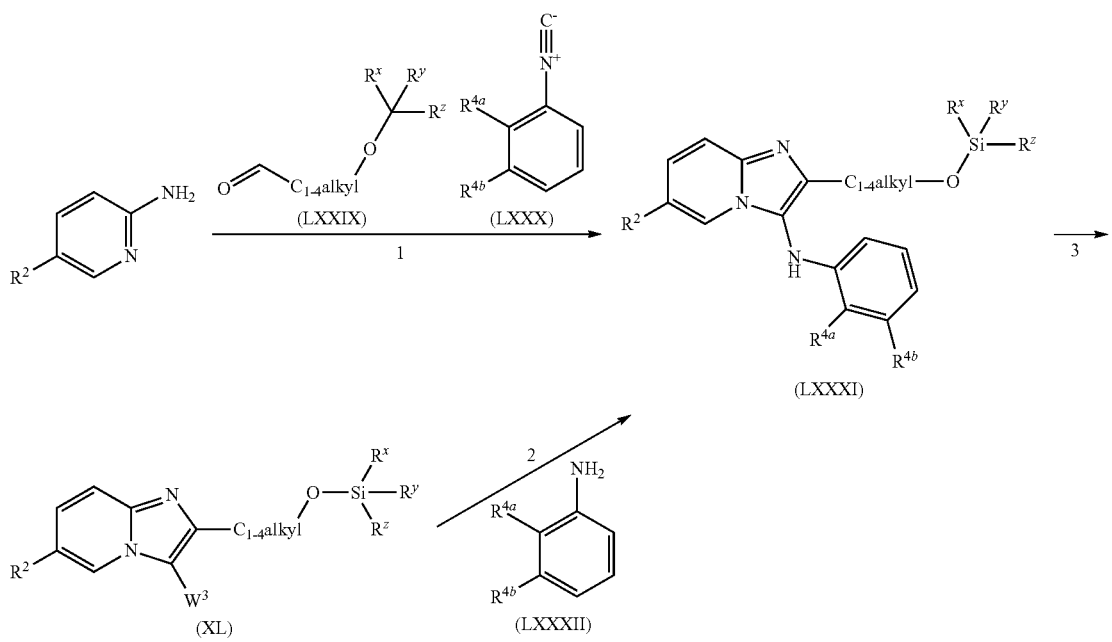

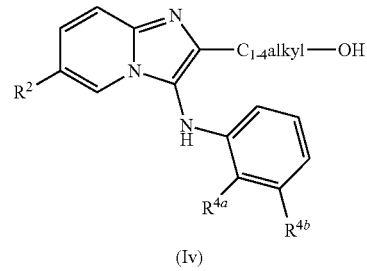

(Iv)

In Scheme 19, the following reaction conditions apply:

1: in the presence of a suitable reagent such as zinc dichloride, in a suitable solvent such as for example tetrahydrofuran, at a suitable temperature such as 120° C., under microwave irradiation;

2: 3: at a temperature such as 100° C. or in a microwave at a temperature of 140° C., in the presence of a suitable catalyst such as for example tris(dibenzylideneacetone)dipalladium(0), a suitable ligand such as for example 2-(Dicyclohexylphosphino)-3,6-dimethoxy-2',4',6'-triisopropyl-1,1'-biphenyl, a suitable base such as for example cesium carbonate, and in a suitable solvent such as for example toluene;

3: In in the presence of a suitable acid such as for example hydrochloric acid, in a suitable solvent such as for example tetrahydrofuran, at a suitable temperature ranging from room temperature to 60° C.; Alternatively, in the presence of a suitable desilylating reagent such as for example tetrabutylammonium fluoride, in a suitable solvent such as for example tetrahydrofuran, at a suitable temperature such as for example room temperature.

In general, compounds of Formula (I) wherein Z represent

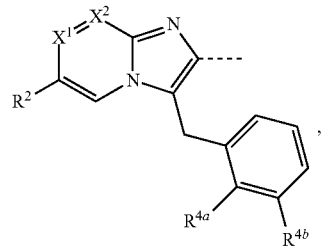

tautomers and stereoisomeric forms thereof, wherein
$X^1$ represents CH or N;
$X^2$ represents CH or N;
provided that maximum one of $X^1$ and $X^2$ represents N;
wherein the other variables are as shown in Formula (Iwa) and (Iwb), can be prepared according to the following reaction Scheme 20, wherein $R^9$ is defined as being H or $CH_3$ and $R^{10}$ is defined as being $—C_{1-4}alkyl\text{-}SO_2—CH_3$ or $—C_{1-4}alkyl\text{-}OH$ and wherein $Het^{1a}$ is defined as being $Het^1$ attached via the nitrogen atom. All other variables in Scheme 20 are defined as above or according to the scope of the present invention.

Scheme 20

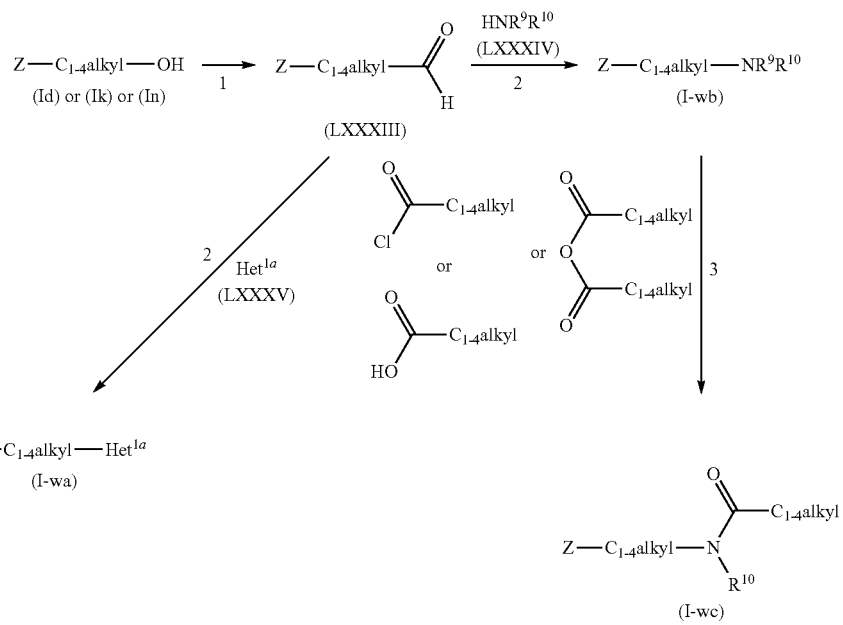

In Scheme 20, the following reaction conditions apply:

1: in the presence of suitable reagents such as for example oxalyl chloride and dimethylsulfoxide, a suitable base such as for example trimethylamine, in a suitable solvent such as for example dichloromethane, at a suitable temperature ranged between −80° C. to room temperature or in the presence of a suitable oxidative reagent such as for example manganese oxide, in a suitable solvent such as for example dichloromethane or toluene, at a suitable temperature ranging from room temperature to 80° C.;

2: in the presence of a suitable reducing agent such as for example sodium triacetoxyborohydride or sodium borohydride, in a suitable solvent such as for example dichloromethane or methanol, dichloroethane, optionally in the presence of a suitable organic base such as for example sodium acetate or a suitable acid such as for example acetic acid, at a suitable temperature ranging from room temperature to 40° C.;

3: in case of an acyl chloride or acyl anhydride, optionally in the presence of a suitable base such as for example triethylamine, and in a suitable solvent such as for example dichloromethane;

in case of a carboxylic acid, in the presence of a suitable coupling reagent such as for example 1-[bis(dimethyl-amino)methylene]-1H-1,2,3-triazolo[4,5-b]pyridinium 3-oxide, a suitable additive such as for example dimethylaminopyridine, a suitable base such as for example diisopropylethylamine, and in a suitable solvent such as for example DMF.

In general, compounds of Formula (I) wherein Z represent

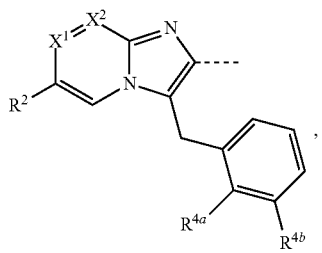

tautomers and stereoisomeric forms thereof, wherein $X^1$ represents CH or N;

$X^2$ represents CH or N;

provided that maximum one of $X^1$ and $X^2$ represents N;

wherein the other variables are as shown in Formula (Ix), can be prepared according to the following reaction Scheme 21. All other variables in Scheme 21 are defined as above or according to the scope of the present invention.

Scheme 21

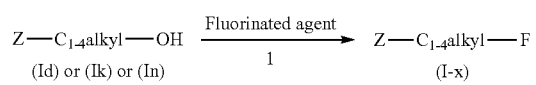

In Scheme 21, the following reaction conditions apply:

1: in the presence of a suitable fluorinated reagent such as for example diethylaminosulfur trifluoride or (diethylamino)difluorosulfonium tetrafluoroborate, optionally in the presence of a suitable salt such as for example trethylamine trihydrofluoride, in a suitable solvent such as for example dichloromethane at a suitable temperature such as room temperature;

In general, compounds of Formula (I) wherein Z represent

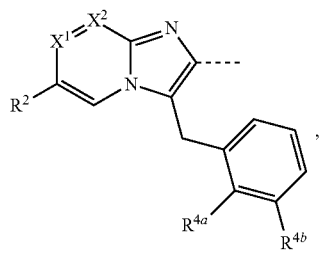

tautomers and stereoisomeric forms thereof, wherein $X^1$ represents CH or N;

$X^2$ represents CH or N;

provided that maximum one of $X^1$ and $X^2$ represents N;

wherein the other variables are as shown in Formula (Iy), can be prepared according to the following reaction Scheme 22. In scheme 22, $R^{11}$ represents —CH(NH$_2$)—C$_{1-4}$alkyl, —CH(NH$_2$)—C$_{1-4}$alkyl-Ar,

or —C$_{1-4}$alkyl-Het$^1$, and PG$^1$ represent a protective group such as for example tert-butoxycarbonyl or benzyloxycarbonyl.

All other variables in Scheme 22 are defined as above or according to the scope of the present invention.

Scheme 22

In Scheme 22, the following reaction conditions apply:

1: in the presence of a suitable coupling reagent such as for example 1-[bis(dimethyl-amino)methylene]-1H-1,2,3-triazolo[4,5-b]pyridinium 3-oxide, a suitable additive such as for example dimethylaminopyridine, a suitable base such as for example diisopropylethylamine, and in a suitable solvent such as for example DMF;

2: in the presence of an acid such as for example trifluoroacetic acid or hydrogen chloride in a suitable solvent such as for example dichloromethane or methanol.

Alternatively, in the presence of palladium on charcoal, in a suitable solvent such as methanol under an atmosphere of hydrogen.

In general, compounds of Formula (I) wherein Z represent

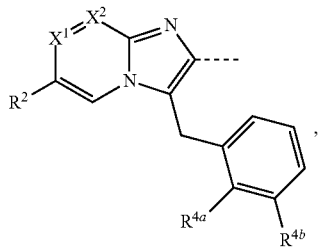

tautomers and stereoisomeric forms thereof, wherein
$X^1$ represents CH or N;
$X^2$ represents CH or N;
provided that maximum one of $X^1$ and $X^2$ represents N;
wherein the other variables are as shown in Formula (Iz), can be prepared according to the following reaction In general, compounds of Formula (I) wherein Z represent

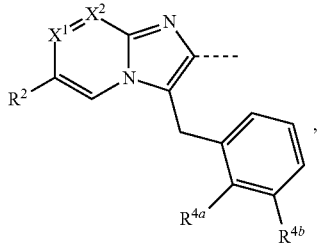

tautomers and stereoisomeric forms thereof, wherein
$X^1$ represents CH or N;
$X^2$ represents CH or N;
provided that maximum one of $X^1$ and $X^2$ represents N;
wherein the other variables are as shown in Formula (Iza), (Izb) and (Izc), can be prepared according to the following reaction Scheme 24.

In scheme 24, (Id), (Ik) and (In) are restricted to (Ida), Ika) and (Ina) in which $R^3$ is restricted to —CH$_2$OH. All other variables in Scheme 24 are defined as above or according to the scope of the present invention.

Scheme 24

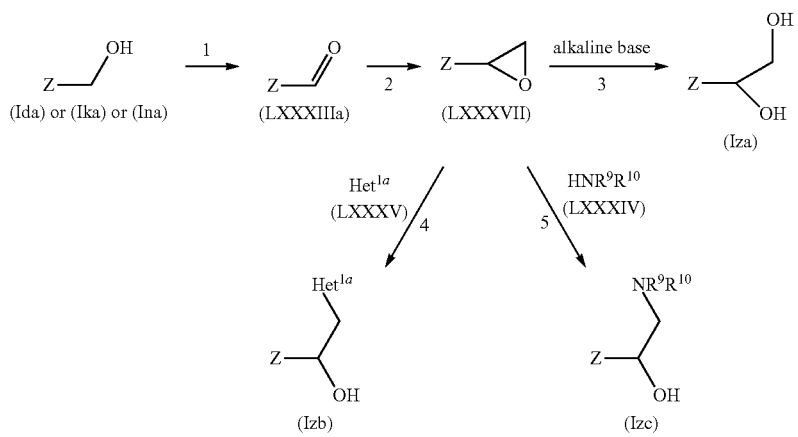

Scheme 23. In scheme 23. Het$^1$ is restricted to Het$^{1b}$ being attached via the carbon atom. All other variables in Scheme 23 are defined as above or according to the scope of the present invention.

Scheme 23

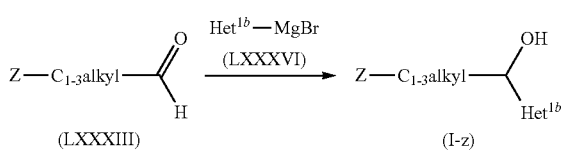

In Scheme 23, the following reaction conditions apply:
1: at a suitable temperature such as for example 0° C. or −78° C., in a suitable solvent such as for example THF;

In Scheme 24, the following reaction conditions apply:
1: in the presence of suitable reagents such as for example oxalyl chloride and dimethylsulfoxide, a suitable base such as for example trimethylamine, in a suitable solvent such as for example dichloromethane, at a suitable temperature ranged between −80° C. to room temperature or in the presence of a suitable oxidative reagent such as for example manganese oxide, in a suitable solvent such as for example dichloromethane or toluene, at a suitable temperature ranging from room temperature to 80° C.;
2: in the presence of suitable reagent such as for example trimethylsulfonium iodide, in the presence of a suitable base such as for example potassium hydroxide, in a suitable solvent such as for example a mixture of acetonitrile and water, at a suitable temperature such as for example 60° C.;
3: in the presence of a suitable alkaline base such as for example sodium hydroxide, in a suitable solvent such as for example a mixture of dioxane and water at a suitable temperature such as for example 80° C.;
4: in a suitable solvent such as for example acetonitrile or dimethylformamide, at a suitable temperature such as for example 80° C., optionally in sealed conditions;

5: in a suitable solvent such as for example acetonitrile or dimethylformamide, at a suitable temperature such as for example 80° C., optionally in sealed conditions.

In general, compounds of Formula (I) wherein Z represent

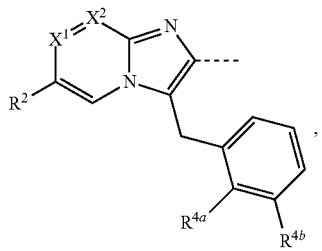

tautomers and stereoisomeric forms thereof, wherein
$X^1$ represents CH or N;
$X^2$ represents CH or N;
provided that maximum one of $X^1$ and $X^2$ represents N;
wherein the other variables are as shown in Formula (Izd), (Ize), (Izf) and (Izh), can be prepared according to the following reaction Scheme 25.

All other variables in Scheme 25 are defined as above or according to the scope of the present invention.

In Scheme 25, the following reaction conditions apply:
1: in the presence of a suitable reagent such as for example di-tert-butyl azodicarboxylate, a suitable phosphine such as for example triphenylphosphine, and in a suitable solvent such as for example THF;
2: at a suitable temperature such as for example 80° C., in a suitable solvent such as for example ethanol;
3: in case of an acyl chloride, in the presence of a suitable base such as for example diisopropylethylamine, and in a suitable solvent such as for example dichloromethane;
  in case of a carboxylic acid, in the presence of a suitable coupling reagent such as for example 1-(3-dimethyl-aminopropyl)-3-ethylcarbodiimide hydrochloride, a suitable additive such as for example 1-hydroxybenzotriazole, a suitable base such as for example triethylamine, and in a suitable solvent such as for example a mixture of THF and dichloromethane;
4: in the presence of a suitable base such as for example diisopropylethylamine, and in a suitable solvent such as for example dichloromethane;
5: in the presence of a suitable coupling reagent such as for example 1-(3-dimethylaminopropyl)-3-ethylcarbodiimide hydrochloride, a suitable additive such as for example 1-hydroxybenzotriazole, a suitable base such as for example triethylamine, and in a suitable solvent such as for example a mixture of THF and dichloromethane.

Scheme 25

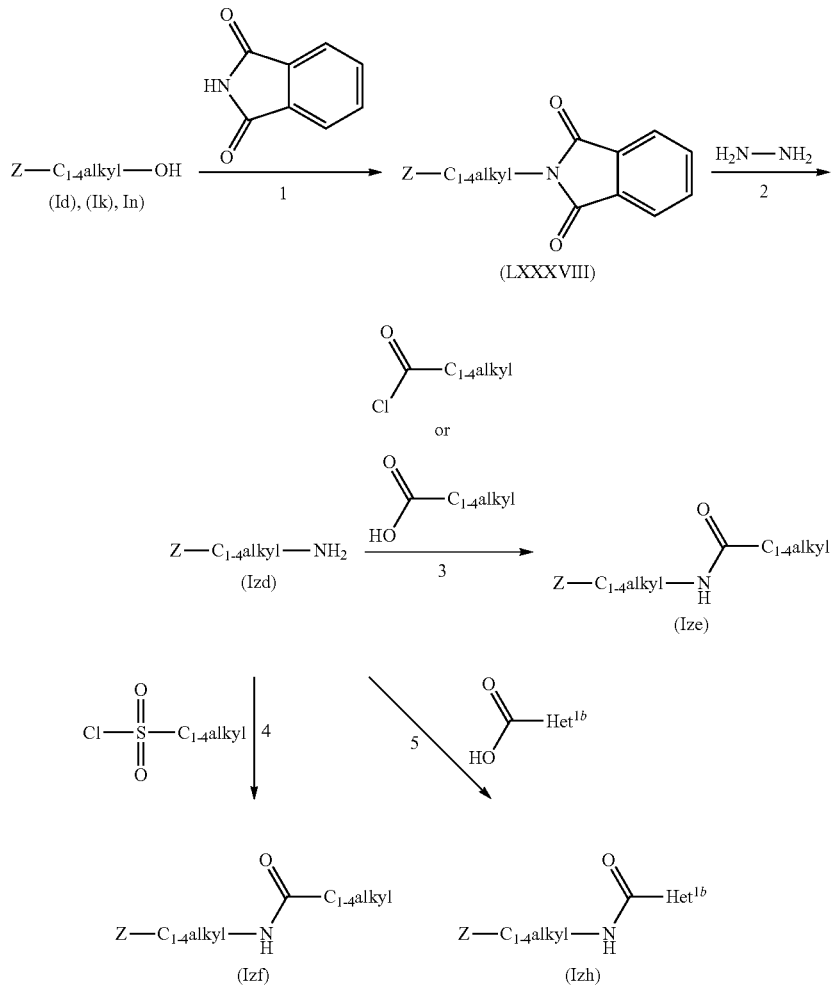

In general, compounds of Formula (I) wherein Z represent

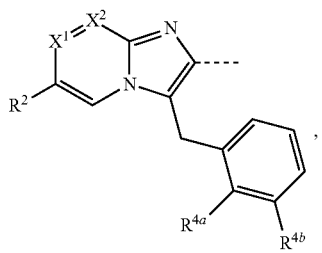

tautomers and stereoisomeric forms thereof, wherein
$X^1$ represents CH or N;
$X^2$ represents CH or N;
provided that maximum one of $X^1$ and $X^2$ represents N;
wherein the other variables are as shown in Formula (Izi) and (Izj), can be prepared according to the following reaction Scheme 26. All other variables in Scheme 26 are defined as above or according to the scope of the present invention.

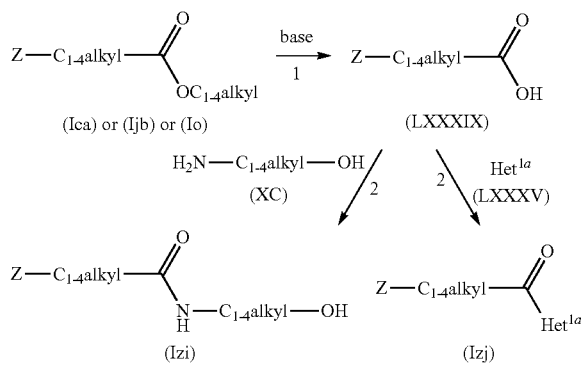

In Scheme 26, the following reaction conditions apply:
1: in the presence of a base such as for example aqueous lithium hydroxide or aqueous sodium hydroxide, in a suitable solvent such as for example methanol, tetrahydrofuran, ethanol;
2: in the presence of a suitable coupling reagent such as for example N,N,N',N'-Tetra-methyl-O—(1H-benzotriazol-1-yl)uronium hexafluorophosphate, O—(Benzotriazol-1-yl)-N,N,N',N'-tetramethyluronium hexafluorophosphate, a suitable base such as for example diisopropylethylamine, in a suitable solvent such as for example dimethylformamide.

In general, compounds of Formula (I) wherein Z represent

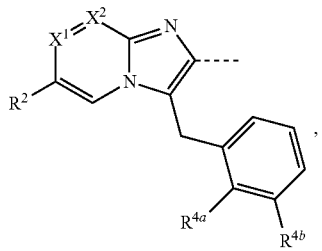

tautomers and stereoisomeric forms thereof, wherein
$X^1$ represents CH or N;
$X^2$ represents CH or N;
provided that maximum one of $X^1$ and $X^2$ represents N;
wherein the other variables are as shown in Formula (Izk), can be prepared according to the following reaction Scheme 27.

In scheme 27, (Icb), Ija) and (Io) are restricted to (Icb1), Ija1) and (Ioa) in which $R^3$ is restricted to —$CO_2C_{1-4}$alkyl. All other variables in Scheme 27 are defined as above or according to the scope of the present invention.

Scheme 27

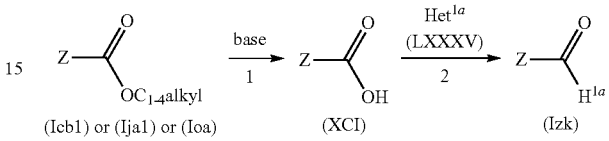

In Scheme 27, the following reaction conditions apply:
1: in the presence of a base such as for example aqueous lithium hydroxide or aqueous sodium hydroxide, in a suitable solvent such as for example methanol, tetrahydrofuran, ethanol;
2: in the presence of a suitable coupling reagent such as for example N,N,N',N'-Tetra-methyl-O—(1H-benzotriazol-1-yl)uronium hexafluorophosphate, O—(Benzotriazol-1-yl)-N,N,N',N'-tetramethyluronium hexafluorophosphate, a suitable base such as for example diisopropylethylamine, in a suitable solvent such as for example dimethylformamide.

In all these preparations, the reaction products may be isolated from the reaction medium and, if necessary, further purified according to methodologies generally known in the art such as, for example, extraction, crystallization, trituration and chromatography.

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

Pharmacology

It has been found that the compounds of the present invention inhibit PI3K kinase activity, and optionally also have PI3Kδ inhibitory activity.

It is therefore anticipated that the compounds according to the present invention or pharmaceutical compositions thereof may be useful for treating or preventing, in particular treating, of diseases such as cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, lung injuries and the like; in particular cancer.

Because the pharmaceutically active compounds of the present invention are active as PI3Kβ inhibitors, they exhibit therapeutic utility in treatment or prevention, in particular treatment, of susceptible neoplasms, particularly those neoplasms that exhibit a PTEN deficiency.

As used herein, the phrase "PTEN deficient" or "PTEN deficiency" shall describe tumors with deficiencies of the tumor suppressor function of PTEN (Phosphatase and Tensin Homolog). Such deficiency includes mutation in the PTEN gene, reduction or absence of PTEN proteins when compared to PTEN wild-type, or mutation or absence of other genes that cause suppression of PTEN function.

"Susceptible neoplasm" as used herein refers to neoplasms which are susceptible to treatment by a kinase inhibitor and particularly neoplasms that are susceptible to treatment by a PI3Kβ inhibitor. Neoplasms which have been associated with inappropriate activity of the PTEN phosphatase and particularly neoplasms which exhibit mutation of PTEN, or mutation of an upstream activator of PI3Kβ kinase or overexpression of an upstream activator of PI3Kβ kinase, and are therefore susceptible to treatment with an PI3Kβ inhibitor, are known in the art, and include both primary and metastatic tumors and cancers. According to an embodiment, description of the treatment of a susceptible neoplasm may be used interchangeably with description of the treatment of a cancer.

According to one embodiment, "susceptible neoplasms" include but are not limited to PTEN-deficient neoplasms listed as follows: brain (gliomas), glioblastomas, leukemias, Bannayan-Zonana syndrome, Cowden disease, Lhermitte-Duclos disease, breast cancer, inflammatory breast cancer, colorectal cancer Wilm's tumor, Ewing's sarcoma., Rhabdomyosarcoma, ependymoma, medulloblastoma, colon cancer, head and neck cancer, liver cancer, kidney cancer, lung cancer, melanoma, squamous cell carcinoma, ovarian cancer, pancreatic cancer, prostate cancer, sarcoma cancer, osteosarcoma, giant cell tumor of bone, thyroid cancer, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, Plasmacytoma, Immunoblastic large cell leukemia, Mantle cell leukemia, Multiple myeloma, Megakaryoblastic leukemia, Acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, cervical cancer, vulval cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), and testicular cancer.

According to an alternative embodiment, the term "susceptible neoplasm" includes and is limited to hormone refractory prostate cancer, non-small-cell lung cancer, endometrial cancer, gastric cancer, melanoma, head and neck cancer, breast cancer, including tripnegative breast cancer, and glioma.

In an embodiment, the term "susceptible neoplasm" includes and is limited to prostate cancer, in particular hormone refractory prostate cancer.

The compounds of the present invention may also have therapeutic applications in sensitising tumour cells for radiotherapy and chemotherapy.

Hence the compounds of the present invention may be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chernotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hemnatoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

The invention relates to compounds of Formula (I) and N-oxides, pharmaceutically acceptable addition salts, and solvates thereof, for use as a medicament.

The invention also relates to compounds of Formula (I) and N-oxides, pharmaceutically acceptable addition salts, and solvates thereof, for use in the inhibition of PI3Kβ kinase activity and optionally also for use in the inhibition of PI3Kδ.

The compounds of the present invention can be "anti-cancer agents", which term also encompasses "anti-tumor cell growth agents" and "anti-neoplastic agents".

The invention also relates to compounds of Formula (I) and N-oxides, pharmaceutically acceptable addition salts, and solvates thereof, for use in the treatment of diseases mentioned above.

The invention also relates to compounds of Formula (I) and N-oxides, pharmaceutically acceptable addition salts, and solvates thereof, for the treatment or prevention, in particular for the treatment, of said diseases.

The invention also relates to compounds of Formula (I) and N-oxides, pharmaceutically acceptable addition salts, and solvates thereof, for the treatment or prevention, in particular in the treatment, of PI3Kβ mediated diseases or conditions.

The invention also relates to compounds of Formula (I) and N-oxides, pharmaceutically acceptable addition salts, and solvates thereof, for the treatment or prevention, in particular in the treatment, of PI3Kβ and optionally PI3Kδ mediated diseases or conditions.

The invention also relates to the use of compounds of Formula (I) and N-oxides, pharmaceutically acceptable addition salts, and solvates thereof, for the manufacture of a medicament.

The invention also relates to the use of compounds of Formula (I) and N-oxides, pharmaceutically acceptable addition salts, and solvates thereof, for the manufacture of a medicament for the inhibition of PI3Kβ.

The invention also relates to the use of compounds of Formula (I) and N-oxides, pharmaceutically acceptable addition salts, and solvates thereof, for the manufacture of a medicament for the inhibition of PI3Kβ and optionally also for the inhibition of PI3Kδ.

The invention also relates to the use of compounds of Formula (I) and N-oxides, pharmaceutically acceptable addition salts, and solvates thereof, for the manufacture of a medicament for the treatment or prevention, in particular for the treatment, of any one of the disease conditions mentioned hereinbefore.

The invention also relates to the use of compounds of Formula (I) and N-oxides, pharmaceutically acceptable addition salts, and solvates thereof, for the manufacture of a medicament for the treatment of any one of the disease conditions mentioned hereinbefore.

The compounds of Formula (I) and N-oxides, pharmaceutically acceptable addition salts, and solvates thereof, can be administered to mammals, preferably humans for the treatment or prevention of any one of the diseases mentioned hereinbefore.

In view of the utility of the compounds of Formula (I) and N-oxides, pharmaceutically acceptable addition salts, and solvates thereof, there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I) or a N-oxide, a pharmaceutically acceptable addition salt, or a solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent cancer or cancer-related conditions, may be administered alone or in combination with one or more additional therapeutic agents. Combination therapy includes administration of a single pharmaceutical dosage formulation which contains a compound of Formula (I), a N-oxide, a pharmaceutically acceptable addition salt, or a solvate thereof, and one or more additional therapeutic agents, as well as administration of the compound of Formula (I), a N-oxide, a pharmaceutically acceptable addition salt, or a solvate thereof, and each additional therapeutic agents in its own separate pharmaceutical dosage formulation. For example, a compound of Formula (I), a N-oxide, a pharmaceutically acceptable addition salt, or a solvate thereof, and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound of Formula (I), a N-oxide, a pharmaceutically acceptable addition salt, or a solvate thereof.

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds of Formula (I) and N-oxides, pharmaceutically acceptable addition salts, and solvates thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing a compound of Formula (I), a N-oxide, a pharmaceutically acceptable addition salt, or a solvate thereof, may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the compounds of Formula (I) and N-oxides, pharmaceutically acceptable addition salts, and solvates thereof, in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), a N-oxide, a pharmaceutically acceptable addition salt, or a solvate thereof, and from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy.

Examples of anti-cancer agents or adjuvants (supporting agents in the therapy) include but are not limited to:
  platinum coordination compounds for example cisplatin optionally combined with amifostine, carboplatin or oxaliplatin;
  taxane compounds for example paclitaxel, paclitaxel protein bound particles (Abraxane™) or docetaxel;
  topoisomerase I inhibitors such as camptothecin compounds for example irinotecan, SN-38, topotecan, topotecan hcl;
  topoisomerase II inhibitors such as anti-tumour epipodophyllotoxins or podophyllotoxin derivatives for example etoposide, etoposide phosphate or teniposide;
  anti-tumour vinca alkaloids for example vinblastine, vincristine or vinorelbine;
  anti-tumour nucleoside derivatives for example 5-fluorouracil, leucovorin, gemcitabine, gemcitabine hcl, capecitabine, cladribine, fludarabine, nelarabine;
  alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;
  anti-tumour anthracycline derivatives for example daunorubicin, doxorubicin optionally in combination with dexrazoxane, doxil, idarubicin, mitoxantrone, epirubicin, epirubicin hcl, valrubicin;
  molecules that target the IGF-1 receptor for example picropodophilin;
  tetracarcin derivatives for example tetrocarcin A;
  glucocorticoiden for example prednisone;
  antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
  estrogen receptor antagonists or selective estrogen receptor modulators or inhibitors of estrogen synthesis for example tamoxifen, fulvestrant, toremifene, droloxifene, faslodex, raloxifene or letrozole;
  aromatase inhibitors such as exemestane, anastrozole, letrazole, testolactone and vorozole;
  differentiating agents such as retinoids, vitamin D or retinoic acid and retinoic acid metabolism blocking agents (RAMBA) for example accutane;
  DNA methyl transferase inhibitors for example azacytidine or decitabine;

antifolates for example pemetrexed disodium;
antibiotics for example antinomycin D, bleomycin, mitomycin C, dactinomycin, carminomycin, daunomycin, levamisole, plicamycin, mithramycin;
antimetabolites for example clofarabine, anminopterin, cytosine arabinoside or methotrexate, azacitidine, cytarabine, floxuridine, pentostatin, thioguanine;
apoptosis inducing agents and antiangiogenic agents such as Bcl-2 inhibitors for example YC 137, BH 312, ABT 737, gossypol, HA 14-1, TW 37 or decanoic acid;
tubuline-binding agents for example combrestatin, colchicines or nocodazole;
kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
farnesyltransferase inhibitors for example tipifarnib;
histone deacetylase (HDAC) inhibitors for example sodium butyrate, suberoylanilide hydroxamic acid (SAHA), depsipeptide (FR 901228), NVP-LAQ824, R306465, JNJ-26481585, trichostatin A, vorinostat;
Inhibitors of the ubiquitin-proteasome pathway for example PS-341, MLN 0.41 or bortezomib;
Yondelis;
Telomerase inhibitors for example telomestatin;
Matrix metalloproteinase inhibitors for example batimastat, marimastat, prinostat or metastat;
Recombinant interleukins for example aldesleukin, denileukin diftitox, interferon alfa 2a, interferon alfa 2b, peginterferon alfa 2b;
MAPK inhibitors;
Retinoids for example alitretinoin, bexarotene, tretinoin;
Arsenic trioxide;
Asparaginase;
Steroids for example dromostanolone propionate, megestrol acetate, nandrolone (decanoate, phenpropionate), dexamethasone;
Gonadotropin releasing hormone agonists or antagonists for example abarelix, goserelin acetate, histrelin acetate, leuprolide acetate;
Thalidomide, lenalidomide;
Mercaptopurine, mitotane, pamidronate, pegademase, pegaspargase, rasburicase;
BH3 mimetics for example ABT-737;
MEK inhibitors for example PD98059, AZD6244, CI-1040;
colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin;
a steroidal cytochrome P450 17alpha-hydroxylase-17,20-lyase inhibitor (CYP17), e.g. abiraterone, abiraterone acetate;
Glycolysis inhibitors, such as 2-deoxyglucose;
mTOR inhibitors such as rapamycins and rapalogs, and mTOR kinase inhibitors;
PI3K inhibitors and dual mTOR/PI3K inhibitors;
autophagy inhibitors, such as chloroquine and hydroxychloroquine;
antibodies that re-activate the immune response to tumors, for example nivolumab (anti-PD-1), lambrolizumab (anti-PD-1), ipilimumab (anti-CTLA4), and MPDL3280A (anti-PD-L1).

The compounds of the invention can also be advantageously combined with anti-androgen therapies including androgen receptor antagonists and inhibitors of androgen biosynthesis in PTEN-negative prostate cancers.

The present invention further relates to a product containing as first active ingredient a compound according to the invention and as further active ingredient one or more anticancer agents, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 mg/m, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter (mg/m²) of body surface area, particularly for vinblastine in a dosage of about 3 to 12 mg/m², for vincristine in a dosage of about 1 to 2 mg/m², and for vinorelbine in dosage of about 10 to 30 mg/m² per course of treatment.

The anti-tumour nucleoside derivative is advantageously administered in a dosage of 200 to 2500 mg per square meter (mg/m²) of body surface area, for example 700 to 1500 mg/m², particularly for 5-FU in a dosage of 200 to 500 mg/m², for gemcitabine in a dosage of about 800 to 1200 mg/m² and for capecitabine in about 1000 to 2500 mg/m² per course of treatment.

The alkylating agents such as nitrogen mustard or nitrosourea is advantageously administered in a dosage of 100 to 500 mg per square meter (mg/m²) of body surface area, for example 120 to 200 mg/m², particularly for cyclophosphamide in a dosage of about 100 to 500 mg/m², for chlorambucil in a dosage of about 0.1 to 0.2 mg/kg, for carmustine in a dosage of about 150 to 200 mg/m², and for lomustine in a dosage of about 100 to 150 mg/m² per course of treatment.

The anti-tumour anthracycline derivative is advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m²) of body surface area, or as known in the art, if different. Trastuzumab is advantageously administered in a dosage of 1 to 5 mg per square meter (mg/m²) of body surface area, particularly 2 to 4 mg/m² per course of treatment.

These dosages may be administered for example once, twice or more per course of treatment, which may be repeated for example every 7, 14, 21 or 28 days.

EXAMPLES

The following examples illustrate the present invention.
When a stereocenter is indicated with 'RS' this means that a racemic mixture was obtained.

Hereinafter, the term 'DCM' means dichloromethane, 'MeOH' means methanol, 'EtOH' means ethanol, 'ACN' means acetonitrile, 'THF' means tetrahydrofuran, 'DMF' means dimethylformamide, 'EtOAc' means ethyl acetate, 'iPrOH' means isopropanol, 'H$_2$O' means water, 'DME' means ethylene glycol dimethyl ether, 'DCE' means dichloroethane, 'DIPE' means diisopropylether, 'K$_2$CO$_3$' means potassium carbonate, 'Cs$_2$CO$_3$' means cesium carbonate, 'K$_3$PO$_4$' means potassium phosphate, 'NH$_4$OH' means ammonia aqueous solution, 'NaHCO$_3$' means sodium bicarbonate, 'NaOH' means sodium hydroxide, 'NaCl' means sodium chloride, 'NH$_4$Cl' means ammonium chloride, 'LiCl' means lithium chloride, 'NH$_4$HCO$_3$' means ammonium bicarbonate, 'HCOONH$_4$' means ammonium formate, 'KOAc' means potassium acetate, 'DIPEA' means diisopropylethylamine, 'n-BuLi' means n-butyllithium, 'iPrNH2' means isopropylamine, 'MgSO$_4$' means magnesium sulfate, 'Na$_2$SO$_4$' means sodium sulfate, 'Na$_2$S$_2$O$_3$' means sodium thiosulfate, 'N$_2$' means nitrogen, 'HCl' means hydrochloric acid, 'TFA' means trifluoroacetic acid, 'NaBH$_4$' means sodium borohydride, 'LiAlH$_4$' means lithium aluminium hydride, 'TBAF' means tetrabutylammonium fluoride, 'CO$_2$' means carbon dioxide, 'CO' means carbon monoxide, 'SFC' means supercritical fluid chromatography, 'HBTU' means N,N,N',N'-tetramethyl-O-(1H-benzotriazol-1-yl)uronium hexafluorophosphate, O—(Benzotriazol-1-yl)-N,N,N', N'-tetramethyluronium hexafluorophosphate, 'PPh$_3$' means triphenylphosphine, 'ZnCl$_2$' means zinc chloride, 'Pd (PPh$_3$)$_4$' means tetrakis(triphenylphosphine)palladium(0), 'Pd(OAc)$_2$' means palladium(II) acetate, 'PdCl$_2$(dppf). DCM' means dichloro [1,1'-bis(diphenylphosphino) ferrocene]palladium(II) dichloromethan adduct, 'Celite®' means diatomaceous earth, 'RuPhos' means 2-dicyclohexylphosphino-2',6'-diisopropoxy-1,1'-biphenyl, 'BrettPhos precatalyst first gen' (CAS 1148148-01-9) means chloro[2-(dicyclohexylphosphino)-3,6-dimethoxy-2',4',6'-triisopropyl-1, 1'-biphenyl][2-(2-aminoethyl)phenyl]-palladium(II), 'Binap' means Rac-bis(diphenylphosphino)-1,1'-binapthyl, 'rt' means room temperature, '(K)' means Kofler, 'DSC' means differential scanning calorimetry. 'M.P.' means melting point.

A. Preparation of the Intermediate Compounds

Example A1

Preparation of Intermediate 1:

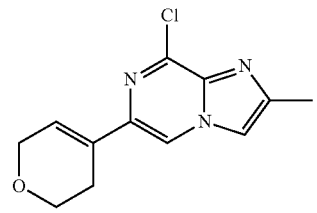 [SMILES: Cc1cn2cc(C3=CCOCC3)nc(Cl)c2n1]

A mixture of 6-iodo-8-chloro-2-methyl-imidazo[1,2-a] pyrazine (WO 2011/110545) (3 g; 10.22 mmol), 3,6-dihydro-4-(4,4,5,5-tetramethyl-1,3,2-dioxaborolan-2-yl)-2H-pyran (2.41 g; 11.45 mmol), K$_3$PO$_4$ (6.51 g; 30.67 mmol) in H$_2$O (18 mL) and 1,4-dioxane (180 mL) was carefully purged with N$_2$. PdCl$_2$(dppf).DCM (920 mg; 1.12 mmol) was added and the reaction mixture was purged once again with N$_2$. The reaction mixture was heated at 80° C. for 24 h. The solution was cooled, poured into cooled water. EtOAc was added and the mixture was filtered through a pad of Celite®. The product was extracted with EtOAc, the organic layer was dried over MgSO$_4$, filtered and evaporated to dryness. The residue (5 g) was purified by chromatography over silica gel (Irregular SiOH; 20-45 μm; 450 g; mobile phase: 65% heptane, 5% MeOH (+10% NH$_4$OH), 35% EtOAc). The pure fractions were collected and the solvent was evaporated to give 1.6 g (63%) of intermediate 1.
Alternative Pathway:

A mixture of 6-bromo-8-chloro-2-methyl-imidazo[1,2-a] pyrazine (WO2010 089292) (1 g; 4.06 mmol), 3,6-dihydro-4-(4,4,5,5-tetramethyl-1,3,2-dioxaborolan-2-yl)-2H-pyran (0.96 g; 4.54 mmol), K$_3$PO$_4$ (2.6 g; 12.2 mmol) in 1,4- dioxane (30 mL) and H₂O (3 mL) was carefully purged with nitrogen. PdCl₂(dppf).DCM (0.37 g; 0.45 mmol) was added and the reaction mixture was purged once again with nitrogen. The reaction mixture was heated at 80° C. for 24 h. The solution was cooled down to rt, poured into cooled water. EtOAc was added and the mixture was filtered through a pad of Celite®. The product was extracted with EtOAc, the organic layer was dried over MgSO₄, filtered and evaporated to dryness. The residue (1.5 g) was purified by chromatography over silica gel (Irregular SiOH; 20-45 µm; 450 g; mobile phase: 65% heptane, 5% MeOH (+10% NH₄OH), 35% EtOAc). The pure fractions were collected and the solvent was evaporated to give 600 mg (59%) of intermediate 1.

Preparation of Intermediate 2:

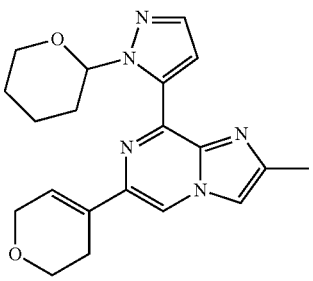 [SMILES: Cc1cn2cc(C3=CCOCC3)nc(-c3ccnn3C3CCCCO3)c2n1]

A mixture of intermediate 1 (1 g; 4 mmol), 1-(tetrahydropyran-2-yl)-1H-pyrazole-5-boronic acid pinacol ester (1.7 g; 6 mmol), K₃PO₄ (2.55 g; 12 mmol) in 1,4-dioxane (66 mL) and H₂O (6.6 mL) was carefully purged with N₂. PdCl₂(dppf).DCM (0.36 g; 0.44 mmol) was added and the reaction mixture was purged once again with N₂. The reaction mixture was heated at 80° C. for 24 h. The solution was cooled down to rt, poured onto cooled water. EtOAc was added and the mixture was filtered through a pad of Celite®. The product was extracted with EtOAc and the organic layer was dried over MgSO₄, filtered and evaporated to dryness. The residue (2.2 g) was purified by chromatography over silica gel (15-40 µm; 120 g; eluent: 99% DCM, 1% MeOH, 0.1% NH₄OH). The pure fractions were collected and the solvent was evaporated. The residue was crystallized with diethylether. The precipitate was filtered and dried to give 1.23 g (84%) of intermediate 2.

Preparation of Intermediate 3:

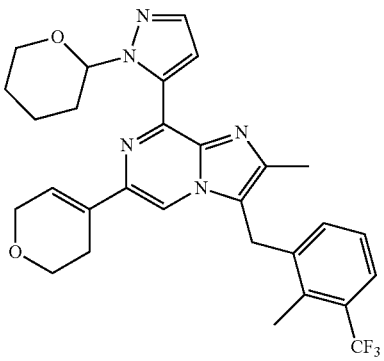 [SMILES: Cc1nc2c(-c3ccnn3C3CCCCO3)nc(C3=CCOCC3)cn2c1Cc1cccc(C(F)(F)F)c1C]

A mixture of intermediate 2 (1.23 g; 3.4 mmol), 1-(chloromethyl)-2-methyl-3-(trifluoromethyl-benzene (0.96 g; 4.6 mmol), K₂CO₃ (0.7 g; 5 mmol) in 1,4-dioxane (125 mL) was purged with N₂. Then, PPh₃ (0.35 g; 1.35 mmol) and Pd(OAc)₂ (0.15 g; 0.67 mmol) was added and heated at 100° C. overnight in a sealed tube. The solution was poured onto cooled water. EtOAc was added and the mixture was filtered through a pad of Celite®. The product was extracted with EtOAc, the organic layer was dried over MgSO₄, filtered and evaporated to dryness. The residue (2.55 g) was purified by chromatography over silica gel (15-40 µm; 120 g; eluent: 60% heptane, 5% MeOH, 35% EtOAc). The pure fractions were collected and the solvent was evaporated to give 1.29 g (71%) of intermediate 3.

Example A2

Preparation of Intermediate 4:

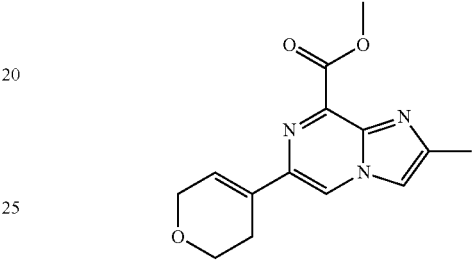

Intermediate 1 (1 g; 4 mmol), Pd(OAc)₂ (0.19 g; 0.4 mmol), 1,3-bis(diphenyl-phosphino)propane (165 mg; 0.4 mmol), KOAc (0.79 g; 8.01 mmol) in MeOH (70 mL) were heated in an autoclave at 120° C. under an atmosphere of CO [CO-gas (5 bars)] for 8 h and at rt overnight. The mixture was filtered through a pad of Celite® and the filtrate was evaporated to dryness. The residue (2.5 g) was purified by chromatography over silica gel (Irregular SiOH; 20-45 µm; 450 g; mobile phase: 0.3% NH₄OH, 97% DCM, 3% MeOH). The pure fractions were collected and the solvent was evaporated to give 725 mg (66%) of intermediate 4.

Preparation of Intermediate 5:

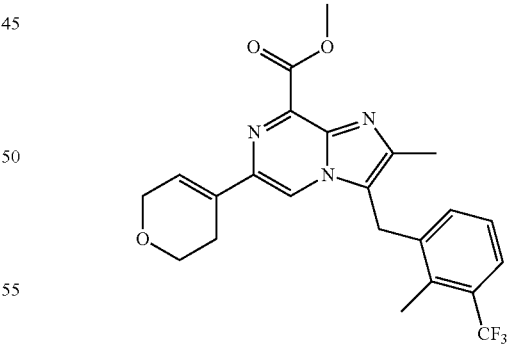

Intermediate 5 was prepared according to an analogous procedure as described for the synthesis of intermediate 3, using intermediate 4 and 1-(chloromethyl)-2-methyl-3-(trifluoromethyl-benzene as starting materials. The crude was purified by chromatography over silica gel (irregular bare silica; 150 g; mobile phase: 98% DCM, 2% MeOH). The pure fractions were collected and the solvent was evaporated to give 300 mg (25%) of intermediate 5.

Example A3

Preparation of Intermediate 6:

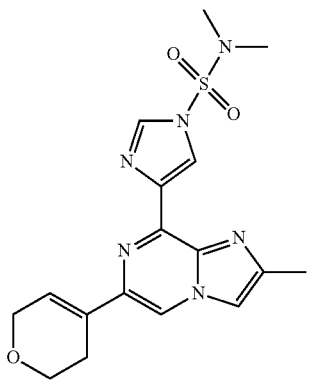 [SMILES: Cc1cn2cc(C3=CCOCC3)nc(-c3cn(S(=O)(=O)N(C)C)cn3)c2n1]

A mixture of intermediate 1 (0.9 g; 3.6 mmol), N,N-dimethyl-4-(4,4,5,5-tetramethyl-1,3,2-dioxaborolan-2-yl)-1H-Imidazole-1-sulfonamide (1.4 g; 4.7 mmol), $K_2CO_3$ (1 g; 7.2 mmol) in $H_2O$ (15.5 mL) and 1.4-dioxane (62 mL) was carefully purged with $N_2$. $PdCl_2$(dppf). DCM (0.3 g; 0.36 mmol) was added and the reaction mixture was purged once again with $N_2$. The reaction mixture was heated at 80° C. for 24 h. The solution was cooled down to rt, poured onto cooled water. EtOAc was added and the mixture was filtered through a pad of Celite®. The product was extracted with EtOAc, the organic layer was dried over $MgSO_4$, filtered and evaporated to dryness. The residue (2.1 g) was purified by chromatography over silica gel (15-40 µm; 80 g; eluent: 95% DCM, 5% MeOH, 0.1% $NH_4OH$). The pure fractions were collected and the solvent was evaporated to give 1.28 g (91%) of intermediate 6.

Preparation of Intermediate 7:

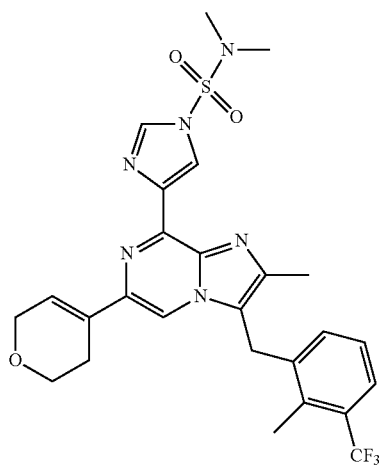 [SMILES: Cc1nc2c(-c3cn(S(=O)(=O)N(C)C)cn3)nc(C3=CCOCC3)cn2c1Cc1cccc(C(F)(F)F)c1C]

Intermediate 7 was prepared according to an analogous procedure as described for the synthesis of intermediate 3, using intermediate 6 and 1-(chloromethyl)-2-methyl-3-(trifluoromethyl)-benzene as starting materials. The crude was purified by chromatography over silica gel (irregular SiOH; 15-40 µm; 300 g; mobile phase: 0.1% $NH_4OH$, 96% DCM, 4% MeOH). The pure fractions were collected and the solvent was evaporated to give 750 mg (40%) of intermediate 7.

Example A5

Preparation of Intermediate 9:

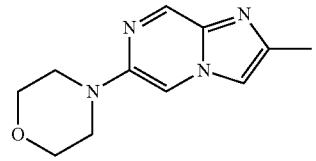 [SMILES: Cc1cn2cc(N3CCOCC3)ncc2n1]

A mixture of 2-amino-5-(morpholino)pyrazine (1 g; 2.5 mmol) and chloro-2-propanone (0.9 mL; 11 mmol) in EtOH (50 mL) was heated at 80° C. for 4 h in a sealed glassware, then overnight at rt. The solution was evaporated to dryness. The residue (1.2 g) was purified by chromatography over silica gel (15-40 µm; 120 g; eluent: 98% DCM, 2% MeOH). The pure fractions were collected and the solvent was evaporated to give 330 mg (27%) of intermediate 9.

Example A6

Preparation of Intermediate 10:

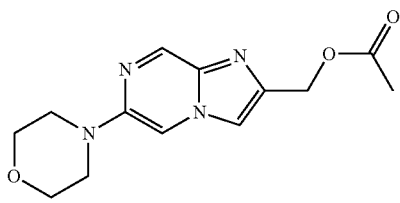 [SMILES: CC(=O)OCc1cn2cc(N3CCOCC3)ncc2n1]

The experiment was performed 6 times on 1 g (5.55 mmol) of 2-amino-5-(morpholino)-pyrazine.
A mixture of 2-amino-5-(morpholino)pyrazine (1 g; 5.55 mmol), 1-acetoxy-3-chloroacetone (1.15 mL; 9.83 mmol) and molecular sieves 4 Å (1 g) in DME (30 mL) was heated at 80° C. overnight. The mixture was cooled down to rt. DCM was added and the mixture was filtered through a pad of Celite®. The organic layer was evaporated to dryness. The residue (14.15 g) was purified by chromatography over silica gel (Irregular SiOH; 20-45 µm; 450 g; mobile phase: 43% heptane, 7% MeOH, 50% EtOAc). The pure fractions were collected and the solvent was evaporated to give 1.1 g (12%) of intermediate 10.

Example A7

Preparation of Intermediate 11:

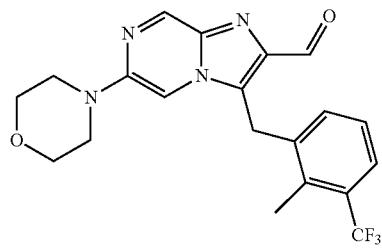 [SMILES: Cc1c(Cc2c(C=O)nc3cnc(N4CCOCC4)cn23)cccc1C(F)(F)F]

A mixture of compound 9 (0.36 g; 0.9 mmol) and manganese oxide (0.78 g; 9 mmol) in DCM (25 mL) was stirred at rt overnight. The mixture was filtered through a pad of Celite® and the filtrate was evaporated to give 360 mg (quantitative) of intermediate 11.

The crude product was used without purification in the next step.

Example A8

Preparation of Intermediate 12:

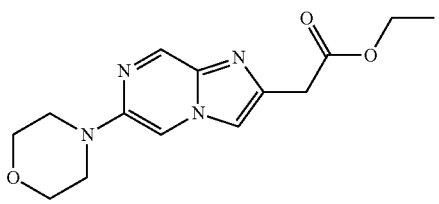

The experiment was performed 3 times on 1 g (5.55 mmol) of 2-amino-5-(morpholino)-pyrazine.

In a sealed tube, ethyl 4-chloroacetatoacetate (1.36 mL; 9.99 mmol) was added to a mixture of 2-amino-5-(morpholino)pyrazine (1 g; 5.55 mmol) and molecular sieves 4 Å (1 g) in DME (30 mL). The reaction mixture was heated at 80° C. overnight. The mixture was cooled down to rt, then filtered through a pad of Celite® and the filtrate was evaporated to dryness. The residue (6 g) was purified by chromatography over silica gel (15-40 µm; 220 g; mobile phase: 0.1% $NH_4OH$, 98% DCM, 2% MeOH). The pure fractions were collected and the solvent was evaporated to give 1.45 g (30%) of intermediate 12.

Preparation of Intermediate 13:

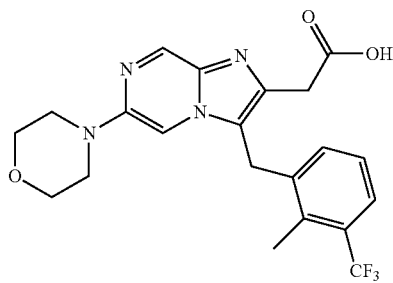 [SMILES: Cc1c(Cc2c(CC(=O)O)nc3cnc(N4CCOCC4)cn23)cccc1C(F)(F)F]

Lithium hydroxide monohydrate (490 mg; 6.49 mmol) was added to a mixture of compound 17 (0.6 g; 1.3 mmol) in $H_2O$ (2 mL) and MeOH (10 mL) at rt for 24 h.

MeOH was eliminated by evaporation, ice-water and water were added followed by 3N aqueous solution of HCl dropwise, the solution was stirred at rt for 3 h. The precipitate was filtered off, washed with water then diethylether and dried under vacuum to give 350 mg (62%) of intermediate 13.

Example A9

Preparation of Intermediate 14:

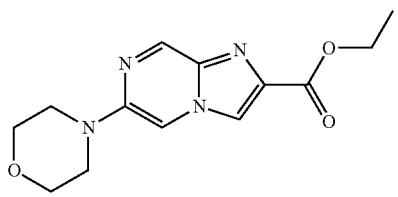 [SMILES: CCOC(=O)c1cn2cc(N3CCOCC3)ncc2n1]

In sealed glassware, a mixture of 2-amino-5-(morpholino)pyrazine (2 g; 11.10 mmol), ethyl bromopyruvate (1.39 mL; 11.10 mmol) and $NaHCO_3$ (2.05 g; 24.42 mmol) in ACN (110 mL) was stirred at 60° C. overnight. After cooling down to rt, the mixture was filtered through a pad of Celite® and the filtrate was evaporated to dryness. The residue was purified by chromatography over silica gel (irregular SiOH; 120 g; solid deposit, mobile phase: from 100% DCM to 50% DCM, 50% EtOAc). The pure fractions were collected and the solvent was evaporated to give 750 mg (24%, beige solid) of intermediate 14.

Example A10

Preparation of Intermediate 16:

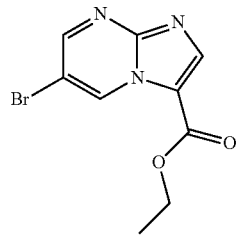

Ethyl bromopyruvate (242 g; 1.24 mol) was added to the mixture of 2-amino-5-bromo-pyrimidine (180 g; 1.03 mol) in DMF (2 L) and the reaction mixture was stirred at rt (25° C.) for 2 days. The solvent was concentrated. Then, the residue was adjusted at pH to 3 with a saturated aqueous solution of NaOH (30%) and the precipitate was filtered to give the crude product 1. The filtrate was extracted with EtOAc (4×500 mL) and the combined organic layer was evaporated. The resulting residue and the crude product 1 (400 g) were combined and purified by chromatography over silica gel (gradient: ether acetate/petrol ether 0/100 to 30/70) to give 58.3 g (21%) of intermediate 16.

Alternative Preparation of Intermediate 16:

2-amino-5-bromoprimidine (15 g; 73.5 mmol) and ethyl bromopyruvate (11.07 mL; 88.2 mmol) were added to ethanol (320 mL). This reaction mixture was refluxed overnight. Then, additional ethyl bromopyruvate (11.07 mL; 88.2 mmol) was added and the reaction mixture was refluxed one more night. The reaction mixture was cooled down to rt, diluted with water and basified until pH 9 with sodium carbonate. The aqueous layer was extracted with DCM. The organic layer was dried over $MgSO_4$, filtered and concentrated. The residue was purified by silica gel chromatography (gradient: DCM 100% to DCM 95% MeOH 5%). The fractions containing the product were mixed and concentrated. The resulting residue was dissolve in ethyl ether and the precipitate was filtered to afford 7 g (35%) of intermediate 16.

Preparation of Intermediate 18:

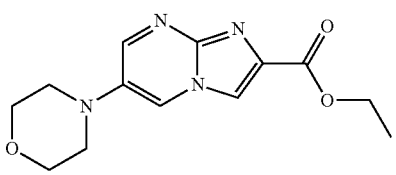 [SMILES: CCOC(=O)c1cn2cc(N3CCOCC3)cnc2n1]

Morpholine (400 mL) was added to a mixture of intermediate 16 (20 g; 74.05 mmol) and DIPEA (18.4 mL; 111.08 mmol). The reaction mixture was stirred at rt for 24 h. The crude was evaporated under vacuum (sticky brown residue). The residue was taken up with DCM and the paste was filtered off before the purification. The residue was purified by chromatography over silica gel (silica 20-45 µm; 330 g; gradient: from 100% DCM to 90% DCM, 10% MeOH, 0.1% NH₄OH). The pure fractions were collected and the solvent was evaporated. The resulting residue (10 g) was purified by chromatography over silica gel (silica 20-45 µm; 120 g; gradient: from 100% DCM to 90% DCM, 10% MeOH, 0.1% NH₄OH). The pure fractions were collected and the solvent was evaporated to give 3.3 g (16%) of intermediate 18.

Example A11

Preparation of Intermediate 21:

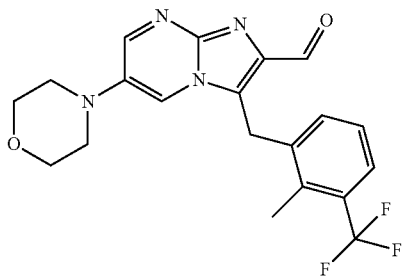 [SMILES: Cc1c(Cc2c(C=O)nc3ncc(N4CCOCC4)cn23)cccc1C(F)(F)F]

A mixture of compound 18 (1.13 g; 2.78 mmol), manganese oxide (2.42 g; 27.81 mmol) in toluene (23 mL) was heated to 80° C. for 12 h. The mixture was cooled down to rt, diluted in DCM and filtered through a pad of Celite® which was washed with DCM. The filtrate was evaporated until dryness to give 0.67 g (76%) of intermediate 21. The product was used without purification in the next step.
Preparation of Intermediate 22:

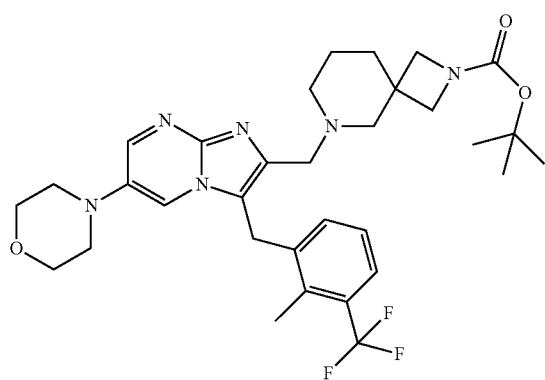 [SMILES: Cc1c(Cc2c(CN3CCCC4(C3)CN(C(=O)OC(C)(C)C)C4)nc3ncc(N4CCOCC4)cn23)cccc1C(F)(F)F]

A mixture of intermediate 21 (271 mg; 0.67 mmol) and tert-butyl 2,6-diazaspiro-[3.5]nonane-2-carboxylate oxalate salt (453 mg; 1.36 mmol) were dissolved in DCM (3 mL) and stirred at 40° C. for 1 h. Then, sodium triacetoxyborohydride (360 mg; 1.7 mmol) was added and the reaction mixture was stirred at 40° C. for 1h30. The mixture was poured into an aqueous solution of NaHCO₃. The organic layer was washed with water and brine, dried over MgSO₄, filtered and evaporated under vacuum. The residue was purified by chromatography over silica gel (gradient: from 100% DCM to 90% DCM, 10% MeOH). The pure fractions were collected and evaporated under vacuum to give 176 mg (38%, solid) of intermediate 22.

Example A12

Preparation of Intermediate 23:

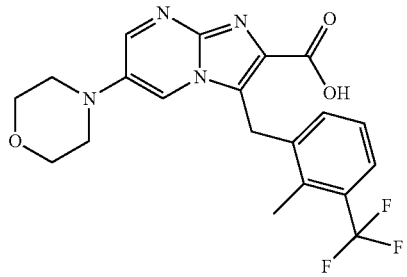 [SMILES: Cc1c(Cc2c(C(=O)O)nc3ncc(N4CCOCC4)cn23)cccc1C(F)(F)F]

Compound 51 (176 mg; 0.39 mmol) was dissolved in THF (2 mL) and H₂O (1 mL). Then, NaOH (31 mg; 0.79 mmol) was added. The reaction mixture was stirred at rt for 12 h. The solvent were removed and the residue (165 mg) was used without purification in the next step.

Example A14

Preparation of Intermediate 25:

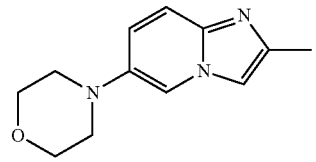 [SMILES: Cc1cn2cc(N3CCOCC3)ccc2n1]

In a Schlenk reactor, to a solution of 6-bromo-2-methylimidazo[1,2-a]pyridine (1.26 g; 5.95 mmol) in dry 2-methyl-2-butanol (25.1 mL) were added morpholine (1.26 mL; 14.3 mmol) and Cs₂CO₃ (3.88 g; 11.9 mmol). The mixture was purged under vacuum and back-filled with N₂ (×3). Then, RuPhos (167 mg; 0.36 mmol) and BrettPhos precatalyst first gen (285 mg; 0.36 mmol) were added. The mixture was purged under vacuum, back-filled with N₂ and heated at 100° C. overnight. Then, more morpholine (500 µL; 5.68 mmol), RuPhos (66 mg; 0.14 mmol) and BrettPhos precatalyst first gen (113 mg; 0.14 mmol) were added and the mixture was stirred at 100° C. overnight. The mixture was filtered through a pad of Celite® and the cake was rinsed with DCM (×2). The filtrate was washed with water, brine, dried over MgSO₄, filtered and evaporated under vacuum. The residue (1.8 g, dark green gum) was purified by chromatography over silica gel (Irregular SiOH 20-45 µm; 450 g; mobile phase: 43% heptane, 7% MeOH (+10% NH₄OH), 50% DCM). The pure fractions were collected and the solvent was evaporated to give 405 mg (41%, beige powder) of intermediate 25.
Preparation of Intermediate 26:

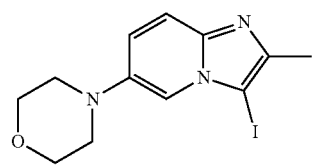 [SMILES: Cc1nc2ccc(N3CCOCC3)cn2c1I]

To a solution of intermediate 25 (405 mg; 1.86 mmol) in ACN (10 mL) at 0° C. was added dropwise a solution of N-iodosuccinimide (440 mg; 1.96 mmol) in ACN (8.6 mL). The reaction mixture was stirred at 0° C. for 30 min. The mixture was evaporated under vacuum and the residue was taken-up in DCM and 10% aqueous solution of K$_2$CO$_3$. The layers were separated and the product was extracted with DCM. The combined organic layers were washed with brine, dried over MgSO$_4$, filtered and evaporated under vacuum. The residue (1.4 g, brown powder) was purified by chromatography over silica gel (irregular SiOH 30 μm; 40 g; mobile phase: from 100% DCM to 96% DCM, 4% MeOH, 0.4% NH$_{40}$H). The pure fractions were collected and the solvent was evaporated to give 633 mg (96%, green powder) of intermediate 26.

Example A15

Preparation of Intermediate 27:

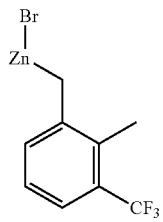

In a dried flask, zinc dust (3.36 g; 51.37 mmol) was suspended in dry THF (50 mL) under N$_2$. The suspension was warmed to 60° C. and then, 1,2-dibromoethane (171 μL; 1.98 mmol) was added. The mixture was stirred at 60° C. for 20 min and cooled down to rt. Chlorotrimethylsilane (200 μL; 1.58 mmol) was added and the reaction mixture was stirred at rt for 20 min. At 0° C., 1-(bromomethyl)-2-methyl-3-(trifluoromethyl)-benzene (10 g; 39.52 mmol) was added dropwise and the reaction mixture was stirred at rt for 2 h. The crude product was used (M=0.565 mol/L) directly in the next step without any further treatment.

Example A16

Preparation of Intermediate 28:

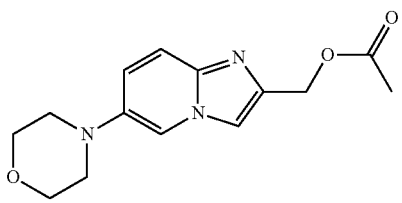 [SMILES: CC(=O)OCc1cn2cc(N3CCOCC3)ccc2n1]

In a Schlenk reactor, to a solution of 2-amino-5-(morpholino)pyridine (2 g; 11.2 mmol) in DMF (40 mL) was added 1-acetoxy-3-chloroacetone (2.23 mL; 19 mmol). The reaction mixture was stirred at 120° C. for 3 h. The mixture was evaporated under vacuum. The residue was taken-up in DCM and washed with a saturated solution of NaHCO$_3$. The layers were separated and the aqueous layer was extracted with DCM (×2). The combined organic layers were washed with brine, dried over MgSO$_4$, filtered and evaporated under vacuum. The residue (3.03 g, black oil) was purified by chromatography over silica gel (Irregular SiOH; 20-45 μm; 450 g; mobile phase: 43% heptane, 7% MeOH (+10% NH$_4$OH), 50% DCM). The pure fractions were collected and the solvent was evaporated to give 880 mg (29%, brown powder) of intermediate 28.

Preparation of Intermediate 29:

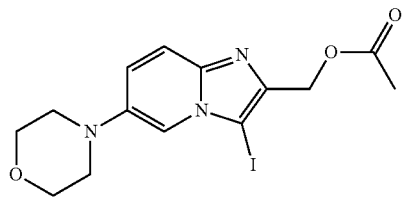 [SMILES: CC(=O)OCc1nc2ccc(N3CCOCC3)cn2c1I]

Intermediate 29 was prepared according to an analogous procedure as described for the synthesis of intermediate 26, using intermediate 28 as starting material. The crude (1.4 g, brown powder) was purified by chromatography over silica gel (irregular SiOH; 15-40 μm; 50 g; gradient: from 100% DCM to 96% DCM, 4% MeOH, 0.4% NH$_4$OH). The pure fractions were collected and the solvent was evaporated to give 1.14 g (79%, green powder) of intermediate 29.

Preparation of Intermediate 30 and compound 28:

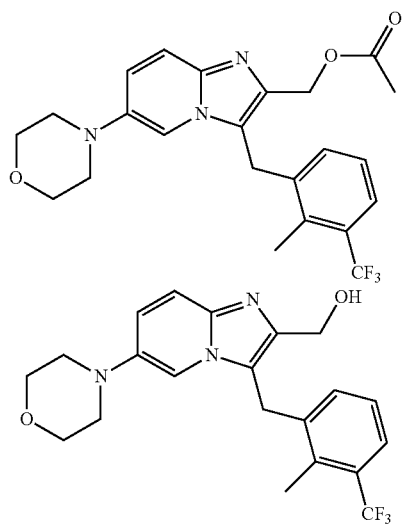

In a Schlenk reactor, to a solution of intermediate 29 (1.07 g; 2.67 mmol) in dry THF (26.8 mL) was added bis(tri-tert-butylphosphine)palladium(0) (68 mg; 0.13 mmol). The mixture was carefully degassed in vacuum and back-filled with N$_2$ (×3). Then, intermediate 27 (8.5 mL; 4.8 mmol) was added and the mixture was carefully degassed under vacuum and back-filled with N$_2$ (×3). The reaction mixture was stirred at 60° C. for 3 h. The mixture was diluted in DCM and filtered on silica. The filtrate was evaporated under vacuum and the residue was taken-up in DCM and water. The layers were separated and the aqueous layer was extracted with DCM. The combined organic layers were dried over MgSO$_4$, filtered and evaporated under vacuum. The residue (1.3 g, green oil) was purified by chromatography over silica gel (irregular SiOH 15-40 μm; 50 g; gradient: from 100% DCM to 96% DCM, 4% MeOH, 0.4% NH$_4$OH). The fractions containing the compound were collected and the solvent was evaporated. The residue (750 mg, green oil) was then purified by chromatography over silica gel (irregular SiOH 30 µm; 40 g; gradient: from 100% DCM to 96% DCM, 4% MeOH, 0.4% NH₄OH). The fractions containing the product were collected and the solvent was evaporated to give 436 mg (37%, green crystals) of intermediate 30 and 104 mg (beige powder) of fraction 1. This fraction was triturated in diethylether/heptane (2:1). The precipitate was filtered off and dried to give 60 mg (6%, white powder) of compound 28.

Example A17

Preparation of Intermediate 31:

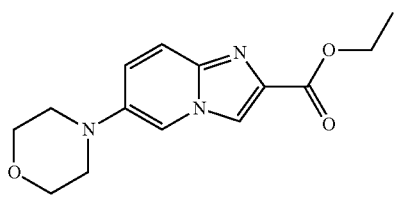 [SMILES: CCOC(=O)c1cn2cc(N3CCOCC3)ccc2n1]

The experiment was performed twice on 500 mg (2.79 mmol) of 2-amino-5-(morpholino)pyridine.

In a microwave vial, to a solution of 2-amino-5-(morpholino)pyridine (500 mg; 2.79 mmol) in EtOH (12.5 mL) was added ethyl bromopyruvate (0.89 mL; 7.12 mmol). The reaction mixture was heated at 120° C. using one single mode microwave (Biotage Initiator) with a power output ranging from 0 to 400 W for 30 min fixed hold time. The two reactions were combined and evaporated under vacuum. The residue was taken-up in DCM and a saturated solution of NaHCO₃. The layers were separated and the aqueous layer was extracted with DCM (×2). The organic layers were combined, dried over MgSO₄, filtered and evaporated under vacuum. The residue (2.45 g, brown oil) was purified by chromatography over silica gel (irregular SiOH 15-40 µm; 80 g; gradient: from 80% DCM, 20% EtOAc to 100% EtOAc). The pure fractions were collected and the solvent was evaporated to give 857 mg (56%, brown powder) of intermediate 31.

Preparation of Intermediate 32:

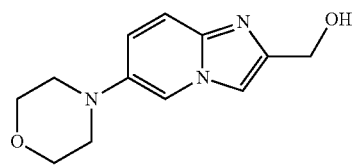 [SMILES: OCc1cn2cc(N3CCOCC3)ccc2n1]

In sealed tube, to a solution of intermediate 31 (800 mg; 2.91 mmol) in dry THF (29 mL) at 0° C. was added dropwise lithium borohydride (4M in THF) (1.45 mL; 5.81 mmol). The reaction mixture was stirred at 50° C. overnight. The mixture was quenched with a 1N aqueous solution of HCl and stirred at rt for 1 h. The mixture was basified with a saturated solution of NaHCO₃. The mixture was concentrated and the concentrate was extracted with DCM (×8), then with DCM/MeOH (9:1) (×3). The organic layers were combined, dried over MgSO₄, filtered and evaporated in vacuum to give 613 mg (90%, white powder) of intermediate 32.

Preparation of Intermediate 33:

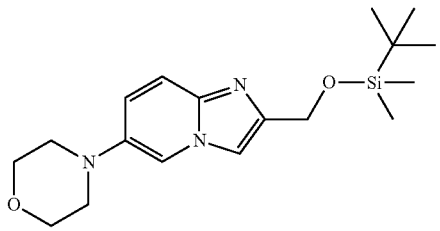 [SMILES: CC(C)(C)[Si](C)(C)OCc1cn2cc(N3CCOCC3)ccc2n1]

To a solution of intermediate 32 (600 mg; 2.57 mmol) and imidazole (263 mg; 3.86 mmol) in DMF (25.7 mL) was added tert-butyldimethylchlorosilane (582 mg; 3.86 mmol). The reaction mixture was stirred at rt for 3 h. The mixture was evaporated under vacuum and the residue was taken-up in DCM and water. The layers were separated and the product was extracted with DCM (×2). The combined organic layers were washed with brine (×2), dried over MgSO₄, filtered and evaporated under vacuum. The residue (677 mg, blue oil) was purified by chromatography over silica gel (Irregular SiOH 15-40 µm; 30 g; gradient: from 100% DCM to 20% DCM, 80% EtOAc). The pure fractions were collected and the solvent was evaporated to give 572 mg (64%, blue oil) of intermediate 33.

Preparation of Intermediate 34:

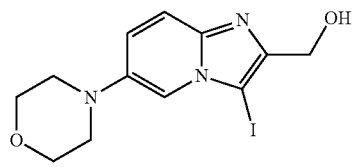 [SMILES: OCc1nc2ccc(N3CCOCC3)cn2c1I]

To a solution of intermediate 29 (543 mg; 1.35 mmol) in EtOH (7 mL) and THF (7 mL) was added NaOH (1M in H₂O) (6.77 mL; 6.77 mmol). The solution was stirred at rt for 3 h, concentrated under vacuum and then neutralized with a 1N aqueous solution of HCl. The product was extracted with DCM (×2), then DCM/MeOH (95:5) (×2). The combined organic layers were dried over MgSO₄, filtered and evaporated in vacuum to give 461 mg (95%, grey solid) of intermediate 34. The product was used without purification in the next step.

Preparation of Intermediate 35:

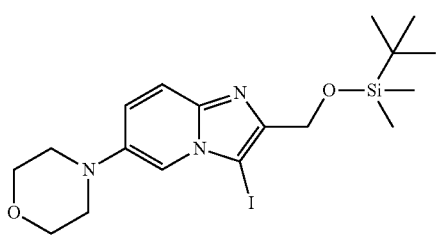 [SMILES: CC(C)(C)[Si](C)(C)OCc1nc2ccc(N3CCOCC3)cn2c1I]

Intermediate 35 was prepared according to an analogous procedure as described for the synthesis of intermediate 26, using intermediate 33 as starting material. The reaction mixture was stirred at rt for 1 h. The crude (775 mg, brown solid) was purified by chromatography over silica gel (irregular SiOH 15-40 µm; 50 g; gradient: from 100% DCM to 70% DCM, 30% EtOAc). The pure fractions were collected and the solvent was evaporated to give 589 mg (76%, reddish solid) of intermediate 35.

Alternative Pathway:

Intermediate 35 was prepared according to an analogous procedure as described for the synthesis of intermediate 33, using intermediate 34 as starting material. The reaction mixture was stirred at rt for 18 h. The product (566 mg, 93%, brown solid) was used without purification in the next step.

Preparation of Intermediate 36:

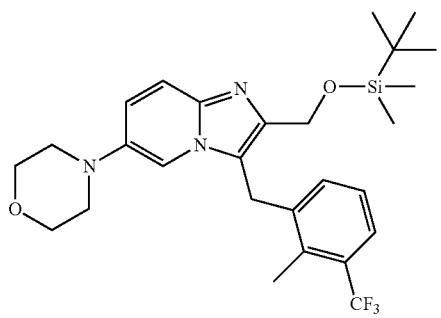 [SMILES: Cc1c(Cc2c(CO[Si](C)(C)C(C)(C)C)nc3ccc(N4CCOCC4)cn23)cccc1C(F)(F)F]

Intermediate 36 was prepared according to an analogous procedure as described for the synthesis of intermediate 30, using intermediate 35 and intermediate 27 as starting materials. The reaction mixture was stirred at 60° C. for 1 h. The crude (775 mg, brown solid) was purified by chromatography over silica gel (regular SiOH 30 μm; 120 g; gradient: from 100% DCM to 96% DCM, 4% MeOH, 0.4% NH$_4$OH). The pure fractions were collected and the solvent was evaporated to give 1.19 g (95%, brown solid) of intermediate 36.

Example A18

Preparation of Intermediate 37:

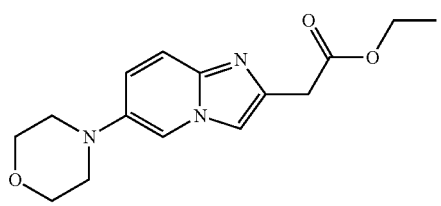 [SMILES: CCOC(=O)Cc1cn2cc(N3CCOCC3)ccc2n1]

In a sealed reactor, to a solution of 2-amino-5-(morpholino)-pyridine (500 mg; 2.79 mmol) in DME (15 mL) were added ethyl 4-chloroacetoacetate (0.75 mL; 5.58 mmol) and molecular sieves 4 Å (1 g). The reaction mixture was stirred at 80° C. for 4 h. The mixture was cooled down to rt, poured into ice-water and filtered through a pad of Celite®. The cake was rinsed with EtOAc. The filtrate was basified with a 10% aqueous solution of K$_2$CO$_3$ and the product was extracted with EtOAc. The combined organic layers were washed with brine, dried over MgSO$_4$ and evaporated under vacuum. The residue (820 mg, black oil) was purified by chromatography over silica gel (irregular SiOH 30 μm; 40 g; mobile phase: from 100% DCM to 96% DCM, 4% MeOH). The pure fractions were collected and the solvent was evaporated. The residue was taken-up with diethylether and the solvent was evaporated to give 306 mg (38%, brown solid) of intermediate 37.

Preparation of Intermediate 38:

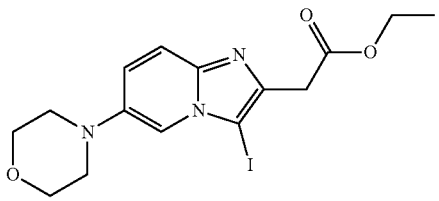 [SMILES: CCOC(=O)Cc1nc2ccc(N3CCOCC3)cn2c1I]

Intermediate 38 was prepared according to an analogous procedure as described for the synthesis of intermediate 26, using intermediate 37 as starting material. The crude (585 mg, brown oil) was combined with smaller batch coming from a reaction preformed on 100 mg of intermediate 37 and the resulting residue was purified by chromatography over silica gel (irregular SiOH 30 μm; 40 g; gradient: from 100% DCM to 96% DCM, 4% MeOH, 0.4% NH$_4$OH). The pure fractions were collected and the solvent was evaporated to give 528 mg (61%, brown powder) of intermediate 38.

Example A19

Preparation of Intermediate 39:

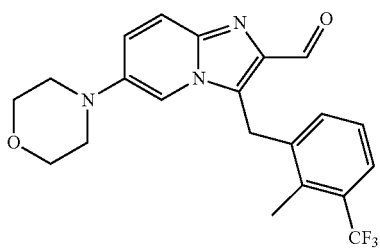 [SMILES: Cc1c(Cc2c(C=O)nc3ccc(N4CCOCC4)cn23)cccc1C(F)(F)F]

To a solution of compound 28 (630 mg; 1.55 mmol) in DCM (36 mL) was added manganese oxide (1.35 g; 15.5 mmol). The mixture was heated at reflux for 18 h. The mixture was cooled down to rt and filtered through a pad of Celite® which was rinsed with DCM. The filtrate was evaporated under vacuum. The residue was then coevaporated with diethylether (×2) to give 566 mg (89%, beige powder) of intermediate 39.

Preparation of Intermediate 40:

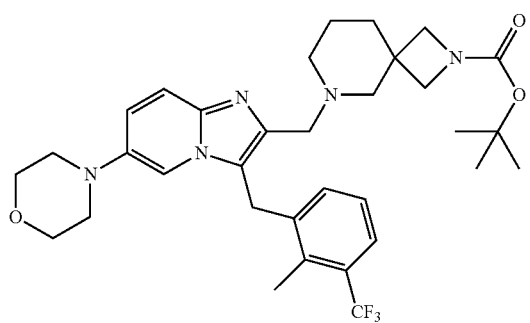 [SMILES: Cc1c(Cc2c(CN3CCCC4(C3)CN(C(=O)OC(C)(C)C)C4)nc3ccc(N4CCOCC4)cn23)cccc1C(F)(F)F]

In a microwave vial, to a solution of intermediate 39 (75 mg; 0.19 mmol) in MeOH (1.86 mL) was added 2,6-Diazaspiro[3.5] nonane-2-carboxylic acid, 1,1-dimethyl-ethyl ester, ethanedioate (2:1) (101 mg; 0.37 mmol). The reaction mixture was stirred at rt overnight. The mixture was evaporated under vacuum. The residue (180 mg) was taken-up in DCE (1.77 mL) and then, potassium acetate (18 mg; 0.19 mmol) was added. After 30 min at rt, sodium triacetoxyborohydride (59 mg; 0.28 mmol) was added and the mixture was stirred at rt for 1 h. The mixture was evaporated under vacuum and the residue was taken-up in DCM and water. The layers were separated and the organic layer was washed with brine, dried over MgSO$_4$, filtered and evaporated in vacuum. The residue (130 mg, brown oil) was purified by chromatography over silica gel (irregular SiOH 30 μm; 4 g; mobile phase: 99% DCM, 1% MeOH, 0.1% NH$_4$OH to 95% DCM, 5% MeOH, 0.5% NH$_4$OH). The pure fractions were collected and the solvent was evaporated to give 101 mg (77%, green oil) of intermediate 40.

Preparation of Intermediate 41:

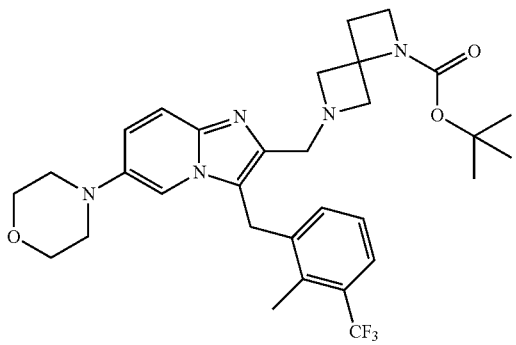 [SMILES: Cc1c(Cc2c(CN3CC4(CCN4C(=O)OC(C)(C)C)C3)nc3ccc(N4CCOCC4)cn23)cccc1C(F)(F)F]

In a microwave vial, to a solution of intermediate 39 (80 mg; 0.20 mmol) and 1-N-boc-1,6-diazaspiro[3.3]heptane oxalic acid salt (2:1) (53 mg; 0.11 mmol) in DCE (2 mL) was added potassium acetate (39 mg; 0.40 mmol). The reaction mixture was stirred at rt for 1 h. Sodium triacetoxyborohydride (63 mg; 0.30 mmol) was added and the mixture was stirred at rt for 1h30. DCM and water were added. The layers were separated and the aqueous layer was basified with a 10% aqueous solution of NaHCO$_3$. The product was extracted with DCM. The organic layers were combined, dried over MgSO$_4$, filtered and evaporated under vacuum. The residue (109 mg, blue oil) was purified by chromatography over silica gel (irregular SiOH 30 μm; 4 g; mobile phase: from 100% DCM to 95% DCM, 5% MeOH, 0.5% NH$_{40}$H). The pure fractions were collected and the solvent was evaporated to give 85 mg (73%, grey solid) of intermediate 41.

Example A20

Preparation of Intermediate 42:

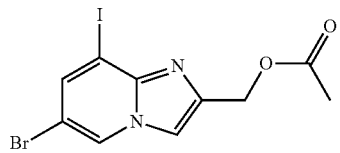 [SMILES: CC(=O)OCc1cn2cc(Br)cc(I)c2n1]

In a sealed tube, a solution of 2-amino-5-bromo-3-iodopyridine (10 g; 33.5 mmol) in 1-acetoxy-3-chloroacetone (35 mL; 298 mmol) was heated at 60° C. for 20 h then at 80° C. for 3 h. After cooling down to rt, the crude was poured into water, slowly neutralized with solid K$_2$CO$_3$ and extracted with EtOAc (×3). The combined organic layer were dried over MgSO$_4$, filtered and evaporated under vacuum. The residue (32.6 g, dark pink oil) was purified by chromatography over silica gel (Irregular SiOH 15-40 μm; 330 g; gradient: from 100% DCM to 90% DCM, 10% EtOAc). The pure fractions were collected and the solvent was evaporated to give 9.64 g (73%, pink oil which crystallized upon standing) of intermediate 42.

Preparation of Intermediate 43:

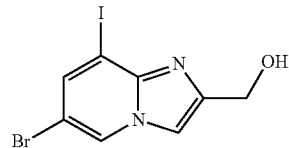 [SMILES: OCc1cn2cc(Br)cc(I)c2n1]

To a solution of intermediate 42 (9.64 g; 24.4 mmol) in EtOH (120 mL) and THF (120 mL) was added NaOH (1M in H$_2$O) (122 mL; 122 mmol). The solution was stirred at rt for 96 h then evaporated under vacuum. The residue (brown solid) was diluted in water and neutralized with a 1N aqueous solution of HCl. The solid was filtered on a glass frit, washed with water and dried under vacuum to give 5.47 g (64%, pale brown solid) of intermediate 43.

Preparation of Intermediate 44:

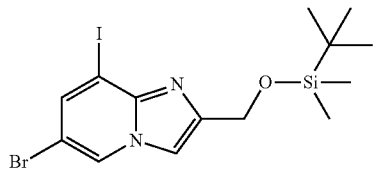 [SMILES: CC(C)(C)[Si](C)(C)OCc1cn2cc(Br)cc(I)c2n1]

Tert-butyldimethylchlorosilane (3.50 g; 23.2 mmol) was added to a suspension of intermediate 43 (5.47 g; 15.5 mmol) and imidazole (1.58 g; 23.2 mmol) in DCM (155 mL) at rt. The mixture was stirred at rt for 18 h then DMF (50 mL) was added and the mixture was stirred for 5 h (intermediate 43 wasn't soluble in DCM). Imidazole (1.58 g; 23.2 mmol), tert-butyldimethylchlorosilane (3.50 g; 23.2 mmol) and DMF (50 mL) were then added. The mixture was turned into solution after a few minutes and was stirred at rt for 18 h. The crude was poured in water then DCM and a saturated aqueous solution of NaHCO$_3$ were added. The organic layer was separated and the aqueous layer was extracted with DCM (×2). The combined organic layers were dried over MgSO$_4$, filtered and evaporated under vacuum. The residue (7.72 g, brown oil) was purified by chromatography over silica gel (Regular SiOH 30 μm; 200 g; gradient: from 100% DCM to 90% DCM, 10% EtOAc). The pure fractions were collected and the solvent was evaporated to give 6.22 g (86%, pink solid) of intermediate 44.

Preparation of Intermediate 45:

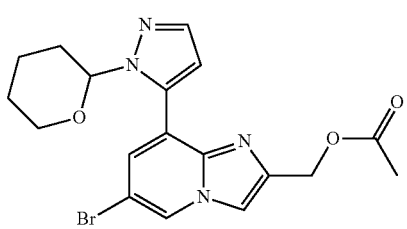 [SMILES: CC(=O)OCc1cn2cc(Br)cc(-c3ccnn3C3CCCCO3)c2n1]

In a Schlenk tube, a solution of intermediate 42 (1.40 g; 3.54 mmol), 1-(tetrahydro-2H-pyran-2-yl)-1H-pyrazole-5-boronic acid pinacol ester (1.18 g; 4.25 mmol) and potassium phosphate (2.26 g; 10.6 mmol) in 1,4-dioxane (25 mL) and H$_2$O (8 mL) was purged with N$_2$. PdCl$_2$(dppf).DCM (290 mg; 0.35 mmol) was added. The reaction mixture was purged again with N$_2$ and heated at 80° C. for 1 h. After cooling down to rt, the crude was partitioned between EtOAc and water. The organic layer was separated, dried over MgSO$_4$, filtered and evaporated under vacuum. The residue (brown) was purified by chromatography over silica gel (Regular SiOH 30 µm; 80 g; gradient: from 100% DCM to 70% DCM, 30% EtOAc). The pure fractions were collected and the solvent was evaporated to give 1.26 g (85%, pale orange oil) of intermediate 45.

Preparation of Intermediate 46:

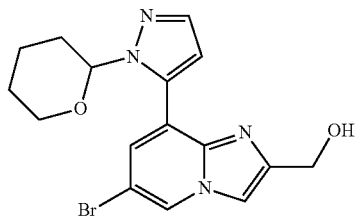 [SMILES: OCc1cn2cc(Br)cc(-c3ccnn3C3CCCCO3)c2n1]

Intermediate 46 was prepared according to an analogous procedure as described for the synthesis of intermediate 34, using intermediate 45 as starting material. The product (461 mg, 95%, grey solid) was used directly without purification in the next step.

Preparation of Intermediate 47:

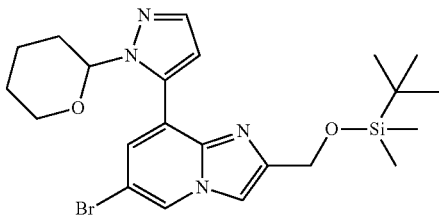 [SMILES: CC(C)(C)[Si](C)(C)OCc1cn2cc(Br)cc(-c3ccnn3C3CCCCO3)c2n1]

Intermediate 47 was prepared according to an analogous procedure as described for the synthesis of intermediate 45, using intermediate 44 and 1-(tetrahydro-2H-pyran-2-yl)-1H-pyrazole-5-boronic acid pinacol ester as starting materials. The residue (787 mg, brown oil) was purified by chromatography over silica gel (Irregular SiOH 15-40 µm; 30 g; gradient: from 100% DCM to 97% DCM, 3% MeOH). The pure fractions were collected and the solvent was evaporated to give 450 mg (86%, yellow oil) of intermediate 47.

Alternative Pathway:

Intermediate 47 was prepared according to an analogous procedure as described for the synthesis of intermediate 44, using intermediate 46 as starting material. Only DCM was use as solvent. The residue (brown oil) was purified by chromatography over silica gel (Irregular SiOH 15-40 µm; 40 g; gradient: from 100% DCM to 90% DCM, 10% EtOAc). The pure fractions were collected and the solvent was evaporated to give 1 g (73%, yellow oil) of intermediate 47.

Preparation of Intermediate 48:

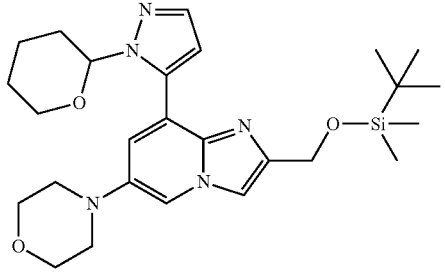 [SMILES: CC(C)(C)[Si](C)(C)OCc1cn2cc(N3CCOCC3)cc(-c3ccnn3C3CCCCO3)c2n1]

In a sealed tube, a mixture of intermediate 47 (1 g; 2.04 mmol), morpholine (215 µL; 2.44 mmol) and Cs$_2$CO$_3$ (1.33 g; 4.07 mmol) in 2-methyl-2-butanol (8.6 mL) was purged with N$_2$. RuPhos (48 mg; 102 µmol) and BrettPhos precatalyst first gen (81 mg; 102 µmol) were added. The reaction mixture was purged with N$_2$ and heated at 100° C. for 18 h. After cooling down to rt, the crude was partitioned between EtOAc and water. The organic layer was separated, dried over MgSO$_4$, filtered and evaporated under vacuum. The residue (1.21 g, brown oil) was purified by chromatography over silica gel (Irregular SiOH 15-40 µm; 50 g; gradient: from 100% DCM to 80% DCM, 20% acetone). The pure fractions were collected and the solvent was evaporated to give 398 mg (39%, pale yellow foam) of intermediate 48.

Preparation of Intermediate 49:

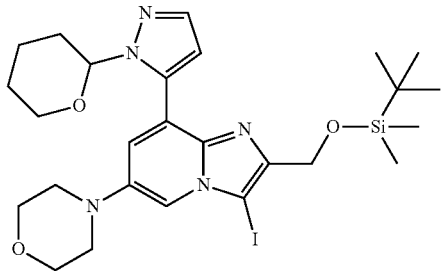 [SMILES: CC(C)(C)[Si](C)(C)OCc1nc2c(-c3ccnn3C3CCCCO3)cc(N3CCOCC3)cn2c1I]

To a solution of intermediate 48 (430 mg; 0.86 mmol) in DCM (8.6 mL) at 0° C. was added N-iodosuccinimide (204 mg; 0.91 mmol). The solution was allowed to warm to rt and stirred for 1 h. Water and a 10% aqueous solution of Na$_2$S$_2$O$_3$ were added to the crude. Then, the organic layer was separated, dried over MgSO$_4$, filtered and evaporated under vacuum. The residue (brown oil) was purified by chromatography over silica gel (Irregular SiOH 15-40 µm; 30 g; gradient: from 100% DCM to 98% DCM, 2% iPrOH). The pure fractions were collected and the solvent was evaporated to give 404 mg (75%, pale yellow foam) of intermediate 49.

Preparation of Intermediate 50:

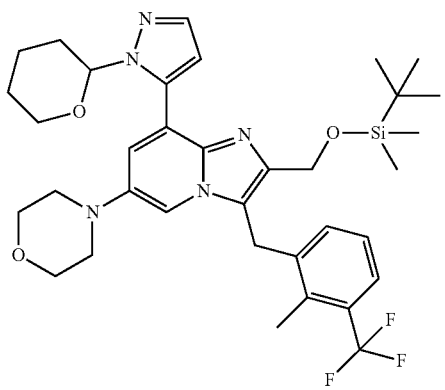 [SMILES: Cc1c(Cc2c(CO[Si](C)(C)C(C)(C)C)nc3c(-c4ccnn4C4CCCCO4)cc(N4CCOCC4)cn23)cccc1C(F)(F)F]

Intermediate 50 was prepared according to an analogous procedure as described for the synthesis of intermediate 30, using intermediate 49 and intermediate 27 as starting material. The reaction mixture was stirred at 60° C. for 1 h. The residue (brown oil) was purified by chromatography over silica gel (irregular SiOH 15-40 μm; 30 g; gradient: from 100% DCM to 50% DCM, 50% EtOAc). The pure fractions were collected and the solvent was evaporated to give 227 mg (53%) of intermediate 50.

Example A21

Preparation of Intermediate 51:

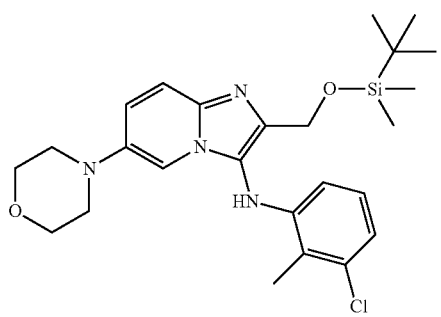 [SMILES: Cc1c(Cl)cccc1Nc1c(CO[Si](C)(C)C(C)(C)C)nc2ccc(N3CCOCC3)cn12]

In a microwave vial, to a solution of 2-amino-5-(morpholino)pyridine (300 mg; 1.67 mmol) in 1.4-dioxane (10 mL) were added ZnCl$_2$ (1M in diethylether) (0.084 mL; 0.08 mmol), (tert-butyldimethylsilyloxy)acetaldehyde (0.319 mL; 1.67 mmol) and 3-chloro-2-methyl phenylisocyanide (0.23 mL; 1.67 mmol). The vessel was closed and the mixture was heated at 120° C. using one single mode microwave (Biotage Initiator EXP 60) with a power output ranging from 0 to 400 W for 15 min [fixed hold time]. The reaction was quenched with a saturated solution of NaHCO$_3$ and extracted with DCM (×3). The combined organic layers were dried over MgSO$_4$, filtered and evaporated under vacuum. The residue was purified by chromatography over silica gel (irregular SiOH 15-40 μm; 12 g; mobile phase: from 100% DCM to 95% DCM, 5% MeOH). The pure fractions were collected and the solvent was evaporated. The residue (300 mg, oil) was triturated in diethylether and evaporated. The residue (300 mg, sticky solid) was purified by chromatography over silica gel (irregular SiOH 15-40 μm; 12 g; mobile phase: from 80% heptane, 20% EtOAc to 60% heptane, 40% EtOAc). The pure fractions were collected and the solvent was evaporated to give 144 mg (oil which crystallized upon standing) of intermediate 51.

Example A22

Preparation of Intermediate 52:

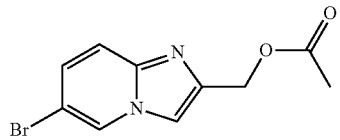

In a Schlenk reactor, 1-acetoxy-3-chloroacetone (5.78 mL; 49.1 mmol) was added to a solution of 5-bromo-2-pyridinamine (5 g; 28.9 mmol) in DMF (110 mL). The solution was heated at 120° C. for 3 h then at 80° C. for 18 h. After cooling down to rt, the solvent was removed under vacuum. The residue was taken-up in DCM and washed with a 10% aqueous solution of NaHCO$_3$. The layers were separated and the aqueous layer was extracted with DCM (×2). The combined organic layers were washed with a saturated aqueous solution of NaCl, dried over MgSO$_4$, filtered and evaporated under vacuum. The residue (9.10 g, brown oil) was purified by chromatography over silica gel (Irregular SiOH 15-40 μm; 330 g; mobile phase: 100% DCM to 95% DCM, 5% MeOH). The pure fractions were collected and the solvent was evaporated to give 4.80 g (62%, red solid) of intermediate 52.

Preparation of Intermediate 53:

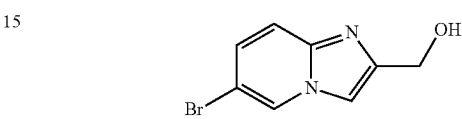

Intermediate 53 was prepared according to an analogous procedure as described for the synthesis of intermediate 43, using intermediate 52 as starting material. The reaction mixture was stirred at rt for 1 h, then evaporated under vacuum. The residue was neutralized with a 1N aqueous solution of HCl and extracted with DCM (×2). The mixture was filtered on a glass frit to give 348 mg (17%, off-white solid) of intermediate 29. The filtrate was transferred in a separatory funnel, the organic layer was separated and the aqueous layer was extracted with DCM (×2). The combined organic layers were dried over MgSO$_4$, filtered and evaporated under vacuum to give 1.34 g (67%, off-white solid) of intermediate 53. The product (84%, global yield) was used without purification in the next step.

Preparation of Intermediate 54:

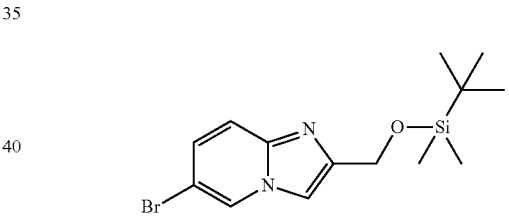

Intermediate 54 was prepared according to an analogous procedure as described for the synthesis of intermediate 44, using intermediate 53 as starting material. Only DMF was used as solvent. The reaction mixture was stirred at rt for 18 h. The residue (2.96 g) was purified by chromatography over silica gel (Regular SiOH 30 μm; 200 g; gradient: from 100% DCM to 90% DCM, 10% EtOAc). The pure fractions were collected and the solvent was evaporated to give 2.11 g (84%) of intermediate 54.

Preparation of Intermediate 55:

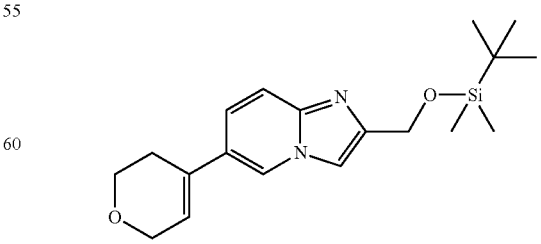

In a sealed tube, a solution of intermediate 54 (2.11 g; 6.18 mmol), 3,6-dihydro-2H-pyran-4-boronic acid pinacol ester (1.95 g; 9.27 mmol) and potassium phosphate (3.94 g; 18.5 mmol) in 1,4-dioxane (41 mL) and H₂O (12 mL) was purged with N₂. PdCl₂(dppf).DCM (506 mg; 0.62 mmol) was added. The mixture was purged again with N₂ and heated at 80° C. for 18 h. After cooling down to rt, water and EtOAc were added to the crude and the mixture was filtered through a pad of Celite®. The filtrate was transferred in a separatory funnel. The organic layer was separated and the aqueous layer was extracted with EtOAc (×2). The combined organic layers were dried over MgSO₄, filtered and evaporated under vacuum. The residue (4.12 g, brown oil) was purified by chromatography over silica gel (irregular SiOH 15-40 µm; 150 g; gradient: from 100% DCM to 70% DCM, 30% EtOAc). The pure fractions were collected and the solvent was evaporated to give 2.49 g (95%, as a pale brown solid) of intermediate 55.

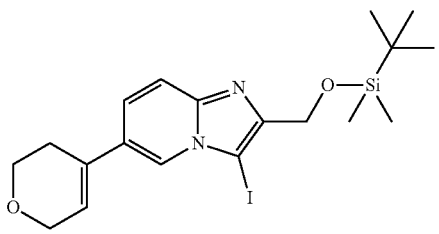 [SMILES: CC(C)(C)[Si](C)(C)OCc1nc2ccc(C3=CCOCC3)cn2c1I]

Preparation of Intermediate 56:

To a solution of intermediate 55 (2.49 g; 5.85 mmol) in ACN (60 mL) at 0° C. was slowly added N-iodosuccinimide (1.38 g; 6.15 mmol). The reaction mixture was allowed to warm to rt and stirred for 1 h. The mixture was evaporated under vacuum. Then, the residue was taken-up in DCM and a saturated aqueous solution of NaHCO₃. The layers were separated and the aqueous layer was extracted with DCM (×2). The combined organic layers were dried over MgSO₄, filtered and evaporated under vacuum to give 2.92 g (98%, pale brown solid) of intermediate 56 which was used without any further purification in the next step.

Preparation of Intermediate 57:

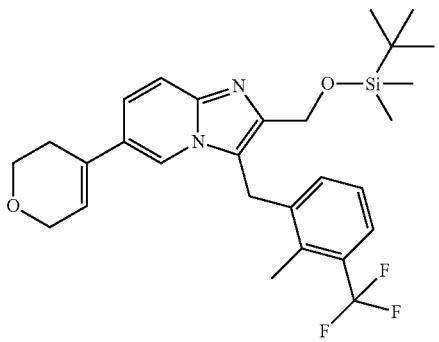 [SMILES: Cc1c(Cc2c(CO[Si](C)(C)C(C)(C)C)nc3ccc(C4=CCOCC4)cn23)cccc1C(F)(F)F]

Intermediate 57 was prepared according to an analogous procedure as described for the synthesis of intermediate 30, using intermediate 56 and intermediate 27 as starting material. The reaction mixture was stirred at 60° C. for 2 h. The residue (brown oil) was purified by chromatography over silica gel (irregular SiOH 15-40 µm; 220 g; gradient: from 100% DCM to 70% DCM, 30% EtOAc). The pure fractions were collected and the solvent was evaporated. The residue (2.99 g, pale brown foam) was purified by chromatography over silica gel (irregular SiOH 40 µm; 120 g; mobile phase: 99% DCM, 1% MeOH). The pure fractions were collected and the solvent was evaporated to give 1.5 g (51%, pale brown solid) of intermediate 57 and 500 mg (25%, brown oil) of intermediate 55.

Example A23

Preparation of Intermediate 59:

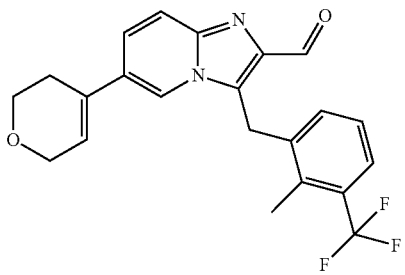 [SMILES: Cc1c(Cc2c(C=O)nc3ccc(C4=CCOCC4)cn23)cccc1C(F)(F)F]

Intermediate 59 was prepared according to an analogous procedure as described for the synthesis of intermediate 39, using compound 47 and manganese oxide as starting material. The filtrate was evaporated to give 956 mg (brown foam) of intermediate 59. The product was used directly without any further purification in the next step.

Example A24

Preparation of Intermediate 60:

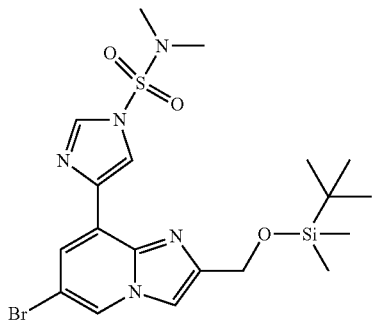 [SMILES: CN(C)S(=O)(=O)n1cnc(-c2cc(Br)cn3cc(CO[Si](C)(C)C(C)(C)C)nc23)c1]

Intermediate 60 was prepared according to an analogous procedure as described for the synthesis of intermediate 45, using intermediate 44 and 1-(N,N-dimethylsulfamoyl)-imidazole-4-boronic acid pinacol ester as starting materials. The residue (yellow oil) was purified by chromatography over silica gel (Irregular SiOH 15-40 µm; 30 g; solid deposit: gradient: from 100% DCM to 80% DCM, 20% EtOAc). The pure fractions were collected and the solvent was evaporated to give 414 mg (75%, yellow solid) of intermediate 60.

Preparation of Intermediate 61:

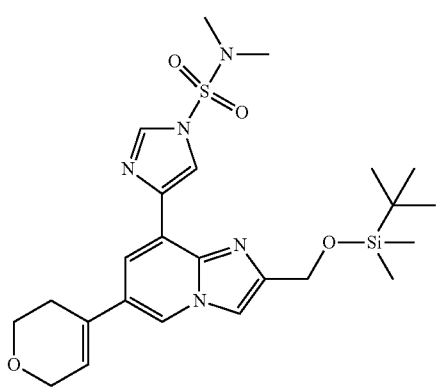 [SMILES: CN(C)S(=O)(=O)n1cnc(-c2cc(C3=CCOCC3)cn3cc(CO[Si](C)(C)C(C)(C)C)nc23)c1]

Intermediate 61 was prepared according to an analogous procedure as described for the synthesis of intermediate 55, using intermediate 60 and 3,6-dihydro-2H-pyran-4-boronic acid pinacol ester as starting material. The reaction mixture was stirred at 80° C. for 2 h. The residue (405 mg, brown oil) was purified by chromatography over silica gel (Irregular SiOH 15-40 µm; 24 g; gradient: from 100% DCM to 95% DCM, 5% iPrOH). The pure fractions were collected and the solvent was evaporated to give 213 mg (84%, yellow oil) of intermediate 61.

Preparation of Intermediate 62:

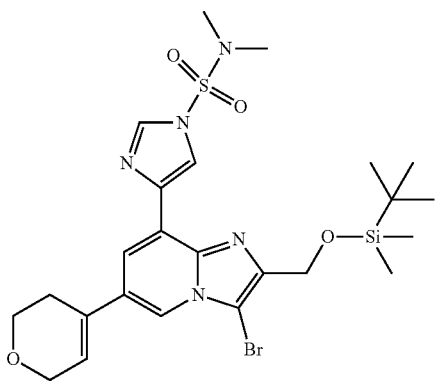 [SMILES: CN(C)S(=O)(=O)n1cnc(-c2cc(C3=CCOCC3)cn3c(Br)c(CO[Si](C)(C)C(C)(C)C)nc23)c1]

To a solution of intermediate 61 (152 mg; 0.29 mmol) in DCM (1 mL) at 0° C. was added N-bromosuccinimide (55 mg; 0.31 mmol). The solution was allowed to warm to rt and stirred for 3 h. A saturated solution of NaHCO$_3$ was added. Then, the layers were separated and the aqueous layer was extracted with DCM. The combined organic layers were dried over MgSO$_4$, filtered and evaporated under vacuum. The residue (163 mg, brown oil) was combined with another batch coming from a reaction performed on 50 mg of intermediate 37 and was purified by chromatography over silica gel (irregular SiOH 15-40 µm; 10 g; gradient: from 100% DCM to 50% DCM, 50% EtOAc). The pure fractions were collected and the solvent was evaporated to give 159 mg (68%, beige solid) of intermediate 62.

Preparation of Intermediate 63:

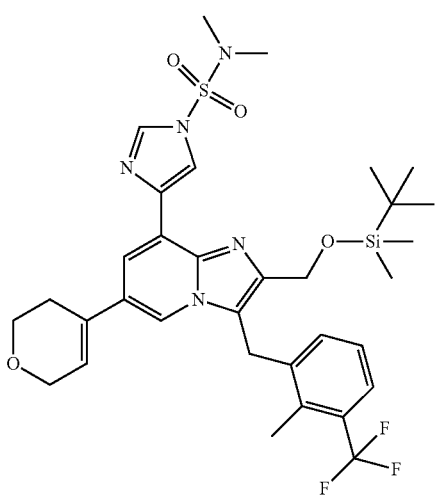 [SMILES: Cc1c(Cc2c(CO[Si](C)(C)C(C)(C)C)nc3c(-c4cn(S(=O)(=O)N(C)C)cn4)cc(C4=CCOCC4)cn23)cccc1C(F)(F)F]

Intermediate 63 was prepared according to an analogous procedure as described for the synthesis of intermediate 30, using intermediate 62 and intermediate 27 as starting materials. The reaction mixture was stirred at rt for 2 h. The residue (167 mg, off-white solid) was purified by chromatography over silica gel (irregular SiOH 15-40 µm; 10 g; mobile phase: 100% EtOAc). The pure fractions were collected and the solvent was evaporated to give 68 mg (41%, yellow solid) of intermediate 63.

Example A25

Preparation of Intermediate 64:

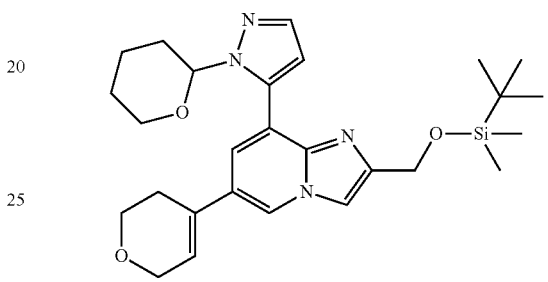

Intermediate 64 was prepared according to an analogous procedure as described for the synthesis of intermediate 55, using intermediate 47 and 3,6-dihydro-2H-pyran-4-boronic acid pinacol ester as starting materials. The reaction mixture was stirred at 80° C. for 2 h. The residue (620 mg, brown residue) was purified by chromatography over silica gel (Irregular SiOH 15-40 µm; 30 g; gradient: from 100% DCM to 90% DCM, 10% EtOAc). The pure fractions were collected and the solvent was evaporated to give 412 mg (68%, yellow oil) of intermediate 64.

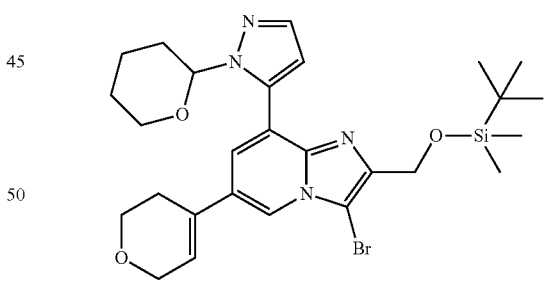

Preparation of Intermediate 65:

To a solution of intermediate 64 (300 mg; 0.61 mmol) in DCM (6 mL) at 0° C. was added N-bromosuccinimide (113 mg; 0.64 mmol). The solution was allowed to warm to rt and stirred for 1 h. The crude was combined with another batch coming from a reaction performed on 50 mg of intermediate 64 and washed with a 10% aqueous solution of K$_2$CO$_3$. The organic layer was separated, washed with water, dried over MgSO$_4$, filtered and evaporated under vacuum to give 338 mg (83%, pale brown solid) of intermediate 65. The product was used without any further purification in the next step.

Preparation of Intermediate 66 and Intermediate 67:

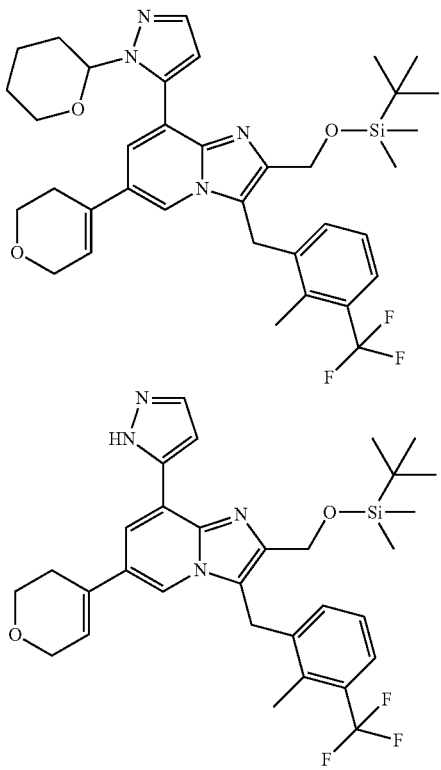

Intermediate 66 and intermediate 67 were prepared according to an analogous procedure as described for the synthesis of intermediate 30, using intermediate 65 and intermediate 27 as starting materials. The reaction mixture was stirred at 60° C. for 1 h. The residue was taken-up in DCM/MeOH (50/50) and filtered through a pad of Celite® which was washed with DCM/MeOH (50/50). The filtrate was evaporated under vacuum to give 739 mg (brown residue) of mixture two intermediates 66 and 67. The mixture was used without any further purification in the next step.

Example A26

Preparation of Intermediate 68:

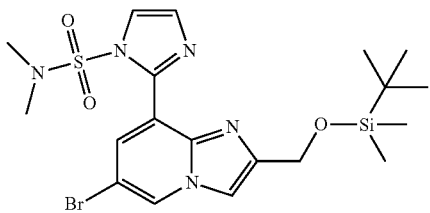 [SMILES: CN(C)S(=O)(=O)n1ccnc1-c1cc(Br)cn2cc(CO[Si](C)(C)C(C)(C)C)nc12]

n-BuLi (1.6M in hexane) (2 mL; 3.21 mmol) was added dropwise to a solution of 1-(dimethylsulfamoyl)imidazole (563 mg; 3.21 mmol) in THF (32 mL) at −78° C. The reaction mixture was stirred for 30 min. Then, a solution of $ZnCl_2$ (2M in THF) (3.21 mL; 6.42 mmol) was added. The reaction mixture was allowed to warm to rt over 30 min and was added to a previously degassed mixture of intermediate 44 (1 g; 2.14 mmol) and Pd(PPh$_3$)$_4$ (247 mg; 214 µmol) and the reaction mixture was heated at 90° C. for 1 h. After cooling down to rt, EtOAc and a mixture of H$_2$O and a saturated aqueous solution of NaHCO$_3$(50/50) were added to the crude. The aqueous layer was separated and extracted with EtOAc. The combined organic layers were dried over MgSO$_4$, filtered and evaporated under vacuum. The residue (1.67 g, brown oil) was purified by chromatography over silica gel (Irregular SiOH 15-40 µm; 50 g; gradient: from 100% DCM to 95% DCM, 5% MeOH). The pure fractions were collected and the solvent was evaporated to give 606 mg (55%, pale yellow oil) of intermediate 68.

Preparation of Intermediate 69:

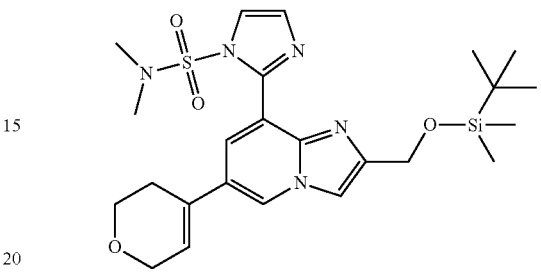

Intermediate 69 was prepared according to an analogous procedure as described for the synthesis of intermediate 55, using intermediate 68 and 3,6-dihydro-2H-pyran-4-boronic acid pinacol ester as starting materials. The residue (897 mg, brown oil) was purified by chromatography over silica gel (Irregular SiOH 15-40 µm; 50 g; gradient: from 100% DCM to 95% DCM, 5% MeOH). The pure fractions were collected and the solvent was evaporated to give 390 mg (64%) of intermediate 69.

Preparation of Intermediate 70:

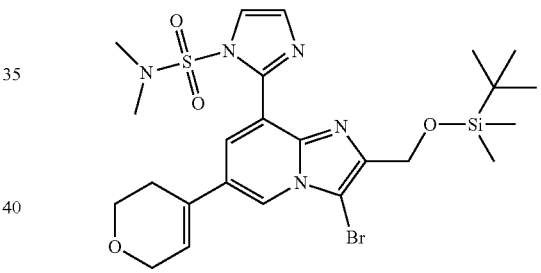

Intermediate 70 was prepared according to an analogous procedure as described for the synthesis of intermediate 65, using intermediate 69 as starting material. The organic layer was separated, washed with water, dried over MgSO$_4$, filtered and evaporated under vacuum to give 444 mg (99%, pale yellow foam) of intermediate 70. The product was used without any further purification in the next step.

Preparation of Intermediate 71:

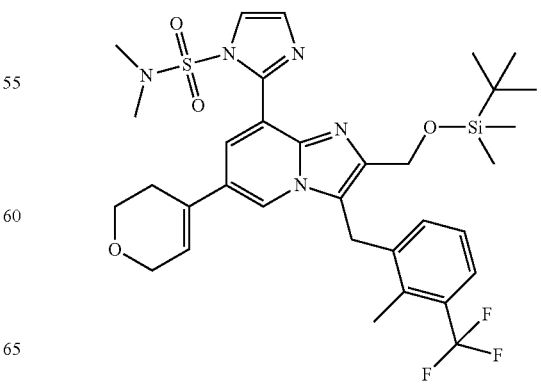

Intermediate 71 were prepared according to an analogous procedure as described for the synthesis of intermediate 30, using intermediate 70 and intermediate 27 as starting materials. The reaction mixture was stirred at 60° C. for 2 h. After cooling down to rt, bis(tri-tert-butylphosphine)palladium(0) (18 mg; 34.4 μmol) and intermediate 3 (608 μL; 0.344 mmol) were added again. The reaction mixture was purged with $N_2$ (×3) and heated at 60° C. for 2 h. The residue (1.05 g, brown oil) was purified by chromatography over silica gel (Irregular SiOH 15-40 μm; 40 g; gradient: from 100% DCM to 95% DCM, 5% MeOH). The pure fractions were collected and the solvent was evaporated to give 386 mg (68%, yellow solid) of intermediate 71.

Example A27

Preparation of Intermediate 72:

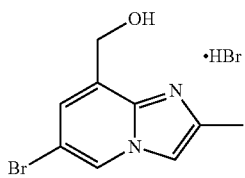

In a sealed tube, to a solution of 2-amino-5-bromo-3-pyridinemethanol hydrobromide (1:1) (4.5 g; 16 mmol) in DMF (50 mL) were added chloroacetone (3 mL; 17 mmol) and DIPEA (2.2 mL; 27 mmol). The reaction mixture was stirred at 130° C. for 18 h. After cooling down, the mixture was evaporated in vacuum. The residue was taken up with DCM which lead to precipitation. The solid was filtered off to give 2.19 g (43%, beige solid) of intermediate 72 (HBr salt).

Preparation of Intermediate 73:

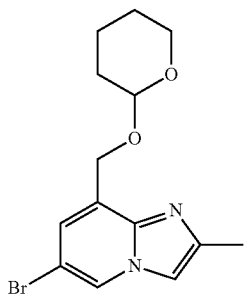 [SMILES: Cc1cn2cc(Br)cc(COC3CCCCO3)c2n1]

In a sealed tube, to a mixture of intermediate 72 (600 mg; 1.86 mmol) in DCM (12 mL) and DMF (1.5 mL) were added pyridinium p-toluenesulfonate (47 mg; 0.19 mmol) and 3,4-dihydro-2H-pyran (2 mL; 22 mmol), and the reaction mixture was stirred at 50° C. for 4 h. Then, the reaction mixture was cooled down and evaporated under reduced pressure. The residue (1.24 g, brown oil which crystallized upon standing) was taken up with DCM, washed twice with a saturated solution of $NaHCO_3$, brine, dried over $MgSO_4$, filtered and evaporated under vacuum. The residue was purified by chromatography over silica gel (regular SiOH 15-40 μm; 40 g; dry loading on Celite®; gradient: from 100% DCM to 95% DCM, 5% MeOH). The pure fractions were collected and the solvent was evaporated to give 557 mg (78%, red oil) of intermediate 73 and 241 mg (white solid) of intermediate 72.

Preparation of Intermediate 74:

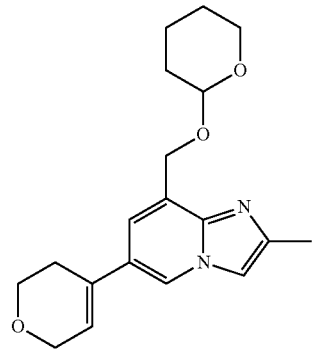 [SMILES: Cc1cn2cc(C3=CCOCC3)cc(COC3CCCCO3)c2n1]

Intermediate 74 was prepared according to an analogous procedure as described for the synthesis of intermediate 55, using intermediate 73 and 3,6-dihydro-2H-pyran-4-boronic acid pinacol ester as starting materials. The residue (1.24 g, brown oil) was purified by chromatography over silica gel (regular SiOH 30 μm; 80 g; gradient: from 100% DCM to 95% DCM, 5% MeOH). The pure fractions were collected and the solvent was evaporated to give 430 mg (65%, brown oil) of intermediate 74.

Preparation of Intermediate 75:

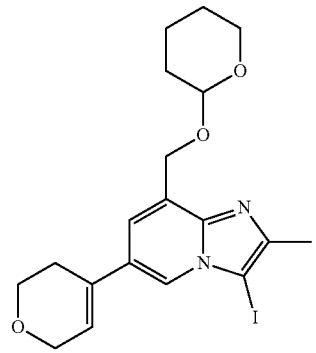 [SMILES: Cc1nc2c(COC3CCCCO3)cc(C3=CCOCC3)cn2c1I]

Intermediate 75 was prepared according to an analogous procedure as described for the synthesis of intermediate 56, using intermediate 74 as starting material. The organic layer was concentrated at 10 mL of DCM solution. ACN (15 mL) was added and the solution was evaporated slowly at 0-5° C., leading to precipitation. The precipitate was filtered off and dried to give 339 mg (67%, pale brown solid) of intermediate 75.

Preparation of Intermediate 76:

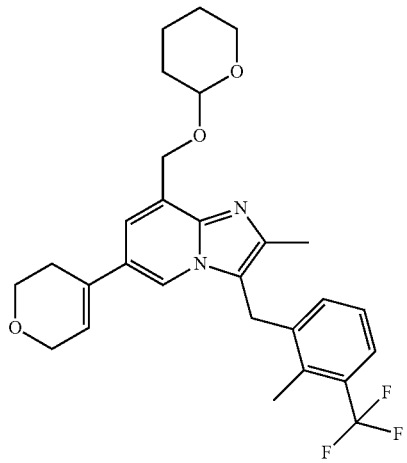 [SMILES: Cc1nc2c(COC3CCCCO3)cc(C3=CCOCC3)cn2c1Cc1cccc(C(F)(F)F)c1C]

Intermediate 76 were prepared according to an analogous procedure as described for the synthesis of intermediate 30, using intermediate 75 and 4 equivalents of intermediate 27 as starting materials. The reaction mixture was stirred at 60° C. for 2 h. The residue (810 mg, brown oil) was sonicated in DCM. The solid was filtered off and the filtrate was purified by chromatography over silica gel (regular SiOH 30 µm; 80 g; gradient: from 100% DCM to 95% DCM, 5% MeOH). The pure fractions were collected and the solvent was evaporated to give 196 mg (67%, off-white solid) of intermediate 76.

Example A28

Preparation of Intermediate 77:

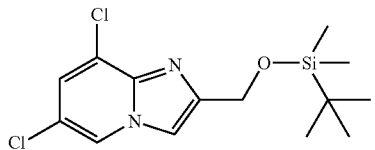 [SMILES: CC(C)(C)[Si](C)(C)OCc1cn2cc(Cl)cc(Cl)c2n1]

Tert-butyldimethylsilyl chloride (20.83 g; 138.22 mmol) was added to a solution of 6,8-dichloro-imidazo[1,2-a]pyridine-2-methanol (10 g; 46.07 mmol) and imidazole (9.41 g; 138.22 mmol) in DMF (100 mL) at rt. The reaction mixture was stirred at rt for 18 h. The solution was poured into water and a 10% aqueous solution of NaHCO₃ (50/50). DCM was added, the organic layer was separated and the aqueous layer was extracted with DCM (2×). The combined organic layers were dried over MgSO₄, filtered and evaporated under vacuum. The residue (brown oil) was purified by chromatography over silica gel (SiOH 20-45 µm; 330 g; gradient: from 90% heptane, 10% EtOAc to 70% heptane, 30% EtOAc). The pure fractions were collected and the solvent was evaporated to give 14.6 g (96%) of intermediate 77.

Preparation of Intermediate 78:

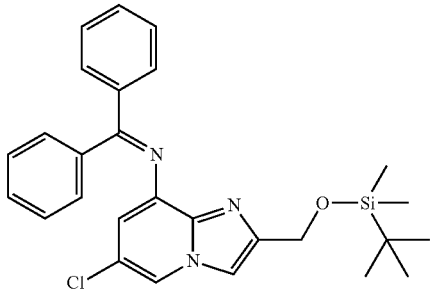 [SMILES: CC(C)(C)[Si](C)(C)OCc1cn2cc(Cl)cc(N=C(c3ccccc3)c3ccccc3)c2n1]

In a sealed glassware, a mixture of intermediate 77 (14 g; 42.26 mmol), benzophenone imine (6.38 mL; 38.03 mmol), Cs₂CO₃ (41.3 g; 126.77 mmol), Binap (1.32 g; 2.11 mmol) and Pd(OAc)₂ (474 mg; 2.11 mmol) in 1,4-dioxane (150 mL) was heated at 100° C. for 16 h. After cooling down to rt, water and EtOAc were added. The mixture was extracted with EtOAc (3×), dried over MgSO₄ and evaporated to dryness. The residue (25 g) was purified by chromatography over silica gel (SiOH 20-45 µm; 330 g; gradient: from 100% heptane to 60% heptane, 40% EtOAc). The fractions were collected and the solvent was evaporated. The residue (17.6 g) was purified by chromatography over silica gel (SiOH 20-45 µm; 220 g; gradient: from 100% heptane to 70% heptane, 30% EtOAc). The pure fractions were collected and the solvent was evaporated to give 1.65 g (8%) of intermediate 54 and 12.2 g which was purified by chromatography over silica gel (SiOH 20-45 µm; 220 g; gradient: from 100% to heptane to 80% heptane, 20% EtOAc). The pure fractions were collected and the solvent was evaporated to give 8.4 g and 2.4 g (12%) of intermediate 78.

Preparation of Intermediate 79:

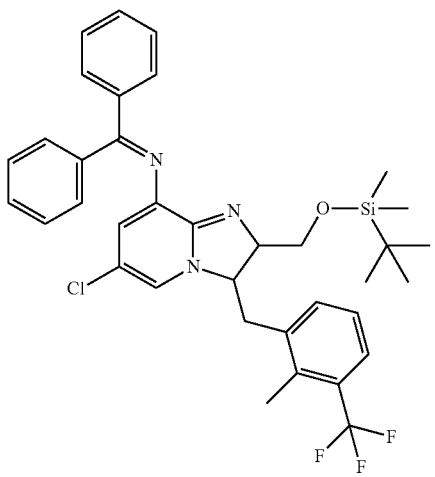 [SMILES: Cc1c(CC2C(CO[Si](C)(C)C(C)(C)C)N=C3C(N=C(c4ccccc4)c4ccccc4)=CC(Cl)=CN32)cccc1C(F)(F)F]

Under nitrogen in a sealed tube, a mixture of intermediate 78 (1.5 g; 3.15 mmol), 1-(chloromethyl)-2-methyl-3-(trifluoromethyl)-benzene (0.99 g; 4.73 mmol) and K₂CO₃ (0.65 g; 4.73 mmol) in 1,4-dioxane (11 mL) was degassed under N₂. Then, PPh₃ (0.165 g; 0.63 mmol) and Pd(OAc)₂ (71 mg; 0.32 mmol) were added. The reaction mixture was heated at 100° C. overnight. The residue (3.3 g) was purified by chromatography over silica gel (SiOH 20-45 µm; 80 g; gradient: from 100% heptane to 70% heptane, 30% EtOAc). The pure fractions were collected and the solvent was evaporated to give 1.2 g (35%; 60% of purity evaluated by LCMS) of intermediate 79 and 0.4 g (17%; 87% of purity evaluated by LCMS) of intermediate 79.

Preparation of Intermediate 80:

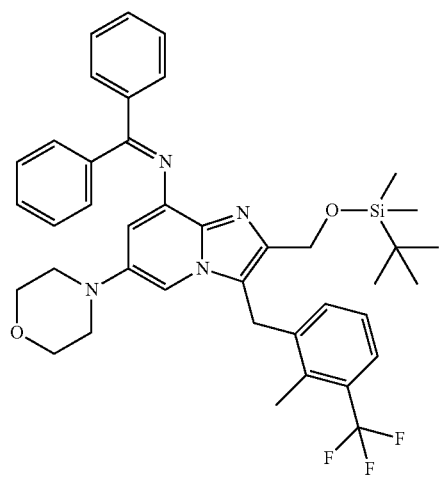 [SMILES: Cc1c(Cc2c(CO[Si](C)(C)C(C)(C)C)nc3c(N=C(c4ccccc4)c4ccccc4)cc(N4CCOCC4)cn23)cccc1C(F)(F)F]

In a sealed tube, a mixture of intermediate 79 (600 mg; 0.93 mmol), morpholine (97.7 µL; 1.11 mmol) and Cs₂CO₃

(603 mg; 1.85 mmol) in 2-methyl-2-butanol (4 mL) was degassed with N$_2$. Ruphos (21.6 mg; 0.05 mmol) and Brettphos precatalyst first gen (37 mg; 0.05 mmol) were added. The reaction mixture was degassed with N$_2$ and heated at 100° C. for 18 h. After cooling down to rt, the mixture was partitioned between EtOAc and water. The organic layer was separated, dried over MgSO$_4$, filtered and the solvent was evaporated under vacuum. The residue (520 mg) was purified by chromatography over silica gel (SiOH 20-45 μm; 24 g; gradient: from 100% heptane to 70% heptane, 30% EtOAc). The pure fractions were collected and the solvent was evaporated to give 68 mg (11%) of intermediate 80.

Preparation of Intermediate 81:

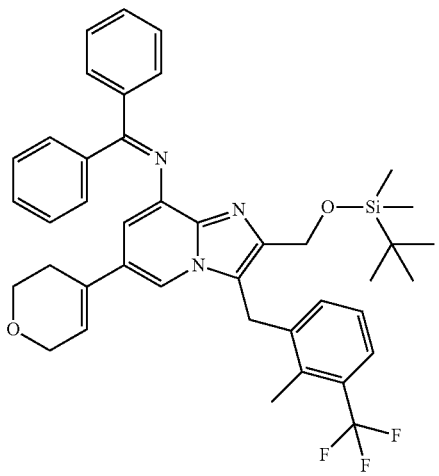 [SMILES: Cc1c(Cc2c(CO[Si](C)(C)C(C)(C)C)nc3c(N=C(c4ccccc4)c4ccccc4)cc(C4=CCOCC4)cn23)cccc1C(F)(F)F]

A mixture of intermediate 79 (0.6 g; 0.93 mmol), 3,6-dihydro-2H-pyran-4-boronic acid pinacol ester (218 mg; 1.04 mmol), potassium phosphate (589 mg; 2.78 mmol) in water (1.62 mL) and 1,4-dioxane (7.72 mL) was carefully purged with N$_2$. Pd.Cl$_2$(dppf).DCM (83 mg; 0.10 mmol) was added and the reaction mixture was purged once again with N$_2$. The reaction mixture was heated at 80° C. for 18 h. The solution was cooled, poured into cooled water and EtOAc was added. The mixture was filtered through a pad of Celite®. The product was extracted with EtOAc. The organic layer was dried over MgSO$_4$, filtered and evaporated to dryness. The residue (1.7 g) was purified by chromatography over silica gel (SiOH 20-45 μm; 24 g; gradient: from 100% heptane to 70% heptane, 30% EtOAc). The pure fractions were collected and the solvent was evaporated to give 50 mg (8%) of intermediate 81.

Example A29

Preparation of Intermediate 82:

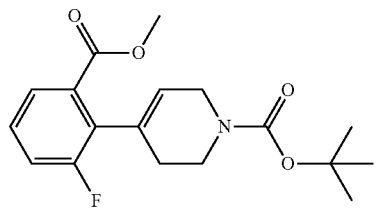 [SMILES: COC(=O)c1cccc(F)c1C1=CCN(C(=O)OC(C)(C)C)CC1]

The reaction was performed twice on the same quantity of 2-bromo-3-fluoro-benzoic acid methyl ester:

A mixture of 2-bromo-3-fluoro-benzoic acid methyl ester (24.34 g; 104.45 mmol), tert-butyl 4-(4,4,5,5-tetramethyl-1,3,2-dioxaborolan-2-yl)-5-6-dihydropyridine-1(2H)-carboxylate (48.44 g; 156.67 mmol) and K$_3$PO$_4$ (66.5 g; 313.34 mmol) in 1,4-dioxane (250 mL) and water (75 mL) was degassed under N$_2$. PdCl$_2$(dppf).DCM (4.27 g; 5.22 mmol) was added and the reaction mixture was heated at 100° C. overnight. The mixture was poured into water and filtered through a pad of Celite®. The organic layer was extracted with DCM, separated, dried over MgSO$_4$, filtered and concentrated to dryness. The residue (55.6 g) was purified by chromatography over silica gel (Irregular SiOH 15-40 μm; 220 g; mobile phase: 100% DCM). The pure fractions were collected and the solvent was evaporated until dryness. The residue (37.9 g) was crystallized from pentane. The precipitate was filtered off and dried under vacuum to give 17.6 g (50%) of intermediate 82.

Preparation of Intermediate 83:

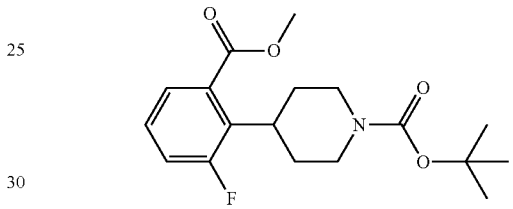

A mixture of intermediate 82 (16.5 g; 49.2 mmol) and palladium hydroxide (1.4 g; 9.84 mmol) in MeOH (170 mL) was hydrogenated in a Parr reactor (2 atmospheres) for 12 h at rt. After uptake of H$_2$, the catalyst was filtered through a pad of Celite®, washed with DCM and the filtrate was concentrated to give 16.4 g (99%) of intermediate 83.

Preparation of Intermediate 84:

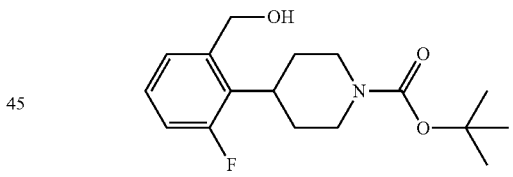

LiAlH$_4$ (1.85 g; 48.61 mmol) was added portionwise to a mixture of intermediate 83 (16.4 g; 48.61 mmol) in THF (200 mL) at 5° C. under N$_2$. The mixture was stirred at 5° C. for 3 h. EtOAc followed by H$_2$O was added dropwise to the mixture at −5° C. The suspension was filtered through a pad of Celite®. The organic layer was separated, dried over MgSO$_4$, filtered and the solvent was evaporated to give 15.18 g of intermediate 84.

Preparation of Intermediate 85:

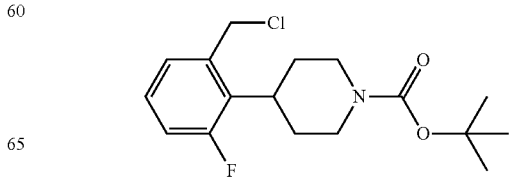

Triethylamine (3.37 mL; 24.24 mmol) followed by methanesulfonyl chloride (1.88 mL; 24.24 mmol) were slowly added to a solution of intermediate 84 (5 g; 16.16 mmol) in DCM (60 mL) at 0° C. The mixture was stirred at rt overnight. Water was added and the product was extracted with DCM. The organic layer was dried over MgSO$_4$, filtered and the solvent was evaporated. The residue (5.8 g) was purified by chromatography over silica gel (Irregular SiOH 15-40 µm; 40 g; gradient: from 80% heptane, 20% EtOAc to 60% heptane, 40% EtOAc). The pure fractions were collected and the solvent was evaporated until dryness to give 3.26 g (61%) of intermediate 85.

Preparation of Intermediate 86:

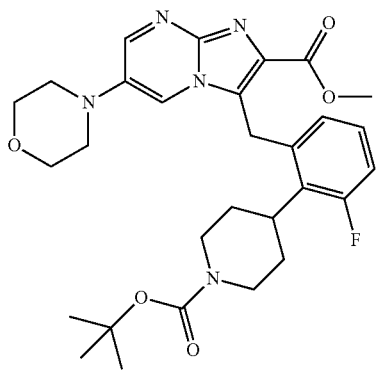 [SMILES: COC(=O)c1nc2ncc(N3CCOCC3)cn2c1Cc1cccc(F)c1C1CCN(C(=O)OC(C)(C)C)CC1]

In a microwave vial, a mixture of intermediate 19 (1 g; 3.61 mmol), intermediate 85 (574 mg; 1.75 mmol) and K$_2$CO$_3$ (0.75 g, 5.43 mmol) in dry 1,4-dioxane (10 mL) was degassed and back-filled with N$_2$ (3×). Pd(OAc)$_2$ (83 mg, 0.36 mmol) and PPh$_3$ (190 mg, 0.72 mmol) were added. The mixture was degassed and back-filled with N$_2$ (3×) and heated at 100° C. for 18 h. After cooling down to rt, the mixture was poured into water and the resulting aqueous layer was extracted with DCM. The organic layers were combined, washed with brine (2×), dried over MgSO$_4$, filtered and evaporated. The residue (1 g) was purified by chromatography over silica gel (Irregular SiOH 15-40 µm; 40 g; gradient: from 100% DCM to 95% DCM, 5% MeOH). The pure fractions were collected and the solvent was evaporated until dryness to give 0.672 g (68%) of intermediate 86.

B. Preparation of the Final Compounds

Example B1

Preparation of Compound 1:

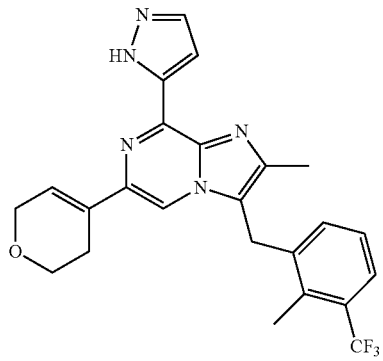 [SMILES: Cc1nc2c(-c3ccn[nH]3)nc(C3=CCOCC3)cn2c1Cc1cccc(C(F)(F)F)c1C]

The mixture of intermediate 3 (0.44 g; 0.82 mmol) and HCl (4M in dioxane) (4 mL) in 1,4-dioxane (44 mL) was heated at 80° C. for 1h30. The mixture was cooled and diethylether was added. Then, a precipitate was filtered and dried. The residue (255 mg) was taken up with DCM and H$_2$O and basified with K$_2$CO$_3$ solid. The mixture was stirred at rt for 30 min. The organic layer was extracted, dried over MgSO$_4$ and evaporated to give 40 mg (8%) of compound 1. M.P.: 240° C. (DSC).

Preparation of Compound 6:

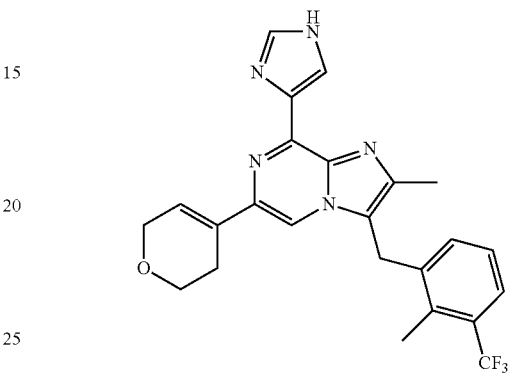

Intermediate 7 (720 mg; 1.28 mmol) was dissolved in 1,4-dioxane (25 mL) and HCl (6M in water) (8.3 mL) was added. The reaction mixture was heated at 100° C. for 2 h, cooled to rt, diluted with EtOAc and basified with NH$_4$OH. The organic layer was decanted, washed with brine, dried over MgSO$_4$, filtered and evaporated to dryness. The residue (0.5 g) was purified by chromatography over silica gel (irregular SiOH; 15-40 µm; 20 g; mobile phase: 0.5% NH$_4$OH, 90% DCM, 10% MeOH). The pure fractions were collected and the solvent was evaporated. The residue (115 mg) was crystallized from diethylether. The precipitate was filtered and dried to give 90 mg (15%) of compound 6. M.P.: 197° C. (DSC).

Example B2

Preparation of Compound 2:

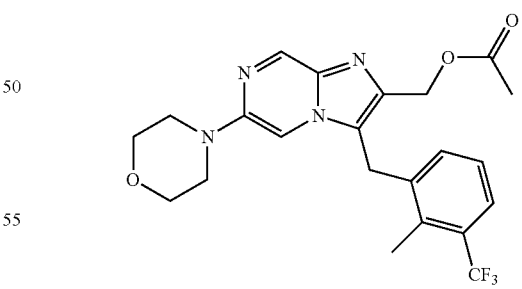

Compound 2 was prepared according to an analogous procedure as described for the synthesis of intermediate 3, using intermediate 10 and 1-(chloromethyl)-2-methyl-3-(trifluoromethyl-benzene as starting materials. The crude was purified by chromatography over silica gel (15-40 µm; 120 g; mobile phase: 60% heptane, 40% EtOAc). The pure fractions were collected and the solvent was evaporated to give 400 mg (37%) of compound 2.

Example B3

Preparation of Compound 3:

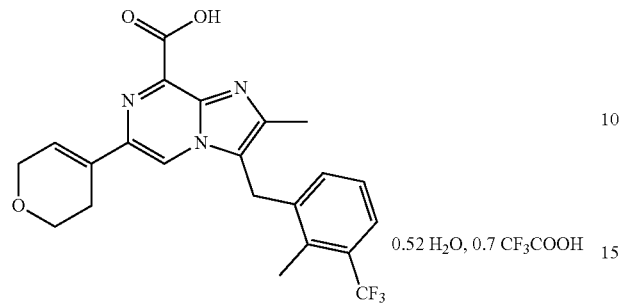

0.52 H$_2$O, 0.7 CF$_3$COOH

Lithium hydroxide monohydrate (53 mg; 1.3 mmol) was added to a mixture of intermediate 5 (113 mg; 0.25 mmol) in H$_2$O (0.3 mL) and THF (5 mL) at rt. The reaction mixture was stirred at rt for 4 h. THF was evaporated and H$_2$O was added. The aqueous layer was acidified with 3N aqueous solution of HCl and the product was extracted with EtOAc. The organic layer was dried over MgSO$_4$ and evaporated to dryness. The residue (152 mg) was purified by Reverse phase (C18 10 μm; 30*150 mm; gradient: from 80% TFA 0.05%, 20% ACN to 0% TFA 0.05%, 100% ACN). The pure fractions were collected and the solvent was evaporated. The residue (41 mg) was freeze-dried with ACN/water 20/80 to give 33 mg (30%, white powder) of compound 3. M.P.: 80° C. (gum, K).

Example B4

Preparation of compound 4:

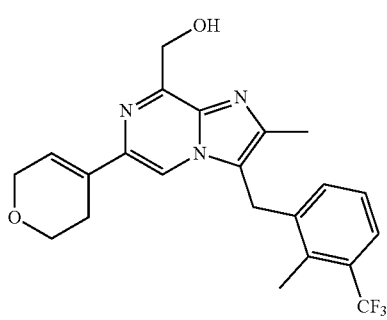 [SMILES: Cc1nc2c(CO)nc(C3=CCOCC3)cn2c1Cc1cccc(C(F)(F)F)c1C]

Under N$_2$ at 10° C., LiAlH$_4$ (65 mg; 1.7 mmol) was added to a solution of intermediate 5 (0.1 g; 0.4 mmol) in THF (8 mL). The solution was allowed to slowly rise to rt and stirred for 20 h. Ice-water and EtOAc were added, then mixture was filtered through a pad of Celite®. The product was extracted with EtOAc, the organic layer was dried over MgSO$_4$, filtered and evaporated to dryness. The residue (110 mg) was purified by chromatography over silica gel (Spherical bare silica 5 μm 150×30.0 mm; gradient: from 0.2% NH$_4$OH, 98% DCM, 2% MeOH to 1.2% NH$_4$OH, 88% DCM, 12% MeOH). The pure fractions were collected and the solvent was evaporated. The residue (8 mg) was freeze-dried with ACN/water 20/80 to give 7.6 mg (4%, yellow powder) of compound 4. M.P.: 80° C. (gum, K).

Example B5

Preparation of Compound 5:

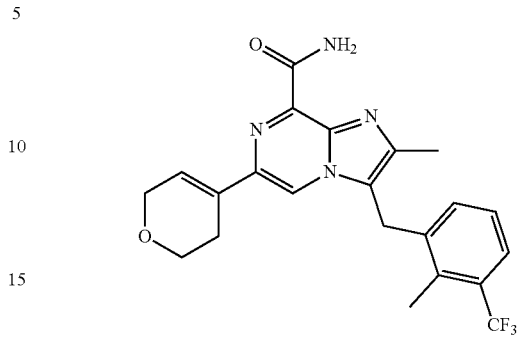

In a sealed tube, intermediate 5 (110 mg; 0.2 5 mmol) and ammonia (7N in MeOH) (5 mL) were heated at 90° C. overnight. The mixture was cooled down to rt and evaporated to dryness. The residue (109 mg) was purified by chromatography over silica gel (irregular SiOH; 15-40 μm; 24 g; mobile phase: 99% DCM, 1% MeOH). The pure fractions were collected and the solvent was evaporated. The residue (96 mg) was crystallized from diethylether. The precipitate was filtered and dried to give 37 mg (35%) of compound 5. M.P: 257° C. (DSC).

Example B7

Preparation of compound 8:

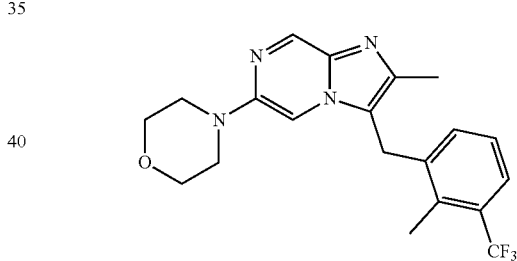

A mixture of intermediate 9 (0.3 g; 1.38 mmol), 1-(bromomethyl)-2-methyl-3-(trifluoromethyl)-benzene (0.49 g; 1.92 mmol), K$_2$CO$_3$ (0.29 g; 2.06 mmol) in 1,4-dioxane (50 mL) was purged with N$_2$. Then, PPh$_3$ (0.14 g; 0.55 mmol) and Pd(OAc)$_2$ (62 mg; 0.28 mmol) was added. The reaction mixture was stirred at 100° C. overnight in a sealed tube. The solution was cooled down to rt, poured into cooled water and EtOAc was added. The mixture was filtered through a pad of Celite® and the product was extracted with EtOAc. The organic layer was dried over MgSO$_4$, filtered and evaporated to dryness. The residue (900 mg) was purified by chromatography over silica gel (irregular 15-40 μm; 50 g; mobile phase: 43% heptane, 7% MeOH (+10% NH$_4$OH), 50% EtOAc). The pure fractions were collected and the solvent was evaporated. The residue (175 mg) was purified by achiral SFC (NH$_2$ 5 μm; 150*30 mm; mobile phase: 91% CO$_2$, 9% MeOH (0.3% iPrNH$_2$)). The pure fractions were collected and the solvent was evaporated. The residue (28 mg) was freeze-dried with ACN/water 20/80 to give 26 mg (5%, beige powder) of compound 8. M.P.: 80° C. (gum, K).

Preparation of Compound 50:

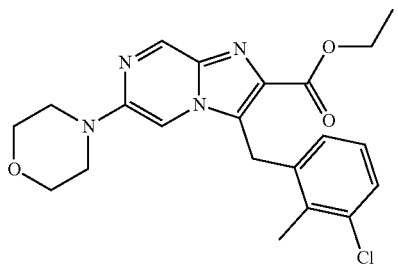 [SMILES: CCOC(=O)c1nc2cnc(N3CCOCC3)cn2c1Cc1cccc(Cl)c1C]

In sealed tube, to a solution of intermediate 14 (730 mg; 2.64 mmol) in 1,4-dioxane (26 mL) were added 1-chloro-3-(chloromethyl)-2-methylbenzene (694 mg; 3.96 mmol) and $K_2CO_3$ (1.10 g; 7.93 mmol). The mixture was carefully degassed under vacuum and back-filled with $N_2$ (×3). Then, Pd(OAc)$_2$ (89 mg; 0.13 mmol) and PPh$_3$ (69 mg; 0.26 mmol) were added and the mixture was carefully again degassed under vacuum and back-filled with $N_2$ (×3). The reaction mixture was stirred at 100° C. overnight. The mixture was combined with another batch (from 50 mg of intermediate 14). The mixture was filtered through a pad of Celite® and the cake was washed with DCM. The filtrate was evaporated under vacuum and the residue was taken-up in DCM and water. The layers were separated and the aqueous layer was extracted with DCM. The organic layers were combined, washed with brine, dried over MgSO$_4$, filtered and evaporated under vacuum. The residue (2.2 g, brown oil) was purified by chromatography over silica gel (irregular SiOH; 15-40 μm; 80 g; gradient: from 70% DCM, 30% EtOAc to 100% EtOAc). The pure fractions were collected and the solvent was evaporated to give 483 mg (41%, green solid) of compound 50.

Preparation of Compound 51:

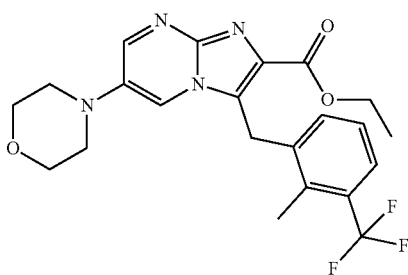 [SMILES: CCOC(=O)c1nc2ncc(N3CCOCC3)cn2c1Cc1cccc(C(F)(F)F)c1C]

The reaction was performed 5 times on 1.17 g (4.24 mmol) of intermediate 18 In sealed tube, a mixture of intermediate 18 (1.17 g; 4.24 mmol), 1-(chloromethyl)-2-methyl-3-(trifluoromethyl)-benzene (0.88 g; 4.2 mmol) and $K_2CO_3$ (0.88 g; 6.4 mmol) in dry 1,4-dioxane (10.6 mL) was degassed and back-filled with $N_2$ (×3). Pd(OAc)$_2$ (97 mg; 0.42 mmol) and PPh$_3$ (220 mg; 0.85 mmol) were added and the mixture was again degassed and back-filled with $N_2$ (×3). The reaction mixture was heated at 100° C. for 18 h. Then, the reaction mixture was cooled down to rt, then all batches were combined and poured into water (~500 mL). The resulting aqueous mixture was extracted with EtOAc (4×250 mL). The combined organic layers were washed with brine (×2), dried over MgSO$_4$, filtered through a pad of Celite® which was washed with DCM and EtOAc. Then, the filtrate was evaporated in vacuum. The residue was triturated with diethylether. The resulting solid was filtered, rinsed with cold diethylether and dried under vacuum to give 5.05 g (50%, pale brown solid) of compound 51.

Preparation of Compound 52:

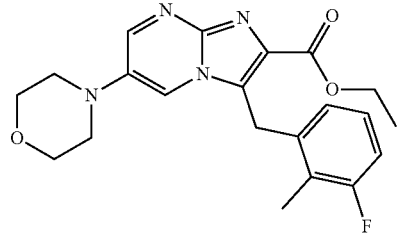 [SMILES: CCOC(=O)c1nc2ncc(N3CCOCC3)cn2c1Cc1cccc(F)c1C]

The reaction was performed twice on 1.17 g (4.22 mmol) of intermediate 18. In a microwave vial, a mixture of intermediate 18 (1.17 g; 4.22 mmol), 1-(chloromethyl)-3-fluoro-2-methylbenzene (0.67 g; 4.2 mmol) and $K_2CO_3$ (0.87 g; 6.3 mmol) in dry 1,4-dioxane (10.6 mL) was degassed and back-filled with $N_2$ (×3). Palladium (II) acetate (97 mg; 0.42 mmol) and PPh$_3$ (221 mg; 0.84 mmol), then more 1,4-dioxane (2.5 mL) were added. The reaction mixture was again degassed and back-filled with $N_2$ (×3), heated at 100° C. for 18 h and cooled down to rt. All batches were combined and poured into water (200 mL). The resulting aqueous mixture was extracted with EtOAc (4×100 mL). The combined organic layers were washed with brine (2×), dried over MgSO$_4$, filtered through a pad of Celite® which was rinsed with EtOAc and the filtrate was evaporated under vacuum. The residue (wet beige solid) was sonicated and triturated in diethylether. The resulting solid was filtered, rinsed with cold diethylether and dried under vacuum (30° C. for 40 h) to give 2.35 g (70%, off-white solid) of compound 52.

Example B9

Preparation of Compound 10:

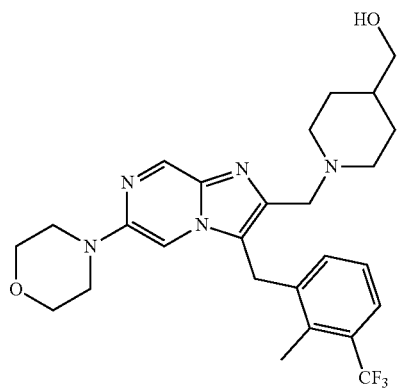 [SMILES: Cc1c(Cc2c(CN3CCC(CO)CC3)nc3cnc(N4CCOCC4)cn23)cccc1C(F)(F)F]

A mixture of intermediate 11 (0.16 g; 0.4 mmol), 4-piperidinemethanol (93 mg; 0.81 mmol) in MeOH (7.5 mL) and THF (4 mL) was stirred at rt for 1h30. NaBH$_4$ (8 mg; 0.2 mmol) was added and the solution was stirred for 30 min. H$_2$O and DCM were added. The organic layer was extracted, dried over MgSO$_4$ and evaporated to dryness. The residue (167 mg) was purified by chromatography over silica gel (Spherical bare silica 5 μm 150×30.0 mm; gradient: from 95% DCM, 5% MeOH (+10% NH$_4$OH) to 82% DCM, 18%

MeOH (+10% NH$_4$OH)). The pure fractions were collected and the solvent was evaporated. The residue (81 mg) was crystallized from diethylether. The precipitate was filtered and dried to give 51 mg (25%) of compound 10. M.P.: 198° C. (K).

Preparation of Compound 11:

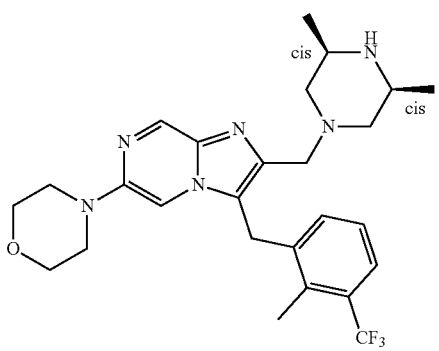 [SMILES: Cc1c(Cc2c(CN3C[C@@H](C)N[C@@H](C)C3)nc3cnc(N4CCOCC4)cn23)cccc1C(F)(F)F]

Compound 11 was prepared according to an analogous procedure as described for the synthesis of compound 10, using intermediate 11 and cis-2,6-dimethylpiperazine as starting materials. The crude was purified by chromatography over silica gel (irregular 15-40 μm; 40 g; mobile phase: 94% DCM, 6% MeOH, 0.6% NH$_4$OH). The pure fractions were collected and the solvent was evaporated. The residue (56 mg) was purified by achiral SFC (CHIRALPAK IC 5 μm 250×20 mm, Mobile phase: 60% CO$_2$, 40% MeOH (0.3% iPrNH$_2$)). The pure fractions were collected and the solvent was evaporated. The residue (42 mg) was purified again by achiral SFC (CYANO 6 μm 150×21.2 mm, Mobile phase: 80% CO$_2$, 20% MeOH (0.3% iPrNH$_2$)). The pure fractions were collected and the solvent was evaporated. The residue (22 mg) was freeze-dried with ACN/water 20/80 to give 20 mg (9%, white powder) of compound 11. M.P.: 80° C. (gum, K).

Preparation of Compound 12:

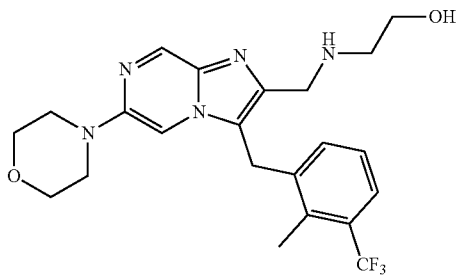 [SMILES: Cc1c(Cc2c(CNCCO)nc3cnc(N4CCOCC4)cn23)cccc1C(F)(F)F]

Compound 12 was prepared according to an analogous procedure as described for the synthesis of compound 10, using intermediate 11 and ethanolamine as starting materials. The crude was purified by chromatography over silica gel (Spherical bare silica 5 μm; 150×30.0 mm; gradient: from 95% DCM, 5% MeOH (+10% NH$_4$OH) to 82% DCM, 18% MeOH (+10% NH$_4$OH)). The pure fractions were collected and the solvent was evaporated. The residue (121 mg) was purified by chromatography over silica gel (irregular 15-40 μm; 24 g; mobile phase: 90% DCM, 10% MeOH, 0.1% NH$_4$OH). The pure fractions were collected and the solvent was evaporated. The residue (42 mg) was freeze-dried with ACN/water 20/80 to give 40 mg (28%, white powder) of compound 12. M.P.: 80° C. (gum, K).

Example B10

Preparation of Compound 13:

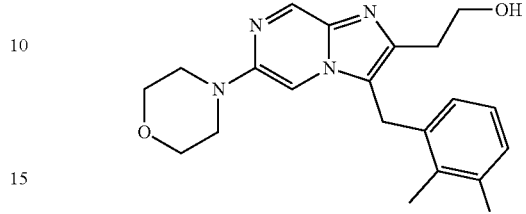

To a suspension of LiAlH$_4$ (140 mg; 3.68 mmol) in anhydrous THF (5 mL) at 0°-5° C. under N$_2$, a solution of compound 17(850 mg; 1.84 mmol) in anhydrous THF (15 mL) was added dropwise and the mixture was stirred for 2 h at 10° C. EtOAc was added dropwise followed by carefully 2 mL of a 3N aqueous solution of NaOH and water (2 mL). EtOAc was added. Then, the mixture was filtered through of pad of Celite®. The organic layer was decanted, dried over MgSO$_4$, filtered and evaporated to dryness. The residue (0.7 g) was purified by chromatography over silica gel (irregular SiOH; 15-40 μm; 40 g; mobile phase: 0.1% NH$_4$OH, 96% DCM, 4% MeOH). The pure fractions were collected and the solvent was evaporated to give 215 mg (28%) of compound 13. M.P.: 142° C. (K).

Example B11

Preparation of Compound 14:3

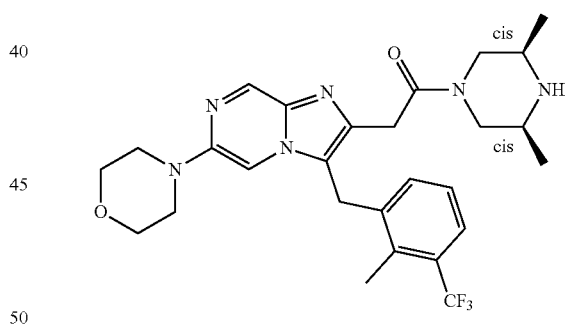

At 10° C., HBTU (153 mg; 0.4 mmol) was added to a mixture of intermediate 13 (175 mg; 0.4 mmol), cis-2,6-dimethylpiperazine (69 mg; 0.6 mmol), DIPEA (0.21 mL; 1.21 mmol) in DMF dry (5 mL). The reaction mixture was stirred for 48 h. The solution was poured into H$_2$O and extracted with EtOAc (×2). The organic layer was washed with brine. The organic layer was dried over MgSO$_4$, filtered and evaporated to dryness. The crude product was crystallized with diethylether. Then, the precipitate was filtered and dried. The precipitate (0.34 g) was purified by chromatography over silica gel (irregular bare silica 40 g; mobile phase: 0.5% NH$_4$OH, 95% DCM, 5% MeOH). The pure fractions were collected and the solvent was evaporated. The residue (130 mg) was freeze-dried with ACN/water 20/80 to give 106 mg (50%, white powder) of compound 14. M.P.: 80° C. (gum, K).

Preparation of Compound 15:

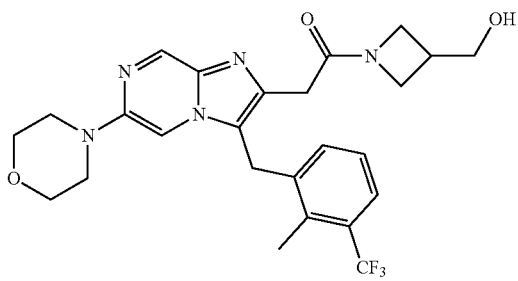 [SMILES: Cc1c(Cc2c(CC(=O)N3CC(CO)C3)nc3cnc(N4CCOCC4)cn23)cccc1C(F)(F)F]

Compound 15 was prepared according to an analogous procedure as described for the synthesis of compound 14, using intermediate 13 and 3-(hydroxymethyl)azetidine as starting materials. The crude was crystallized from diethylether. Then, the precipitate was filtered and dried. The precipitate (0.21 g) was purified by chromatography over silica gel (irregular bare silica 40 g; mobile phase: 0.7% NH$_4$OH, 93% DCM, 7% MeOH). The pure fractions were collected and the solvent was evaporated. The residue (60 mg) was freeze-dried with ACN/water 20/80 to give 51 mg (25%, white powder) of compound 15. M.P.: 80° C. (gum, K).

Example B12

Preparation of Compound 16:

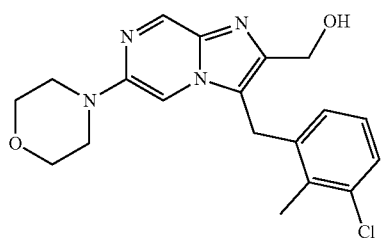 [SMILES: Cc1c(Cl)cccc1Cc1c(CO)nc2cnc(N3CCOCC3)cn12]

In sealed tube, to a solution of compound 50 (430 mg; 1.04 mmol) in dry THF (10 mL) at 0° C. was added dropwise lithium borohydride (4M in THF) (518 μL; 2.07 mmol). The mixture was stirred at rt for 2 h. The mixture was diluted with EtOAc and quenched with 10% aqueous solution of NH$_4$Cl. The mixture was combined with another batch coming from a reaction performed on 50 mg of compound 50. The layers were separated and the product was extracted with EtOAc (×2). The combined organic layers were dried over MgSO$_4$, filtered and evaporated under vacuum. The residue (355 mg, brown oil) was purified by chromatography over silica gel (irregular SiOH; 15-40 μm; 50 g; gradient: from 100% DCM to 92% DCM, 8% MeOH). The pure fractions were collected and the solvent was evaporated. The residue (77 mg, red solid) was purified by reverse phase (C18 5 μm; 30*150 mm; gradient: from 80% (aq. NH$_4$HCO$_3$ 0.5%), 20% ACN to 100% ACN). The pure fractions were collected and the solvent was evaporated. The residue (36 mg, colorless oil) was freeze-dried with MeOH/water 20/80 to give 36 mg (white solid). This fraction was purified by chromatography over silica gel (Spherical bare silica 5 μm; 150×30.0 mm; gradient: from 98% DCM, 2% MeOH, 0.2% NH$_4$OH to 87% DCM, 13% MeOH, 1.3% NH$_4$OH). The pure fractions were collected and the solvent was evaporated. The residue (16 mg, colorless oil) was freeze-dried with ACN/water 23/77 to give 13 mg (3%, white solid) of compound 16. M.P.: 184° C. (DSC).

Example B13

Preparation of Compound 17:

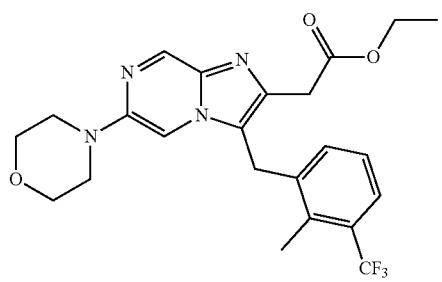 [SMILES: CCOC(=O)Cc1nc2cnc(N3CCOCC3)cn2c1Cc1cccc(C(F)(F)F)c1C]

Compound 17 was prepared according to an analogous procedure as described for the synthesis of intermediate 3, using intermediate 12 and 1-(chloromethyl)-2-methyl-3-(trifluoromethyl-benzene as starting materials. The crude was taken-up with diethylether. The precipitate was filtered off and dried under vacuum to give 530 mg (24%) of compound 17. M.P.: 135° C. (Mettler Toledo).

Example B14

Preparation of Compound 18:

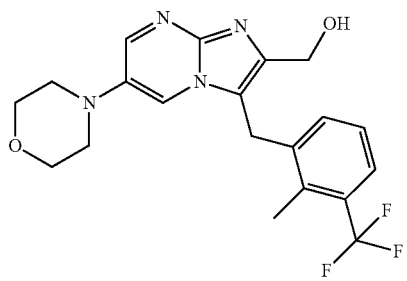 [SMILES: Cc1c(Cc2c(CO)nc3ncc(N4CCOCC4)cn23)cccc1C(F)(F)F]

Diisobutylaluminium hydride (1M in DCM) (54 mL; 54 mmol) was added dropwise to a solution of compound 51 (5.04 g; 10.7 mmol) in THF (200 mL) at −5° C. under N$_2$. The resulting brown mixture was then allowed to gently reach rt and stirred for 16 h. More diisobutylaluminium hydride (1M in DCM) (18 mL; 18 mmol) was added at −5° C. and the mixture was gently allowed to reach rt and stirred for an additional 3 h. The resulting mixture was gently poured into distilled water at 0° C. under stirring and the aqueous layers was extracted with DCM (4×300 mL) and then DCM/MeOH (90/10, 200 mL). The combined organic layers were dried over MgSO$_4$ and the resulting suspension was filtered through a pad of Celite® then evaporated. The residue (5.6 g brown residue) was purified by chromatography over silica gel (regular SiOH 30 μm; 200 g; dry loading Celite®; gradient: from 99% DCM, 1% MeOH to 96% DCM, 4% MeOH). Fractions containing product were combined and DCM was evaporated under vacuum resulting in the precipitation of a solid in remaining MeOH. This solid was filtered (1.41 g, off-white solid) and was recrystallized in a minimum of hot EtOH (~200 mL) with slow cooling.

The solid was filtered, rinsed with cool EtOH and dried under high vacuum at 60° C. for 4 h to give 1.16 g (27%, white solid) of compound 18. M.P.: 231° C. (DSC).

Preparation of Compound 25:

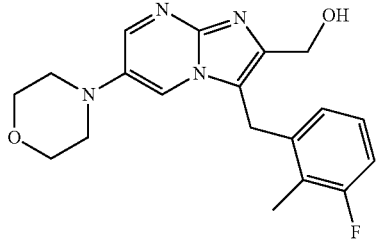 [SMILES: Cc1c(F)cccc1Cc1c(CO)nc2ncc(N3CCOCC3)cn12]

Diisobutylaluminium hydride (1M in DCM) (30 mL; 30 mmol) was added dropwise over 1 h to a solution of compound 52 (1.98 g; 4.97 mmol) in THF (93 mL) at −10° C. under stirring and $N_2$. The resulting brown mixture was then allowed to gently reach rt and stirred for 18 h. The brown solution was then placed at 0° C., quenched by dropwise addition of EtOAc (50 mL), followed by a 15% aqueous solution of Rochelle's salt (~100 mL). The mixture was stirred for 2 h and extracted with EtOAc (twice). The combined organic layers were dried over $MgSO_4$, filtered and evaporated under vacuum. The residue (2.75 g, orange sticky compound) was combined with another batch coming from a reaction performed on 350 mg (0.88 mmol) of compound 52. The mixture of residue was purified by chromatography over silica gel (regular SiOH; m, 80 g; dry loading (Celite®), gradient: from 100% DCM to 90% DCM, 10% MeOH). The pure fractions were collected and the solvent was evaporated. The residue (1.1 g, off-white solid) was recrystallized in a minimum of hot EtOH (~150 mL) with slow cooling down to rt (over ~6 h), then slow cooling down to 14° C. over 2 h in order to maximize crystallization yield. The resulting solid was filtered, washed with a minimum of cold diethylether and dried to give 883 mg (42%, white solid) of compound 25. M.P.: 210° C. (DSC).

The filtrate was evaporated in vacuum to give an additional batch of 228 mg of compound 25 (11%, not totally pure, beige solid).

Preparation of Compound 48:

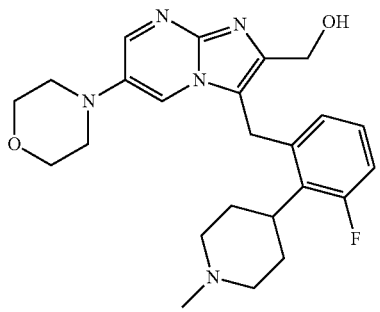 [SMILES: CN1CCC(c2c(F)cccc2Cc2c(CO)nc3ncc(N4CCOCC4)cn23)CC1]

Compound 48 was prepared according to an analogous procedure as described for the synthesis of compound 18, using intermediate 86 as starting material (crystallized from DIPE; 43 mg, 1%). M.P.: 222° C. (DSC).

Example B15

Preparation of Compound 19:

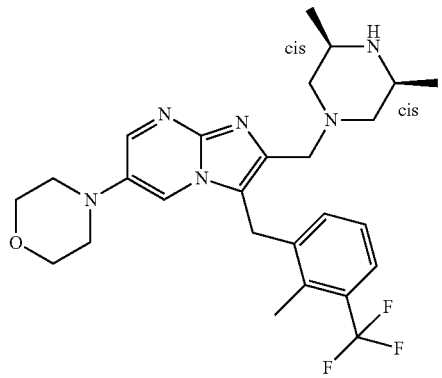 [SMILES: Cc1c(Cc2c(CN3C[C@@H](C)N[C@@H](C)C3)nc3ncc(N4CCOCC4)cn23)cccc1C(F)(F)F]

A mixture of intermediate 21 (174 mg; 0.43 mmol) and cis-2,6-dimethylpiperazine in MeOH (3 mL) was stirred at rt for 2 h. Then, $NaBH_4$ (24 mg; 0.65 mmol) was added and the reaction mixture was stirred at rt overnight. More cis-2,6-dimethylpiperazine (1.5 eq.) was added and the reaction mixture was stirred 6 h at 30° C. The reaction mixture was heated at 60° C. for 1 h. $NaBH_4$ was added and the mixture was stirred at rt for 1 h. The solvent was removed and the crude was purified by chromatography over silica gel (silica, gradient: from 100% DCM to 90% DCM, 10% MeOH). The pure fractions were collected and the solvent was evaporated to give 40 mg (18%) of compound 19. M.P.: 263° C. (MP50 Mettler Toledo).

Preparation of Compound 21:

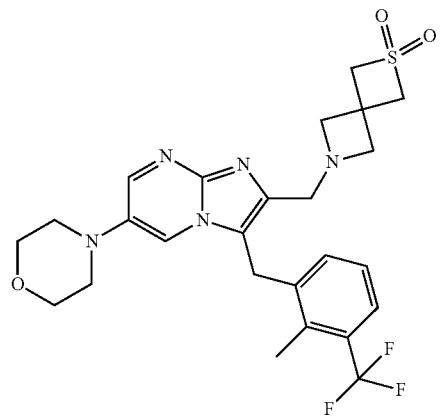 [SMILES: Cc1c(Cc2c(CN3CC4(C3)CS(=O)(=O)C4)nc3ncc(N4CCOCC4)cn23)cccc1C(F)(F)F]

Sodium triacetoxyborohydride (0.157 g; 0.74 mmol) was added to a mixture of intermediate 21 (0.2 g; 0.50 mmol), 2-thia-6-aza-spiro[3.3]heptane2,2-dioxide (trifluoroacetate) (0.193 g; 0.74 mmol), sodium acetate (61 mg; 0.74 mmol) in DCE (5 mL). The reaction mixture was stirred overnight at rt. The solution was poured into a mixture of $H_2O$ and $NaHCO_3$, then extracted with DCM. The organic layer was dried over $MgSO_4$, filtered and evaporated until dryness. The residue (0.248 g) was purified by chromatography over silica gel (Spherical bare silica 5 μm 150×30.0 mm; gradient: from 98% DCM, 2% MeOH, 0.2% $NH_4OH$ to 88% DCM, 12% MeO, 1.2% $NH_4OH$). The pure fractions were collected and the solvent was evaporated until dryness. The residue (0.025 g) was crystallized from DIPE. The precipitate was filtered off and dried under vacuum to give 0.015 g (6%) of compound 21. M.P.: 228° C. (kofler).
Preparation of Compound 22:

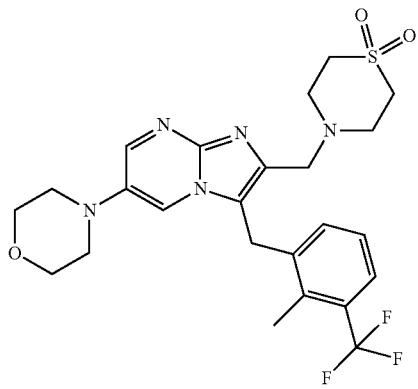 [SMILES: Cc1c(Cc2c(CN3CCS(=O)(=O)CC3)nc3ncc(N4CCOCC4)cn23)cccc1C(F)(F)F]

Compound 22 was prepared according to an analogous procedure as described for the synthesis of compound 21, using intermediate 21 and thiomorpholine 1,1-dioxide as starting material. The residue (286 mg) was purified by chromatography over silica gel (irregular SiOH 15-40 μm; 40 g; gradient: from 100% DCM to 95% DCM, 5% MeOH, 0.1% NH$_4$OH). The pure fractions were collected and the solvent was evaporated. The residue (0.165 g) was crystallized from DIPE and 10% of ACN. The precipitate was filtered off and dried in vacuum to give 0.048 g (15%) of compound 22. M.P.: 225° C. (kofler).
Preparation of Compound 24 and Compound 24a

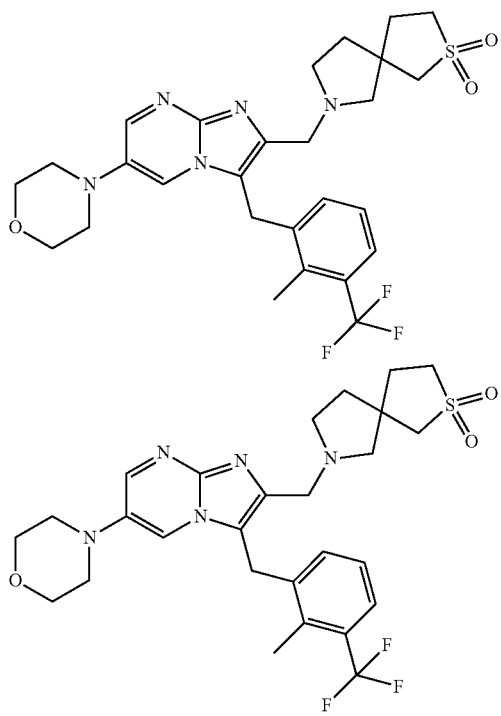

1.63 HCl, 0.71 H$_2$O

A solution of intermediate 21 (250 mg; 0.62 mmol) and 2-thia-7-azaspiro[4,4]nonane 2,2-dioxide hydrochloride (130.88 mg; 0.62 mmol) in MeOH (16.6 mL) was stirred at rt. AcOH (722 μL; 12.61 mmol) was added dropwise followed by portionwise addition of sodium borohydride (39 mg; 0.62 mmol). The reaction mixture was stirred at rt for 16 h. The reaction mixture was poured to 10% aqueous solution of K$_2$CO$_3$ and extracted with DCM. The organic layer was dried over MgSO$_4$, filtered and the solvent was evaporated. The residue was purified by chromatography over silica gel (SiOH 20-45 μm; 24 g; gradient: 98% DCM, 2% MeOH, 0.1% NH$_4$OH to 95% DCM, 5% MeOH, 0.1% NH$_4$OH). The pure fractions were collected and the solvent was evaporated to give 125 mg of amorphous compound 24. This fraction was dissolved in ACN (5 mL) at rt, then HCl (4M in 1,4-dioxane) (500 μL) was added dropwise and the reaction mixture was stirred at rt for 16 h. No salt precipitation occurred. The solvent was then evaporated under reduced pressure and the resulting solid was triturated in diisopropylether, filtered and dried under vacuum to give 75 mg (19%) of compound 24a (1.63 HCl 0.71 H$_2$O).
Preparation of Compound 26:

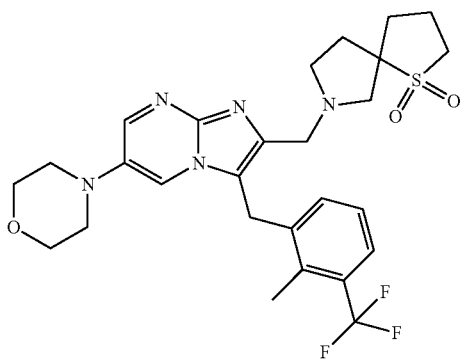 [SMILES: Cc1c(Cc2c(CN3CCC4(CCCS4(=O)=O)C3)nc3ncc(N4CCOCC4)cn23)cccc1C(F)(F)F]

Compound 26 was prepared according to an analogous procedure as described for the synthesis of compound 24, using intermediate 21 and 1-thia-7-azaspiro[4,4]nonane 1,1-dioxide hydrochloride as starting material. The residue was purified by chromatography over silica gel (SiOH 20-45 μm; 24 g; gradient: 98% DCM, 2% MeOH, 0.1% NH$_4$OH to 95% DCM, 5% MeOH, 0.1% NH$_4$OH). The pure fractions were collected and the solvent was evaporated to give 130 mg of amorphous solid compound 26. This fraction was dissolved in ACN (2 mL) and the mixture was heated until fully dissolve. The reaction mixture was cooling down to rt, the resulting precipitate was filtered, washed with small amount diisopropylether and dried to give 90 mg (26%, white solid) of compound 26. M.P.: 200° C. (DSC).

Example B16

Preparation of Compound 20:

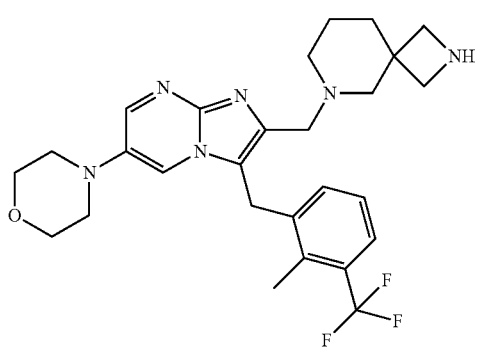 [SMILES: Cc1c(Cc2c(CN3CCCC4(CNC4)C3)nc3ncc(N4CCOCC4)cn23)cccc1C(F)(F)F]

TFA (1 mL) was added to a solution of intermediate 22 in DCM (3 mL). The reaction mixture was stirred at rt for 1 h. The solvents were removed and the crude residue was washed twice with toluene. The product was purified by chromatography over silica gel (silica; gradient: from 100% DCM to 90% DCM, 10% MeOH 0.1% NH$_4$OH). The pure fractions were collected and evaporated to give 6 mg (4%) of compound 20.

Preparation of Compound 53:

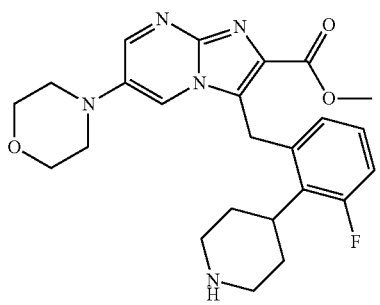 [SMILES: COC(=O)c1nc2ncc(N3CCOCC3)cn2c1Cc1cccc(F)c1C1CCNCC1]

TFA (1.32 mL; 17.76 mmol) was added dropwise to a solution of intermediate 86 (672 mg; 1.18 mmol) in DCM (10 mL) at 0° C. The solution was allowed to warm to rt and was stirred at rt overnight. The mixture was poured into water, basified with an aqueous solution of K$_2$CO$_3$ 10% and the compound was extracted with DCM. The organic layer was separated, dried over MgSO$_4$, filtered and evaporated. The residue (0.57 g) was purified by chromatography over silica gel (Irregular SiOH 15-40 µm; 40 g; gradient: from 100% DCM to 90% DCM, 10% MeOH). The pure fractions were collected and the solvent was evaporated to give 0.22 g (40%) of compound 53.

Example B17

Preparation of Compound 23:

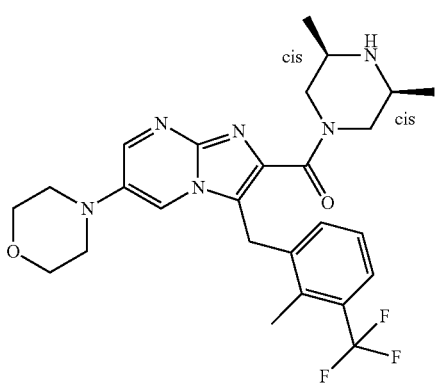 [SMILES: Cc1c(Cc2c(C(=O)N3C[C@@H](C)N[C@@H](C)C3)nc3ncc(N4CCOCC4)cn23)cccc1C(F)(F)F]

The reaction was performed twice on 165 mg (0.39 mmol) of intermediate 23. A solution of cis-2,6-dimethylpiperazine (93 mg; 0.79 mmol) in dry DMF was added to a solution of intermediate 23 (165 mg; 0.39 mmol), HBTU (447 mg; 1.18 mmol) and DIPEA (0.205 mL; 1.18 mmol) in dry DMF (5 mL). The reaction mixture was stirred at rt for 1 h. Drops of ammonia (7N in MeOH) were added and EtOAc was poured in the reaction mixture. The two batches were combined for the work-up. The resulting organic layer was washed with water, then brine. The organic layer was evaporated. The residue (203 mg) was purified by chromatography over silica gel (SiOH; gradient: from 100% DCM to 90% DCM, 10% MeOH). The pure fractions were collected and evaporated. The residue was crystallized from diethylether. The precipitate was filtered off and dried to give 19 mg (5%) of compound 23. M.P.: 130° C. (MP50 Mettler Toledo).

Example B18

Preparation of Compound 27:

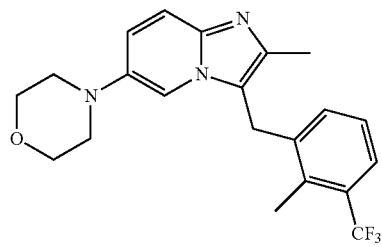 [SMILES: Cc1nc2ccc(N3CCOCC3)cn2c1Cc1cccc(C(F)(F)F)c1C]

In a Schlenk reactor, to a solution of intermediate 26 (630 mg; 1.78 mmol) in THF (17.8 mL) was added bis(tri-tert-butylphosphine)palladium(0) (46 mg; 0.09 mmol). The mixture was carefully degassed under vacuum and back-filled with N$_2$ (3×). Then, intermediate 27 (5.67 mL; 3.21 mmol) was added and the mixture was carefully degassed under vacuum and back-filled with N$_2$ (×3). The reaction mixture was stirred at 60° C. for 3 h. The mixture was diluted in DCM and filtered over a pad of silica gel. The silica was rinsed with DCM and the filtrate was evaporated in vacuum to give a residue which was taken-up in DCM and water. The layers were separated and the aqueous layer was extracted with DCM. The combined organic layers were dried over MgSO$_4$, filtered and evaporated in vacuum. The residue (900 mg, brown oil) was purified by chromatography over silica gel (irregular SiOH 30 µm; 40 g; mobile phase: from 100% DCM to 96% DCM, 4% MeOH, 0.4% NH$_4$OH). The pure fractions were collected and the solvent was evaporated. The residue (720 mg, green oil) was triturated in diethylether/heptane. Then, the precipitate was filtered and dried to give 605 mg (87%, white powder). A part of this fraction (112 mg) was freeze-dried with ACN/water (20/80) to give 103 mg. The residue (103 mg) was purified by achiral SFC (CYANO 6 µm 150×21.2 mm; mobile phase: 85% CO$_2$, 15% MeOH (0.3% iPrNH$_2$)). The pure fractions were collected and the solvent was evaporated. The residue (36 mg, purple solid) was freeze-dried with ACN/water (16/84) to give 35 mg (5%, white fluffy solid) of compound 27. M.P.: 162° C. (DSC).

Example B19

Preparation of Compound 28:

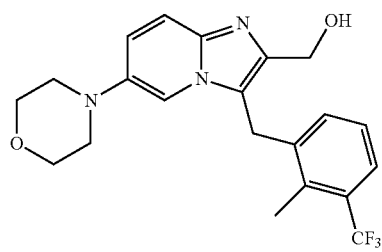

To a solution of intermediate 30 (390 mg; 0.87 mmol) in THF (4.3 mL) and EtOH (4.3 mL) was added NaOH (1M in H₂O) (1.74 mL; 1.74 mmol). The reaction mixture was stirred at rt overnight. The mixture was evaporated under vacuum and the residue was taken-up in DCM and water. The aqueous layer was acidified with NH₄Cl solid. The layers were separated and the aqueous layer was extracted with DCM. The combined organic layers were dried over MgSO₄, filtered and the solvent was evaporated in vacuum to give 343 mg (97%, white solid) of compound 28. M.P.: 196° C. (DSC).

Alternative Preparation:

To a solution of intermediate 36 (1.19 g; 2.29 mmol) in THF (23 mL) at 0° C. was added dropwise tetrabutylammonium fluoride (1M in THF) (2.52 mL; 2.52 mmol). The reaction mixture was warmed to rt and stirred for 2 h. Then, more tetrabutylammonium fluoride (1M in THF) (4.58 mL; 4.58 mmol) was added and the mixture was stirred at rt for 2 h. The mixture was poured onto a saturated solution of NaHCO₃ and the aqueous layer was extracted with EtOAc (×2). The combined organic layers were dried over MgSO₄, filtered and evaporated under vacuum. The residue (yellow solid) was taken-up in EtOAc and washed with water (×2). The organic layer was dried over MgSO₄, filtered and evaporated in vacuum to give 631 mg (68%, beige solid) of compound 28.

Alternative Preparation: See A16 (Together with Intermediate 30)

Preparation of Compound 47:

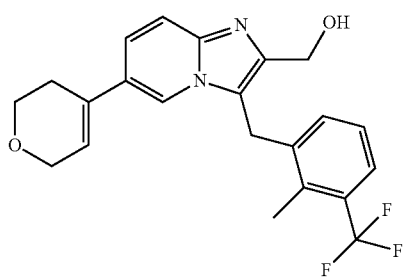 [SMILES: Cc1c(Cc2c(CO)nc3ccc(C4=CCOCC4)cn23)cccc1C(F)(F)F]

To a solution of intermediate 57 (1.5 g; 2.90 mmol) in THF (29 mL) was added HCl (3M in H₂O) (1.94 mL; 5.81 mmol). The solution was stirred at rt for 3 h, then cooled down to 0° C. and slowly neutralized with solid K₂CO₃. The mixture was extracted with DCM (×3) then with EtOAc (×2). The combined organic layers were dried over MgSO₄, filtered and evaporated in vacuum to give 1.05 g (90%, beige solid) of compound 47.

Example B20

Preparation of compound 30:

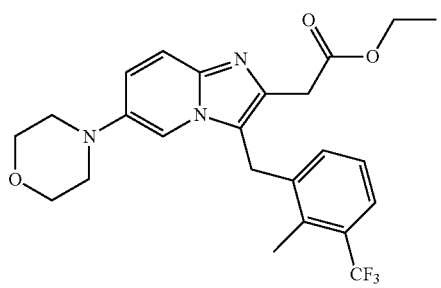 [SMILES: CCOC(=O)Cc1nc2ccc(N3CCOCC3)cn2c1Cc1cccc(C(F)(F)F)c1C]

In a Schlenk reactor, to a solution of intermediate 38 (475 mg; 1.14 mmol) in THF (11.5 mL) was added bis(tri-tert-butylphosphine)palladium(0) (29 mg; 0.06 mmol). The mixture was carefully degassed under vacuum and back-filled with N₂ (×3). Then, intermediate 27 (3.64 mL; 2.06 mmol) was added and the mixture was carefully degassed under vacuum and back-filled with N₂ (×3). The reaction mixture was stirred at rt overnight. The mixture was quenched with NH₄Cl solid and filtered through a pad of Celite®. The Celite® was washed with EtOAc and the filtrate was evaporated under vacuum. The residue (600 mg, red oil) was combined with a batch coming from a reaction performed 50 mg of intermediate 14 and the resulting residue was purified by chromatography over silica gel (irregular SiOH 15-40 µm; 50 g; gradient: from 100% DCM to 95% DCM, 5% MeOH). The pure fractions were collected and the solvent was evaporated. The residue (376 mg, green oil) was purified by chromatography over silica gel (Spherical bare silica 5 µm 150×30.0 mm; gradient: from 98% DCM, 2% MeOH (+10% NH₄OH) to 86% DCM, 14% MeOH (+10% aq. NH₄OH)). The pure fractions were collected and the solvent was evaporated. The residue (66 mg) was purified by Reverse phase (X-Bridge-C18 5 µm 30*150 mm; gradient: from 70% (aq. NH₄HCO₃ 0.5%), 30% ACN to 100% ACN). The pure fractions were collected and the solvent was evaporated. The residue (18 mg, colorless oil) was freeze-dried with ACN/water 23/77 to give 17 mg (3%, white fluffy solid) of compound 30. M.P.: 176° C. (DSC).

Example B21

Preparation of Compound 31:

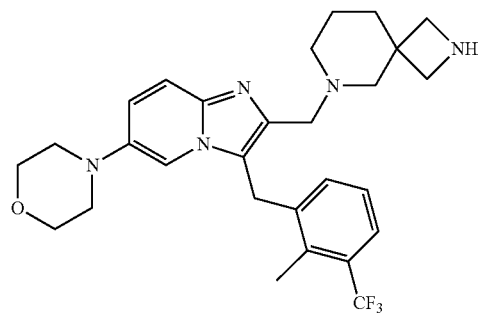 [SMILES: Cc1c(Cc2c(CN3CCCC4(CNC4)C3)nc3ccc(N4CCOCC4)cn23)cccc1C(F)(F)F]

To a solution of intermediate 40 (101 mg; 0.14 mmol) in DCM (1.44 mL) at 0° C. was added TFA (110 µL; 1.44 mmol). The mixture was warmed to rt and stirred at rt overnight. Then, more TFA (110 µL; 1.44 mmol) was added dropwise and the mixture was stirred at rt for 3 h. NaOH (1M in H₂O) (2.88 mL; 2.88 mmol) was added and the mixture was stirred at rt for 1 h. The layers were separated and the organic layer was washed with brine, dried over MgSO₄, filtered and evaporated under vacuum. The residue (220 mg, green oil) was taken up in THF (0.72 mL) and EtOH (0.72 mL) and NaOH (1M in H₂O) (0.72 mL, 0.72 mmol) was added. The mixture was stirred at 50° C. for 2 h. The mixture was evaporated under vacuum and the residue was taken-up in DCM and water. The aqueous layer was neutralized with 10% aqueous solution of NH₄Cl and the product was extracted with DCM (×2). The combined organic layers were dried over MgSO₄, filtered and evaporated in vacuum. The residue (143 mg, yellow powder was purified by chromatography over silica gel (Spherical bare silica 5 µm 150×30.0 mm; gradient: from 92% DCM, 8%

MeOH, 0.8% NH4OH to 76% DCM, 24% MeOH, 2.4% NH4OH). The pure fractions were collected and the solvent was evaporated. The residue (32 mg, colorless oil) was freeze-dried with ACN/water (20/80) to give 31 mg (42%, white powder) of compound 31.

Preparation of compound 32:

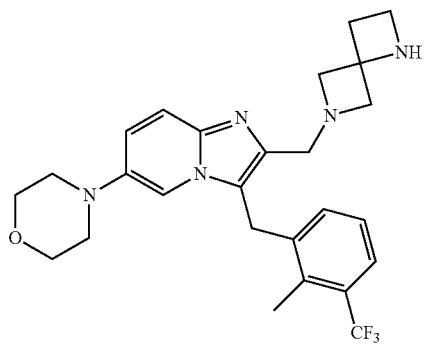 [SMILES: Cc1c(Cc2c(CN3CC4(CCN4)C3)nc3ccc(N4CCOCC4)cn23)cccc1C(F)(F)F]

To a solution of intermediate 41(85 mg; 0.15 mmol) in DCM (1.45 mL) at 0° C. was added TFA (0.111 mL; 1.45 mmol). The mixture was warmed to rt and stirred at rt overnight. More TFA (0.111 mL; 1.45 mmol) was added and the mixture was stirred at rt over the weekend. NaOH (1M in H2O) (3.63 mL; 3.63 mmol) was added and the reaction mixture was stirred at rt for 2 h. The layers were separated and the organic layer was washed with brine, dried over MgSO4, filtered and evaporated in vacuum. The residue (70 mg, green oil) was purified by chromatography over silica gel (Spherical bare silica 5 μm 150×30.0 mm; gradient: from 92% DCM, 8% MeOH, 0.8% NH4OH to 76% DCM, 24% MeOH, 2.4% NH4OH). The pure fractions were collected and the solvent was evaporated. The residue (10 mg, colorless oil) was freeze-dried with ACN/water 23/77 to give 8 mg (11%, white fluffy solid) of compound 32.

Example B22

Preparation of Compound 33:

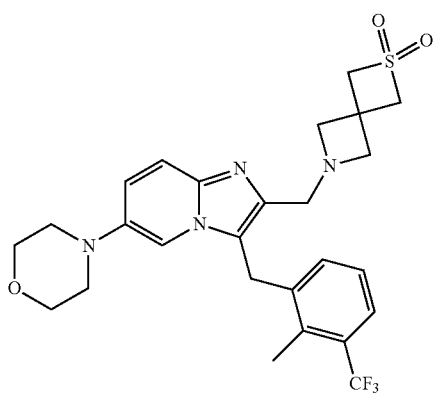 [SMILES: Cc1c(Cc2c(CN3CC4(C3)CS(=O)(=O)C4)nc3ccc(N4CCOCC4)cn23)cccc1C(F)(F)F]

To a solution of intermediate 39 (305 mg; 0.76 mmol) in MeOH (7.5 mL) was added 2-thia-6-aza-spiro[3.3]heptane2,2-dioxide trifluoroacetate) (217 mg; 0.83 mmol). The mixture was stirred at rt for 1 h. Then, sodium triacetoxyborohydride (481 mg; 2.27 mmol) was added and the mixture was stirred at rt overnight. The mixture was taken-up in DCM and a saturated solution of NaHCO3 was added. The layers were separated and the aqueous layer was extracted with DCM. The combined organic layers were dried over MgSO4, filtered and evaporated in vacuum. The residue (420 mg, pale green solid) was triturated in DCM/diethylether (1:9). The precipitate was filtered and dried under vacuum to give 302 mg (75%, white solid) of compound 33. M.P.: 196° C. (DSC).

Preparation of Compound 34:

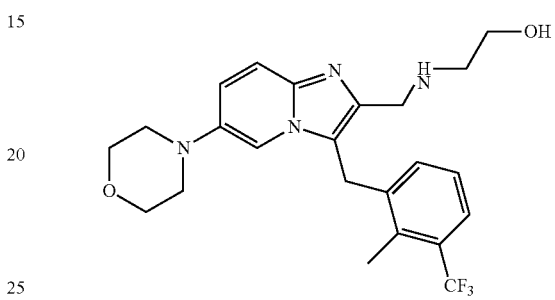

In a microwave vial, to a solution of intermediate 39(566 mg; 1.40 mmol) in MeOH (14 mL) was added 2-aminoethanol (168 μL; 2.81 mmol). The mixture was stirred at rt for 1h30. Then, NaBH4 (27 mg; 0.70 mmol) was added and the reaction mixture was stirred at rt overnight. The mixture was evaporated under vacuum. Then, the residue was taken up in DCM and 1N aqueous solution of HCl. The layers were separated and the aqueous layer was basified with a saturated solution of NaHCO3 and extracted with DCM (×2). The combined organic layers were dried over MgSO4, filtered and evaporated under vacuum. The residue (532 mg, beige solid) was purified by chromatography over silica gel (Spherical bare silica 5 μm 150×30.0 mm; gradient: from 96% DCM, 4% MeOH, 0.4% NH4OH to 83% DCM, 17% MeOH 1.7% NH4OH). The pure fractions were collected and the solvent was evaporated. The residue (436 mg, beige powder) was triturated in diethylether/DCM (9:1) and the solvent was evaporated under vacuum. The solid was dried in vacuum (50° C., 24 h) to give 400 mg (64%, white powder) of compound 34. M.P.: 147° C. (DSC).

Preparation of Compound 35:

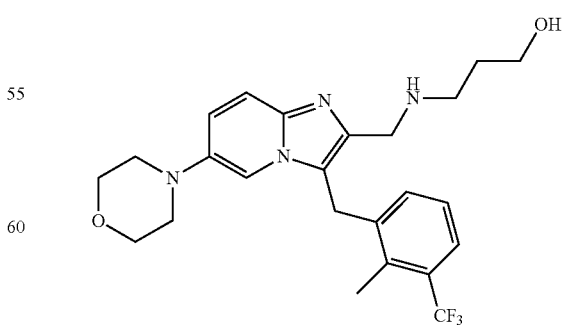

Compound 35 was prepared according to an analogous procedure as described for the synthesis of compound 33, using intermediate 39 and 3-amino-1-propanol as starting material. The residue (76 mg) was purified by chromatography over silica gel (irregular SiOH 30 µm; 4 g; gradient: from 100% DCM to 96% DCM, 4% MeOH, 0.4% NH₄OH). The pure fractions were collected and the solvent was evaporated. The residue (56 mg, green oil) was purified by chromatography over silica gel (Spherical bare silica 5 µm 150×30.0 mm; gradient: from 97% DCM, 3% MeOH, 0.3% NH₄OH to 85% DCM, 15% MeOH, 1.5% NH₄OH). The pure fractions were collected and the solvent was evaporated. The residue (28 mg) was purified by Reverse phase (X-Bridge-C18 µm 30*15 mm; gradient: from 80% (aq. NH₄HCO₃ 0.5%), 20% ACN to 0% (aq. NH₄HCO₃ 0.5%), 100% ACN). The pure fractions were collected and the solvent was evaporated. The residue (17 mg, white solid) was freeze-dried with ACN/water 20/80 to give 16 mg (19%, white fluffy powder) of compound 35. M.P.: 133° C. (DSC).

Preparation of Compound 40:

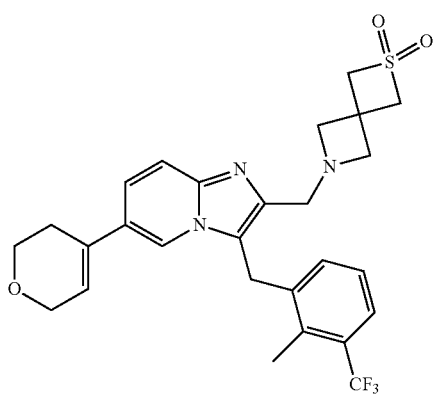 [SMILES: Cc1c(Cc2c(CN3CC4(C3)CS(=O)(=O)C4)nc3ccc(C4=CCOCC4)cn23)cccc1C(F)(F)F]

To a solution of intermediate 59 (500 mg; 1.25 mmol) in MeOH (12 mL) was added 2-thia-6-aza-spiro[3.3]heptane2,2-dioxide trifluoroacetate (359 mg; 1.37 mmol) and sodium triacetoxyborohydride (794 mg; 3.75 mmol). The reaction mixture was stirred at rt for 3 h, then evaporated under vacuum. The residue was taken-up in DCM and a saturated aqueous solution of NaHCO₃ was added. The layers were separated and the aqueous layer was extracted with DCM. The combined organic layers were dried over MgSO₄, filtered and evaporated under vacuum. The residue (701 mg; pale brown foam) was purified by chromatography over silica gel (irregular SiOH 15-40 µm; 30 g; gradient: from 100% DCM to 95% DCM, 5% MeOH). The pure fractions were collected and the solvent was evaporated. The residue (413 mg, off-white solid) was purified by chromatography over silica gel (irregular SiOH 15-40 µm; 30 g; gradient: from 100% heptane to 50% heptane, 50% (iPrOH/NH₄OH: 95/5)). The pure fractions were collected and the solvent was evaporated. The residue (318 mg, off-white solid) was purified by chromatography over silica gel (irregular SiOH 15-40 µm; 24 g; gradient: from 100% DCM to 95% DCM, 5% (iPrOH/NH₄OH: 95/5)). The pure fractions were collected and the solvent was evaporated to give 287 mg (39%, white solid) of compound 40. M.P.: 184° C. (DSC).

Example B23

Preparation of Compound 38:

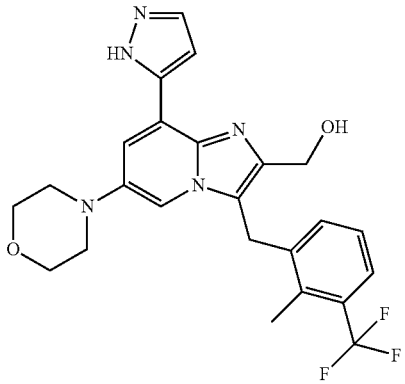 [SMILES: Cc1c(Cc2c(CO)nc3c(-c4ccn[nH]4)cc(N4CCOCC4)cn23)cccc1C(F)(F)F]

To a solution of intermediate 50 (227 mg; 0.34 mmol) in THF (3 mL) was added HCl (6M in H₂O) (565 µL; 3.39 mmol). The solution was heated at 60° C. for 18 h then, additional HCl (6M in H₂O) (395 µL; 2.37 mmol) was added and the solution was heated at 60° C. for 18 h. The solution was neutralized with 1M aqueous solution of NaOH. The aqueous layer was extracted with DCM (×3) and the combined organic layers were dried over MgSO₄, filtered and evaporated under vacuum. The residue was purified by chromatography over silica gel (Irregular SiOH 15-40 µm; 10 g; gradient: from 100% DCM to 90% DCM, 10% MeOH, 0.1% NH₄OH). The pure fractions were collected and the solvent was evaporated. The residue (48 mg, pale brown solid) was purified by Reverse phase (X-Bridge-C18 5 m 30*150 mm; gradient: from 75% H₂O (0.5% HCOONH₄ pH4.5), 25% ACN to 0% H₂O (0.5% HCOONH₄ pH4.5), 100% ACN). The pure fractions were collected and the solvent was evaporated. The residue (19 mg, off-white solid) was purified by chromatography over silica gel (Spherical bare silica 5 µm 150×30.0 mm; gradient: from 50% heptane, 3% MeOH (+10% NH₄OH), 47% EtOAc to 0% heptane, 25% MeOH (+10% NH₄OH), 75% EtOAc). The pure fractions were collected and the solvent was evaporated to give 10 mg (6%, white solid) of compound 38.

Preparation of Compound 41:

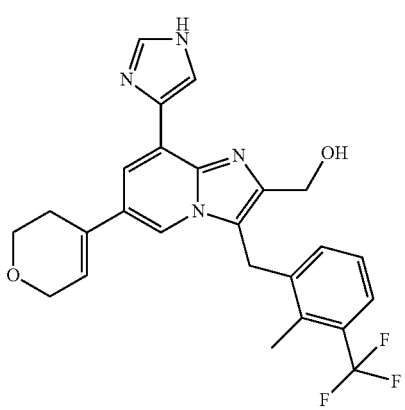 [SMILES: Cc1c(Cc2c(CO)nc3c(-c4c[nH]cn4)cc(C4=CCOCC4)cn23)cccc1C(F)(F)F]

To a mixture of intermediate 63 (68 mg; 98.6 μmol) in THF (980 μL) was added HCl (6M in H₂O) (82 μL; 0.49 mmol). The mixture was heated at 60° C. for 18 h. After cooling down to rt, the reaction mixture was cooled down to 0° C., slowly neutralized with solid K₂CO₃ and transferred in a separatory funnel. EtOAc and water were added; The organic layer was separated and the aqueous layer was extracted with EtOAc (×2). The combined organic layers were dried over MgSO₄, filtered and evaporated under vacuum. The residue (43 mg, yellow residue) was purified by chromatography over silica gel (Irregular SiOH 15-40 μm; 4 g; gradient: from 100% DCM to 90% DCM, 10% MeOH/, 0.1% NH₄OH). The pure fractions were collected and the solvent was evaporated. The residue (pale yellow film) was triturated in diethylether. The precipitate was filtered and dried under vacuum. The resulting residue (17 mg, pale brown solid) was purified by Reverse phase (X-Bridge-C18 5 μm; 30*150 mm; gradient: from 75% H₂O (NH₄HCO₃ 0.5%), 25% ACN to 35% H₂O (NH₄HCO₃ 0.5%), 65% ACN). The pure fractions were collected and the solvent was evaporated. The residue (colorless film) was freeze-dried with ACN/water (20/80) to give 5 mg (24%, white fluffy solid) of compound 41.

Preparation of Compound 42:

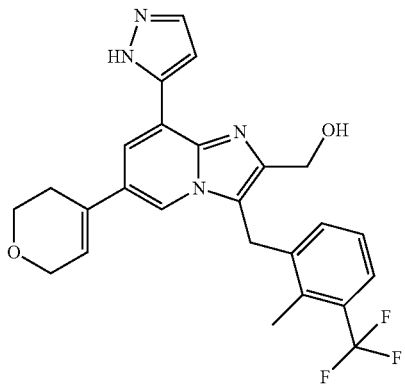 [SMILES: Cc1c(Cc2c(CO)nc3c(-c4ccn[nH]4)cc(C4=CCOCC4)cn23)cccc1C(F)(F)F]

To a mixture of intermediate 66 and intermediate 67 (739 mg; 1.27 mmol; 33% purity) in THF (3 mL) was added HCl (6M in H₂O) (0.837 mL; 5.02 mmol). The mixture was heated at 50° C. for 1 h. More HCl (6M in H₂O) (0.837 mL; 5.02 mmol) was added and the solution was heated at 50° C. for 1 h. More HCl (6M in H₂O) (1.67 mL; 10.0 mmol) was added and the solution was heated at 60° C. for 96 h. The crude was then cooled down to 0° C., slowly neutralized with solid K₂CO₃ and extracted with DCM (×3). The combined organic layers were dried over MgSO₄, filtered and evaporated under vacuum. The residue (551 mg, brown oil) was purified by chromatography over silica gel (Irregular SiOH 15-40 μm; 10 g; gradient: from 100% DCM to 90% DCM, 10% MeOH, 0.1% NH₄OH). The pure fractions were collected and the solvent was evaporated. The residue (551 mg, off-white solid) was triturated in diethylether. The solid was filtered and dried under vacuum at 50° C. for 18 h. The residue (110 mg, off-white solid) was solubilized in a mixture of acetone and MeOH, evaporated under vacuum and dried under vacuum at 50° C. for 18 h to give 65 mg (33%, off-white solid) of compound 42. M.P.: 238° C. (DSC).

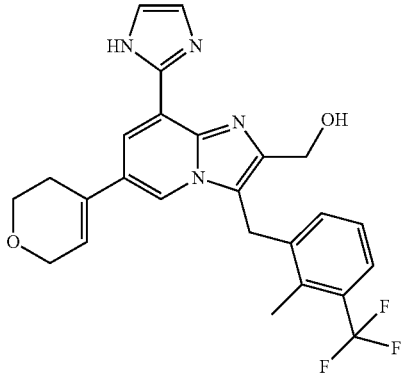 [SMILES: Cc1c(Cc2c(CO)nc3c(-c4ncc[nH]4)cc(C4=CCOCC4)cn23)cccc1C(F)(F)F]

Preparation of Compound 43:

Compound 43 was prepared according to an analogous procedure as described for the synthesis of compound 41, using intermediate 71 as starting material. The reaction mixture was stirred at 60° C. for 1 h. The residue (241 mg) was purified by chromatography over silica gel (irregular SiOH 15-40 μm; 10 g; gradient: from 100% DCM to 95% DCM, 5% MeOH, 0.5% NH₄₀H). The pure fractions were collected and the solvent was evaporated. The residue was triturated with diethylether. The precipitate was filtered and dried under vacuum to give 96 mg (37%, off-white solid) of compound 43. M.P.: 247° C. (DSC).

Example B24

Preparation of Compound 39:

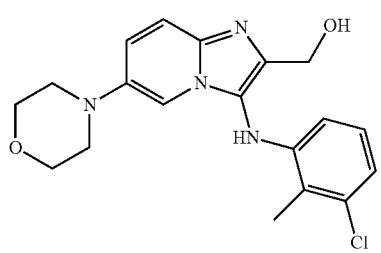 [SMILES: Cc1c(Cl)cccc1Nc1c(CO)nc2ccc(N3CCOCC3)cn12]

To a solution of intermediate 51 (144 mg; 0.30 mmol) in THF (3 mL) was added dropwise TBAF (1M in THF) (0.325 mL; 0.33 mmol). The reaction mixture was stirred at rt for 1 h and poured onto a saturated solution of NaHCO₃. The aqueous layer was extracted with EtOAc (×3) and the combined organic layers were washed with brine, dried over MgSO₄ and filtered under vacuum. The residue (solid) was triturated in ACN. The solid was filtered and dried to give 60 mg (54% off-white solid) of compound 39. M.P.: 257° C. (DSC).

Example B25

Preparation of compound 44:

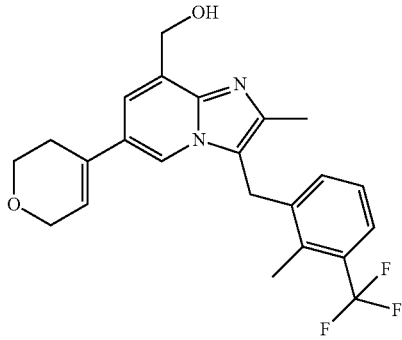 [SMILES: Cc1nc2c(CO)cc(C3=CCOCC3)cn2c1Cc1cccc(C(F)(F)F)c1C]

To a solution of intermediate 76 (176 mg; 0.26 mmol) in THF (5 mL) was added HCl (3M in H$_2$O) (0.88 mL; 2.6 mmol). The reaction mixture was stirred at rt for 18 h then diluted with EtOAc and the mixture was slowly basified with a saturated solution of NaHCO$_3$ until pH=8. The aqueous layer was extracted with EtOAc (×3). The combined organic layers were dried over MgSO$_4$, filtered and evaporated. The residue (200 mg, solid) was purified by chromatography over silica gel (regular SiOH 30 µm; 25 g; dry loading on Celite®; gradient: from 100% DCM to 95% DCM, 5% MeOH). The pure fractions were collected and the solvent was evaporated to give 73 mg (66%, white solid) of compound 44. M.P.: 199° C. (DSC).

Example B26

Preparation of Compound 45:

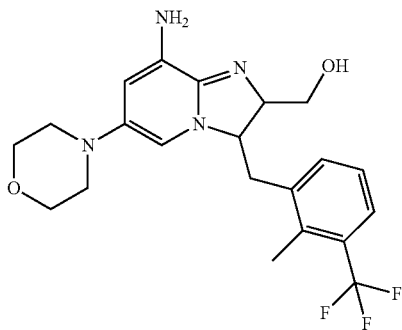 [SMILES: Cc1c(CC2C(CO)N=C3C(N)=CC(N4CCOCC4)=CN32)cccc1C(F)(F)F]

In a round bottom flask, intermediate 80 (68 mg; 0.10 mmol) was diluted in THF (3.7 mL). Then, HCl (1M in H$_2$O) (0.97 mL; 0.97 mmol) was added and the reaction mixture was stirred overnight at rt. The reaction mixture was poured onto iced water, neutralized with K$_2$CO$_3$ and the aqueous layer was extracted with EtOAc. The organic layers were combined, dried over MgSO$_4$, filtered and the solvent was evaporated to dryness. The residue (40 mg) was purified by chromatography over silica gel (SiOH 15 µm; 24 g; gradient: from 98% DCM, 2% MeOH, 0.1% NH$_4$OH to 90% DCM, 10% MeOH, 0.1% NH$_4$OH). The pure fractions were collected and the solvent was evaporated to give 18 mg (44%) of compound 45.

Preparation of Compound 46:

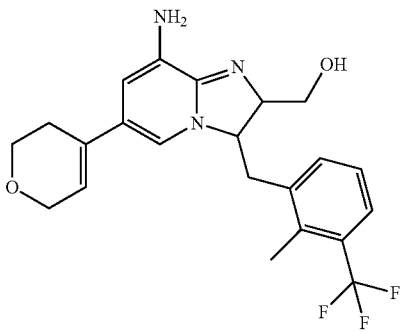 [SMILES: Cc1c(CC2C(CO)N=C3C(N)=CC(C4=CCOCC4)=CN32)cccc1C(F)(F)F]

Compound 46 was prepared according to an analogous procedure as described for the synthesis of compound 45, using intermediate 81 as starting material (5 mg, 28%. M.P.: 223° C. (K).

C: Conversion

Example C1

Preparation of Compound 29:

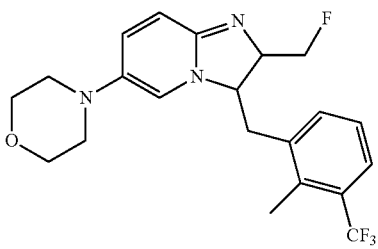 [SMILES: Cc1c(CC2C(CF)N=C3C=CC(N4CCOCC4)=CN32)cccc1C(F)(F)F]

In sealed tube, to a suspension of (diethylamino)difluorosulfonium tetrafluoroborate (34 mg; 0.15 mmol) in DCM (0.92 mL) at 0° C. were added compound 28 (40 mg; 0.10 mmol) and triethylamine trihydrofluoride (24 µL; 0.15 mmol). The reaction mixture was warmed to rt and stirred for 2 h. The mixture was combined with a reaction performed on 20 mg of compound 28. The mixture was neutralized with 10% aqueous solution of K$_2$CO$_3$. The layers were separated and the organic layer was dried over MgSO$_4$, filtered and evaporated under vacuum. The residue (61 mg) was purified by chromatography over silica gel (irregular SiOH 30 µm; 4 g; mobile phase: from 100% DCM to 96% DCM, 4% MeOH, 0.4% NH$_4$OH). The pure fractions were collected and the solvent was evaporated. The residue (21 mg, white gum) freeze-dried with ACN/water 20/80 to give 14 mg (23%, white solid) of compound 29. M.P.: 177° C. (DSC).

Preparation of Compound 36:

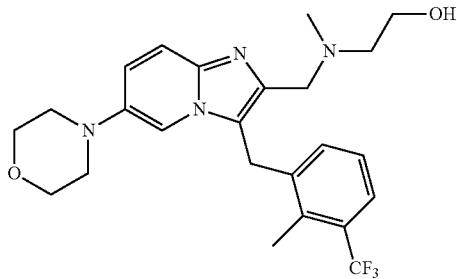

To a solution of compound 34 (80 mg; 0.18 mmol) in MeOH (1.8 mL) were added formaldehyde (80 µL; 1.07 mmol) and acetic acid (61 µL; 1.07 mmol). The reaction mixture was stirred at rt for 30 min. Then, sodium triacetoxyborohydride (227 mg; 1.07 mmol) was added. The reaction mixture was stirred at rt overnight. The mixture was evaporated under vacuum, then the residue was taken-up in DCM and a saturated solution of NaHCO$_3$ was added. The layers were separated and the aqueous layer was extracted with DCM. The combined organic layers were dried over MgSO$_4$, filtered and evaporated under vacuum. The residue (91 mg, green oil) was purified by chromatography over silica gel (irregular bare silica 150 g; gradient: from 95% DCM, 5% MeOH, 0.5% NH$_4$OH to 82% DCM, 18% MeOH, 1.8% NH$_4$OH). The pure fractions were collected and the solvent was evaporated. The residue (51 mg, colorless oil) was freeze-dried with ACN/water 23/77 to give 41 mg (white solid) which turn into an oil. This fraction was solubilized in EtOAc (5 mL), transferred in another container, evaporated under vacuum and dried (50° C.) to give 35 mg (42%, colorless oil) of compound 36.

Preparation of Compound 37:

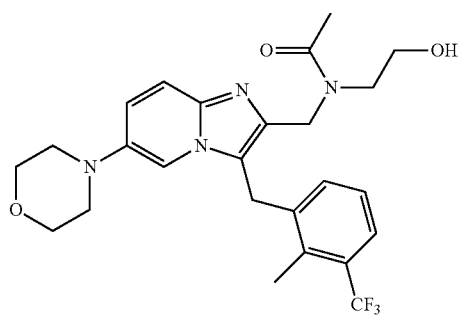 [SMILES: CC(=O)N(CCO)Cc1nc2ccc(N3CCOCC3)cn2c1Cc1cccc(C(F)(F)F)c1C]

To a solution of compound 34(80 mg; 0.18 mmol) in DCM (1.5 mL) at 0° C. was added dropwise a solution of acetic anhydride (17 µL; 0.18 mmol) in DCM (0.3 mL). The reaction mixture was warmed to rt and stirred for 1h30. Then, a saturated solution of NaHCO$_3$ was added. The layers were separated and the aqueous layer was extracted with DCM. The combined organic layers were dried over MgSO$_4$, filtered and evaporated under vacuum. The residue (82 mg, blue solid) was purified by chromatography over silica gel (irregular bare silica 150 g; gradient: from 95% DCM, 5% MeOH, 0.5% NH$_4$OH to 82% DCM, 18% MeOH, 1.8% NH$_4$OH). The pure fractions were collected and the solvent was evaporated. The residue (23 mg, colorless oil) was freeze-dried with ACN/water 20/80 to give 21 mg (24%, white fluffy solid) of compound 37. M.P.: 172° C. (DSC).

Example C2

Preparation of Compound 9:

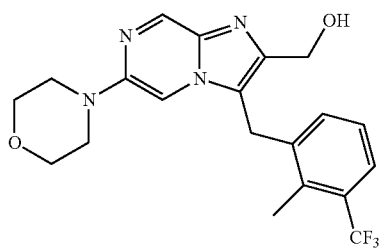 [SMILES: Cc1c(Cc2c(CO)nc3cnc(N4CCOCC4)cn23)cccc1C(F)(F)F]

Lithium hydroxide monohydrate (35 mg; 0.84 mmol) was added to a mixture of compound 2 (75 mg; 0.17 mmol) in H$_2$O (0.2 mL) and MeOH (2 mL) at room temperature and the solution was stirred at rt overnight. H$_2$O and EtOAc were added. The organic layer was dried over MgSO$_4$ and evaporated to dryness. The residue (117 mg) was taken up with diethylether. Then, a precipitate was filtered and dried to give 30 mg (44%) of compound 9. M.P.: 195° C. (K).

Example C3

Preparation of Compound 49

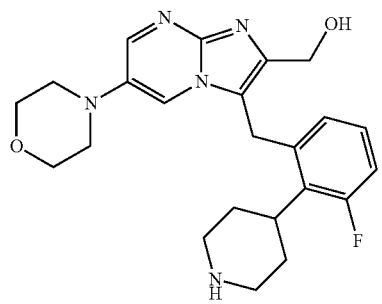 [SMILES: OCc1nc2ncc(N3CCOCC3)cn2c1Cc1cccc(F)c1C1CCNCC1]

Compound 49 was prepared according to an analogous procedure as described for the synthesis of compound 18, using compound 53 as starting material (crystallized from DIPE; 19 mg, 9%). M.P.: 224° C. (DSC).

Analytical Part

LCMS (Liquid Chromatography/Mass Spectrometry)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times (R$_t$) and ions. If not specified differently in the table of data, the reported molecular ion corresponds to the [M+H]$^+$ (protonated molecule) and/or [M−H]$^−$ (deprotonated molecule). In case the compound was not directly ionizable the type of adduct is specified (i.e. [M+NH$_4$]$^+$, [M+HCOO]$^−$, etc. . . . ). For molecules with multiple isotopic patterns (Br, Cl, . . . ), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE

LCMS Method codes (Flow expressed in mL/min; column temperature (T) in °C.; Run time in minutes).

| Method code | Instrument | Column | Mobile phase | gradient | Flow Column T | Run time |
|---|---|---|---|---|---|---|
| Method 1 | Waters: Acquity UPLC ®-DAD and Quattro Micron ™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min held for 1.94 min, back to 84.2% A in 0.73 min, held for 0.73 min. | 0.343 40 | 6.2 |
| Method 2 | Agilent: 1100-DAD and MSD | YMC: Pack ODS-AQ (3 μm, 4.6 × 50 mm) | A: HCOOH 0.1% in water, B: $CH_3CN$ | 95% A to 5% A in 4.8 min, held for 1 min, back to 95% A in 0.2 min, held for 1.0 min. | 2.6 35 | 6 |
| Method 3 | Agilent 1290 Infinity DAD TOF-LC/MS G6224A | YMC-pack ODS-AQ C18 (50 × 4.6 mm, 3 μm) | A: 0.1% HCOOH in H2O B: CH3CN | 94.51% A to 5% A in 4.8 min, held for 1.0 min, back to 95% A in 0.2 min, held for 0.2 min. | 2.6 35 | 6.0 |

Melting Points

For a number of compounds, melting points (MP) were determined with a DSC1 (Mettler-Toledo). Melting points were measured with a temperature gradient of 10° C./minute. Maximum temperature was 350° C. Values are peak values."

For a number of compounds, melting points were obtained with a Kofler hot bench, consisting of a heated plate with linear temperature gradient, a sliding pointer and a temperature scale in degrees Celsius.

For a number of compounds, melting points were obtained with or a MP50 (Mettler Toledo) with which melting points were measured with a temperature gradient of 10° C./minute. Starting temperature was 50° C. and maximum temperature was 300° C.

The NMR experiments were carried out using a Bruker Avance 500 III using internal deuterium lock and equipped with reverse triple-resonance ($^1H$, $^{13}C$, $^{15}N$ TXI) probe head. Chemical shifts (δ) are reported in parts per million (ppm).

TABLE

| N° | Compound | MP | Kofler (K), DSC or Mettler Toledo (M) | Rt | [M + H]$^+$ | Method HPLC |
|---|---|---|---|---|---|---|
| 1 | 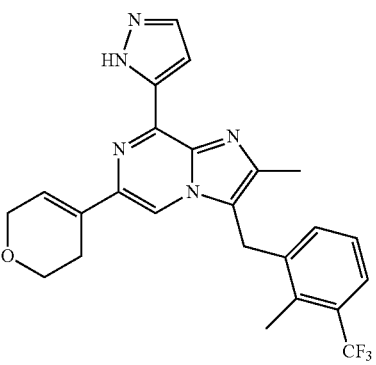 [SMILES: Cc1nc2c(-c3ccn[nH]3)nc(C3=CCOCC3)cn2c1Cc1cccc(C(F)(F)F)c1C] | 240 | DSC | 3.28 | 454 | 1 |
| 2 | 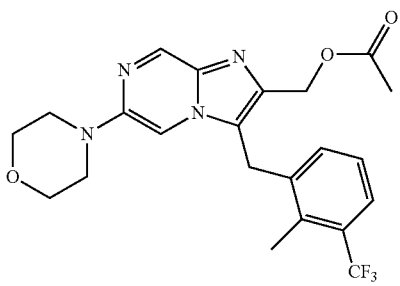 [SMILES: CC(=O)OCc1nc2cnc(N3CCOCC3)cn2c1Cc1cccc(C(F)(F)F)c1C] | — | — | — | — | — |

TABLE-continued

| N° | Compound | MP | Kofler (K), DSC or Mettler Toledo (M) | Rt | [M + H]+ | Method HPLC |
|---|---|---|---|---|---|---|
| 3 | (structure) 0.52 H2O 0.7 CF3COOH | 80 (gum) | K | 2.18 | 431 | 1 |
| 4 | (structure) | 80 (gum) | K | 2.87 | 418 | 1 |
| 5 | (structure) | 257 | DSC | 2.79 | 431 | 1 |
| 6 | (structure) | 197 | DSC | 2.95 | 454 | 1 |

TABLE-continued

| N° | Compound | MP | Kofler (K), DSC or Mettler Toledo (M) | Rt | [M + H]⁺ | Method HPLC |
|---|---|---|---|---|---|---|
| 8 | | 80 (gum) | K | 2.92 | 390 | 1 |
| 9 | | 195 | K | 2.54 | 406 | 1 |
| 10 | | 198 | K | 2.52 | 504 | 1 |
| 11 | | 80 (gum) | K | 2.41 | 503 | 1 |
| 12 | | 80 (gum) | K | 2.36 | 450 | 1 |

TABLE-continued

| N° | Compound | MP | Kofler (K), DSC or Mettler Toledo (M) | Rt | [M + H]⁺ | Method HPLC |
|---|---|---|---|---|---|---|
| 13 | | 142 | K | 2.57 | 421 | 1 |
| 14 | | 80 (gum) | K | 2.40 | 531 | 1 |
| 15 | | 80 (gum) | K | 2.34 | 504 | 1 |
| 16 | | 184 | DSC | 2.46 | 372 | 1 |
| 17 | | 135 | M | — | — | — |

TABLE-continued

| N° | Compound | MP | Kofler (K), DSC or Mettler Toledo (M) | Rt | [M + H]⁺ | Method HPLC |
|---|---|---|---|---|---|---|
| 18 | | 231 | DSC | 2.45 | 407 | 1 |
| 19 | | 263 | M | 2.00 | 503 | 2 |
| 20 | | — | — | 1.89 | 515 | 2 |
| 21 | | 228 | K | 2.52 | 536 | 1 |

TABLE-continued
| N° | Compound | MP | Kofler (K), DSC or Mettler Toledo (M) | Rt | [M + H]+ | Method HPLC |
|---|---|---|---|---|---|---|
| 22 | 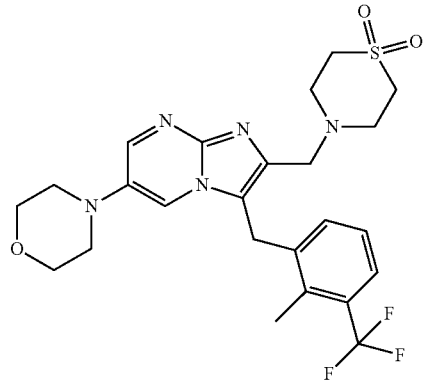 [SMILES: Cc1c(Cc2c(CN3CCS(=O)(=O)CC3)nc3ncc(N4CCOCC4)cn23)cccc1C(F)(F)F] | 225 | K | 2.56 | 524 | 1 |
| 23 | 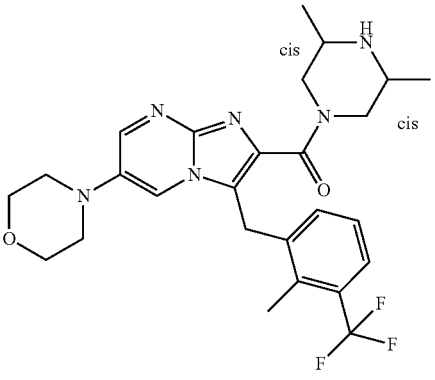 [SMILES: Cc1c(Cc2c(C(=O)N3CC(C)NC(C)C3)nc3ncc(N4CCOCC4)cn23)cccc1C(F)(F)F] | 130 | M | 2.15 | 517 | 3 |
| 24 | 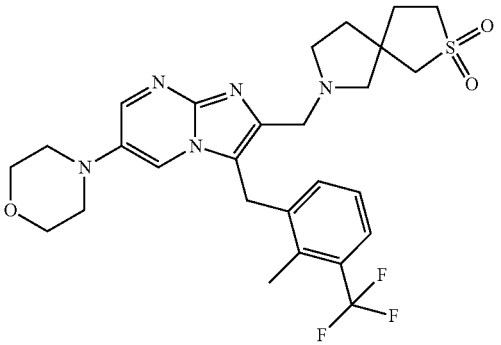 [SMILES: Cc1c(Cc2c(CN3CCC4(CCS(=O)(=O)C4)C3)nc3ncc(N4CCOCC4)cn23)cccc1C(F)(F)F] | — | — | 2.62 | 564 | 1 |
| 24a | 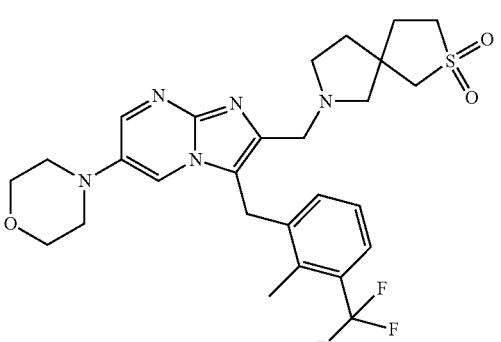<br>1.63 HCl, 0.71 H$_2$O | — | — | 2.62 | 564 | 1 |

TABLE-continued

| N° | Compound | MP | Kofler (K), DSC or Mettler Toledo (M) | Rt | [M + H]+ | Method HPLC |
|---|---|---|---|---|---|---|
| 25 | | 210 | DSC | 2.19 | 357 | 1 |
| 26 | | 200 | DSC | 2.68 | 564 | 1 |
| 27 | | 162 | DSC | 2.93 | 390 | 1 |
| 28 | | 196 | DSC | 2.57 | 406 | 1 |
| 29 | | 177 | DSC | 2.91 | 407 | 1 |

TABLE-continued

| N° | Compound | MP | Kofler (K), DSC or Mettler Toledo (M) | Rt | [M + H]+ | Method HPLC |
|---|---|---|---|---|---|---|
| 30 | | 176 | DSC | 2.99 | 462 | 1 |
| 31 | | — | — | 2.57 | 514 | 1 |
| 32 | | — | — | 2.42 | 486 | 1 |
| 33 | | 196 | DSC | 2.64 | 535 | 1 |

TABLE-continued
| N° | Compound | MP | Kofler (K), DSC or Mettler Toledo (M) | Rt | [M + H]⁺ | Method HPLC |
|---|---|---|---|---|---|---|
| 34 | 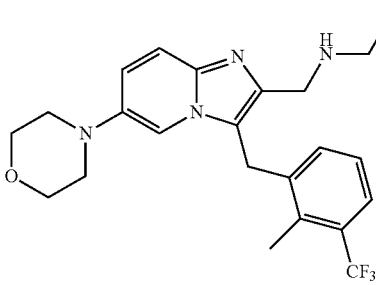 | 147 | DSC | 2.38 | 449 | 1 |
| 35 | 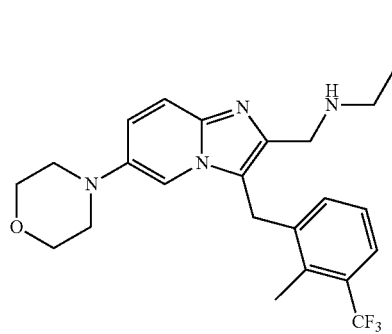 | 133 | DSC | 2.38 | 463 | 1 |
| 36 | 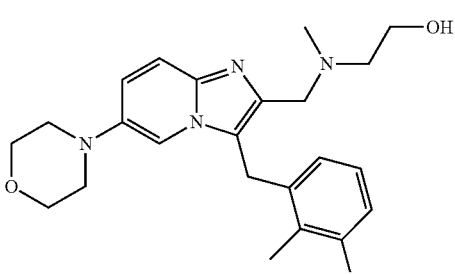 | — | — | 2.50 | 463 | 1 |
| 37 | 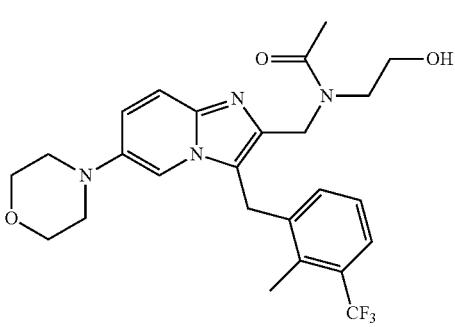 [SMILES: CC(=O)N(CCO)Cc1nc2ccc(N3CCOCC3)cn2c1Cc1cccc(C(F)(F)F)c1C] | 172 | DSC | 2.49 | 491 | 1 |

TABLE-continued

| N° | Compound | MP | Kofler (K), DSC or Mettler Toledo (M) | Rt | [M + H]+ | Method HPLC |
|---|---|---|---|---|---|---|
| 38 | | — | — | 2.72 | 472 | 1 |
| 39 | | 257 | DSC | 2.48 | 373 | 1 |
| 40 | | 184 | DSC | 2.78 | 532 | 1 |
| 41 | | — | — | 2.65 | 469 | 1 |

TABLE-continued

| N° | Compound | MP | Kofler (K), DSC or Mettler Toledo (M) | Rt | [M + H]+ | Method HPLC |
|---|---|---|---|---|---|---|
| 42 | | 238 | DSC | 2.85 | 469 | 1 |
| 43 | | 247 | DSC | 2.79 | 469 | 1 |
| 44 | | 199 | DSC | 2.91 | 417 | 1 |
| 45 | | — | — | 2.54 | 421 | 1 |

TABLE-continued

| N° | Compound | MP | Kofler (K), DSC or Mettler Toledo (M) | Rt | [M + H]+ | Method HPLC |
|---|---|---|---|---|---|---|
| 46 | | 223 | K | 2.68 | 418 | 1 |
| 47 | | — | — | — | — | — |
| 48 | | 222 | DSC | 1.63 | 440 | 1 |
| 49 | | 224 | DSC | 1.55 | 426 | 1 |
| 50 | | — | — | — | — | — |

TABLE-continued

| N° | Compound | MP | Kofler (K), DSC or Mettler Toledo (M) | Rt | [M + H]+ | Method HPLC |
|----|----------|-----|------|-----|--------|------|
| 51 | *structure* | — | — | — | — | — |
| 52 | *structure* | — | — | — | — | — |
| 53 | *structure* | — | — | — | — | — |

Co. No. means compound number;
Retention time (R$_t$) in min;
MP means melting point (° C.);
dec means decomposition;
n.d. means not determined.

Compound 1: $^1$H NMR (500 MHz, DMSO-d$_6$) δ ppm 13.71 (br s, 1H) 8.04 (s, 1H) 7.71 (br s, 1H) 7.52-7.64 (m, 2H) 7.09-7.31 (m, 2H) 6.86 (br d, J=7.6 Hz, 1H) 4.49 (s, 2H) 4.30 (br s, 2H) 3.82 (br t, J=5.2 Hz, 2H) 2.48 (br s, 3H) 2.44 (br s, 2H) 2.31 (s, 3H)

Compound 21: $^1$H NMR (500 MHz, DMSO-d$_6$) δ ppm 8.59 (d, J=2.8 Hz, 1H) 7.81 (d, J=2.5 Hz, 1H) 7.56 (d, J=7.9 Hz, 1H) 7.23 (t, J=7.7 Hz, 1H) 6.77 (d, J=7.9 Hz, 1H) 4.41 (s, 2H) 4.20 (s, 4H) 3.63-3.80 (m, 4H) 3.54 (s, 2H) 3.28 (s, 4H) 2.95-3.02 (m, 4H) 2.47 (s, 3H)

Compound 46: $^1$H NMR (500 MHz, DMSO-d$_6$) δ ppm 7.53 (d, J=7.9 Hz, 1H) 7.14-7.25 (m, 2H) 6.81 (d, J=7.9 Hz, 1H) 6.42 (s, 1H) 6.05 (br s, 1H) 5.60 (s, 2H) 4.95 (t, J=5.5 Hz, 1H) 4.52 (d, J=5.4 Hz, 2H) 4.41 (s, 2H) 4.17 (br d, J=2.5 Hz, 2H) 3.74 (t, J=5.4 Hz, 2H) 2.24 (br s, 2H)

Compound 39: $^1$H NMR (400 MHz, DMSO-d$_6$) δ ppm 7.44 (d, J=9.6 Hz, 1H) 7.35 (s, 1H) 7.26 (dd, J=9.6, 2.0 Hz, 1H) 7.14 (d, J=1.5 Hz, 1H) 6.83-6.95 (m, 1H) 6.74-6.83 (m, 1H) 5.88 (d, J=8.1 Hz, 1H) 4.81 (t, J=5.6 Hz, 1H) 4.39 (d, J=5.6 Hz, 2H) 3.60-3.77 (m, 4H) 2.85-2.97 (m, 4H) 2.41 (s, 3H)

Pharmacology

Enzyme Binding Assays (KINOMEscan®)

Kinase enzyme binding affinities of compounds disclosed herein were determined using the KINOMEscan technology performed by DiscoveRx Corporation, San Diego, Calif., USA (www.kinomescan.com). Table A reports the obtained Kd values (nM), with the Kd being the inhibitor binding constant:

| No | Kd PIK3Cα_h (nM) | Kd PIK3Cβ_h (nM) | Kd PIK3Cδ_h (nM) | Kd PIK3Cγ_h (nM) | Kd MTOR_h (nM) |
|----|------|------|------|------|------|
| 1 | 288 | 1.6 | 69 | 1061 | 935 |
| 2 | — | — | — | — | — |
| 3 | 11482 | 1.4 | 468 | >30200 | >30200 |

-continued

| No | Kd PIK3Cα_h (nM) | Kd PIK3Cβ_h (nM) | Kd PIK3Cδ_h (nM) | Kd PIK3Cγ_h (nM) | Kd MTOR_h (nM) |
|---|---|---|---|---|---|
| 4 | 12023 | 7.6 | 3020 | 14791 | >30200 |
| 5 | 1820 | 4.7 | 891 | 6310 | 12303 |
| 6 | 343 | 5.5 | 682 | 4704 | 2172 |
| 8 | 25119 | 1175.0 | 19498 | >30200 | >30200 |
| 9 | 22387 | 35.0 | 4266 | >30200 | >30200 |
| 10 | >30200 | 41.0 | 4266 | >30200 | >30200 |
| 11 | >30200 | 120.0 | 8128 | >30200 | >30200 |
| 12 | >30200 | 68.0 | 5495 | >30200 | >30200 |
| 13 | 20417 | 126.0 | 14125 | >30200 | >30200 |
| 14 | >30200 | 155.0 | 15136 | >30200 | >30200 |
| 15 | >30200 | 141.0 | 11220 | >30200 | >30200 |
| 16 | 7586 | 25.0 | 1318 | 25119 | 28184 |
| 17 | — | — | — | — | — |
| 18 | 3504 | 1.4 | 442 | 15254 | 17896 |
| 19 | 16596 | 4.2 | 1230 | >30200 | >30200 |
| 20 | >30200 | 76.0 | 7244 | >30200 | >30200 |
| 21 | 1479 | 0.4 | 123 | >30200 | >30200 |
| 22 | 1445 | 3.1 | 631 | >30200 | >30200 |
| 23 | >30200 | 8.7 | 1479 | >30200 | >30200 |
| 24 | 2570 | 11.0 | 1413 | >30200 | >30200 |
| 24a | >30200 | 6.5 | 759 | >30200 | >30200 |
| 25 | 5888 | 8.9 | 759 | 7244 | 5623 |
| 26 | 4169 | 6.8 | 697 | >30200 | >30200 |
| 27 | 9550 | 363.0 | 2570 | >30200 | >30200 |
| 28 | 5370 | 13.0 | 794 | 16982 | 17783 |
| 29 | 6918 | 126.0 | 2138 | 14454 | >30200 |
| 30 | >10000 | 631.0 | 5754 | >30200 | >10000 |
| 31 | >30200 | 20.0 | 1349 | >30200 | >30200 |
| 32 | 7244 | 2.2 | 324 | 8511 | 27542 |
| 33 | 589 | 3.0 | 316 | >30200 | >30200 |
| 34 | 16934 | 9.0 | 741 | >30200 | 23175 |
| 35 | 22387 | 5.8 | 575 | >30200 | 21878 |
| 36 | >30200 | 22.0 | 2138 | >30200 | >30200 |
| 37 | 10233 | 20.0 | 1445 | >30200 | 23988 |
| 38 | 2951 | 71.0 | 2042 | 4365 | 2291 |
| 39 | 468 | 0.5 | 141 | 11220 | 3981 |
| 40 | 302 | 0.3 | 44 | >30200 | 12883 |
| 41 | 96 | 1.1 | 13 | 324 | 200 |
| 42 | 525 | 2.5 | 186 | 1072 | 151 |
| 43 | 585 | 0.9 | 35 | 1920 | 1674 |
| 44 | 7244 | 1.7 | 562 | 21380 | 17783 |
| 45 | 14454 | 91.0 | 3467 | 15849 | 18621 |
| 46 | 8427 | 16.0 | 1065 | 6463 | 5890 |
| 47 | — | — | — | — | — |
| 48 | 9550 | 49.0 | 4786 | 12883 | >30200 |
| 49 | 2570 | 15.0 | 2239 | 15849 | >30200 |

Cellular Assays:

Cellular activity of PI3Kβ inhibitors was determined by quantifying the phosphorylation of Akt in PC-3 cells. Akt phosphorylated at Ser473 and Thr308 were measured using an enzyme-linked immunosorbent assay (ELISA; Meso Scale Discovery (MSD), Gaithersburg, Md.) and specific primary antibodies from MSD.

On day 1, PC3 cells (ATCC #CRL-14351) were seeded into PerkinElmer MW96 plates at 25.000 cells per well, in 75 μl complete culture medium (DMEM high glucose, AQmedia™, D0819, Sigma-Aldrich) containing 10% heat inactivated FCS and incubated at 37° C., 50% CO2 during 24 hours. On day 2, compound or DMSO (0.3%) was added and cells were further incubated for 60 min at 37° C., 5% CO2 in a total volume of 100 μl of medium.

The phosphoprotein assay was executed according to vendor instructions in the Phospho-Akt (Ser473) Assay Whole Cell Lysate Kit (MSD #K15100D-3) and the Phospho-Akt (Thr308) Assay Whole Cell Lysate Kit (MSD #K151DYD-3) using the lysis, blocking and wash buffer provided.

Briefly, at the end of the cell treatment period, media were removed by aspiration and adherent cells were lysed in 50 μl ice-cold lysis buffer. MSD plates are supplied pre-coated with capture antibodies for Phospho-Akt (Ser473 and Thr308). After blocking, lysates from tissue culture plates were added and plates were washed. Then, a solution containing the detection antibody (anti-total Akt conjugated with an electrochemiluminescent compound-MSD Sulfo-tag label) was added. The signals were detected using an MSD SECTOR Imager 6000 and are proportional to the phospho-Akt titres.

Data were processed. The percentage of inhibition was plotted against the log concentration of test compounds, and the sigmoidal log concentration-effect curve of best fit was calculated by nonlinear regression analysis. From these concentration-response curves, the $IC_{50}$ values were calculated. Five concentrations were used for curve fitting.

Table B reports the obtained $IC_{50}$ values (nM):

| Co. No. | $IC_{50}$ pAkt_S473 (nM) | $IC_{50}$ pAkt_Thr308 (nM) |
|---|---|---|
| 1 | 14 | 7 |
| 2 | — | — |
| 3 | — | >513 |

-continued

| Co. No. | IC$_{50}$ pAkt_S473 (nM) | IC$_{50}$ pAkt_Thr308 (nM) |
|---|---|---|
| 4 | >513 | 479 |
| 5 | ~87 | ~65 |
| 6 | 185 | 59 |
| 8 | >513 | >513 |
| 9 | ~427 | 501 |
| 10 | >513 | >513 |
| 11 | >513 | >513 |
| 12 | >513 | >513 |
| 13 | >513 | >513 |
| 14 | >513 | >513 |
| 15 | — | — |
| 16 | 347 | ~245 |
| 17 | — | — |
| 18 | 72 | 43 |
| 19 | 380 | 186 |
| 20 | >513 | >513 |
| 21 | 15 | 17 |
| 22 | 214 | ~79 |
| 23 | 389 | ~219 |
| 24 | 288 | ~174 |
| 24a | 347 | 170 |
| 25 | 195 | 120 |
| 26 | 479 | 71 |
| 27 | >513 | 417 |
| 28 | 182 | ~83 |
| 29 | 155 | 50 |
| 30 | — | — |
| 31 | 479 | >513 |
| 32 | 191 | ~178 |
| 33 | 16 | 15 |
| 34 | 110 | 70 |
| 35 | 74 | 89 |
| 36 | ~224 | ~132 |
| 37 | 282 | ~282 |
| 38 | >513 | >513 |
| 39 | ~40 | 28 |
| 40 | 15 | ~10 |
| 41 | 14 | 14 |
| 42 | 76 | ~20 |
| 43 | 52 | ~59 |
| 44 | 135 | 83 |
| 45 | 145 | 166 |
| 46 | 32 | 18 |
| 47 | — | — |
| 48 | >513 | >513 |
| 49 | >513 | >513 |

Prophetic Composition Examples

"Active ingredient" (a.i.) as used throughout these examples relates to a compound of Formula (I), including any tautomer or stereoisomeric form thereof, or a N-oxide, a pharmaceutically acceptable addition salt or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:

1. A compound of Formula (I)

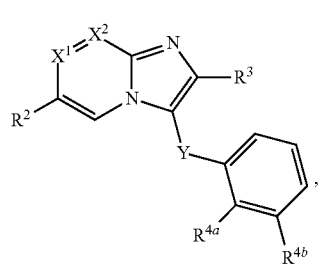

(I)

a tautomer or a stereoisomeric form thereof, wherein
X$^1$ represents CH;
X$^2$ represents N;
Y represents —CH$_2$— or NH—;
R$^2$ represents

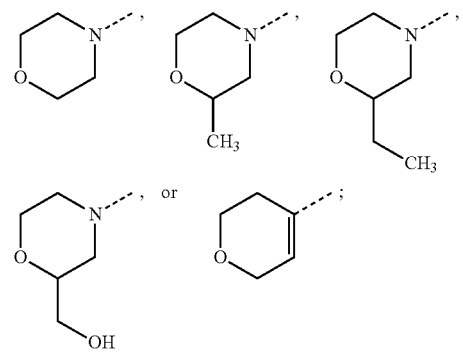

R$^3$ represents C$_{1-4}$alkyl; —C(=O)—O—C$_{1-4}$alkyl; —C(=O)—Het$^1$; —CH(OH)—CH$_2$—R$^q$; C$_{1-4}$alkyl substituted on the same carbon atom with one OH and with one Het$^1$; or C$_{1-4}$alkyl substituted with one substituent selected from the group consisting of halo, —OH, —NH$_2$, —O—(C=O)—C$_{1-4}$alkyl, —(C=O)—O—C$_{1-4}$alkyl, -NH-(C=O)—C$_{1-4}$alkyl, —NH—(SO$_2$)—C$_{1-4}$alkyl, —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, —N(C═O—C$_{1-4}$alkyl)-C$_{1-4}$alkyl-OH, —(C═O)—NH—C$_{1-4}$alkyl-OH,
—O—(C═O)—CH(NH$_2$)—C$_{1-4}$alkyl, —O—(C═O)—CH(NH$_2$)—C$_{1-4}$alkyl-Ar,

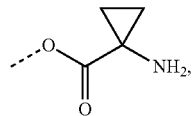

—NH—C$_{1-4}$alkyl-OH, Het$^1$, —O—C(═O)—C$_{1-4}$alkyl-Het$^1$, —C(═O)—Het$^1$, and —NH—C(═O)—Het$^1$;

R$^q$ represents Het$^1$, halo, —OH, —NH$_2$, —O—(C═O)—C$_{1-4}$alkyl, —NH—(C═O)—C$_{1-4}$alkyl,
NH—(SO$_2$)—C$_{7-4}$alkyl, —N(CH$_3$)—C$_{1-4}$alkyl-SO$_2$—CH$_3$, —NH—C$_{1-4}$alkyl-SO$_2$—CH$_3$,
N(CH$_3$)—C$_{1-4}$alkyl-OH, —O—(C═O)—CH(NH$_2$)—C$_{1-4}$alkyl,
O—(C═O)—CH(NH$_2$)—C$_{1-4}$alkyl-Ar,

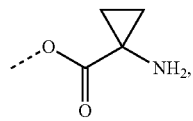

or —NH—C$_{1-4}$alkyl-OH;

Ar represents phenyl optionally substituted with one hydroxy;

R$^{4a}$ represents hydrogen, C$_{1-4}$alkyl, Het$^a$, or C$_{1-4}$alkyl substituted with one or more substituents each independently selected from the group consisting of —OH, —NR$^5$R$^6$ and Het$^a$;

R$^{4b}$ represents hydrogen, halo, C$_{1-4}$alkyl, or C$_{1-4}$alkyl substituted with one or more halo substituents;

or R$^4$a and R$^{4b}$ are taken together to form together with the phenyl ring to which they are attached a structure of Formula (a-1), (a-2), (a-3), (a-4) or (a-5):

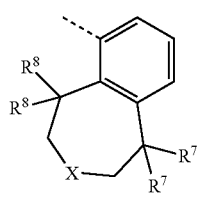
(a-1)

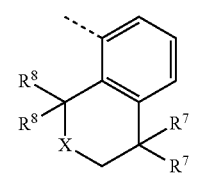
(a-2)

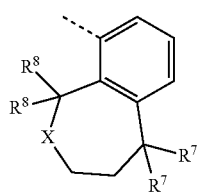
(a-3)

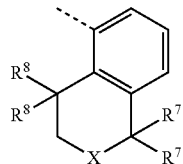
(a-4)

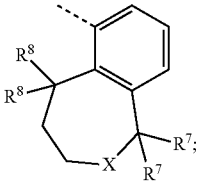
(a-5)

X represents —NH—, —O—, —N(C$_{1-3}$alkyl)-, or —N(hydroxyC$_{1-3}$alkyl)-;

both R$^7$ substituents are the same and are selected from the group consisting of hydrogen, fluoro and methyl; or both R$^7$ substituents are taken together to form together with the common carbon atom to which they are attached a cyclopropyl, cyclobutyl or oxetanyl;

both R$^8$ substituents are the same and are selected from the group consisting of hydrogen and methyl; or both R$^8$ substituents are taken together to form together with the common carbon atom to which they are attached a cyclopropyl, cyclobutyl or oxetanyl;

R$^5$ represents hydrogen, C$_{1-6}$alkyl, or C$_{1-6}$alkyl substituted with one —OH;

R$^6$ represents hydrogen, C$_{1-6}$alkyl, or C$_{1-6}$alkyl substituted with one —OH;

Het$^1$ represents a 4-, 5- or 6-membered saturated heterocyclyl containing at least one heteroatom each independently selected from O, S, S(═O)$_p$ and N; said 4-, 5- or 6-membered saturated heterocyclyl is optionally substituted with one or two substituents each independently selected from the group consisting of halo, —NH$_2$, C$_{1-4}$alkyl, —S(═O)$_2$—C$_{1-6}$alkyl, —C$_{1-4}$alkyl-S(═O)$_2$—C$_{1-6}$alkyl hydroxyl, C$_{1-4}$alkyloxy, fluoro, cyano and C$_{1-4}$alkyl substituted with one hydroxy; or two substituents on the same carbon atom of said 4-, 5- or 6-membered saturated heterocyclyl are taken together to form together with the common carbon atom to which they are attached Ring A;

Ring A represents cyclobutyl, cyclopentyl, cyclohexyl or a 4-, 5- or 6-membered saturated heterocyclyl containing at least one heteroatom each independently selected from O, S, S(═O)$_p$ and N; said cyclobutyl, cyclopentyl, cyclohexyl or 4-, 5- or 6-membered saturated heterocyclyl is optionally substituted with one or two C$_{1-4}$alkyl substituents, with one C$_{1-4}$alkyl and one hydroxy substituent, or with one hydroxy substituent;

each Het$^a$ independently represents a 4-, 5- or 6-membered saturated heterocyclyl containing at least one heteroatom each independently selected from O, S, S(═O)$_p$ and N; said 4-, 5- or 6-membered saturated heterocyclyl is optionally substituted with one or two substituents each independently selected from the group consisting of C$_{1-4}$alkyl, —S(═O)$_2$-C$_{1-6}$alkyl, hydroxy, —C$_{1-4}$alkyl-S(═O)$_2$—C$_{1-6}$alkyl, and C$_{1-4}$alkyl substituted with one hydroxy; or two substituents on the same carbon atom of said 4-, 5- or 6-membered saturated heterocyclyl are taken together to form together with the common carbon atom to which they are attached Ring B;

Ring B represents cyclobutyl, cyclopentyl, cyclohexyl or a 4-, 5- or 6-membered saturated heterocyclyl containing at least one heteroatom each independently selected from O, S, S(=O)$_p$ and N; said cyclobutyl, cyclopentyl, cyclohexyl or 4-, 5- or 6-membered saturated heterocyclyl is optionally substituted with one or two C$_{1-4}$alkyl substituents, with one C$_{1-4}$alkyl and one hydroxy substituent, or with one hydroxy substituent;
p represents 1 or 2;
or a N-oxide, a pharmaceutically acceptable addition salt thereof.

2. The compound according to claim 1, wherein
R$^3$ represents C$_{1-4}$alkyl; —C(=O)—Het$^1$; C$_{1-4}$alkyl substituted on the same carbon atom with one —OH and with one Het$^1$; or C$_{1-4}$alkyl substituted with one substituent selected from the group consisting of halo, —OH, —NH$_2$, —O—(C=O)—C$_{1-4}$alkyl, —(C=O)—O—C$_{1-4}$alkyl, —NH—(C=O)—C$_{1-4}$alkyl, —NH—(SO$_2$)—C$_{1-4}$alkyl, —N(CH$_3$)—C$_{1-4}$alkyl-SO$_2$—CH$_3$, -NH-C$_{1-4}$alkyl-SO$_2$—CH$_3$, -N(CH$_3$)—C$_{1-4}$alkyl-OH, —N(C=O—C$_{1-4}$alkyl)-C$_{1-4}$alkyl-OH, —(C=O)—NH—C$_{1-4}$alkyl-OH, —O—(C=O)—CH(NH$_2$)—C$_{1-4}$alkyl,

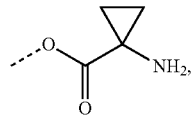

—NH—C$_{1-4}$alkyl-OH, Het$^1$,

O—C(=O)—C$_{1-4}$alkyl-Het$^1$, —C(=O)—Het$^1$ and —NH—C(=O)—Het$^1$;
each Het$^a$ independently represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of C$_{1-4}$alkyl, —S(=O)$_2$—C$_{1-6}$alkyl, hydroxy, —C$_{1-4}$alkyl-S(=O)$_2$—C$_{1-6}$alkyl, and C$_{1-4}$alkyl substituted with one hydroxyl.

3. The compound according to claim 1, wherein R$^2$ represents

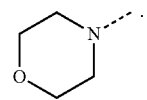

4. The compound according to claim 1, wherein Y represents —CH$_2$—.

5. A pharmaceutical composition comprising a pharmaceutically acceptable carrier and a compound according to claim 1.

* * * * *